(12) United States Patent
Bennett et al.

(10) Patent No.: US 12,403,204 B2
(45) Date of Patent: Sep. 2, 2025

(54) GENE THERAPY FOR OCULAR DISORDERS

(71) Applicant: The Trustees of the University of Pennsylvania, Philadelphia, PA (US)

(72) Inventors: Jean Bennett, Bryn Mawr, PA (US); Jeannette Bennicelli, Philadelphia, PA (US); Junwei Sun, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 505 days.

(21) Appl. No.: 17/369,525

(22) Filed: Jul. 7, 2021

(65) Prior Publication Data

US 2021/0330816 A1 Oct. 28, 2021

Related U.S. Application Data

(62) Division of application No. 16/061,530, filed as application No. PCT/US2016/066402 on Dec. 13, 2016, now Pat. No. 11,090,392.

(60) Provisional application No. 62/266,789, filed on Dec. 14, 2015.

(51) Int. Cl.
*A61K 48/00* (2006.01)
*A61K 9/00* (2006.01)
*C07K 14/47* (2006.01)
*C12N 15/86* (2006.01)

(52) U.S. Cl.
CPC ........ *A61K 48/0058* (2013.01); *A61K 9/0048* (2013.01); *C07K 14/47* (2013.01); *C12N 15/86* (2013.01); *C12N 2750/14143* (2013.01); *C12N 2799/022* (2013.01); *C12N 2799/04* (2013.01); *C12N 2800/107* (2013.01); *C12N 2800/22* (2013.01); *C12N 2840/002* (2013.01); *C12N 2840/007* (2013.01)

(58) Field of Classification Search
CPC ................................................ A61K 48/0058
See application file for complete search history.

(56) References Cited

U.S. PATENT DOCUMENTS

| | | |
|---|---|---|
| 5,139,941 A | 8/1992 | Muzyczka et al. |
| 5,478,745 A | 12/1995 | Samulski et al. |
| 5,741,683 A | 4/1998 | Zhou et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,629,322 B2 | 12/2009 | Kleinschmidt et al. |
| 7,790,449 B2 | 9/2010 | Gao et al. |
| 7,906,111 B2 | 3/2011 | Wilson et al. |
| 8,147,823 B2 | 4/2012 | Acland et al. |
| 2004/0022766 A1 | 2/2004 | Acland et al. |
| 2007/0036760 A1 | 2/2007 | Wilson et al. |
| 2009/0197338 A1 | 8/2009 | Vandenberghe et al. |
| 2011/0305772 A1 | 12/2011 | Cameron |
| 2013/0317091 A1 | 11/2013 | Ye et al. |
| 2014/0010861 A1 | 1/2014 | Bancel et al. |
| 2014/0087444 A1 | 3/2014 | Bennett et al. |
| 2015/0259395 A1 | 9/2015 | Chalberg et al. |
| 2015/0299864 A1 | 10/2015 | Inoue et al. |
| 2016/0206704 A1 | 7/2016 | MacLaren |

FOREIGN PATENT DOCUMENTS

| | | |
|---|---|---|
| EP | 1310571 | 2/2006 |
| RU | 2444977 C2 | 3/2012 |
| WO | WO-2002/057454 | 7/2002 |
| WO | WO-2003/042397 | 5/2003 |
| WO | WO-2005/033321 | 4/2005 |
| WO | WO-2006/110689 | 10/2006 |
| WO | WO-2010/005533 | 1/2010 |
| WO | WO-2011/034947 A2 | 3/2011 |
| WO | WO-2011/126808 | 10/2011 |
| WO | WO 2012/094560 A2 | 7/2012 |
| WO | WO-2012/114090 | 8/2012 |
| WO | WO-2012/158757 | 11/2012 |
| WO | WO-2013/049493 | 4/2013 |
| WO | WO 2013/063601 A1 | 5/2013 |
| WO | WO-2013/086515 | 6/2013 |
| WO | WO-2014/011210 | 1/2014 |
| WO | WO-2014/124282 | 8/2014 |
| WO | WO-2014/170480 | 10/2014 |

(Continued)

OTHER PUBLICATIONS

Bhosale et al., 2021, Thieme Medical Publishing, pp. 4-7 (Year: 2021).*

(Continued)

*Primary Examiner* — Anoop K Singh
*Assistant Examiner* — David A Montanari
(74) *Attorney, Agent, or Firm* — Howson & Howson LLP; Colleen M. Schaller

(57) ABSTRACT

Compositions and methods are provided for treating ocular disorders in a subject are provided. In one aspect, an adeno-associated viral vector is provided which includes a nucleic acid molecule comprising a sequence encoding CNGA3. In another aspect, an adeno-associated viral vector is provided which includes a nucleic acid molecule comprising a sequence encoding CNGB3. In another aspect, an adeno-associated viral vector is provided which includes a nucleic acid molecule comprising a sequence encoding REP-1. In desired embodiments, the subject is human, cat, dog, sheep, or non-human primate.

10 Claims, 27 Drawing Sheets

Specification includes a Sequence Listing.

(56) References Cited

FOREIGN PATENT DOCUMENTS

| WO | WO-2015/092440 | 6/2015 |
|---|---|---|
| WO | WO 2015/142941 | 9/2015 |
| WO | WO-2015/160893 | 10/2015 |

OTHER PUBLICATIONS

Reichel et al. (2022, BMJ, vol. 106, pp. 1567-1572) (Year: 2022).*
Michalakis et al., 2022, vol. 26, pp. 51-59 (Year: 2022).*
Office Action dated Feb. 28, 2024 issued in Canadian Patent Application No. 3,008,264.
Beltran, W.A. et al., rAAV2/5 gene-targeting to rods: dose-dependent efficiency and complications associated with different promoters, Gene Therapy, vol. 17(9): 1162-74, Sep. 2010.
Buchholz et al., Rapid and Efficient Directed Differentiation of Human Pluripotent Stem Cells Into Retinal Pigmented Epithelium, Stem Cells Translational Medicine, vol. 2:384-393, May 2013.
Buning et al., Recent developments in adeno-associated virus vector technology, J. Gene Med, vol. 10:717-733, 2008.
Cai, X. et al., A 350 bp region of the proximal promoter of RDS drives cell-type specific gene expression, Experimental Eye Research, vol. 91(2):186-94, Aug. 2010.
Cereso, N. et al., Proof of concept for AAV2/5-mediated gene therapy in iPSC-derived retinal pigment epithelium of a choroideremia patient, Molecular Therapy—Methods & Clinical Development; vol. 1:14011, Apr. 2014.
Coussa, R.G. and Traboulsi, E.I, Choroideremia: a review of general findings and pathogenesis, Ophthalmic Genetics, vol. 33(2):57-65, Jun. 2012.
Daber, A novel molecular switch, J Mol Biol, vol. 391(4):661-70, Aug. 2009 (ePub Jun. 2009).
Dalkara, et al., In vivo-directed evolution of a new adeno-associated virus for therapeutic outer retinal gene delivery from the vitreous, Science Translation Medicine, vol. 5(189):189ra76, Jun. 2013.
Damdindorj et al., A Comparative Analysis of Constitutive Promoters Located in Adeno-Associated Viral Vectors, PLoS One, vol. 9(8):e106472, Aug. 2014.
Diehl et al., A Good Practice Guide to the Administration of Substances and Removal of Blood, Including Routes and Volumes Applied Toxicology, vol. 21:15-23, Sep. 2001.
Dominguez et al., Intravenous scAAV9 delivery of a codon-optimized SMN1 sequence rescues SMA mice, Human Molecular Genetics, vol. 20(4):681-693, Nov. 2011.
Genbank Accession No. AY327580, Homo sapiens rhodopsin kinase gene, promoter region, exon 1 and partial cds, Nov. 2003.
GenBank accession No. NM_000390.2, Homo sapiens CHM, Rab escort protein 1 (CHM), transcript variant 1, mRNA: Feb. 2016.
GenBank accession No. NM_001298.2, Homo sapiens cyclic nucleotide gated channel alpha 3 (CNGA3), transcript variant 2, mRNA: Dec. 2018.
GenBank accession No. P24386, RecName: Full=Rab proteins geranylgeranyltransferase component A 1; AltName: Full=Choroideremia protein; AltName: Full=Rab escort protein 1; Short-REP-1; AltName: Full=TCD protein: Dec. 2018.
GenBank accession No. XM_011510554.1, Predicted: Homo sapiens cyclic nucleotide gated channel alpha 3 (CNGA3), transcript variant X1, mRNA: Jan. 2015.
Grieger & Samulski, Adeno-associated virus as a gene therapy vector: Vector development, production and clinical applications, Adv. Biochem. Engin/Biotechnol, vol. 99: 119-145, Oct. 2005.
Guo et al., Rapid and simplified purification of recombinant adeno-associated virus, J Virol Methods, vol. 183(2):139-146, Aug. 2012.
Fisher et al., Transduction with Recombinant Adeno-Associated Virus for Gene Therapy Is Limited by Leading-Strand Synthesis, J. Virol., vol. 70(1):520-532, Jan. 1996.
Kachi et al., Equine infectious anemia viral vector-mediated codelivery of endostatin and angiostatin driven by retinal pigmented epithelium-specific VMD2 promoter inhibits choroidal nevascularization, Human Gene Therapy, vol. 20(1):31-9, Jan. 2009.
Lambard, S. et al., Expression of rod-derived cone viability factor: dual role of CRX in regulating promoter activity and cell-type specificity, PLoS One, vol. 5(10): e13075, Oct. 2010.
Lock et al., Absolute Determination of Single-Stranded and Self-Complementary Adeno-Associated Viral Vector Genome Titers by Droplet Digital PCR, Hum Gene Ther Methods, vol. 25(2):115-25, Apr. 2014.
McCarty et al., Self-complementary recombinant adeno-associated virus (scAAV) vectors promote efficient transduction independently of DNA synthesis, Gene Therapy, vol. 8(16):1248-1254, Aug. 2001.
McLaughlin et al., Adeno-Associated Virus General Transduction Vectors: Analysis of Proviral Structures, J. Virol., vol. 62:1963, Jun. 1988.
Morrissey et al., PRE-1, a cis element sufficient to enhance cone- and rod-specific expression in differentiating zebrafish photoreceptors, BMC Developmental Biology., vol. 11:3, Jan. 2011.
Mowat et al., Tyrosine capsid-mutant AAV vectors for gene delivery to the canine retina from a subretinal or intravitreal approach, Gene Therapy, vol. 21:96-105, Jan. 2014.
Mussolino et al., AAV-mediated photoreceptor transduction of the pig cone-enriched retina, Gene Therapy, vol. 18(7):637-45, Jul. 2011.
Nagata et al., Codon Optimization Effect on Translational Efficiency of DNA Vaccine in Mammalian Cells: Analysis of Plasmid DNA Encoding a CTL Epitope Derived from Microorganisms, Biochemical and Biophysical Research Communications, pp. 445-451, Aug. 1999.
Nathans, J., and Hogness, D.S., Isolation and nucleotide sequence of the gene encoding human rhodopsin, Proceedings of the National Academy of Sciences of the United States of America, vol. 81(15):4851-5, Aug. 1984.
Nicoud, M. et al., Development of photoreceptor-specific promoters and their utility to investigate EIAV lentiviral vector mediated gene transfer to photoreceptors, The Journal of Gene Medicine, vol. 9(12):1015-23, Dec. 2007.
Ogueta, S.B. et al., The human cGMP-PDE beta-subunit promoter region directs expression of the gene to mouse photoreceptors, Invest Ophthalmology & Visual Science, vol. 41(13):4059-63, Dec. 2000.
Shu, X. et al., Functional characterization of the human RPGR proximal promoter, Invest Ophthalmology & Visual Science, vol. 53(7):3951-8, Jun. 2012.
Sochor et al., An Autogenously Regulated Expression System for Gene Therapeutic Ocular Applications, Scientific Reports, vol. 5:17105, Nov. 2015.
Sun, X. et al., Gene therapy with a promoter targeting both rods and cones rescues retinal degeneration caused by AIPL1 mutations, Gene Therapy, vol. 17(1):117-131, Jan. 2010.
Tolmachova, T. et al., CHM/REP1 cDNA delivery by lentiviral vectors provides functional expression of the transgene in the retinal pigment epithelium of choroideremia mice, The Journal of Gene Medicine, vol. 14(3):158-68, Mar. 2012.
Vasireddy, V. et al., AAV-mediated gene therapy for choroideremia: preclinical studies in personalized models, PLoS One, vol. 8(5):e61396, May 2013.
Zhang et al., Adenovirus-adeno-associated virus hybrid for large-scale recombinant adeno-associated virus production, Human Gene Therapy, vol. 20:922-929, Sep. 2009.
International Search Report and Written Opinion issued on International Patent Application No. PCT/US2016/066402, dated Jul. 31, 2017.
Examination Report issued Aug. 9, 2019 in European Patent Application No. 16852859.4.
International Search Report and Written Opinion issued in International Patent Application No. PCT/US2018/037592, date Nov. 5, 2018.
Office Action dated Oct. 22, 2020, issued in corresponding Russian Patent Application No. 2018125468 (including translation provided by local agent).
Office Action dated Dec. 2, 2020, issued in corresponding Japanese Patent Application No. 2018-531202 (including translation provided by local agent).

(56) References Cited

OTHER PUBLICATIONS

Extended European Search Report dated Feb. 19, 2021 issued in European Patent Application No. 20183330.8.
Extended European Search Report dated Feb. 22, 2021 issued in European Patent Application No. 18817402.3.
Restriction Requirement issued in U.S. Appl. No. 16/061,530, dated Jun. 25, 2020.
Applicant's Amendment and Response in U.S. Appl. No. 16/061,530, filed Aug. 25, 2020.
Non-Final Office Action issued in U.S. Appl. No. 16/061,530, dated Nov. 27, 2020.
Applicant's Amendment and Response in U.S. Appl. No. 16/061,530, filed Feb. 25, 2021.
Notice of Allowance issued in U.S. Appl. No. 16/061,530, dated Apr. 7, 2021.
The Five Kingdoms of Life, The Amazing Diversity of Living Systems, Waynes World, Feb. 1998, [retrieved on Apr. 8, 2021], [PDF], Retrieved from the Internet <https://www.waynesword.net/trfeb98.htm>.
Mammal, Wikipedia, [retrieved on Aug. 31, 2022] pp. 1-49, [PDF], Retrieved from the Internet <en.wikipedia.org/wiki/mammal>.
Fumoto et al., Targeted Gene Delivery: Importance of Administration Routes, Novel Gene Therapy Approaches, pp. 3-31, Feb. 2013.
Daya et al., Gene therapy using adeno-associated virus vectors, Clin Microbiol Rev, Oct. 2008;21(4):583-93.
Mingozzi, Immune responses to AAV vectors: overcoming barriers to successful gene therapy, Blood, Jul. 4, 2013;122(1):23-36. Epub Apr. 17, 2013.
Kattenhorn et al., Adeno-Associated Virus Gene Therapy for Liver Disease. Hum Gene Ther. Dec. 2016;27(12):947-961.
Perrin, S., Preclinical research: Make mouse studies work. Nature 507:423-425, Mar. 2014.
Ye et al., Rescue of Cone ERG Function by Treatment with AAV-hCNGB3 Vectors in CNGB3 Knockout Mice, Investigative Ophthalmology & Visual Science, vol. 56(7), Abstract, Jun. 2015.
Non-Final Office Action dated Oct. 17, 2022 issued in U.S. Appl. No. 16/621,627.
Carvalho et al., Long-term and age-dependent restoration of visual function in a mouse model of CNGB3-associated achromatopsia following gene therapy, Human Molecular Genetics, vol. 20(16):3161-3175, May 2011.
Ye et al., Cone-Specific Promoters for Gene Therapy for Achromatopsia and Other Retinal Diseases, Human Gene Therapy, vol. 27(1):72-82, Jan. 2016.
Office Action dated Apr. 2, 2022 issued in corresponding Chinese Patent Application No. 201680081801.2, with unofficial translation provided by local agent.
Office Action dated May 11, 2022 issued in corresponding Japanese Patent Application No. 2019-569784, with unofficial translation provided by local agent.
Office Action dated Jun. 7, 2023 issued in Japanese Patent Application No. 2022-063749, with unofficial translation provided by local agent.

* cited by examiner

QUERY = Native REP-1 (SEQ ID NO: 3)
SUBJECT = Codon-optimized REP-1 (SEQ ID NO: 1)

| Score | Expect | Identities | Gaps | Strand |
|---|---|---|---|---|
| 1267 bits(1404) | 0.0 | 1455/1955(74%) | 4/1955(0%) | Plus/Plus |

```
Query    1  ATGGCGGATACTCTCCCTTCGGAGTTTGATGTGTAATAGGGACGGGTTTGCCTGAA    60
            |||||| |||| || ||| || ||||| ||||  ||| |||||||  ||||||||
Sbjct    1  ATGGCTGATACCCTGCCCTCTGAATTCGACGTGATTGTGAACCGGACTCCCTGAA    60

Query   61  TCCATCATTGCAGCTGCATGTTCAAGAAGTGGCCGGAGAGTTCTGCATGTTGATTCAAGA  120
            ||||||||| ||||||| ||| || ||||| |||||| |||| ||| ||| ||||| ||
Sbjct   61  TCGATCATCGCCGCGGTCCCGGTCCCGGTCCGGCGCGTGCTGCACGTCGATTCGAGA    120

Query  121  AGCTACTATGGAGGAAAACTGGGCCAGTTTTAGCTTTTCAGGACTATTGTCCTGGCTAAAG  180
            |||||||| ||  || || ||||||||||| ||||  ||  ||||| || ||||| |||
Sbjct  121  AGCTACTACGGAGGGAATTGGGCCCTGTTTAGCTTCCTCCGGACTGCTCTCCGGCTGAAG  180

Query  181  GAATACCAGGAAAACAGTGACATTGTAAGTGACAGTCCAGTGTGGCAAGACCAGATCCTT  240
            ||  |||||||| ||| |||  || || || ||||| || ||| ||||||||||| |
Sbjct  181  GAGTATCAGGAGAACTCCGACATTGTCTCCGACTCACCTGTGCAGGACCAGATCCTG  240

Query  241  GAAAATGAAGAAGCCATTGCTCTTAGCAGGAAGACAAAACTATTCAACATGTGGAAGTA  300
            ||||| |||||||||||  ||  ||||||||||||||  ||||||||||| ||||||
Sbjct  241  GAAAACGAGGAAGCAATAGCCCTGAGCCGGAAGGACAAGACCATCCAGCACGTGGAGGTG  300
```

FIG. 2

```
Query  301  TTTTGTTATGCCAGTCAGGATTTGCATGAAGATGTCGAAGAAGCTGGTGTGCACTGCAGAAA  360
            ||||||||||||||||||||||||||||||||||||||||||||||||||||||||||||
Sbjct  301  TTCTGTTATGCCTCCCAAGACCTCCATGAGGACGTGGAGCGTTGCAGAAG              360

Query  361  AATCATGCTCTCTGTGACATCTGCAAACTCCACAGAAGCTGCAGATTCTGCCTTCCTGCCT  420
            ||||||||||||||||||||||||||||||||||||||||||||||||||||||||||||
Sbjct  361  AATCATGCCCCTCGTGACCTCGTGACCTCCGCTAACTCCACCGAGGCAGCCGACAGCGCCTTCCTGCCG  420

Query  421  ACGGAGGATGAGTCATTAAGCACTATGAGCTGTGAAATGCTCACAGAACAAACTCCAAGC   480
            ||||||||||||||||||||||||||||||||||||||||||||||||||||||||||||
Sbjct  421  ACCGAGGATGAATCCCTGTCAACTATGTCGTGCGAAATGCTGACCGAACAGACTCCGAGC   480

Query  481  AGCGATCCAGAGAATGCGCTAGAAGTAAATGGTGCTGAAGTGACAGGGGAAAAAGAAAAC   540
            ||||||||||||||||||||||||||||||||||||||||||||||||||||||||||||
Sbjct  481  TCCGACCCCGAAAAACGCCCTGGAAGTGAACGGAGCGGAAGTGACCGGCGAAAAGGAGAAC   540

Query  541  CATTGTGATGATAAAACTTGTGTGCCATCAACTTCAGCAGAAGACATGAGTGAAAATGTG   600
            ||||||||||||||||||||||||||||||||||||||||||||||||||||||||||||
Sbjct  541  CATTGCGACGACAAGACTTGTGTCCCATCCACTTCCGCGGAGGACATGTCCGAGAATGTG   600

Query  601  CCTATAGCAGAAGATACCACAGAGCAACCAAAGAAAAACAGAATTACTTACTCACAAATT   660
            ||||||||||||||||||||||||||||||||||||||||||||||||||||||||||||
Sbjct  601  CCTATCGCCGAGGACACCACCGACAGCCAAGAGAAGAACAGAATCACGTACAGCCAGATC   660

Query  661  ATTAAAGAAGGCAGGAGATTTAATATTTGATTTAGTATCAAAGCTGCTGTATTCTCGAGGA   720
            ||||||||||||||||||||||||||||||||||||||||||||||||||||||||||||
```

```
Sbjct  1079  ACTTCCTGCACTGTTTGGGGCGCTACGGCAACACTCCGTTCCTCTTCCCGCTGTACGGCC  1138
             ||||||  || ||||||||||||||||||||||||||||||| |||||||||||||||||
Query  1139  AAGGAGAACTCCCCCAGTGTTTCTGCAGGATGTGTGCTGTGTTTGGTGTGGAATTTATTGTC  1198
             |||||||||||||||||||||||||||||||||||||||||||||||||||||||||||||
Sbjct  1139  AGGGAGAGCTGCCTCAGTGTTTCTGCAGTGTGTTCTGCCGGATGTGCGCCGTGTTCGGCGCCGGAATCTACTGTC  1198

Query  1199  TTCGCCATTCAGTACAGTGCCTTGTAGTGGACAAAGAATCCAGAAAATGTAAAGCAATTA  1258
             |||||||||||||||||||||||||||||||||||||||||||||||||||||||||||
Sbjct  1199  TCCGCCACTCGGTCCAGTGCCTGGTGGTGGACAAGGAATCCAGGAAGTGCAAAGCCATTA  1258

Query  1259  TAGATCAGTTTGGTCAGAGAATAATCTCTGAGCATTTCCTGTGGAGGACAGTTACTTTC  1318
             |||||||||||||||||||||||||||||||||||||||||||||||||||||||||
Sbjct  1259  TTGACCAGTTCGGACAACGGATCATTTCCGAGCACTTCTGTGGAGGACTCATACTTCC  1318

Query  1319  CTGAGAACATGTGTCCACGTGTGCAATACAGGCAGATCTCCAGGGCAGTGCTGATTACAG  1378
             ||||||||||||||||||||||||||||||||||||||||||||||||||||||||||
Sbjct  1319  CGGAGAACATGTGCTCTCGGGTCCAGTATCGACAGATTTCCAGGGCGGTGCTCATTACTG  1378

Query  1379  ATAGATCTGTCCTAAAAACAGATTCAGATTCAACAGATTTCCATTTTGACAGTGCCAGCAG  1438
             ||| ||||||||||||||||||||||||||||||||||||||||||||||||||||||
Sbjct  1379  ACCGGAGCCGTCCTCAAGACCGATAGCGACCAGCAGATCTCCATCCTGACCGTGCCGGGG  1438

Query  1439  AGGAACCAGGAACTTTTGCTGTTCGGGTCATTGAGTTATGTTCTTCAACGATGACATGCA  1498
             ||||||||||||||||||||||||||||||||||||||||||||||||||||||||||
Sbjct  1439  AAGAACCCGGCACTTTGCCGTGCCGTGATCGAGCTTTGCTCATCCACCATGACTTGCA  1498
```

FIG. 2 (continued)

```
Query  1499  TGAAAGGCACCTTATTGGTTCATTTGACTTGCACATCTTCTAAAACAGCCAAGAGAAGATT  1558
             ||||||||||||||||||||||||||||||||||||||||||||||||||||||||||||
Sbjct  1499  TGAAAGGCACTTACCTGGTGCACGTGCACCTCGACGTGCACCCTCGAAAACCGCTAGAGAGGACC  1558

Query  1559  TAGAATCAGTTGTGCAGAAATTGTTTGTTCCATATACTGAAATGGAGATAGAAAAATGAAC  1618
             ||||||||||||||||||||||||||||||||||||||||||||||||||||||||||||
Sbjct  1559  TGGAATCCGTCGTCCAAAAGCTGTTCGTTGCCTTACACCGAGATGGAAATTGAAAACGAAC  1618

Query  1619  AAGTAGAAAAAGCCAAGAATTCTGTGGGCCTCTTTACTTCAATATGAGAGATTCGTCAGACA  1678
             ||||||||||||||||||||||||||||||||||||||||||||||||||||||||||||
Sbjct  1619  AAGTGGAGAAGCCCCGCATCCTTTGGGCCCTGTACTTTAACATGCGCGATTCCTCCGATA  1678

Query  1679  TCAGCAGGAGCTGTTATAATGATTTACCATCCAACGTTTATGTCGCTCTGCCTCAGATT  1738
             ||||||||||||||||||||||||||||||||||||||||||||||||||||||||||||
Sbjct  1679  TCTCGCGGTCCTGCTATAACGACTTGCCTTCGAACGTCTACGTCGTCCGGGCCAGACT  1738

Query  1739  GTGGTTTAGGAAATGATAATGCAGTCAAACAGGCTGAAACACTTTTCCAGGAAATCTGCC  1798
             ||||||||||||||||||||||||||||||||||||||||||||||||||||||||||||
Sbjct  1739  GCGGTCTTGGCAACGACAATGCCGTGAAGCAGGCGGAAACACTGTTCCAAGAGATCTGCC  1798

Query  1799  CCAATGAAGATTTCTGTCCCCCTCCACCAAATCCTGAAGACATTATCCTTGATGGAGACA  1858
             ||||||||||||||||||||||||||||||||||||||||||||||||||||||||||||
Sbjct  1799  CTAACGAGGATTTTTGCCCGCCCCAAACCCGAGATATCATCTTGGACGGAGAGACA  1858

Query  1859  GTTTACAGCCAGAGGCTTCAGAATCCAGAGTGCCATACCAGAGGCTAACTCGGAGACTTTCA  1918
             ||||||||||||||||||||||||||||||||||||||||||||||||||||||||||||
Sbjct  1859  GCCTGCAGCCAGAAGCATCCGAGTCCGATCCAGCCGAGTCCCGGAGGCCAACAGCGAAACCTTCA  1918
```

FIG. 2
(continued)

```
Query  1919  AGGAAAGCACAAACCTTGGAAACCTAGAGGAGTCC  1953
             ||||| ||||| || |||||| || |||||| |||||
Sbjct  1919  AGGAGAGCACTAACCTGGGCAACCTGGAAGAGAGTCC  1953
```

Codon optimized (Query) SEQ ID NO: 9 vs. Native (subject) SEQ ID NO: 13 CNGA3

| Score | Expect | Identities | Gaps |
|---|---|---|---|
| 1856 bits(2058) | 0.0 | 1678/2108(80%) | 2/2108(0%) |

```
Query  1    GCGGGCCGCCACCATGGCTAAGATTAACACCCAGTACTCACATCCATCCCGCACTCACCTC  60
            |||||||||||||||||| ||||| || ||||| ||| ||||||||  ||| || |||||
Sbjct  1    GCGGGCCGCCACCATGGCCAAGATCAACACCCAATACTCCCACCCCCTCCGGACCCACCTC  60

Query  61   AAAGTCAAGACCTCCGATCGGGATCTGAACCGGGCTGAGAATGGGCTGTCGCGGCCCAC   120
            || ||||| || ||||||  ||  ||||| || |  ||||| ||| ||||| ||| |||
Sbjct  61   AAGGTAAAAGACCTCAGACCGGGATCTCAATCGCGCTGAAAATGGCCTGTCAGCAGAGCCAC  120

Query  121  TCGTCGTCCGAGGAAAACCAGCAGC-GTGCTCCAGCCATCGCCGGCATGGAAACTAGGGG   179
            |||||  |  ||   ||  || |||   |||||||| || || |||||  || ||  ||
Sbjct  121  TCGTCAAGTGAGGAGAC-ATCGTCAGTGCTGCTGCAGCCATGGAGACCAGAGG        179

Query  180  GCTGGGGACTCCGGACAGGGATCCTTCACTGGACAGGGTATTGCCCGGCTGAGCAGACT   239
            ||||||||||||| || ||||| || ||||| || ||| |||||| |||| ||| ||
Sbjct  180  ACTGGGCTGACTCCGGCGCTGGGTCCTTCACCGGGCAGGGCCTGGGATCGCCAGGCTGTCGCGCT  239

Query  240  GATCTTCCTGCTTCGCGCCGTTGCACCGTGCACCATCAGGACCAGGGACCTGA         299
            ||| || || |||| | |||||||  |||| || ||||| |||||| |||  |
Sbjct  240  CATCTTCTTGCTGCCAGGTGGCTGCCAGGCATGTGCACCAGGACCATGGAGACCAGGA  299
```

```
Query  300  TAGCTTCCCGACCGCTTTAGGGGAGCCGAGCTGAAAGAAGTGTCAAGCCAGGAGTCAAA   359
            ||||||||||||||||||||||||||||||||||||||||||||||||||||||||||
Sbjct  300  TAGCTTCCCGACCGCTTTAGGGGAGCCGAGCTGAAAGAAGTGTCAAGCCAGGAGTCAAA   359

Query  360  CTCTTTTCCTGATCGTTCCGTGGAGCCGAGCTTAAGGAGTGTCCAGCCAAGAAAGCAA   419
            ||||||||||||||||||||||||||||||||||||||||||||||||||||||||||
Sbjct  360  CTCTTTTCCTGATCGTTCCGTGGAGCCGAGCTTAAGGAGTGTCCAGCCAAGAAAGCAA   419

Query  420  CGGGCCAGGCCAAACGTCGGCAGCCCAAGAGCCTGCAGAACCGGGGACGCTCGGCATGGCCGCT   479
            ||||||||||||||||||||||||||||||||||||||||||||||||||||||||||
Sbjct  420  CGGGCCAGGCCAAACGTCGGCAGCCCAAGAGCCTGCAGAACCGGGGACGCTCGGCATGGCCGCT   479

Query  480  TGCCCAGGCAAATGTGGGCAGCCAGGAGCCAGCAGAGGGAGAAGCGCCTGGCCCT   539
            ||||||||||||||||||||||||||||||||||||||||||||||||||||||||||
Sbjct  480  TGCCCAGGCAAATGTGGGCAGCCAGGAGCCAGCAGAGGGAGAAGCGCCTGGCCCT   539

Query  540  CGCAAAGTGCAACACTAACACTTCCAACAACACCGAAGAGGGAAAAGAAAACCAAGAAGAA   599
            ||||||||||||||||||||||||||||||||||||||||||||||||||||||||||
Sbjct  540  CGCAAAGTGCAACACTAACACTTCCAACAACACCGAAGAGGGAAAAGAAAACCAAGAAGAA   599

Query  600  GGCCAAATGCAACACTAACACCAGCAACAACACGGAGGAGGAAGAAGACGAAAAAGAA   659
            ||||||||||||||||||||||||||||||||||||||||||||||||||||||||||
Sbjct  600  GGCCAAATGCAACACTAACACCAGCAACAACACGGAGGAGGAAGAAGACGAAAAAGAA   659

Query  660  GGATGCAATTGTGGTGGACCCTTCCTCCAACCTGTACTACCGCTGGTTGACCGCCATCGC   719
            ||||||||||||||||||||||||||||||||||||||||||||||||||||||||||
Sbjct  660  GGATGCGATCGTGGTGGACCCGTGGAGCCAGCAACCTGTACTACCGCTGCTGACCGCCATCGC   719
```

FIG. 3 (continued)

```
Query  720   GAATAGACTGTGGCAGCACTATAAGACCAACCCAGTTCAAGCTTGACGTGCTCAGCCT   779
             ||||| ||||||||||||| || ||||| |||||||||||||||| || |||||||||
Sbjct  720   CAACAGGCTGTGGCAGCATTACAAGACGACCACGCAGTTCAAGCTGGATGTGTGTCCCT   779

Query  780   TGTGCCGACTGACCTGGCCTACTTGAAAGTCGGAACTAACTACCCGGAAGTCAGATTCAA   839
             ||| ||||||||||||||||||| |||| |||   ||||| ||||| |||||| |||||
Sbjct  780   GGTCCCCACCGACCTGGCTTACTTAAAGGTGGGCACAAACTACCCAGAAGTGAGGTTCAA   839

Query  840   CCGACTCCTGAAGTTCAGCAGGCTGTTCGAGTTCTCTTTGACCGCACCGAGACTCGGACCAA   899
             || ||||| ||||||||||||||| | |||||| |||||||||| ||||||||| | || |
Sbjct  840   CCGCCTACTGAAGTTTTCCCGGCTCTCTTTGAATTCTTTGACCGCACAGAGACAAGGACCAA   899

Query  900   CTACCCCTAACATGTTCCGGATCGGAAATCGGTGCTCTACATACTGATTATCATCCATTG   959
             |||||| ||| |||| |||||| | |||| ||| | || ||||| |||| |||| |||
Sbjct  900   CTACCCCAATATGTCTTCAGGATTGGGAACTTGGTCTCTTGTACATTCTCATCATCCACTG   959

Query  960   GAACGCCTGTATCTATTTCGGATCCCGAACACGGGTTTCGGAACCGATTCCTGGGT   1019
             ||| || ||| |||  |||||||   |||| || |||||||||| ||||||| |
Sbjct  960   GAATGCCTGCATCTACTTTGCCATTTCCAAGTTCATTGGTTTTGGCACAGACTCCTGGGT   1019

Query  1020  GTACCCCGAACACACGTCGCCTGTCCCGGAAGTACATCTACTCCCT   1079
             ||||||| || | || || |||||| ||||||| || |||| |||
Sbjct  1020  CTACCCAAACATCTCAATCCCAGAGCATGGGCGCCCTCCAGGAAGTACATTTACAGTCT   1079

Query  1080  GTACTGGTCCACTCTGACTCTGAACTCCGGGGAAACCCTCCACCCGTGAAGGACGA   1139
             |||| |||||| ||| ||||||||||| || ||||||||| || ||||||| ||
Sbjct  1080  CTACTGGTCCACCTTGACCCTGAACCCCTGACCCCACCCCCGTGAAAGATGA   1139
```

FIG. 3 (continued)

```
Query  1140  AGAGTACCTGTTCGTGGTGGTGGACTTCCCTGGTCGTGGAGTGTTGATTTTCGCCACCATTGT  1199
             ||||||||||||||||||||||||||||||||||||||||||||||||||||||||||||||
Sbjct  1140  AGAGTACCTGTTCGTGGTGGTGGACTTCCCTGGTCGTGGAGTGTTGATTTTCGCCACCATTGT  1199

Query  1200  GGAGTATCTCTTTGTGGTCGTAGACTTCTTGGTGGGTGTTCTGATTTTTGCCAAGCCAA     1259
             |||||||||||||||||||||||||||||||||||||||||||||||||||||||||||
Sbjct  1200  GGAGTATCTCTTTGTGGTCGTAGACTTCTTGGTGGGTGTTCTGATTTTTGCCAAGCCAA     1259

Query  1260  GGGAAACGTGGGCTCCATGATCTCCAACATGAACGGTCGAGAGCTGAGTTCCAAGCCAA     1319
             |||||||||||||||||||||||||||||||||||||||||||||||||||||||||||
Sbjct  1260  GGGAAACGTGGGCTCCATGATCTCCAACATGAACGGTCGAGAGCTGAGTTCCAAGCCAA     1319

Query  1320  GGGCAAATGTGGGCTCCATGATCTCGAATATGAATGCCTCACGGGCAGAGTTCCAGGCCAA  1379
             ||||||||||||||||||||||||||||||||||||||||||||||||||||||||||||
Sbjct  1320  GGGCAAATGTGGGCTCCATGATCTCGAATATGAATGCCTCACGGGCAGAGTTCCAGGCCAA  1379

Query  1380  GATCGACTCCATTAAGCAGTACATGCAGTTCAGAAAGGTCACCAAGGACCTGGAAACCAG   1439
             ||||||||||||||||||||||||||||||||||||||||||||||||||||||||||
Sbjct  1380  GATCGACTCCATTAAGCAGTACATGCAGTTCAGAAAGGTCACCAAGGACCTGGAAACCAG   1439

Query  1440  GATTGATTCCATCAAGCAGTACATGCAGTTCCGCAAGGTCACCAAGGACTTGGAGACGCG   1499
             ||||||||||||||||||||||||||||||||||||||||||||||||||||||||||
Sbjct  1440  GATTGATTCCATCAAGCAGTACATGCAGTTCCGCAAGGTCACCAAGGACTTGGAGACGCG   1499

Query  1500  GGTCATCCGCTGGTTCGACTACCTGTGGGCCAACAAAAAGACTGTGGACGAAAGGAAGT   1559
             |||||||||||||||||||||||||||||||||||||||||||||||||||||||||
Sbjct  1500  GGTCATCCGCTGGTTCGACTACCTGTGGGCCAACAAAAAGACTGTGGACGAAAGGAAGT   1559
```

FIG. 3 (continued)

```
Query  1560  CAAAGAGATGTACATCATCAACGAGGGAAAGCTGGCCGTGGTCGGAGACGACGGCGTGAC  1619
             ||||||||||||||||||||||||||||||||||||||||||||||||||||||||||||
Sbjct  1560  GAAGGAGATGTACATCATCAACGAGGGCAAGCTGGCCGTGGTGGTGCTGATGATGGGGCAC  1619

Query  1620  CCAGTTCGTGTGGCTGTCGGACGGATCCTACTTCGGTGAAATCTCAATCCTCAACATCAA  1679
             ||||||||||||||||||||||||||||||||||||||||||||||||||||||||||||
Sbjct  1620  CCAGTTCGTGTGGTCCTCAGCGATGGCAGCTACTTCGGGGAGATCAGCATTCTGAACATCAA  1679

Query  1680  GGGGTCCAAGTCCGGCAACCGGAGAACTGCCAACATTCGCTCCATCGGATACAGCGACCT  1739
             ||||||||||||||||||||||||||||||||||||||||||||||||||||||||||||
Sbjct  1680  GGGGAGCAAGTCGGGGAACCGCAGGAACATCGGCAGCATTGGCTACTCAGACCT  1739

Query  1740  GTTTTGCCTGTCCAAGGATGACCTGACTGAGGAGGCTCTGACTGAGTACCCTGAAGCGAAGAA  1799
             ||||||||||||||||||||||||||||||||||||||||||||||||||||||||||||
Sbjct  1740  GTTCTGCCTCTCAAAGGACGATCTCATGGAGGCCCTCACCGAGTACCCGAAGCCAAGAA  1799

Query  1800  GGCTTTGGAGGAAAAAGGGGCGGCAGATTCTGATGAAGGACAATTTGATCGACGAGGAGCT  1859
             ||||||||||||||||||||||||||||||||||||||||||||||||||||||||||||
Sbjct  1800  GGCCCTGGAGGAGAAAGACGGCAGATCCTGATGAAAGACAACCTGATCGATGAGGAGCT  1859

Query  1860  CGCACGGGCCGGCAAGGATCTCGAAGAGAAGGTCGAACAGCTGGGTTCTTC  1919
             ||||||||||||||||||||||||||||||||||||||||||||||||||||||||||||
Sbjct  1860  GGCCAGGGGCGGGCAAGGACCTTGAGGAGAAAGTGAGCAGCTGGGGTCCTC  1919

Query  1920  GCTTGATACCCTGCAAACCCGATTCGCGGCGGCTGCTCGCCGAGTACAACGCGACCCAGAT  1979
             ||||||||||||||||||||||||||||||||||||||||||||||||||||||||||||
Sbjct  1920  CCTGGACACCCTGCAGACCAGTTTGCACGCCTCCTGCTGAGTACAACGCCACCCAGAT  1979
```

FIG. 3 (continued)

```
Query  1980  GAAGATGAAGCAGAGACTGTCACAGTTGGAATCCCAAGTCAAGGGCGGAGGCGACAAGCC  2039
             ||||||||||||||||||||||||||||||||||||||||||||||||||||||||||||
Sbjct  1980  GAAGATGAAGCAGAGACTGTCACAGTTGGAATCCCAAGTCAAGGGCGGAGGCGACAAGCC  2039

Query  2040  GCTGGCGGACGGGGAAGTGCCCGGGACGCCACCAAGACTGAGGACAAGCAGCAGTGATC   2099
             ||||||||||||||||||||||||||||||||||||||||||||||||||||||||||||
Sbjct  2040  CCTGGCTGATGGGGAAGTTCCCGGGATGCTACAAAAACAGAGGACAAACAACAGTGATC   2099

Query  2100  ATAGATCT  2107
             ||||||||
Sbjct  2100  ATAGATCT  2107
```

FIG. 3
(continued)

Locations of silent mutations are highlighted
CLUSTAL W (1.83) multiple sequence alignment
CNGB3_with_modified_ends - SEQ ID NO: 23
CNGB3_modified_ORF - SEQ ID NO: 21
native_CNGB3_ORF - SEQ ID NO: 19

CNGB3_with_modified       GCGGCCGCCACCATGTTTAAATCGCTGACAAAAGTCAACAAGGTGAAGCCTATAGGAGAG
CNGB3_modified_ORF        ----------ATGTTTAAATCGCTGACAAAAGTCAACAAGGTGAAGCCTATAGGAGAG
native_CNGB3_ORF          ----------ATGTTTAAATCGCTGACAAAAGTCAACAAGGTGAAGCCTATAGGAGAG
                                    ********************************************

CNGB3_with_modified       AACAATGAGAATGAACAAAGTTCTCGTCGGAATGAAGAAGGCTCTCACCCAAGTAATCAG
CNGB3_modified_ORF        AACAATGAGAATGAACAAAGTTCTCGTCGGAATGAAGAAGGCTCTCACCCAAGTAATCAG
native_CNGB3_ORF          AACAATGAGAATGAACAAAGTTCTCGTCGGAATGAAGAAGGCTCTCACCCAAGTAATCAG
                          ************************************************************

CNGB3_with_modified       TCTCAGCAAACCACAGCCACAGGAAGAGAAAACAAAGGTGAAGAGAAATCTCTCAAAACCAAG
CNGB3_modified_ORF        TCTCAGCAAACCACAGCCACAGGAAGAGAAAACAAAGGTGAAGAGAAATCTCTCAAAACCAAG
native_CNGB3_ORF          TCTCAGCAAACCACAGCCACAGGAAGAGAAAACAAAGGTGAAGAGAAATCTCTCAAAACCAAG
                          **************************************************************

CNGB3_with_modified       TCAACTCCAGTCAGTCTGAAGAGCCAACACACCAACATACAAGACAAACTCTCCAAGAAA
CNGB3_modified_ORF        TCAACTCCAGTCAGTCTGAAGAGCCAACACACCAACATACAAGACAAACTCTCCAAGAAA
native_CNGB3_ORF          TCAACTCCAGTCAGTCTGAAGAGCCAACACACCAACATACAAGACAAACTCTCCAAGAAA
                          ************************************************************

CNGB3_with_modified       AATTCCTCTGGAGATCTGACCACAAACCCTGACCCTCAAAATGCAGCAGAACCAACTGGA
CNGB3_modified_ORF        AATTCCTCTGGAGATCTGACCACAAACCCTGACCCTCAAAATGCAGCAGAACCAACTGGA
native_CNGB3_ORF          AATTCCTCTGGAGATCTGACCACAAACCCTGACCCTCAAAATGCAGCAGAACCAACTGGA
                          ************************************************************

CNGB3_with_modified       ACAGTGCCAGAGCAGAGCAGAATGGACCCCGGGAAAGAAGGTCCAAACAGCCCACAAAAC
CNGB3_modified_ORF        ACAGTGCCAGAGCAGAGCAGAATGGACCCCGGGAAAGAAGGTCCAAACAGCCCACAAAAC
native_CNGB3_ORF          ACAGTGCCAGAGCAGAGCAGAATGGACCCCGGGAAAGAAGGTCCAAACAGCCCACAAAAC
                          ************************************************************

CNGB3_with_modified       AAACCGCCAGCAGCTCCTGTTATAAATGAGTATGCCGATGCCCAGTACACAACCTGGTG

```
native_CNGB3_ORF              TTTGTAAGGAGGAGACATAATAGTGGATTCAAATGAGCTAAGGAAACACTACAGGACT
                              **********************************************************

CNGB3_with_modified_ORF       TCTACAAAATTTCAGTTGGATGTCGCATCAATAATACCATTTGATATTTGCTACCTCTTC
CNGB3_modified_ORF            TCTACAAAATTTCAGTTGGATGTCGCATCAATAATACCATTTGATATTTGCTACCTCTTC
native_CNGB3_ORF              TCTACAAAATTTCAGTTGGATGTCCGCATCAATAATACCATTTGATATTTGCTACCTCTTC
                              **********************************************************

CNGB3_with_modified_ORF       TTTGGGTTTAATCCAATGTTTAGAGCAAATAGGATGTTAAAGTACACTTCATTTTTGAA
CNGB3_modified_ORF            TTTGGGTTTAATCCAATGTTTAGAGCAAATAGGATGTTAAAGTACACTTCATTTTTGAA
native_CNGB3_ORF              TTTGGGTTTAATCCAATGTTTAGAGCAAATAGGATGTTAAAGTACACTTCATTTTTGAA
                              **********************************************************

CNGB3_with_modified_ORF       TTTAATCATCACCTAGAGTCTATAAATGGACAAAGCATATATATCTACAGAGTTATTCGAACA
CNGB3_modified_ORF            TTTAATCATCACCTAGAGTCTATAAATGGACAAAGCATATATATCTACAGAGTTATTCGAACA
native_CNGB3_ORF              TTTAATCATCACCTAGAGTCTATAAATGGACAAAGCATATATATCTACAGAGTTATTCGAACA
                              **********************************************************

CNGB3_with_modified_ORF       ACTGGATACTTGCTGTTTATTCTGCACATTAATGCCTGTGTTTATTACTGGCTTCAAAC
CNGB3_modified_ORF            ACTGGATACTTGCTGTTTATTCTGCACATTAATGCCTGTGTTTATTACTGGCTTCAAAC
native_CNGB3_ORF              ACTGGATACTTGCTGTTTATTCTGCACATTAATGCCTGTGTTTATTACTGGCTTCAAAC
                              **********************************************************

CNGB3_with_modified_ORF       TATGAAGGAATTGGCACTAGATGGGTGTATGATGGGAAGGAAACGAGTATCTGAGA
CNGB3_modified_ORF            TATGAAGGAATTGGCACTAGATGGGTGTATGATGGGAAGGAAACGAGTATCTGAGA
native_CNGB3_ORF              TATGAAGGAATTGGCACTAGATGGGTGTATGATGGGAAGGAAACGAGTATCTGAGA
                              **********************************************************

CNGB3_with_modified_ORF       TGTTATTATTGGGCAGTTCGAACTTTAATTACCATTGGTGGCCTTCCAGAACCACAAACT
CNGB3_modified_ORF            TGTTATTATTGGGCAGTTCGAACTTTAATTACCATTGGTGGCCTTCCAGAACCACAAACT
native_CNGB3_ORF              TGTTATTATTGGGCAGTTCGAACTTTAATTACCATTGGTGGCCTTCCAGAACCACAAACT
                              **********************************************************

CNGB3_with_modified_ORF       TTATTTGAAATTGTTTTTCAACTCTTGAATTTTTTTTCTGGAGTTTTTGTGTTCTCCAGT
CNGB3_modified_ORF            TTATTTGAAATTGTTTTTCAACTCTTGAATTTTTTTTCTGGAGTTTTTGTGTTCTCCAGT
native_CNGB3_ORF              TTATTTGAAATTGTTTTTCAACTCTTGAATTTTTTTTCTGGAGTTTTTGTGTTCTCCAGT
                              **********************************************************

CNGB3_with_modified_ORF       TTAATTGGTCAGATGAGAGATGTGATTGGAGCAGCCAATCAGAACTCAGAACTTCCGC
CNGB3_modified_ORF            TTAATTGGTCAGATGAGAGATGTGATTGGAGCAGCCAATCAGAACTCAGAACTTCCGC
native_CNGB3_ORF              TTAATTGGTCAGATGAGAGATGTGATTGGAGCAGCCAATCAGAACTCAGAACTTCCGC
                              **********************************************************
```

```
CNGB3_with_modified      GCCTGCATGGATGACACCATTGCCTACATGAACAATTACTCCATTCCTAAACTTGTGCAA
CNGB3_modified_ORF       GCCTGCATGGATGACACCATTGCCTACATGAACAATTACTCCATTCCTAAACTTGTGCAA
native_CNGB3_ORF         GCCTGCATGGATGACACCATTGCCTACATGAACAATTACTCCATTCCTAAACTTGTGCAA
                         ************************************************************

CNGB3_with_modified      AAGCGAGTTCGGACTTGGTATGAATATACATGGGACTCTCAAAGAATGCTAGATGAGTCT
CNGB3_modified_ORF       AAGCGAGTTCGGACTTGGTATGAATATACATGGGACTCTCAAAGAATGCTAGATGAGTCT
native_CNGB3_ORF         AAGCGAGTTCGGACTTGGTATGAATATACATGGGACTCTCAAAGAATGCTAGATGAGTCT
                         ************************************************************

CNGB3_with_modified      GATTTGCTTAAGACCCTACCAACTACGGTCCAGTTAGCCCTCGCCATTGATGTGAACTTC
CNGB3_modified_ORF       GATTTGCTTAAGACCCTACCAACTACGGTCCAGTTAGCCCTCGCCATTGATGTGAACTTC
native_CNGB3_ORF         GATTTGCTTAAGACCCTACCAACTACGGTCCAGTTAGCCCTCGCCATTGATGTGAACTTC
                         ************************************************************

CNGB3_with_modified      AGCATCATCAGCAAAGTTGACTTGTTCAAGGGTTGTGATACACAGATGATTTATGACATG
CNGB3_modified_ORF       AGCATCATCAGCAAAGTTGACTTGTTCAAGGGTTGTGATACACAGATGATTTATGACATG
native_CNGB3_ORF         AGCATCATCAGCAAAGTCGACTTGTTCAAGGGTTGTGATACACAGATGATTTATGACATG
                         *****************  *****************************************

CNGB3_with_modified      TTGCTAAGATTGAAATCCGTTCTCTATTTGCCTGGTCGACTTTGTCTGCAAAAGGGAGAA
CNGB3_modified_ORF       TTGCTAAGATTGAAATCCGTTCTCTATTTGCCTGGTCGACTTTGTCTGCAAAAGGGAGAA
native_CNGB3_ORF         TTGCTAAGATTGAAATCCGTTCTCTATTTGCCTGGTCGACTTTGTCTGCAAAAGGGAGAA
                         ************************************************************

CNGB3_with_modified      ATTGGCAAGGAAATGTATATCATCAAGCATGGAGAAGTCCAAGTTCTTGGAGGCCCTGAT
CNGB3_modified_ORF       ATTGGCAAGGAAATGTATATCATCAAGCATGGAGAAGTCCAAGTTCTTGGAGGCCCTGAT
native_CNGB3_ORF         ATTGGCAAGGAAATGTATATCATCAAGCATGGAGAAGTCCAAGTTCTTGGAGGCCCTGAT
                         ************************************************************

CNGB3_with_modified      GGTACTAAAGTTCTGGTTACTCTGAAAAGCTGGGTCGGTGTTTTGGAGAAATCAGCCTTCTA
CNGB3_modified_ORF       GGTACTAAAGTTCTGGTTACTCTGAAAAGCTGGGTCGGTGTTTTGGAGAAATCAGCCTTCTA
native_CNGB3_ORF         GGTACTAAAGTTCTGGTTACTCTGAAAAGCTGGGTCGGTGTTTTGGAGAAATCAGCCTTCTA
                         ************************************************************

CNGB3_with_modified      GCAGCAGGAGGAGGAGGAAACCGTCGAACTGCCAATGTGGTGGCCCACGGGTTTGCCAATCTT
CNGB3_modified_ORF       GCAGCAGGAGGAGGAGGAAACCGTCGAACTGCCAATGTGGTGGCCCACGGGTTTGCCAATCTT
native_CNGB3_ORF         GCAGCAGGAGGAGGAGGAAACCGTCGAACTGCCAATGTGGTGGCCCACGGGTTTGCCAATCTT
                         ************************************************************
```

```
CNGB3_with_modified     AGAGGGACTTCTCGTCAATCACTCATTATCAGCATGGCTCCTTCTGCTGAGGGCGGAGAA
CNGB3_modified_ORF      AGAGGGACTTCTCGTCAATCACTCATTATCAGCATGGCTCCTTCTGCTGAGGGCGGAGAA
native_CNGB3_ORF        AGAGGGACTTCTCGTCAATCACTCATTATCAGCATGGCTCCTCTGCTGAGGGCGGAGAA
                        ********************************************************

CNGB3_with_modified     GAGGTTCTTACTATTGAAGTCAAAGAAAAGGCTAAGCAATGATCATAACTGCAG-MDIFI
CNGB3_modified_ORF      GAGGTTCTTACTATTGAAGTCAAAGAAAAGGCTAAGCAATGA------------------
native_CNGB3_ORF        GAGGTTCTTACTATTGAAGTCAAAGAAAAGGCTAAGCAATAA------------------
                        *****************************************
```

FIG. 4 (continued)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| KanR | 4631...5440 | 810 | => |
| pUC ori | 5612...6200 | 589 | => |
| lamba stuffer | 6437...11,503 | 5067 | == |
| CAP binding site | 11,555...11,576 | 22 | == |
| lac promotor | 11,591...11,621 | 31 | == |
| lac operator | 11,629...11,645 | 17 | == |

Version 2b (V2b)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| KanR | 4631...5440 | 810 | => |
| pUC ori | 5612...6200 | 589 | => |
| CAP binding site | 6488...6509 | 22 | == |
| lac promotor | 6524...6554 | 31 | == |
| lac operator | 6562...6578 | 17 | == |

Version 3a (V3a)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| FRT (minimal) | 4264...4297 | 34 | <= |
| bla txn terminator | 4330...4630 | 301 | == |
| pTF3 | 4421...4446 | 26 | == |
| p15A ori | 5077...5622 | 546 | <= |
| lamba stuffer | 5643...10,709 | 5067 | == |
| KanR | 10,715...11,524 | 810 | <= |
| rnB1 B2 T1 txn terminator | 11,703...11,877 | 175 | <= |
| pTR | 11,778...11,794 | 17 | == |
| FRT (minimal) | 11,909...11,942 | 34 | => |

Version 3a (V3a)

Features

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Kozak | 1859...1864 | 6 | => |
| Human codon optimized CHM (REP-1) | 1865...3826 | 1962 | => |
| bGH poly(A) signal | 3847...4054 | 208 | == |
| 3' ITR | 4104...4233 | 130 | == |
| ITR D segment | 4104...4121 | 18 | == |
| FRT (minimal) | 4264...4297 | 34 | <= |
| bla txn terminator | 4330...4630 | 301 | == |
| pTF3 | 4421...4446 | 26 | == |
| p15A ori | 5077...5622 | 546 | <= |
| KanR | 5644...6453 | 810 | <= |
| rrnB1 B2 T1 txn terminator | 6632...6806 | 175 | <= |
| pTR | 6707...6723 | 17 | == |
| FRT (minimal) | 6838...6871 | 34 | => |

| Feature | Location | Size | Directionality |
|---|---|---|---|
| 5' ITR | 1...130 | 130 | == |
| ITR D segment | 113...130 | 18 | == |
| CMV enhancer | 241...544 | 304 | == |
| Chicken beta-actin promoter | 546...823 | 278 | => |
| CBA exon1 and intron | 824...1795 | 972 | => |
| Human native CHM (REP-1) | 1861...3822 | 1962 | => |
| bGH poly(A) signal | 3836...4043 | 208 | == |
| 3' ITR | 4093...4222 | 130 | == |
| ITR D segment | 4093...4110 | 18 | == |
| FRT (minimal) | 4250...4283 | 34 | <= |
| bla txn terminator | 4316...4616 | 301 | == |
| pTF3 | 4407...4432 | 26 | == |
| lamba stuffer | 4752...9818 | 5067 | == |
| M13 fwd | 9824...9840 | 17 | <= |
| pUC ori | 10,110...10,698 | 589 | <= |
| KanR | 10,822...11,631 | 810 | <= |
| rrnB1 B2 T1 txn terminator | 11,810...11,984 | 175 | <= |
| pTR | 11,885...11,901 | 17 | == |
| FRT (minimal) | 12,016...12,049 | 34 | == |

GENE THERAPY FOR OCULAR DISORDERS

CROSS-REFERENCE TO RELATED APPLICATIONS

This Application is a divisional of U.S. patent application Ser. No. 16/061,530, filed Jun. 12, 2018, which is a US National Stage of PCT/US2016/066402, filed Dec. 13, 2016, and which claims priority to U.S. Provisional Patent Application No. 62/266,789, filed Dec. 14, 2015. Each of these applications are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "16-7660_Seq_Listing_new_ST25.txt".

BACKGROUND OF THE INVENTION

Choroideremia (CHM) is an X-linked inherited retinal disease characterized by the degeneration of photoreceptors, retinal pigment epithelium (RPE) and choriocapillaris. Symptoms develop in the 1st or 2nd decade of life with complaints of poor night vision (nyctalopia) and progressive loss of peripheral vision. Visual fields constrict as the disease progresses. This culminates with loss of central vision (visual acuity) and blindness as early as the fourth decade of life. More than 140 mutations in the CHM gene have been found to cause choroideremia. Mutations may lead to the production of an abnormally small, nonfunctional and/or unstable Rab escort protein-1 (REP-1) protein, a decrease in the protein's function or loss of REP-1 protein production. Lack of normal REP-1 disrupts the ability of Rab proteins to aid in intracellular trafficking. The immobility of proteins and organelles within the cell causes the cells to function poorly and to die prematurely.

The choroideremia gene, CHM, encodes Rab Escort Protein-1 (REP-1), a 653 amino acid protein involved in regulation of membrane trafficking. Since the CHM locus is on the X-chromosome, choroideremia is typically only diagnosed in males. Although female carriers of the disease are usually asymptomatic, retinal exams often reveal a patchy degeneration of the retina and RPE and female individuals can be affected depending on the extent of X-inactivation of the normal X chromosome (lyonization). Coussa, RG, Traboulsi, EI (2012) Choroideremia: a review of general findings and pathogenesis, Ophthalmic Genet 33(2): 57-65, which is incorporated herein by reference. See also, Vasireddy et al, AAV-mediated gene therapy for choroideremia: preclinical studies in personalized models. PLoS One. 2013 May 7;8(5):e61396, which is incorporated herein by reference.

Achromatopsia is a heterogeneous group of autosomal recessive inherited retinal diseases characterized by early onset reduced visual acuity, impaired or complete color blindness, nystagmus, photoaversion and loss of cone photoreceptor function. About 80% of achromatopsia patients show mutations in the alpha or beta subunit (A3 and B3) of the cGMP controlled cation channel cyclic nucleotide-gated channel (CNG) of cone photoreceptors. Homologous to the human disease, Cnga3 deficient mice reveal a loss of cone specific functionality leading to malfunction and degeneration of affected cone photoreceptors.

Therefore, compositions useful for expressing CNGA3 or CNGB3 in human subjects are needed.

SUMMARY OF THE INVENTION

Choroideremia (CHM) is an X-linked retinal degeneration that is symptomatic in the 1st or 2nd decade of life causing nyctalopia and loss of peripheral vision. The disease progresses through mid-life, when most patients become blind. CHM is a favorable target for gene augmentation therapy, as the disease is due to loss of function of a protein necessary for retinal cell health, Rab Escort Protein 1 (REP1), which is encoded by the CHM gene. The CHM cDNA can be packaged in recombinant adeno-associated virus (rAAV), which has an established track record in human gene therapy studies. In addition, there are sensitive and quantitative assays to document REP1 activity, including its ability to prenylate Rab proteins such as Rab27 and to correct a defect in Rab27 localization and trafficking due to lack of prenylation in REP-1 deficient cells.

In one aspect, a codon optimized cDNA sequence encoding Rab Escort Protein-1 (REP-1) is provided. In one embodiment, the codon optimized cDNA sequence is a variant of SEQ ID NO: 3. In another embodiment, the codon optimized cDNA sequence is SEQ ID NO: 1. In another embodiment, the cDNA sequence is codon optimized for expression in humans.

In another aspect, an expression cassette includes a codon optimized nucleic acid sequence that encodes REP-1. In one embodiment, the expression cassette includes the cDNA sequence of SEQ ID NO: 1. In still other embodiments, the REP-1 encoding sequence is positioned between 5' and 3' AAV ITR sequences.

In another embodiment, an adeno-associated virus (AAV) vector is provided. The AAV vector includes an AAV capsid and a nucleic acid sequence comprising AAV inverted terminal repeat sequences and a nucleic acid sequence encoding human Rab Escort Protein-1 (REP-1), and expression control sequences that direct expression of the REP-1 in a host cell. In one embodiment, the REP-1 sequence encodes a full length REP-1 protein. In one embodiment, the REP-1 sequence is the protein sequence of SEQ ID NO: 2.

In one aspect, a codon optimized cDNA sequence encoding cyclic nucleotide gated channel alpha 3 (CNGA3) is provided. In one embodiment, the codon optimized cDNA sequence is a variant of SEQ ID NO: 13 or SEQ ID NO: 15. In another embodiment, the codon optimized cDNA sequence is SEQ ID NO: 9 or SEQ ID NO: 11. In another embodiment, the cDNA sequence is codon optimized for expression in humans.

In another aspect, an expression cassette includes a codon optimized nucleic acid sequence that encodes cyclic nucleotide gated channel alpha 3 (CNGA3). In one embodiment, the expression cassette includes the cDNA sequence of SEQ ID NO: 9, SEQ ID NO: 11, SEQ ID NO: 13, or SEQ ID NO: 15. In still other embodiments, the CNGA3 encoding sequence is positioned between 5' and 3' AAV ITR sequences.

In another aspect, an expression cassette includes a codon optimized nucleic acid sequence that encodes cyclic nucleotide gated channel alpha 3 (CNGB3). In one embodiment, the expression cassette includes the cDNA sequence of SEQ ID NO: 19 or SEQ ID NO: 21 or SEQ ID NO: 23. In still other embodiments, the CNGB3 encoding sequence is positioned between 5' and 3' AAV ITR sequences.

In another embodiment, an adeno-associated virus (AAV) vector is provided. The AAV vector includes an AAV capsid and a nucleic acid sequence comprising AAV inverted terminal repeat sequences and a nucleic acid sequence encoding human CNGA3, and expression control sequences that direct expression of the CNGA3 in a host cell. In one embodiment, the CNGA3sequence encodes a full length CNGA3 protein. In one embodiment, the CNGA3 sequence is the protein sequence of SEQ ID NO: 10, SEQ ID NO: 12 or SEQ ID NO: 14.

In another embodiment, an adeno-associated virus (AAV) vector is provided. The AAV vector includes an AAV capsid and a nucleic acid sequence comprising AAV inverted terminal repeat sequences and a nucleic acid sequence encoding human CNGB3, and expression control sequences that direct expression of the CNGB3 in a host cell. In one embodiment, the CNGB3 sequence encodes a full length CNGB3 protein. In one embodiment, the CNGB3 sequence is the protein sequence of SEQ ID NO: 20.

In another aspect, an adeno-associated virus (AAV) vector is provided which comprises an AAV8 capsid and an expression cassette, wherein said expression cassette comprises nucleic acid sequences encoding REP-1, inverted terminal repeat sequences and expression control sequences that direct expression of REP-1 in a host cell.

In yet another aspect, an adeno-associated virus (AAV) vector is provided which comprises an AAV8 capsid and an expression cassette, wherein said expression cassette comprises nucleic acid sequences encoding CNGA3, inverted terminal repeat sequences and expression control sequences that direct expression of CNGA3 in a host cell.

In yet another aspect, an adeno-associated virus (AAV) vector is provided which comprises an AAV8 capsid and an expression cassette, wherein said expression cassette comprises nucleic acid sequences encoding CNGB3, inverted terminal repeat sequences and expression control sequences that direct expression of CNGB3 in a host cell.

In another aspect, an adeno-associated virus (AAV) vector is provided which comprises an AAV2 capsid and an expression cassette, wherein said expression cassette comprises nucleic acid sequences encoding REP-1, inverted terminal repeat sequences and expression control sequences that direct expression of REP-1 in a host cell.

In yet another aspect, an adeno-associated virus (AAV) vector is provided which comprises an AAV2 capsid and an expression cassette, wherein said expression cassette comprises nucleic acid sequences encoding CNGA3, inverted terminal repeat sequences and expression control sequences that direct expression of CNGA3 in a host cell.

In yet another aspect, an adeno-associated virus (AAV) vector is provided which comprises an AAV2 capsid and an expression cassette, wherein said expression cassette comprises nucleic acid sequences encoding CNGB3, inverted terminal repeat sequences and expression control sequences that direct expression of CNGB3 in a host cell.

In another aspect, a pharmaceutical composition is provided which includes a pharmaceutically acceptable carrier, diluent, excipient and/or adjuvant and a least a viral vector as described herein.

In yet a further aspect a pharmaceutical composition comprises a pharmaceutically acceptable carrier, diluent, excipient and/or adjuvant and the nucleic acid sequence, a plasmid, a vector, or a viral vector, such as the rAAV, described specifically herein.

In another aspect, a method for treating choroideremia is provided. In one embodiment, the method includes administering a composition which includes the AAV vector which encodes REP-1, as described herein, to a subject in need thereof.

In another aspect, a method for treating achromatopsia is provided. In one embodiment, the method includes administering a composition which includes the AAV vector which encodes CNGA3, as described herein, to a subject in need thereof.

In another aspect, a method for treating achromatopsia is provided. In one embodiment, the method includes administering a composition which includes the AAV vector which encodes CNGB3, as described herein, to a subject in need thereof.

In yet another aspect, a plasmid for producing an AAV vector is provided. In one embodiment, the plasmid includes the codon optimized cDNA sequence encoding REP-1 as described herein. In another embodiment, the plasmid includes the codon optimized cDNA sequence encoding CNGA3 as described herein. In another embodiment, the plasmid includes a codon optimized cDNA sequence encoding CNGB3 which is a sequence sharing at least 70% identity with SEQ ID NO: 19 or SEQ ID NO: 21. In one embodiment, the plasmid is modular.

In another aspect, a method of generating a rAAV virus is provided. The method includes culturing a packaging cell carrying the plasmid described herein in the presence of sufficient viral sequences to permit packaging of the gene expression cassette viral genome into an infectious AAV envelope or capsid. In another, aspect, a recombinant AAV produced according to the method is provided.

Other aspects and advantages of the invention will be readily apparent from the following detailed description of the invention.

BRIEF DESCRIPTION OF THE DRAWINGS

FIG. 2 is an alignment of the native REP-1 coding sequence of SEQ ID NO: 1 vs. the codon optimized REP-1 coding sequence of SEQ ID NO: 3.

FIG. 3 is an alignment of the native CNGA3 coding sequence of SEQ ID NO: 13 vs. the codon optimized CNGA3 coding sequence of SEQ ID NO: 9.

FIG. 4 is an alignment of CNGB3 native ORF (SEQ ID NO: 19) vs. CNGB3 modified ORF (SEQ ID NO: 21) vs. CNGB3 modified orf with modified ends (SEQ ID NO: 23). Point mutations are highlighted.

DETAILED DESCRIPTION OF THE INVENTION

Figure 1B:
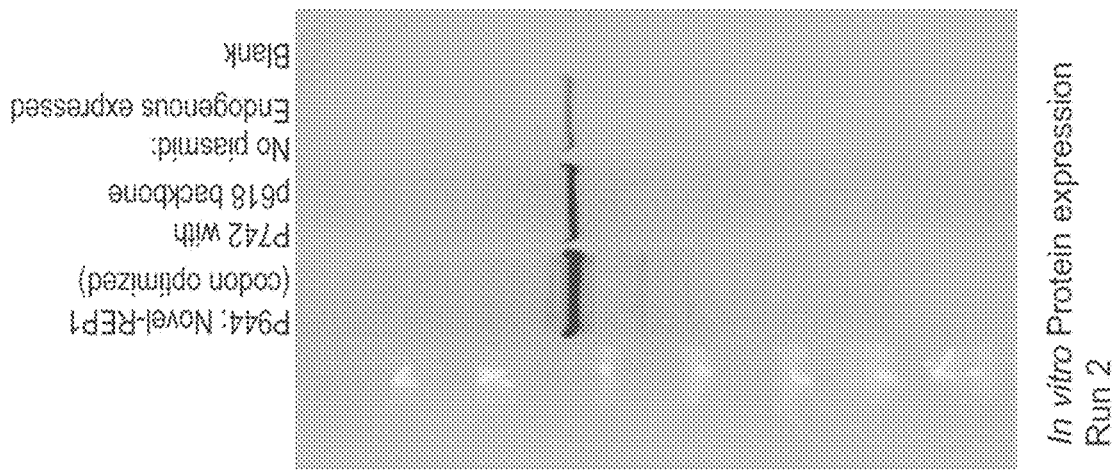
FIG. 1A and FIG. 1B are gels showing REP-1 protein expression in vitro after transfection of cultured 84-31 HEK cells. The first lane of each gel shows expression of codon-optimized REP-1 as described herein, expressed from plasmid p944. The second lane shows expression of native REP-1 from plasmid p742. The third lane shows endogenous expression of REP-1 by 84-31 cells thatwere not transfected with a plasmid. The last lane is a blank. The gels demonstrate that the codon-optimized REP-1 sequence, as described herein, results in a higher level of protein expression than the native REP-1 sequence, and that levels of expression from the exogenously transfected plasmids are many-fold higher than endogenous REP-1 expression.

The methods and compositions described herein involve compositions and methods for delivering optimized CHM encoding REP-1 to mammalian subjects for the treatment of ocular disorders, primarily blinding diseases such as chroroideremia. In addition, methods and compositions described herein involve compositions and methods for delivering optimized CNGA3 or CNGB3 to mammalian subjects for the treatment of ocular disorders, primarily blinding diseases such as achromatopsia. In one embodiment, such compositions involve codon optimization of the REP-1, CNGA3 or CNGB3 coding sequence. It is believed that these features increase the efficacy of the product, and increase safety, since a lower dose of reagent is used. It is anticipated that this optimization of the transgene cassette could theoretically maximize the level of production of the experimental protein compared to levels that can be generated using the endogenous sequence. However, also encompassed herein are compositions which include the native REP1, CNGA3, and CNGB3 coding sequences, as shown in SEQ ID NO: 3, SEQ ID NO: 13 and SEQ ID NO: 19, respectively. It is to be understood that when an embodiment is described for either REP-1, CNGA3 or CNGB3, a similar embodiment is intended to be recited for the other.

Technical and scientific terms used herein have the same meaning as commonly understood by one of ordinary skill in the art to which this invention belongs and by reference to published texts, which provide one skilled in the art with a general guide to many of the terms used in the present application. The definitions contained in this specification are provided for clarity in describing the components and compositions herein and are not intended to limit the claimed invention.

The choroideremia gene, CHM, encodes Rab Escort Protein-1 (REP-1), a 653 amino acid protein thought to be involved in membrane trafficking. As used herein, the terms "REP-1" and "CHM" are used interchangeably when referring to the coding sequence. Since the CHM locus is on the X-chromosome, choroideremia is typically only diagnosed in males. Although female carriers of the disease are usually asymptomatic, retinal exams often reveal a patchy degeneration of the retina and RPE and female individuals can be affected depending on the extent of X-inactivation of the normal X chromosome (lyonization). See, Coussa, cited above. The native amino acid sequence encoding human REP-1 is reported at GenBank accession number P24386, and reproduced here in SEQ ID NO: 2. The native human nucleic acid sequence of CHM is reproduced here at SEQ ID NO: 3 (accession no. NM_000390.2).

Cyclic nucleotide-gated (CNG) ion channels are key mediators underlying signal transduction in retinal and olfactory receptors. Genetic defects in CNGA3 and CNGB3, encoding two structurally related subunits of cone CNG channels, are known to lead to achromatopsia. CNGA3 is a 694 amino acid protein. CNGB is an 809 amino acid protein.

Achromatopsia is a heterogeneous group of congenital, autosomal recessive retinal disorders that manifest by early onset cone photoreceptor dysfunction, severely reduced visual acuity, impaired or complete color blindness and photophobia. The native nucleic acid sequence encoding human CNGA3 is reported at GenBank accession no. XM_011210554.1, and reproduced in SEQ ID NO: 13. The native nucleic acid sequence encoding human CNGA3 is reported at GenBank accession no. XM_011210554.1, and reproduced in SEQ ID NO: 13. The native nucleic acid sequence for the human CNGA3 X1 variant, which includes an additional exon, is reported at GenBank accession no. NM_001298.2, and reproduced in SEQ ID NO: 15. The native nucleic acid sequence encoding human CNGB3 is reproduced in SEQ ID NO: 19.

In certain embodiments of this invention, a subject has an "ocular disorder", for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

As used herein "ocular disorder" includes, cone-rod dystrophies and retinal diseases including, without limitation. Stargardt disease (autosomal dominant or autosomal recessive), retinitis pigmentosa, and pattern dystrophy. In one embodiment, the subject has achromatopsia. In another embodiment, the subject has choroideremia or an X-linked hereditary retinal degeneration. Clinical signs of such ocular diseases include, but are not limited to, decreased peripheral vision, decreased central (reading) vision, decreased night vision, loss of color perception, reduction in visual acuity, decreased photoreceptor function, pigmentary changes, and ultimately blindness.

As used herein, the term "treatment" or "treating" is defined encompassing administering to a subject one or more compounds or compositions described herein for the purposes of amelioration of one or more symptoms of an ocular disease. "Treatment" can thus include one or more of reducing onset or progression of an ocular disease, preventing disease, reducing the severity of the disease symptoms, or retarding their progression, including the progression of blindness, removing the disease symptoms, delaying onset of disease or monitoring progression of disease or efficacy of therapy in a given subject.

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

The terms "percent (%) identity", "sequence identity", "percent sequence identity", or "percent identical" in the context of nucleic acid sequences refers to the bases in the two sequences which are the same when aligned for correspondence. The percent identity is determined by comparing two sequences aligned under optimal conditions over the sequences to be compared. The length of sequence identity comparison may be over the full-length of the REP-1, CNGA3 or CNGB3 coding sequence, or a fragment of at least about 100 to 150 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Commonly available sequence analysis software, more specifically, BLAST or analysis tools provided by public databases may also be used.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

By "engineered" is meant that the nucleic acid sequences encoding the REP-1 or CNGA3 or CNGB3 protein described herein are assembled and placed into any suitable genetic element, e.g., naked DNA, phage, transposon, cosmid, episome, etc., which transfers the REP-1 or CNGA3 or CNGB3 sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

The term "transgene" as used herein means an exogenous or engineered protein-encoding nucleic acid sequence that is under the control of a promoter or expression control sequence in an expression cassette, rAAV genome, recombinant plasmid or production plasmid, vector, or host cell described in this specification. In certain embodiments, the transgene is a human CHM (REP-1) sequence, encoding a functional REP-1 protein. In some embodiments, the transgene is a codon optimized nucleic acid CHM (REP-1) encoding the REP-1 amino acid sequence set forth in SEQ ID NO: 2. In certain embodiments, the transgene is encoded by the sequence set forth in SEQ ID NO: 1. In certain embodiments, the REP-1 transgene is encoded by the sequence set forth in SEQ ID NO: 5. SEQ ID NO: 5 includes modified ends, which include restriction sites for cloning into a plasmid, such as a production plasmid described herein.

In certain embodiments, the transgene is a human CNGA3 sequence, encoding a functional CNGA3 protein. In certain embodiments, the transgene is a codon optimized CNGA3 encoding sequence SEQ ID NO: 10. In certain embodiments, the transgene is encoded by the sequence set forth in SEQ ID NO: 9. In one embodiment, the transgene includes modified ends, such as that shown in SEQ ID NO: 16, SEQ IDNO 17 or SEQ ID NO: 18, which include restriction sites for cloning into a plasmid, such as a plasmid described herein. In certain embodiments, the transgene is a codon optimized CNGA3 encoding sequence SEQ ID NO: 12. In certain embodiments, the transgene is encoded by the sequence set forth in SEQ ID NO: 11. In certain embodiments, the transgene is encoded by the native coding sequence of CNGA3, which is set forth in SEQ ID NO: 13.

In certain embodiments, the transgene is a human CNGB3 sequence, encoding a functional CNGB3 protein. In certain embodiments, the transgene is a codon optimized CNGB3 encoding sequence which is a sequence sharing at least 70% identity with SEQ ID NO: 19 or 21. In certain embodiments, the transgene is encoded by the sequence set forth in SEQ ID NO: 23. SEQ ID NO: 23 includes modified ends, which include restriction sites for cloning into a plasmid, such as a production plasmid described herein. Nucleotides 13 to 2448 of SEQ ID NO: 23 provide the ORF for CNGB3. In certain embodiments, the transgene is a codon optimized CNGB3 encoding sequence SEQ ID NO: 20. In certain embodiments, the transgene is encoded by the sequence set forth in SEQ ID NO: 19. In certain embodiments, the transgene is encoded by the sequence set forth in SEQ ID NO: 21. In certain embodiments, the transgene includes modified ends for cloning into a plasmid, such as the plasmids described herein. SEQ ID NO: 21 is a novel cDNA sequence in which certain silent mutations have been made to the native coding sequence. Further modifications to the native sequence, as described herein, are contemplated by the invention.

In one embodiment, the nucleic acid sequence encoding REP-1, CNGA or CNGB further comprises a nucleic acid encoding a tag polypeptide covalently linked thereto. The tag polypeptide may be selected from known "epitope tags" including, without limitation, a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide.

A "vector" as used herein is a nucleic acid molecule into which an exogenous or heterologous or engineered nucleic acid transgene may be inserted which can then be introduced into an appropriate host cell. Vectors preferably have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes." Certain plasmids are described herein.

"Virus vectors" are defined as replication defective viruses containing the exogenous or heterologous CHM (REP-1) or CNGA3 or CNGB3 nucleic acid transgene(s). In one embodiment, an expression cassette as described herein may be engineered onto a plasmid which is used for drug delivery or for production of a viral vector. Suitable viral vectors are preferably replication defective and selected from amongst those which target ocular cells. Viral vectors may include any virus suitable for gene therapy, including but not limited to adenovirus; herpes virus; lentivirus; retrovirus; parvovirus, etc. However, for ease of understanding, the adeno-associated virus is referenced herein as an exemplary virus vector.

A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In still another embodiment, the expression cassette, including any of those described herein is employed to generate a recombinant AAV genome.

As used herein, the term "host cell" may refer to the packaging cell line in which a recombinant AAV is produced from a production plasmid. In the alternative, the term "host cell" may refer to any target cell in which expression of the transgene is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion.

In certain embodiments herein, the term "host cell" refers to cultures of ocular cells of various mammalian species for in vitro assessment of the compositions described herein. In other embodiments herein, the term "host cell" refers to the cells employed to generate and package the viral vector or recombinant virus. Still in other embodiments, the term "host cell" is intended to reference the ocular cells of the subject being treated in vivo for the ocular disease.

As used herein, the term "ocular cells" refers to any cell in, or associated with the function of, the eye. The term may refer to any one of photoreceptor cells, including rod photoreceptors, cone photoreceptors and photosensitive ganglion cells, retinal pigment epithelium (RPE) cells, Mueller cells, choroidal cells, bipolar cells, horizontal cells, and amacrine cells. In one embodiment, the ocular cells are the photoreceptor cells. In another embodiment, the ocular cells are RPE cells.

"Plasmids" generally are designated herein by a lower case p preceded and/or followed by capital letters and/or numbers, in accordance with standard naming conventions that are familiar to those of skill in the art. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

As used herein, the term "transcriptional control sequence" or "expression control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "operably linked" or "operatively associated" refers to both expression control sequences that are contiguous with the nucleic acid sequence encoding the REP-1 or CNGA3 and/or expression control sequences that act in trans or at a distance to control the transcription and expression thereof.

The term "AAV" or "AAV serotype" as used herein refers to the dozens of naturally occurring and available adeno-associated viruses, as well as artificial AAVs. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, AAV1, AAV2, AAV3, AAV4, AAV5, AAV6, AAV7, AAV8, AAV9, AAV8 bp, AAV7M8 and AAVAnc80, variants of any of the known or mentioned AAVs or AAVs yet to be discovered or variants or mixtures thereof. See, e.g., WO 2005/033321, which is incorporated herein by reference. In another embodiment, the AAV capsid is an AAV8 bp capsid, which preferentially targets bipolar cells. See, WO 2014/024282, which is incorporated herein by reference. In another embodiment, the AAV capsid is an AAV7m8 capsid, which has shown preferential delivery to the outer retina. See, Dalkara et al, In Vivo-Directed Evolution of a New Adeno-Associated Virus for Therapeutic Outer Retinal Gene Delivery from the Vitreous, Sci Transl Med 5, 189ra76(2013), which is incorporated herein by reference. In one embodiment, the AAV capsid is an AAV8 capsid. In another embodiment, the AAV capsid an AAV9 capsid. In another embodiment, the AAV capsid an AAV5 capsid. In another embodiment, the AAV capsid an AAV2 capsid.

As used herein, relating to AAV, the term variant means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used.

The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, VA). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors.

"Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

By "administering" as used in the methods means delivering the composition to the target selected cell which is characterized by the ocular disease. In one embodiment, the method involves delivering the composition by subretinal injection to the RPE, photoreceptor cells or other ocular cells. In another embodiment, intravitreal injection to ocular cells is employed. In still another method, injection via the palpebral vein to ocular cells may be employed. Still other methods of administration may be selected by one of skill in the art given this disclosure. By "administering" or "route of administration" is delivery of composition described herein, with or without a pharmaceutical carrier or excipient, of the subject. Routes of administration may be combined, if desired. In some embodiments, the administration is repeated periodically. The pharmaceutical compositions described herein are designed for delivery to subjects in need thereof by any suitable route or a combination of different routes. Direct delivery to the eye (optionally via ocular delivery, subretinal injection, intra-retinal injection, intravitreal, topical), or delivery via systemic routes, e.g., intraarterial, intraocular, intravenous, intramuscular, subcutaneous, intradermal, and other parental routes of administration. The nucleic acid molecules and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins.

Certain compositions described herein are isolated, or synthetically or recombinantly engineered nucleic acid sequences that provide novel codon-optimized sequences encoding REP-1 or CNGA3 or CNGB3. In one embodiment, an isolated or engineered codon optimized nucleic acid sequence encoding human REP-1 is provided. In one embodiment, the codon-optimized sequence is SEQ ID NO: 1. In another embodiment, the codon optimized sequence includes N-terminal and C-terminal restriction sites for cloning. In one embodiment, such as that disclosed in SEQ ID NO: 5, the REP-1 coding sequence includes an N-terminal NotI restriction site and a C-terminal BamHI restriction site, in addition to a Kozak consensus sequence. In addition, the codon optimized sequence, in some embodiments, includes one or more additional restriction sites to allow for addition of markers, such as an epitope tag. When aligned with the native nucleic acid sequence, the codon optimized REP-1 may have a percent identity of at least 50%, or at least 60%, or at least 70%, or at least 80% or at least 90%, including any integer between any of those ranges. In one embodiment, the codon optimized REP-1 has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%. In one embodiment, when aligned with the native nucleic acid sequence SEQ ID NO: 3, it is revealed that codon optimized REP-1 (SEQ ID NO: 1) has a percent sequence identity of only 74% (see FIG. 2).

In another embodiment, an isolated or engineered codon optimized nucleic acid sequence encoding human CNGA3 is provided. In one embodiment, the codon-optimized sequence is SEQ ID NO: 9. In one embodiment, the codon-optimized sequence is a CNGA3 variant shown in SEQ ID NO: 11. In another embodiment, the codon optimized sequence includes N-terminal and C-terminal restriction sites for cloning. In one embodiment, the CNGA3 coding sequence includes an N-terminal NotI restriction site and a C-terminal BglII restriction site, in addition to a Kozak consensus sequence. Examples of CNGA3 sequences which include such modifications can be found in SEQ ID NO: 16, SEQ ID NO: 17 and SEQ ID NO: 18. In addition, the codon optimized sequence, in some embodiments, includes one or more additional restriction sites to allow for addition of markers, such as an epitope tag. When aligned with the native nucleic acid sequence, the codon optimized CNGA3 may have a percent identity of at least 50%, or at least 60%, or at least 70%, or at least 80% or at least 90%, including any integer between any of those ranges. In one embodiment, the codon optimized CNGA3 has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%. In one embodiment, when aligned with the native nucleic acid sequence SEQ ID NO: 13, it is revealed that codon optimized CNGA3 (SEQ ID NO: 9) has a percent sequence identity of only 80% (see FIG. 3).

In another embodiment, an isolated or engineered codon optimized nucleic acid sequence encoding human CNGB3 is provided. In one embodiment, the codon-optimized sequence is a sequence sharing at least 70% identity with SEQ ID NO: 19 or SEQ ID NO 21. In another embodiment, the codon optimized sequence includes N-terminal and C-terminal restriction sites for cloning, for example, as shown in SEQ ID NO: 23. In addition, the codon optimized sequence, in some embodiments, includes one or more additional restriction sites to allow for addition of markers, such as an epitope tag. When aligned with the native nucleic acid sequence (as shown in SEQ ID NO: 19), the codon optimized CNGB3 may have a percent identity of at least 50%, or at least 60%, or at least 70%, or at least 80% or at least 90%, including any integer between any of those ranges. In one embodiment, the codon optimized CNGB3 has a percent identify with the native sequence of at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99%.

In one embodiment, the optimized nucleic acid sequences encoding the REP-1 or CNGA3 constructs described herein are engineered into any suitable genetic element, e.g., naked DNA, phage, transposon, cosmid, RNA molecule (e.g., mRNA), episome, etc., which transfers the REP-1 or CNGA3 sequences carried thereon to a host cell, e.g., for generating nanoparticles carrying DNA or RNA, viral vectors in a packaging host cell and/or for delivery to a host cells in subject. In one embodiment, the genetic element is a plasmid.

The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

A variety of expression cassettes are provided which employ SEQ ID NOs. 1 or 5 for expression of the REP-1 protein. In one embodiment, an example of a plasmid containing such an expression cassette is shown in SEQ ID NO. 25. In one embodiment, an example of a plasmid containing such an expression cassette is shown in SEQ ID NO. 26. In one embodiment, an example of a plasmid containing such an expression cassette is shown in SEQ ID NO. 27. In one embodiment, an example of a plasmid containing such an expression cassette is shown in SEQ ID NO. 28. In another embodiment, a variety of expression cassettes are provided which employ SEQ ID NOs. 9, 11 or 13 for expression of the CNGA3 protein. In another embodiment, a variety of expression cassettes are provided which employ SEQ ID NOs. 19, 21 or 23 for expression of the CNGAB protein. As used herein, an "expression cassette" refers to a nucleic acid molecule which comprises coding sequences for the optimized REP-1 or CNGA3 or CNGB3 proteins, promoter, and may include other regulatory sequences therefor, which cassette may be engineered into a genetic element or plasmid, and/or packaged into the capsid of a viral vector (e.g., a viral particle). In one embodiment, an expression cassette comprises a codon optimized nucleic acid sequence that encodes REP-1. In one embodiment, the cassette provides the codon optimized REP-1 operatively associated with expression control sequences that direct expression of the codon optimized nucleic acid sequence that encodes REP-1 in a host cell.

In another embodiment, an expression cassette comprises a codon optimized nucleic acid sequence that encodes CNGA3. In one embodiment, the cassette provides the codon optimized CNGA3 operatively associated with expression control sequences that direct expression of the codon optimized nucleic acid sequence that encodes CNGA3 in a host cell.

In another embodiment, an expression cassette comprises a codon optimized nucleic acid sequence that encodes CNGB3. In one embodiment, the cassette provides the codon optimized CNGB3 operatively associated with expression control sequences that direct expression of the codon optimized nucleic acid sequence that encodes CNGB3 in a host cell.

In another embodiment, an expression cassette for use in an AAV vector is provided. In that embodiment, the AAV expression cassette includes at least one AAV inverted terminal repeat (ITR) sequence. In another embodiment, the expression cassette comprises 5' ITR sequences and 3' ITR sequences. In one embodiment, the 5' and 3' ITRs flank the codon optimized nucleic acid sequence that encodes REP-1 or CNGA3 or CNGB3, optionally with additional sequences which direct expression of the codon optimized nucleic acid sequence that encodes REP-1 or CNGA3 or CNGB3 in a host cell. Thus, as described herein, a AAV expression cassette is meant to describe an expression cassette as described above flanked on its 5' end by a 5'AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Each rAAV genome can be then introduced into a production plasmid. In one embodiment, the production plasmid is that described herein, or as described in WO2012/158757, which is incorporated herein by reference. Various plasmids are known in the art for use in producing rAAV vectors, and are useful herein. The production plasmids are cultured in the host cells which express the AAV cap and/or rep proteins. In the host cells, each rAAV genome is rescued and packaged into the capsid protein or envelope protein to form an infectious viral particle.

One type of production plasmid is that shown in SEQ ID NO: 7, which is termed p584. This plasmid is used in the examples for generation of the rAAV-REP-1 vector. Such a plasmid is one that contains a 5' AAV ITR sequence; a selected promoter; a polyA sequence; and a 3' ITR; additionally, it also contains a stuffer sequence, such as lambda.

In one embodiment, a non-coding lambda stuffer region is included in the vector backbone. The nucleic acid sequence encoding REP-1, CNGA3 or CNGB2 are inserted in place of between the selected promoter and the polyA sequence, or a similar, plasmid. An example of p584 which includes the REP-1 encoding sequence can be found in SEQ ID NO: 8. In another embodiment, the production plasmid is modified to optimized vector plasmid production efficiency. Such modifications include addition of other neutral sequences, or deletion of portion(s) of or the entire lambda stuffer sequence to modulate the level of supercoil of the vector plasmid. Such modifications are contemplated herein. In other embodiments, terminator and other sequences are included in the plasmid.

In still a further embodiment, a recombinant adeno-associated virus (AAV) vector is provided for delivery of the REP-1, CNGA3 and CNGB3 constructs and optimized sequences described herein. An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10). These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 vp3. In another embodiment, a self-complementary AAV is used. In one embodiment, it is desirable to utilize an AAV capsid, which shows tropism for the desired target cell, e.g., photoreceptors, RPE or other ocular cells. In one embodiment, the AAV capsid is a tyrosine capsid-mutant in which certain surface exposed tyrosine residues are substituted with phenylalanine (F). Such AAV variants are described, e.g., in Mowat et al, Tyrosine capsid-mutant AAV vectors for gene delivery to the canine retina from a subretinal or intravitreal approach, Gene Therapy 21, 96-105 (January 2014), which is incorporated herein by reference.

For packaging an expression cassette or rAAV genome or production plasmid into virions, the ITRs are the only AAV components required in cis in the same construct as the transgene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or engineered obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99:119-145; Buning et al., 2008, "Recent developments in adeno-associated virus vector technology,"

J. Gene Med. 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

The rAAV vectors comprise an AAV capsid and an AAV expression cassette comprising sequences encoding REP-1 or CNGA3 or CNGB3, such as described above. In certain embodiments, the rAAV expression cassette comprises AAV inverted terminal repeat sequences and a codon optimized nucleic acid sequence that encodes REP-1 or CNGA3 or CNGB3, and expression control sequences that direct expression of the encoded proteins in a host cell. The rAAV expression cassette, in other embodiments, further comprises one or more of an intron, a Kozak sequence, a polyA, and post-transcriptional regulatory elements. Such rAAV vectors for use in pharmaceutical compositions for delivery to the eye, may employ a capsid from any of the many known AAVs identified above.

Other conventional components of the expression cassettes and vectors include other components that can be optimized for a specific species using techniques known in the art including, e.g, codon optimization, as described herein. The components of the cassettes, vectors, plasmids and viruses or other compositions described herein include a promoter sequence as part of the expression control sequences. In another embodiment, the promoter is cell-specific. The term "cell-specific" means that the particular promoter selected for the recombinant vector can direct expression of the optimized REP-1 or CNGA3 or CNGB3 transgene in a particular ocular cell type. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In one embodiment, the photoreceptor-specific promoter is a human rhodopsin kinase promoter. The rhodopsin kinase promoter has been shown to be active in both rods and cones. See, e.g., Sun et al, Gene Therapy with a Promoter Targeting Both Rods and Cones Rescues Retinal Degeneration Caused by AIPL1 Mutations, Gene Ther. 2010 January; 17(1): 117-131, which is incorporated herein by reference in its entirety. In one embodiment, the promoter is modified to add one or more restriction sites to facilitate cloning.

In another embodiment, the promoter is a human rhodopsin promoter. In one embodiment, the promoter is modified to include restriction on the ends for cloning. See, e.g, Nathans and Hogness, Isolation and nucleotide sequence of the gene encoding human rhodopsin, PNAS, 81:4851-5 (August 1984), which is incorporated herein by reference in its entirety. In another embodiment, the promoter is a portion or fragment of the human rhodopsin promoter. In another embodiment, the promoter is a variant of the human rhodopsin promoter.

Other exemplary promoters include the human G-protein-coupled receptor protein kinase 1 (GRK1) promoter (Genbank Accession number AY327580). In another embodiment, the promoter is a 292 nt fragment (positions 1793-2087) of the GRK1 promoter (See, Beltran et al, Gene Therapy 2010 17:1162-74, which is hereby incorporated by reference in its entirety). In another preferred embodiment, the promoter is the human interphotoreceptor retinoid-binding protein proximal (IRBP) promoter. In one embodiment, the promoter is a 235 nt fragment of the hIRBP promoter. In one embodiment, the promoter is the RPGR proximal promoter (Shu et al, IOVS, May 2102, which is incorporated by reference in its entirety). Other promoters useful in the invention include, without limitation, the rod opsin promoter, the red-green opsin promoter, the blue opsin promoter, the cGMP-β-phosphodiesterase promoter (Qgueta et al, IOVS, Invest Ophthalmol Vis Sci. 2000 December;41 (13): 4059-63), the mouse opsin promoter (Beltran et al 2010 cited above), the rhodopsin promoter (Mussolino et al, Gene Ther, July 2011, 18(7): 637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12): 1015-23); the NXNL2/NXNL1 promoter (Lambard et al, PLoS One, October 2010, 5(10):e13025), the RPE65 promoter; the retinal degeneration slow/peripherin 2 (Rds/perph2) promoter (Cai et al, Exp Eye Res. 2010 August;91(2): 186-94); and the VMD2 promoter (Kachi et al, Human Gene Therapy, 2009(20:31-9)). Each of these documents is incorporated by reference herein in its entirety. In another embodiment, the promoter is selected from human human EF1α promoter, rhodopsin promoter, rhodopsin kinase, interphotoreceptor binding protein (IRBP), cone opsin promoters (red-green, blue), cone opsin upstream sequences containing the red-green cone locus control region, cone transducing, and transcription factor promoters (neural retina leucine zipper (Nrl) and photoreceptor-specific nuclear receptor Nr2e3, bZIP).

In another embodiment, the promoter is a ubiquitous or consistutive promoter. An example of a suitable promoter is a hybrid chicken β-actin (CBA) promoter with cytomegalovirus (CMV) enhancer elements. In another embodiment, the promoter is the CB7 promoter. Other suitable promoters include the human β-actin promoter, the human elongation factor-1α promoter, the cytomegalovirus (CMV) promoter, the simian virus 40 promoter, and the herpes simplex virus thymidine kinase promoter. See, e.g., Damdindorj et al, (August 2014) A Comparative Analysis of Constitutive Promoters Located in Adeno-Associated Viral Vectors. PLoS ONE 9(8):e106472. Still other suitable promoters include viral promoters, constitutive promoters, regulatable promoters [see, e.g., WO 2011/126808 and WO 2013/04943]. Alternatively a promoter responsive to physiologic cues may be utilized in the expression cassette, rAAV genomes, vectors, plasmids and viruses described herein. In one embodiment, the promoter is of a small size, under 1000 bp, due to the size limitations of the AAV vector. In another embodiment, the promoter is under 400 bp. Other promoters may be selected by one of skill in the art. In one embodiment, the REP-1 construct incorporates a ubiquitous promoter. In another embodiment, the CNGA3 construct incorporates a photoreceptor-specific promoter. In one embodiment, the REP-1 construct includes a CBA promoter with CMV enhancer elements.

In another embodiment, the promoter is an inducible promoter. The inducible promoter may be selected from known promoters including the rapamycin/rapalog promoter, the ecdysone promoter, the estrogen-responsive promoter, and the tetracycline-responsive promoter, or heterodimeric repressor switch. See, Sochor et al, An Autogenously Regulated Expression System for Gene Therapeutic Ocular Applications. Scientific Reports, 2015 Nov. 24; 5:17105 and Daber R, Lewis M., A novel molecular switch. J Mol Biol. 2009 Aug. 28;391(4): 661-70, Epub 2009 Jun. 21 which are both incorporated herein by reference in their entirety.

In other embodiments, the cassette, vector, plasmid and virus constructs described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein. Examples of suitable polyA sequences include, e.g., SV40, bovine growth hormone (bGH), and TK polyA. Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), amongst others. In one embodiment, a Kozak sequence is included upstream of the transgene coding sequence to enhance translation from the correct initiation codon. In another embodiment, CBA exon 1 and intron are included in the expression cassette. In one embodiment, the transgene is placed under the control of a hybrid chicken β actin (CBA) promoter. This promoter consists of the cytomegalovirus (CMV) immediate early enhancer, the proximal chicken β actin promoter, and CBA exon 1 flanked by intron 1 sequences.

In one embodiment, the expression cassette contains a 5' ITR, CBA promoter, CMV enhancer, CBA exon 1 and intron, kozak sequence, human codon optimized CHM sequence (SEQ ID NO: 1), bGH poly A and 3' ITR.

In yet other aspects, these nucleic acid sequences, vectors, expression cassettes and rAAV viral vectors are useful in a pharmaceutical composition, which also comprises a pharmaceutically acceptable carrier, buffer, diluent and/or adjuvant, etc. Such pharmaceutical compositions are used to express the optimized REP-1 or CNGA3 or CNGB3 in the ocular cells through delivery by such recombinantly engineered AAVs or artificial AAVs.

To prepare these pharmaceutical compositions containing the nucleic acid sequences, vectors, expression cassettes and rAAV viral vectors, the sequences or vectors or viral vector is preferably assessed for contamination by conventional methods and then formulated into a pharmaceutical composition suitable for administration to the eye. Such formulation involves the use of a pharmaceutically and/or physiologically acceptable vehicle or carrier, particularly one suitable for administration to the eye, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In one exemplary specific embodiment, the composition of the carrier or excipient contains 180 mM NaCl, 10 mM NaPi, pH7.3 with 0.0001%-0.01% Pluronic F68 (PF68). The exact composition of the saline component of the buffer ranges from 160 mM to 180 mM NaCl. Optionally, a different pH buffer (potentially HEPES, sodium bicarbonate, TRIS) is used in place of the buffer specifically described. Still alternatively, a buffer containing 0.9% NaCl is useful.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The pharmaceutical compositions containing at least one replication-defective rAAV virus, as described herein, can be formulated with a physiologically acceptable carrier, diluent, excipient and/or adjuvant, for use in gene transfer and gene therapy applications. In the case of AAV viral vectors, quantification of the genome copies ("GC"), vector genomes ("VG"), or virus particles may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). In another method the effective dose of a recombinant adeno-associated virus carrying a nucleic acid sequence encoding the optimized REP-1 or CNGA3 transgene is measured as described in S.K. Mclaughlin et al, 1988 J. Virol., 62:1963, which is incorporated by reference in its entirety.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the codon optimized nucleic acid sequences encoding REP-1 or CNGA3 or CNGB3 as described herein that is in the range of about $1.0 \times 10^9$ GC to about $1.0 \times 10^{15}$ GC including all integers or fractional amounts within the range. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per dose including all integers or fractional amounts within the range. In another embodiment, the compositions are formulated to contain at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per dose including all integers or fractional amounts within the range. In another embodiment, the compositions are formulated to contain at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range. In one embodiment, for human application the dose can range from $1\times10^{10}$ to about $1\times10^{12}$ GC per dose including all integers or fractional amounts within the range. All dosages may be measured by any known method, including as measured by oqPCR or digital droplet PCR (ddPCR) as described in, e.g., M. Lock et al, Hum Gene Ther Methods. 2014 April;25(2):115-25. doi: 10.1089/hgtb.2013.131, which is incorporated herein by reference.

These above doses may be administered in a variety of volumes of carrier, excipient or buffer formulation, ranging from about 25 to about 1000 microliters, including all numbers within the range, depending on the size of the area to be treated, the viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is between about 700 and 1000 µL.

In one embodiment, the viral constructs may be delivered in doses of from at least $1\times10^9$ to about least $1\times10^{11}$ GCs in volumes of about 1 µL to about 3 µL for small animal subjects, such as mice. For larger veterinary subjects having eyes about the same size as human eyes, the larger human dosages and volumes stated above are useful. See, e.g., Diehl et al, J. Applied Toxicology, 21:15-23 (2001) for a discussion of good practices for administration of substances to various veterinary animals. This document is incorporated herein by reference.

It is desirable that the lowest effective concentration of virus or other delivery vehicle be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the particular ocular disorder and the degree to which the disorder, if progressive, has developed.

Yet another aspect described herein is a method for treating, retarding or halting progression of blindness in a mammalian subject having, or at risk of developing, choroideremia. In one embodiment, a rAAV carrying the REP-1 codon optimized sequences, preferably suspended in a physiologically compatible carrier, diluent, excipient and/or adjuvant, may be administered to a desired subject including a human subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of ocular diseases, and may also involve administration via the palpebral vein or other intravenous or conventional administration routes.

Yet another aspect described herein is a method for treating, retarding or halting progression of blindness in a mammalian subject having, or at risk of developing, achromatopsia. In one embodiment, an rAAV carrying the CNGA3 or CNGB3 native, modified or codon optimized sequence, preferably suspended in a physiologically compatible carrier, diluent, excipient and/or adjuvant, may be administered to a desired subject including a human subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of ocular diseases, and may also involve administration via the palpebral vein or other intravenous or conventional administration routes.

For use in these methods, the volume and viral titer of each dosage is determined individually, as further described herein, and may be the same or different from other treatments performed in the same, or contralateral, eye. The dosages, administrations and regimens may be determined by the attending physician given the teachings of this specification. In one embodiment, the composition is administered in a single dosage selected from those above listed in a single affected eye. In another embodiment, the composition is administered as a single dosage selected from those above listed in a both affected eyes, either simultaneously or sequentially. Sequential administration may imply a time gap of administration from one eye to another from intervals of minutes, hours, days, weeks or months. In another embodiment, the method involves administering the compositions to an eye two or more dosages (e.g., split dosages). In another embodiment, multiple injections are made in different portions of the same eye. In another embodiment, a second administration of an rAAV including the selected expression cassette (e.g., CHM containing cassette) is performed at a later time point. Such time point may be weeks, months or years following the first administration. Such second administration is, in one embodiment, performed with an rAAV having a different capsid than the rAAV from the first administration. In another embodiment, the rAAV from the first and second administration have the same capsid.

In still other embodiments, the compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

In certain embodiments of the invention it is desirable to perform non-invasive retinal imaging and functional studies to identify areas of the rod and cone photoreceptors to be targeted for therapy. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, etc, depending upon the species of the subject being treated, their physical status and health and the dosage. In view of the imaging and functional studies, in some embodiments of the invention one or more injections are performed in the same eye in order to target different areas of the affected eye. The volume and viral titer of each injection is determined individually, as further described herein, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged ocular cells is impacted. In another embodiment, the volume and/or concentration of the rAAV composition is a greater amount, in order reach larger portions of the eye, including non-damaged photoreceptors.

In one embodiment of the methods described herein, a one-time intra-ocular delivery of a composition as described herein, e.g., an AAV delivery of an optimized REP-1 cassette, is useful in preventing vision loss and blindness in a subject at risk of developing choroideremia. In another embodiment of the methods described herein, a one-time intra-ocular delivery of a composition as described herein, e.g., an AAV delivery of an optimized CNGA3 or CNGB3 cassette, is useful in preventing vision loss and blindness in a subject at risk of developing achromatopsia.

Thus, in one embodiment, the composition is administered before disease onset. In another embodiment, the composition is administered prior to the initiation of vision impairment or loss. In another embodiment, the composition is administered after initiation of vision impairment or loss. In yet another embodiment, the composition is administered when less than 90% of the rod and/or cones or photoreceptors are functioning or remaining, as compared to a non-diseased eye.

In another embodiment, the method includes performing additional studies, e.g., functional and imaging studies to determine the efficacy of the treatment. For examination in animals, such tests include retinal and visual function assessment via electroretinograms (ERGs) looking at rod and cone photoreceptor function, optokinetic nystagmus, pupillometry, water maze testing, light-dark preference, optical coherence tomography (to measure thickness of various layers of the retina), histology (retinal thickness, rows of nuclei in the outer nuclear layer, immunofluorescence to document transgene expression, cone photoreceptor counting, staining of retinal sections with peanut agglutinin-which identifies cone photoreceptor sheaths).

Specifically for human subjects, following administration of a dosage of a compositions described in this specification, the subject is tested for efficacy of treatment using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), and reading speed test. Other useful post-treatment efficacy test to which the subject is exposed following treatment with a pharmaceutical composition described herein are functional magnetic resonance imaging (fMRI), full-field light sensitivity testing, retinal structure studies including optical coherence tomography, fundus photography, fundus autofluorescence, adaptive optics laser scanning ophthalmoscopy, mobility testing, test of reading speed and accuracy, microperimetry and/or ophthalmoscopy. These and other efficacy tests are described in U.S. Pat. No. 8,147,823; in co-pending International patent application publication WO 2014/011210 or WO 2014/124282, incorporated by reference.

In yet another embodiment, any of the above described methods is performed in combination with another, or secondary, therapy. In still other embodiments, the methods of treatment of these ocular diseases involve treating the subject with the composition described in detail herein in combination with another therapy, such as antibiotic treatment, palliative treatment for pain, and the like. The additional therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In one embodiment, a method of generating a recombinant rAAV comprises obtaining a plasmid containing an AAV expression cassette as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver the codon optimized REP-1 or CNGA3 or CNGB3 in the expression cassettes and genomes described above and in the examples below.

In yet another embodiment, a vector comprising any of the expression cassettes described herein is provided. As described above, such vectors can be plasmids of variety of origins and are useful in certain embodiments for the generation of recombinant replication defective viruses as described further herein.

In one another embodiment, the vector is a plasmid that comprises an expression cassette, wherein the expression cassette comprises AAV inverted terminal repeat sequences and a codon optimized nucleic acid sequence that encodes REP-1, and expression control sequences that direct expression of the encoded protein in a host cell.

In another embodiment, the vector is a plasmid that comprises an expression cassette, wherein the expression cassette comprises AAV inverted terminal repeat sequences and a codon optimized nucleic acid sequence that encodes CNGA3, and expression control sequences that direct expression of the encoded protein in a host cell.

In another embodiment, the vector is a plasmid that comprises an AAV expression cassette, wherein the expression cassette comprises AAV inverted terminal repeat sequences and a codon optimized nucleic acid sequence that encodes CNGB3, and expression control sequences that direct expression of the encoded protein in a host cell.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

Example 1—Differentiation of Pluripotent Stem Cells into RPE

Choroideremia lacks a relevant mouse model and there is no canine model, therefore, transduction and expression is tested in a human retinal cell model of the disease. Because it is impossible to obtain retinal cells from a living patient, RPE are generated from induced pluripotent stem cells. Pluripotent stem cells are directed to RPE using the protocol described by Buchholz et al, Rapid and Efficient Directed Differentiation of Human Pluripotent Stem Cells Into Retinal Pigmented Epithelium, Stem Cells Translational Medicine, 2013; 2:384-393 which is incorporated by reference in its entirety. See also, Cereso et al, Proof of concept for AAV2/5-mediated gene therapy in iPSC-derived retinal pigment epithelium of a choroideremia patient, Molecular Therapy—Methods & Clinical Development (2014) 1, 14011, which is incorporated by reference in its entirety. Other methods for producing RPE are known in the art.

Briefly, the human induced pluripotent stem cell line is maintained in Dulbecco's Modified Eagle's Medium: Nutrient Mixture F-12 (DMEM/F12) containing 2mMGlutaMAX-I, 20% knockout serum replacement, 0.1 mM Modified Eagle's Medium Non-Essential Amino Acids (MEM NEAA), 0.1 mM β-mercaptoethanol and 4 ng/ml bFGF on a mitomycin C-treated or irradiated mouse embryonic fibroblast feeder layer.

Pluripotent stem cells are passaged directly onto Matrigel (BD Biosciences) in DMEM/F12 with 1×B27, 1×N2, and 1×NEAA (Invitrogen). From days 0 to 2, 50 ng/ml Noggin, 10 ng/ml Dkk1, 10 ng/ml IGF1 and 10 mM nicotinamide are added to the base medium. From days 2 to 4, 10 ng/ml Noggin, 10 ng/ml Dkk1, 10 ng/ml IGF1, 5 ng/ml bFGF and 10mMnicotinamide are added to the base medium. From days 4 to 6, 10 ng/ml Dkk1, 10 ng/ml IGF1 and 100 ng/ml Activin A (R&D Systems) are added to the base medium. From days 6 to 14, 100 ng/ml Activin A, 10 µM SU5402 (EMD Millipore, Darmstadt, Germany), and 1 mM VIP are added to the base medium. Control experiments are performed in base media alone (DMEM/F12, B27, N2, and NEAA).

The cells are mechanically enriched by scraping away cells with non-RPE morphology. Subsequently, the remaining RPE are digested using TrypLE Express (Invitrogen) for 5 minutes at 37° C. The cells are passed through a 30-µm single-cell strainer and seeded onto Matrigel-coated tissue culture plastic, Transwell membranes or CC2-treated chambered slides. Enriched cells are cultured in DMEM-high glucose with 1% fetal bovine serum (FBS), GlutaMAX, and sodium pyruvate for 30 days.

Example 2—Cells Transduced with AAV-REP-1

Briefly, AAV2/8CMV.CBA-REP-1 viral vector incorporating REP-1 codon optimized sequences are produced by transient transfection of HEK293 cells, and the viral particles are precipitated from either the supernatant using polyethylene glycol. See, e.g., Guo et al, Rapid and simplified purification of recombinant adeno-associated virus, J Virol Methods. 2012 August; 183(2): 139-146, which is incorporated herein by reference. The vectors are purified by double CsCl centrifugation, dialyzed, and titered by dot blot assay.

For the prenylation experiments, RPE are seeded in 24-well plates, and $1.2 \times 10^6$ cells are estimated at confluence. Cells are transduced with 100,000 vg per cell, and prenylation assays are performed at 4 weeks posttransduction. Experiments are performed in triplicate.

Example 3—Prenylation

An in vitro prenylation assay is performed as described in Vasireddy et al, PLoS One. 2013 May 7;8(5): e61396, cited above, using [3H]-geranylgeranyl pyrophosphate (GGPP) (Perkin Elmer, Boston, MA, USA) as a prenyl group donor, in the presence of recombinant Rab geranylgeranyl transferase and RAB27. Incorporation of radiolabeled prenyl groups into the RAB27 protein is measured by scintillation counting. For consistency the control values are normalized to 100 and used as the base value. All experiments are performed in triplicate, and statistical comparison of prenylation between experimental and control groups is evaluated using the two-tailed unpaired student's t-test.

Briefly, 48 hr post transduction, transduced REP cells are washed with cold PBS. Cell pellets are collected and washed thoroughly with cold PBS. Cells are lysed on ice for 30 min using RIPA+Protease inhibitors. In an alternative protocol, cells are sonicated. Cytosolic fractions are collected by centrifuging the lysate at 75,000-100,000 g for 1-2 h at 4° C.

Stocks are prepared for the prenylation reaction as follows.

| | STOCKS prepared | FINAL CONCENTRATION REQUIRED |
|---|---|---|
| Rab GGTase | 16.63 uM - (GGTAse-a) | 0.05 uM |
| | 14.59 uM - (GGTASE-b) | |
| Rab 27a | 25.93 uM | 4 uM |
| 3H GGPP | 22.2 | 5 uM |
| NP40 | | 1 mM |
| DTT | 10 mM | 1 mM |

-continued

| STOCKS prepared | | FINAL CONCENTRATION REQUIRED |
|---|---|---|
| HEPES | 1M | 50 mM |
| Mgcl2 | 100 mM | 5 mM |

Final reaction volume used for prenylation is 25 μL

| Rab GGTase a | 0.075 ul |
|---|---|
| Rab Ggtaseb | 0.085 ul |
| [³H]-geranylgeranyl pyrophosphate (GGPP) | 5.68 ul |
| NP40 | 0.15 ul |
| DTT | 2.5 ul |
| HEPES | 1.25 ul |
| MgCl2 | 1.25 ul |
| Rab 27a | 3.12 ul |
| Cytosolic Fraction (Cell lysate) | 10.89 ul |

The reaction mixture is incubated at 37° C. for 30 min. The reaction is stopped by adding 9:1 ethanol/HCL, and incubated for 30 minutes. The proteins are collected on glass fiber filter papers (Whatman papers) by vacuum filtration (0.1 ml). The filters are washed carefully with cold phosphate buffer—3 times to remove unbound material. The membranes are dried carefully. The filters are placed in 5 ml scintillation cocktail and scinitillation counting is performed. See also, Tolmachova et al, CHM/REP1 cDNA delivery by lentiviral vectors provides functional expression of the transgene in the retinal pigment epithelium of choroideremia mice, The Journal of Gene Medicine, 2012; 14-158-68, which is incorporated herein by reference in its entirety.

Assays for CNGA3 or CNGB3 proof-of-concept may include use of a spontaneous mutant animal model (for example, the Cnga3–/– mouse or the Awassi sheep). The mouse model could be bred with an "all-cone" photoreceptor mouse, the Nrl–/– mouse, to obtain double knockouts. The latter (Cnga3–/–Nrl–/–) mouse may expedite identification of efficacy. Efficacy could be measured by pupillometry, measures of visual acuity and contrast (for example, using optokinetics), electroretinograms, and visual behavior. Ultimately, histology will document expression of the transgene with improved outcomes on the other measures. Hsitologic approaches will also be used to document any effects of the intervention on cone photoreceptors (total number of cone photoreceptors, density, location, etc).

Similar to choroideremia as discussed above, assays for proof-of-concept for gene augmentation therapy for CNGA3- or CNGB3-associated achromatopsia may include use of induced pluripotent stem cell (iPSC) models. The iPSC models, generated from patients with achromatopsia due to CNGA3 or CNGB3 mutations, will be differentiated into retinal precursors and/or photoreceptor cells in vitro. The wildtype CNGA3 (or CNGB3) cDNA will be delivered to these cells using recombinant AAV and the cells will be analyzed for biogenesis and preservation of function of the relevant (Cyclic nucleotide-gated, CNG) channel comprised by these subunits. Channel function will be assessed by electrophysiology on membrane patches. Restoration of the channel should rescue cGMP-activated currents. Additional studies can test for sensitivity of channel function before and after delivery of the wildtype CNG cDNA to physiological ligands.

Example 4: In Vitro Expression of AAV.Codon-Optimized Human CHM

The objective of this study was to evaluate the ability of AAV mediated CHM expression after gene delivery using a series of next generation AAV 2 and AAV8 vectors encoding the codon optimized CHM gene (SEQ ID NO: 1) in 84-31 and COS-7 cell lines.

To maximize the expression of CHM, a codon optimized CHM sequence was produced (SEQ ID NO: 1). The codon optimized plasmid was synthesized and used in the creation of all the next generation CHM transgene expression cassettes. To overcome the potential problem of contamination of non-functional AAV genomes, a non-coding lambda stuffer region was included in the vector backbone. Incorporation of stuffer not only increases the length of the plasmid, but also diminishes the possibility of plasmid DNA backbone contamination while packaging the AAV. The impact of incorporating a stuffer region in the vector backbone to eliminate the plasmid DNA impurities was carried out as an independent study. Two recombinant AAV proviral plasmids (high and low copy) backbones were used to generate the different constructs. The high copy plasmid was designed based on the pUC vector origin. The low copy plasmid was designed based on the p15A origin. To further enhance the translation from the correct initiation codon, a Kozak sequence upstream of the start codon was incorporated.

A total of four plasmids have been engineered for the current study and those described in the following examples (Table 1). In addition, a plasmid carrying the CHM native sequence, which is currently being used in a clinical trial, was also generated (version 1). Plasmid maps for each of Version 2a, 2b, 3a and 3b, and Version 1 are shown in FIGS. 6-10, respectively.

TABLE 1

| Plasmid features | | | | | | |
|---|---|---|---|---|---|---|
| Name | REP Sequence | Lambda insert | Kozak Sequence | Origin | Copy number | Promoter/Intron |
| Version 1 (V1) | Native | Present | Absent | pUC | High copy | CMV-CBA promoter + Enhancer extension |
| Version 2a (V2a) | Codon-optimized | Present | present | pUC | High copy | CMV-CBA promoter + Enhancer extension |
| Version 2b (V2b) | Codon-optimized | Not Present | present | pUC | High copy | CMV-CBA promoter + Enhancer extension |
| Version 3a (V3a) | Codon-optimized | Present | present | p15A | Low copy | CMV-CBA promoter + Enhancer extension |
| Version 3b (V3b) | Codon-optimized | Not Present | present | p15A | Low copy | CMV-CBA promoter + Enhancer extension |

The in vitro expression of these constructs was tested in COS-7 and 84-31 cell lines. The engineered features of the next-generation CHM constructs are depicted in Table.1.

Recombinant AAV proviral high and low copy plasmids were generated by cloning the codon optimized human CHM cDNA (hCHM) (SEQ ID NO: 1) into the transgene cassette. The transgene was placed under the control of a hybrid chicken β actin (CBA) promoter. This promoter consists of the cytomegalovirus (CMV) immediate early enhancer, the proximal chicken β actin promoter, and CBA exon 1 flanked by intron 1 sequences. The proviral high and low copy number plasmids also contain AAV inverted terminal repeats and a PolyA sequence. The next generation plasmid backbones used in the current study contain a lambda phage fragment stuffer followed by the kanamycin bacterial selection gene. Additional plasmids lack the stuffer but contain the kanamycin selection gene. The high-copy number vector is similar to that of pUC plasmids (~300 copies/bacterial cell). The low copy number plasmid (~10 copies/bacterial cell) has an origin of p15A. To enhance translation from the correct initiation codon, all next generation constructs contain a KOZAK consensus sequence upstream of the start codon, ATG. The generated plasmids are sequence verified using primers that can specifically target either the promoter+enhancer extension sequence or the codon optimized CHM sequence. The plasmid maps and sequences of all five constructs are shown in FIGS. 6-10.

Standard triple transfection with calcium phosphate was used to generate AAV vectors listed below (see Table 2 for vector qualification). Both AAV2 and AAV8 serotypes of the vectors were generated to ensure the results are serotype-independent.

TABLE 2

Summary of AAV2 and AAV8 vectors generated and concentration of viral stocks

| Name | Serotype | Plasmid name | Lot number | Stock Conc. (vg/ml) |
|---|---|---|---|---|
| AAV2.V1 | AAV 2 | Version 1 (V1) | KA 892* | 4.47E+12 |
| AAV2.V2a | AAV 2 | Version 2a (V2a) | CT 239 | 2.16E+12 |
| AAV2.V2b | AAV 2 | Version 2b (V2b) | CT 238 | 7.40E+12 |
| AAV2.V3a | AAV 2 | Version 3a (V3a) | CT 258 | 4.82E+12 |
| AAV2.V3b | AAV 2 | Version 3b (V3b) | CT 256 | 5.91E+12 |
| AAV8.V1 | AAV 8 | Version 1 (V1) | KA 808* | 1.39E+13 |
| AAV8.V2a | AAV 8 | Version 2a (V2a) | CT 245 | 1.04E+13 |
| AAV8.V2b | AAV 8 | Version 2b (V2b) | CT 244 | 1.11E+13 |
| AAV8.V3a | AAV 8 | Version 3a (V3a) | CT 259 | 8.67E+12 |
| AAV8.V3b | AAV 8 | Version 3b (V3b) | CT 255 | 1.36E+13 |

The 84-31 cell line is a subclone of 293 HEK cell line (human embryonic kidney cells) and constitutively expresses adenovirus E4 proteins to enhance transduction of AAV virus. COS-7 cells are fibroblast like cell lines that are derived from monkey kidney tissues. Both 84-31 cells and COS-7 cells were plated, separately, in 6-well cell culture plates and transduced with one of the ten test articles (either AAV2 or AAV8) at five different multiplicity of infection (MOIs). After 36-48 hours, cells were harvested, lysed and protein samples were prepared for SDS-PAGE followed by Western blot analysis to detect the expression of exogenous CHM.

Both 84-31 and COS-7 cells were cultured in Dulbecco's modified Eagle medium (DMEM)-high glucose with 10% fetal bovine serum, and 1% penicillin/streptomycin at 37° C. in an environment supplied with 5% CO2. The day before transduction (18-24 h before) cells at a density of 3E5 were seeded in 2 ml of cell culture media in each well of a 6-well cell culture dish. Seeded cells were incubated at 37° C. in an environment supplied with 5% CO2. Wells of both COS-7 and 84-31 cells were infected with AAV vectors listed below at various multiplicities of infection (MOI) (Table 3 and Table 4). No virus was added to negative control cells (untransduced cells). Briefly, the tissue culture media was removed and a fresh 2 ml aliquot of media was added to each well of the 6 well culture dish. Then the predetermined amount of AAV vector was measured (directly from the stock) and added to each well (Table 3 and Table 4). For an MOI of 1E4, 1 μL of respective virus stock was diluted to 10 μL with cell culture media. From this solution, the predetermined volume of the virus was added to respective well (Table 3 and 4). Cells were incubated with the AAV virus for 36-48 hours at 37° C. with 5% CO2 till harvesting. Cells were observed under microscope before harvesting to check for abnormalities.

TABLE 3

Infection dose of four next generation AAV2 and AAV8 hCHM vectors in COS-7 cells.

| Vector Used | Cell Line | Cell Density | Vector Used (μL) | MOI |
|---|---|---|---|---|
| No AAV | COS-7 | 3E5 | — | — |
| AAV2.V2a | COS-7 | 3E5 | 1.5 | 1E4 |
| | COS-7 | 3E5 | 15 | 1E5 |
| | COS-7 | 3E5 | 45 | 3E5 |
| | COS-7 | 3E5 | 75 | 5E5 |
| | COS-7 | 3E5 | 150 | 1E6 |
| AAV2.V2b | COS-7 | 3E5 | 4.2 (front a 1 to 10 dilution of the stock) | 1E4 |
| | COS-7 | 3E5 | 4.2 | 1E5 |
| | COS-7 | 3E5 | 12.6 | 3E5 |
| | COS-7 | 3E5 | 21 | 5E5 |
| | COS-7 | 3E5 | 42 | 1E6 |
| AAV8.V2a | COS-7 | 3E5 | 2.9 (from a 1 to 10 dilution of the stock) | 1E4 |
| | COS-7 | 3E5 | 2.88 | 1E5 |
| | COS-7 | 3E5 | 8.65 | 3E5 |
| | COS-7 | 3E5 | 14.42 | 5E5 |
| | COS-7 | 3E5 | 28.85 | 1E6 |
| AAV8.V2b | COS-7 | 3E5 | 2.7 (front a 1 to 1b dilution of the stock) | 1E4 |
| | COS-7 | 3E5 | 2.7 | 1E5 |
| | COS-7 | 3E5 | 8.1 | 3E5 |
| | COS-7 | 3E5 | 13.5 | 5E5 |
| | COS-7 | 3E5 | 27 | 1E6 |

TABLE 4

Infection rates of four next generation AAV2 and AAV8 hCHM vectors in 84-31 cells.

| Vector Used | Cell Line | Cell Density | Vector Used (μL) | MOI |
|---|---|---|---|---|
| No AAV | 84-31 | 3E5 | — | — |
| AAV2.V2a | 84-31 | 3E5 | 1.5 | 1E4 |
| | 84-31 | 3E5 | 15 | 1E5 |
| | 84-31 | 3E5 | 45 | 3E5 |
| | 84-31 | 3E5 | 75 | 5E5 |
| | 84-31 | 3E5 | 150 | 1E6 |
| AAV2.V2b | 84-31 | 3E5 | 4.2 (from a 1 to 10 dilution of the stock) | 1E4 |
| | 84-31 | 3E5 | 4.2 | 1E5 |
| | 84-31 | 3E5 | 12.6 | 3E5 |
| | 84-31 | 3E5 | 21 | 5E5 |
| | 84-31 | 3E5 | 42 | 1E6 |

TABLE 4-continued

Infection rates of four next generation AAV2 and AAV8 hCHM vectors in 84-31 cells.

| Vector Used | Cell Line | Cell Density | Vector Used (µL) | MOI |
|---|---|---|---|---|
| AAV8.V2a | 84-31 | 3E5 | 2.9 (from a 1 to 10 dilution of the stock) | 1E4 |
| | 84-31 | 3E5 | 2.88 | 1E5 |
| | 84-31 | 3E5 | 8.65 | 3E5 |
| | 84-31 | 3E5 | 14.42 | 5E5 |
| | 84-31 | 3E5 | 28.85 | 1E6 |
| AAV8.V2b | 84-31 | 3E5 | 2.7 (from a 1 to 10 dilution of the stock) | 1E4 |
| | 84-31 | 3E5 | 2.7 | 1E5 |
| | 84-31 | 3E5 | 8.1 | 3E5 |
| | 84-31 | 3E5 | 13.5 | 5E5 |
| | 84-31 | 3E5 | 27 | 1E6 |

First, both, the COS7 and 84-31 cell lines were used to test if the in vitro expression of CHM is cell line independent. Once the independence was established, all subsequent experiments were carried out only in 84-31 cells, which have shown superior transduction efficiency with AAV. Wells of 84-31 cells were infected with the AAV vectors listed below at various MOI (see table 3 and 4).

Western blot analysis: 1. Cell lysates were prepared. The AAV transduced cells along with the untreated control cells, were harvested 36-48 h post-infection after a thorough PBS wash. Cells were then lysed on ice using RIPA buffer with protease inhibitors. Cell lysates were cleared by centrifuging at 13,000 rpm for 10 min. 2. Quantification and preparation of proteins. Protein quantification of the cell lysates was carried out using ThermoFisher Micro BCA™ Protein Assay Kit following manufacturer's instructions. Protein concentration was determined by taking OD reading at 562 nm. To evaluate the in vitro expression of CHM, between 40-60 ug of measured protein was loaded on 4-12% Bis-Tris gels. 3. SDS-PAGE and blotting SDS-PAGE and western blot analysis were carried out according to known protocols. Briefly, the protein gels were transferred on to a nitrocellulose membrane, blocked in milk and incubated with the primary antibodies. Antihuman REP-1 2F1 antibody (2F1, 1:1000 dilution) and one of the following: anti-GAPDH antibody (1:1000 dilution), anti actin antibody (1:1000 dilution) or anti-Tubulin antibody (1:5000 dilution) was used as primary antibodies for each blot. After washing the blot, HRP conjugated anti-mouse IgG antibody and/or anti-rabbit IgG antibody at a concentration of 1:5000 were used as secondary antibodies. The blots were developed by chemiluminescence using ECL reagents according to the manufacturer's instructions. Controls: 1. Loading controls: One of the following: anti-Actin antibody, anti-tubulin antibody or anti-GAPDH antibody was used as a loading control to demonstrate equal loading of protein in each well of the gels. Anti-Tubulin antibody detects a protein of ~51 kDa. Anti-Actin antibody detects a protein of ~42 kDa, and anti-GAPDH antibody detects a protein of ~39 kDa. Initial blots were probed with either anti-tubulin antibody or anti-Actin antibody or anti-GAPDH antibody depending up on their availability. After initial experiments, to be consistent, anti-GAPDH antibody was used as the loading control. 2. Positive control: After the production of hREP-1 protein was established in AAV2.V2a transduced COS-7 cells, the AAV2.V2a-Cos-7 cell lysates were used as positive control in later western blot experiments. 3. Negative control: Untreated cells were used as negative control. Analyses of western blot results of REP-1 protein production in various cell lines are summarized in Table. 5.

TABLE 5

Figure 1A:
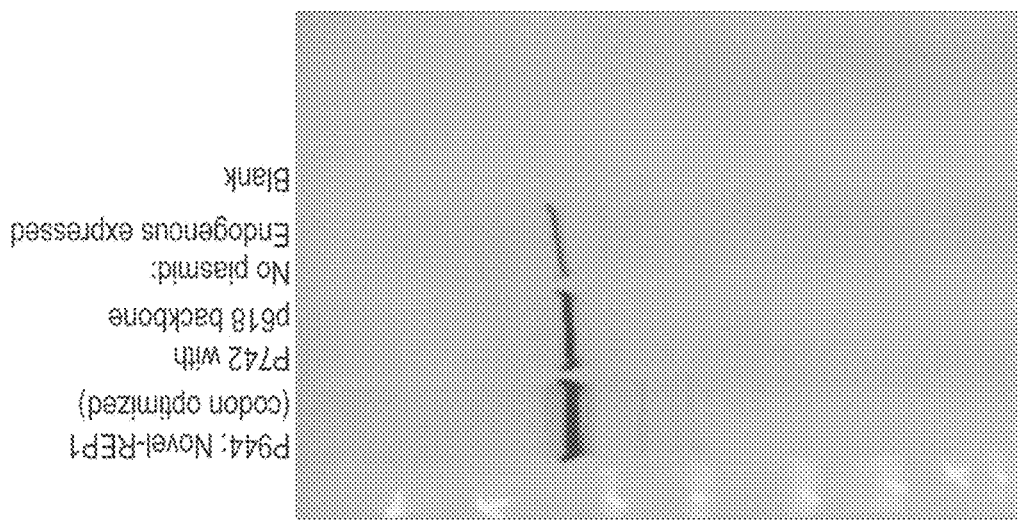
Figure 5:
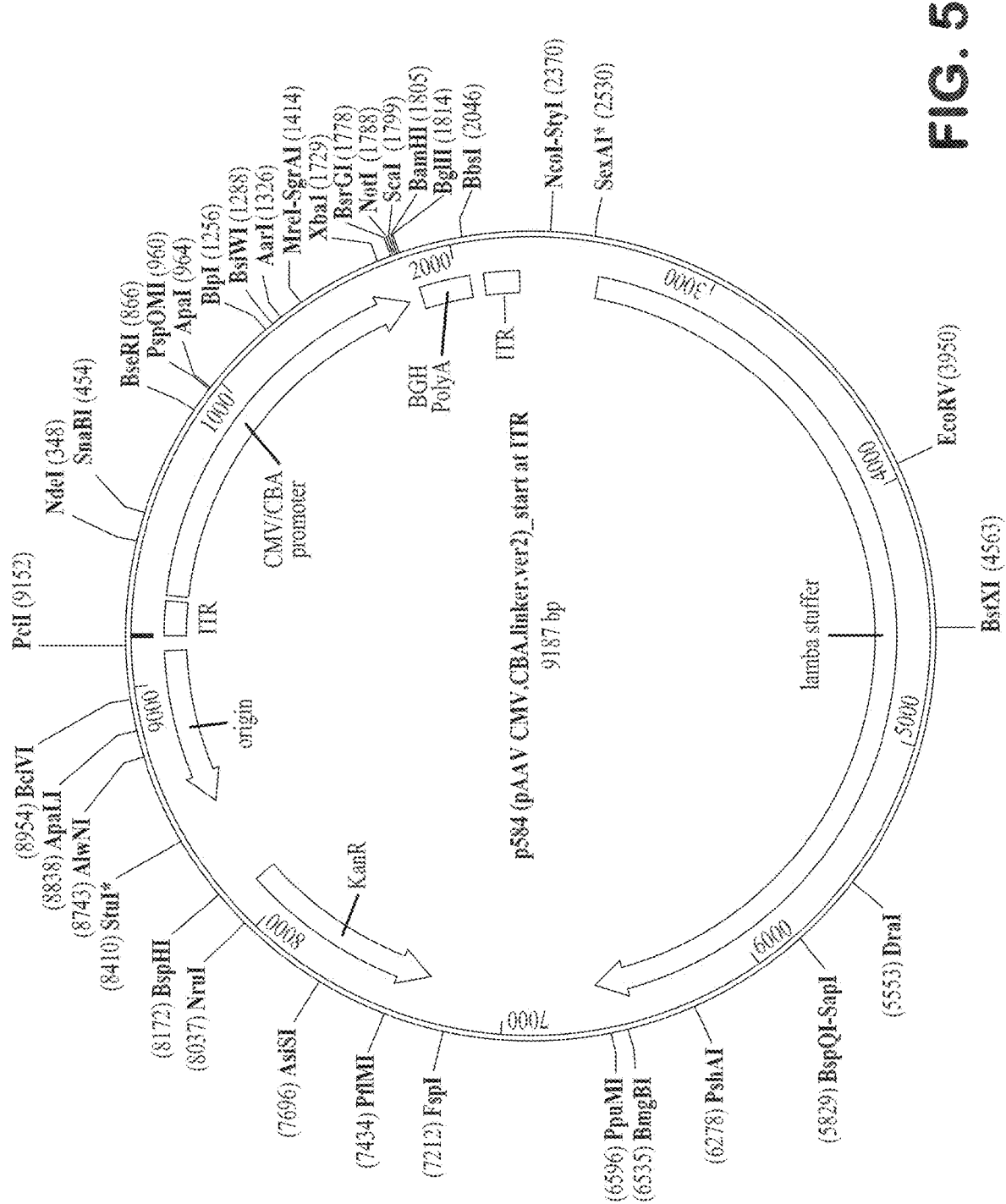
FIG. 5 is a plasmid map of p584, described herein. The sequence of p584 is shown in SEQ ID NO: 7.
Figure 6:
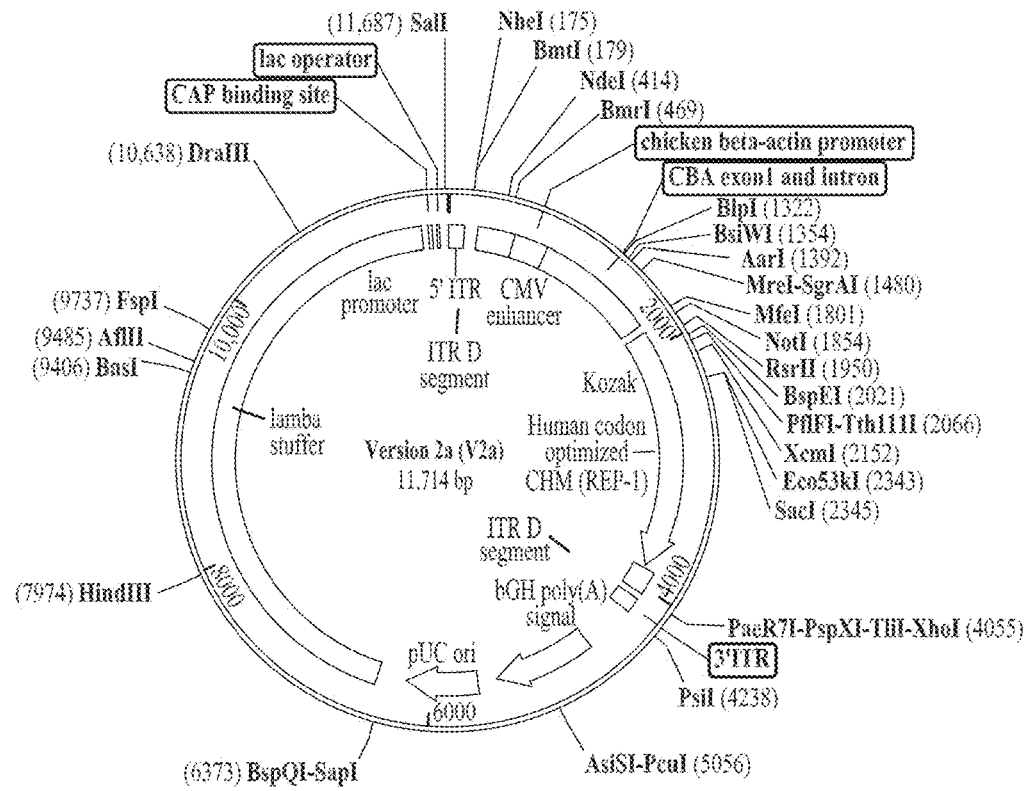
FIG. 6 is a plasmid map of AAV.hCHMco. Version 2a, described herein. The sequence of Version 2a is shown in SEQ ID NO: 25.
Figure 7:
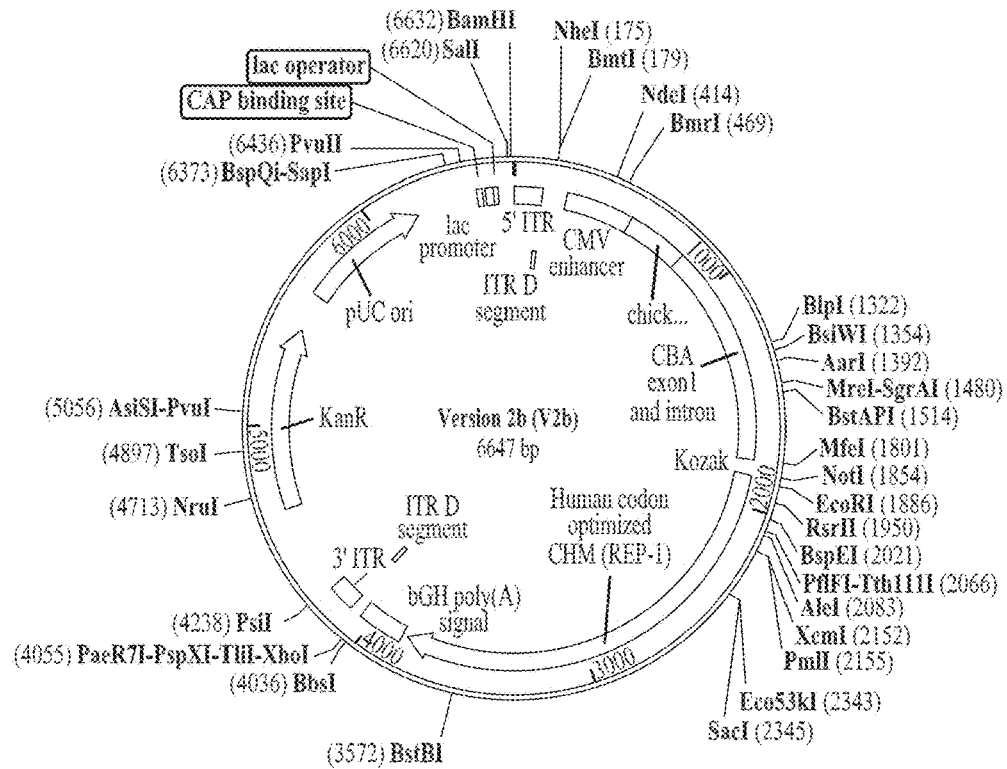
FIG. 7 is a plasmid map of AAV.hCHMco. Version 2b, described herein. The sequence of Version 2b is shown in SEQ ID NO: 26.
Figure 8:
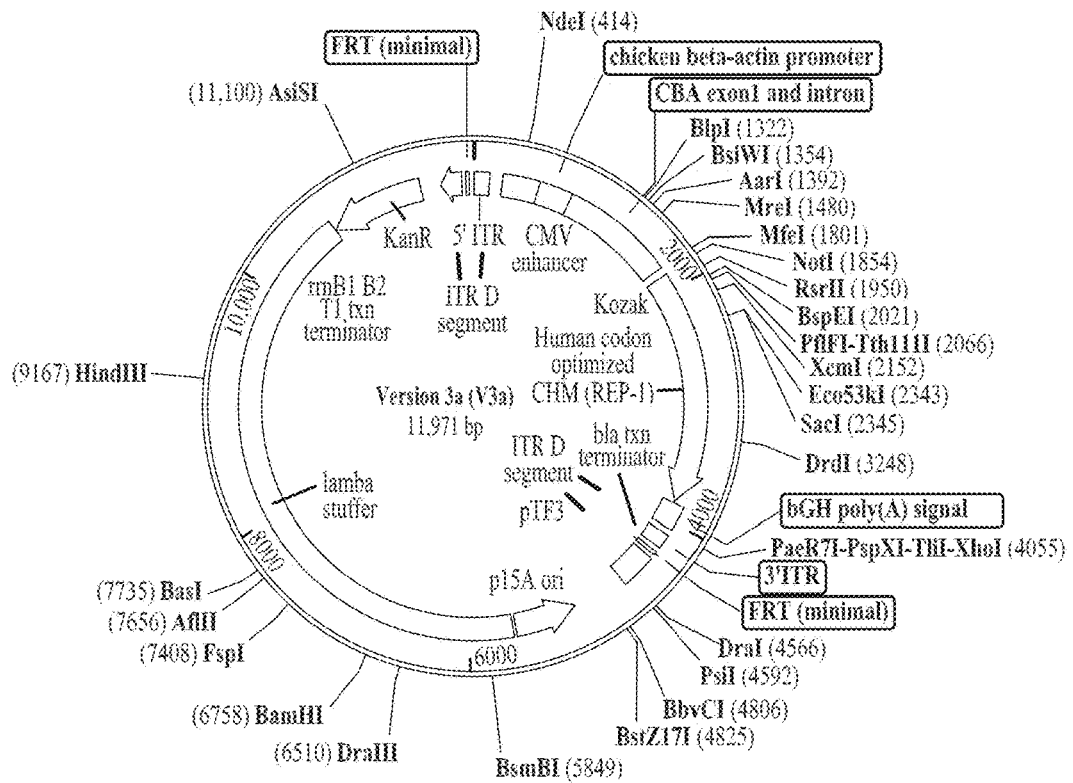
FIG. 8 is a plasmid map of AAV.hCHMco. Version 3a, described herein. The sequence of Version 3a is shown in SEQ ID NO: 27.
Figure 9:
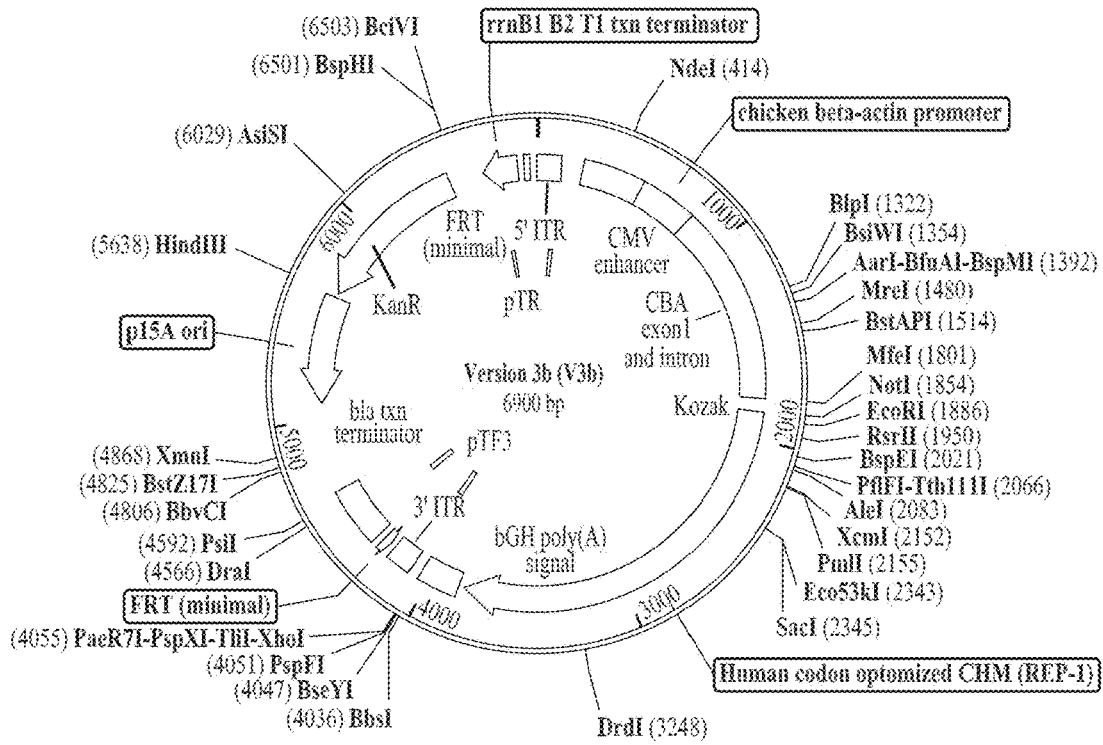
FIG. 9 is a plasmid map of AAV.hCHMco. Version 3b, described herein. The sequence of Version 3b is shown in SEQ ID NO: 28.
Figure 10:
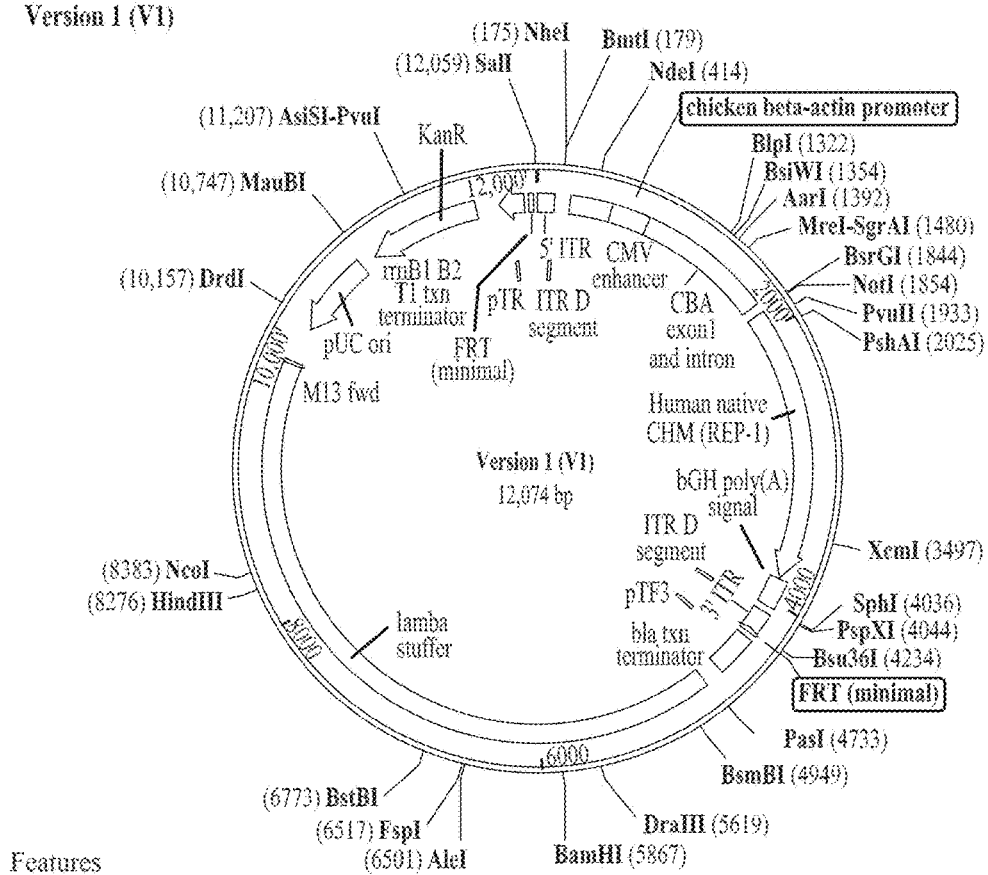
FIG. 10 is a plasmid map of AAV.hCHM. Version 1, described herein. The sequence of Version 1 is shown in SEQ ID NO: 29.

| Name | Serotype | Cell Line | FIG. | MOI Used | CHM Expression (Observation) |
|---|---|---|---|---|---|
| AAV2.V2a | AAV2 | COS-7 | FIG. 1 | 1E4-1E6 | Detectable expession of CHM at all MOIs tested |
| AAV2.V2a | AAV2 | 84-31 | FIG. 1 | 1E4-1E6 | |
| AAV2.V2b | AAV2 | COS-7 | FIG. 2 | 1E4-1E6 | |
| AAV2.V2b | AAV2 | 84-31 | FIG. 2 | 1E4-1E6 | |
| AAV2.V3a | AAV2 | 84-31 | FIG. 3 | 1E4-1E6 | |
| AAV2.V3b | AAV2 | 84-31 | FIG. 3 | 1E4-1E6 | |
| AAV2.V2a | AAV8 | COS-7 | FIG. 4 | 1E4-1E6 | Detectable expession of CHM at MOI of 1E5-1E6. |
| AAV2.V2a | AAV8 | 84-31 | FIG. 4 | 1E4-1E6 | |
| AAV2.V2b | AAV8 | COS-7 | FIG. 5 | 1E4-1E6 | Detectable expession of CHM above MOI of 3E5-1E6 |
| AAV2.V2b | AAV8 | 84-31 | FIG. 5 | 1E4-1E6 | |
| AAV2.V3a | AAV8 | 84-31 | FIG. 6 | 1E4-1E6 | Detectable expession of CHM above MOI of 3E5-1E6 |
| AAV8.V3b | AAV8 | 84-31 | FIG. 6 | 1E4-1E6 | |

Monoclonal human REP-1-specific antibody, detected one single ~75-80 kDa hREP-1 protein in cells transduced with next generation AAV2.copt.CHM/AAV8.copt.CHM. A 75-80 kDa band was not observed in cell lysates of untreated control cells. Probing of the blots with either anti-Actin/antitubulin/anti-GAPDH antibody showed a band of equal density in all lanes of the western blot including in untreated controls. Anti-actin antibody detected a protein molecular weight band at ~42 kDa, anti-tubulin antibody detected a protein at ~51 kDa, and anti-GAPDH antibody detected a protein at ~39 kDa. All antibodies detected only specific bands of expected size molecular weight. No nonspecific bands were observed in any of the blots. A pre-stained molecular weight marker was used to compare the molecular weights of protein of interest.

Briefly, REP-1 protein was observed at the expected size in COS-7 and 84-31 cells transduced with AAV2.V2a, AAV2.V2b, AAV2.hCHM.V3a and AAV2.hCHM.V3b. Untreated controls did not reveal the presence of expected size human REP-1 protein. Labeling the blot with anti-actin antibody detected a protein band of equal intensity in all lanes of the gel at ~42 kDa. Pre-stained protein ladder was used to compare the molecular weights of REP-1 and Actin. Data not shown.

The results indicate that AAV2 and AAV8 serotype vectors containing next generation plasmids are able to transduce 84-31 and COS-7 cells efficiently. Expression of CHM in the next generation plasmids was in the detectable range, and demonstrated a dose dependent trend. Transduction of cells with the next generation hCHM viruses resulted in production of REP-1 protein of the predicted size.

Example 5: Comparison of in Vitro Protein Expression of AAV.Codon-Optimized.Human CHM with AAV Native.Human CHM The objective of this study was to delineate transduction efficiency of AAV vectors (serotype 2 and 8) containing various versions of the CHM-containing transgene cassettes by measuring levels of REP-1 protein in a 84-31 cell line based study model.

Plasmids and Vectors: A total of 5 transgene plasmids were compared either in AAV2 or AAV8: Version 1 (previously being used in an on-going clinical trial) and four next generation versions (V2a, V2b, V3a, and V3b). The plasmids were engineered as described in Example 4, and the features thereof are shown in Table 1. Table 2 above shows a summary of AAV2 and AAV8 vectors generated and concentration of viral stocks.

Study Design (e.g. Treatment Groups)

1. In a pilot experiment, COS-7 and 84-31 cells were transduced with AAV2.hCHM.Version1, Version2a and Version 2b. Western blot was performed to compare transduction efficiency levels in the two cells lines.

2. 84-31 cells, plated in 6-well plates were transduced with one of the 10 test articles (Version 1, 2a, 2b, 3a and 3b in either AAV2 or AAV8 background) at an MOI of 3E5. After 36-48 hours, cells were harvested and lysed. The lysate was loaded on SDS-PAGE, and subjected to further Western blot analyses. Levels of REP-1 protein are compared amongst all construct versions. Two separate plates were setup for each AAV2.CHM or AAV8.CHM experiments were analyzed, separately.

Test Material Administration 3.4.1 Cell Culture 83-41 cells and COS-7, both were cultured in Dulbecco's modified Eagle medium (DMEM)-high glucose with 10% fetal bovine serum, and 1% penicillin/streptomycin at 37° C. in an environment supplied with 5% CO2.

3.4.2 Preparation of Cells for Transduction:

The day before transduction (18-24 h before) 83-41 and COS-7 cells were seeded at a density of 3E5 in 2 ml of cell culture media per well in a 6-well cell culture dish. The seeded cells were incubated at 37° C. in an environment supplied with 5% CO2.

3.4.3 Transduction:

Wells of 84-31 cells and Cos-7 were infected with AAV vectors as described below at an MOI of 3E5 (see Table 6 for the pilot experiment and Table 7 for the second set of experiments). No virus was added to the negative (untransduced) control. Briefly, first, the tissue culture media was removed and replaced with 2 ml fresh media/well in each the wells in the 6 well cell culture dish. Then the predetermined amount of AAV vector (see table 2 for vector volumes used for transduction) was measured (from the stock) and directly added to each well. Cells were incubated with the AAV virus for 36-48 hours at 37° C. with 5% CO2 until harvesting. Cells were observed under microscope before harvesting to check any abnormality. Western blot analysis was performed as described in Example 4.

TABLE 6

Pilot Experiment: Infection doses of AAV2.hCHM.V1, 2a, 2b in 84-31 and COS-7 cells.

| Vector Used | Cell Line | Cell density | Vector used (µL) | MOI |
|---|---|---|---|---|
| None | 84-31 | 3E5 | 0 | 0 |
| AAV2.V1 | 84-31 | 3E5 | 13.42 | 3E5 |
| AAV2.V2b | 84-31 | 3E5 | 8.11 | 3E5 |
| AAV2.V2a | 84-31 | 3E5 | 27.78 | 3E5 |
| AAV2.V1 | COS-7 | 3E5 | 13.42 | 3E5 |
| AAV2.V2b | COS-7 | 3E5 | 8.11 | 3E5 |
| AAV2.V2a | COS-7 | 3E5 | 27.78 | 3E5 |
| None | COS-7 | 3E5 | 0 | 0 |

TABLE 7

Infection doses of AAV.hCHM next generation vectors and V1 (AAV2 and AAV8) in 84-31 cells

| Vector Used | Cell Line | Cell density | Vector used (µL) | MOI |
|---|---|---|---|---|
| None | 84-31 | 3E5 | 0 | 0 |
| AAV8.V2a | 84-31 | 3E5 | 5.77 | 3E5 |
| AAV8.V2b | 84-31 | 3E5 | 5.41 | 3E5 |
| AAV8.V3a | 84-31 | 3E5 | 6.92 | 3E5 |
| AAV8.V3b | 84-31 | 3E5 | 4.41 | 3E5 |
| AAV8.V1 | 84-31 | 3E5 | 4.32 | 3E5 |
| None | 84-31 | 3E5 | 0 | 0 |
| AAV2.V2a | 84-31 | 3E5 | 27.78 | 3E5 |
| AAV2.V2b | 84-31 | 3E5 | 8.11 | 3E5 |
| AAV2.V3a | 84-31 | 3E5 | 12.45 | 3E5 |
| AAV2.V3b | 84-31 | 3E5 | 10.15 | 3E5 |
| AAV2.V1 | 84-31 | 3E5 | 13.42 | 3E5 |

Results: Comparison of the Expression of Native hCHM (AAV2.hCHM.V1) Versus Codon-Optimized CHM AAV2a and 2b Vectors in 84-31 and COS-7 Cells In this experiment 84-31 and COS-7 cells were transduced with either no vector (untreated control), AAV2.hCHM.Version1, AAV2.hCHM.Version2a or AAv2.hCHM.Version2b. Western blot analysis with an anti-human REP-1 antibody, showed that REP-1 protein levels were detectable at ~75-80 kDa in all AAV2 (V1, V2a, V2b) transduced samples and in both cells lines (Data not shown). A slightly better protein expression was seen in 84-31 cell line (Table 8). Anti-REP1 antibody detected negligible amount of REP-1 protein in untreated cells. Labeling of the blot with GAPDH antibody detected a band at ~39 kDa in all cell lysates, including the untreated cells.

Densitometric evaluation (quantification of the protein level) of the blots using ImageJ software demonstrated that after normalizing the values to the expression of endogenous GAPDH protein the transduction efficiency was similar in 84-31 and COS-7 cells. (See Table 8 for results.) Based on this, the 84-31 cell line, which is from human origin was used for further experiments.

In conclusion, AAV2.V1, AAV2.V2a and AAv2. V2b induced the production of REP-1 protein in both, 84-31 and COS-7 cells with similar transduction efficiency.

| | | REP1 | GAPDH | GAPDH NORMALIZED TO GAPDH OF V1 | REP-1 NORMALIZED TO RESPECTIVE GAPDH | REP-1 NORMALIZED TO REP-1 OF V1 (%) |
|---|---|---|---|---|---|---|
| 84-31 | AAV2.V1 | 23416.844 | 19350.773 | 1 | 23416.844 | 100 |
| | AAV2.V2b | 36626.765 | 20357.894 | 1.011 | 36203.838 | 154.605 |
| | AAV2.V2a | 31114.844 | 20315.945 | 1.009 | 30819.0684 | 131.610 |

|  |  | REP1 | GAPDH | GAPDH NORMALIZED TO GAPDH OF V1 | REP-1 NORMALIZED TO RESPECTIVE GAPDH | REP-1 NORMALIZED TO REP-1 OF V1 (%) |
|---|---|---|---|---|---|---|
|  |  |  | Molecular weight Marker |  |  |  |
| COS7 | AAV2.V1 | 12880.459 | 15479.288 | 1 | 12880.459 | 100 |
|  | AAV2.V2b | 19209.823 | 14321.167 | 0.711 | 26991.925 | 209.557 |
|  | AAV2.V2a | 15132.602 | 13145.924 | 0.849 | 17818.595 | 138.338 |

Comparison of the expression of native CHM versus codon-optimized CHM AAV2 vectors in 84-31 cells: Using an anti-human REP-1 antibody, the Western blot analysis of the 84-31 cells transduced with AAV2.hCHM.V2a, V3a, V2b, V3b and V1 detected a band at ~75-80 kDa in all conditions (Data not shown). Anti-REP1 antibody detected negligible amount of REP-1 protein in untreated cells. Labeling of the blot with GAPDH antibody detected a band at ~39 kDa in all cell lysates, including the untreated cells. Densitometric evaluation (quantification of the expression level) of the blots using ImageJ software demonstrated an increase in the expression of AAV2.hCHM.V2a, 3a, 2b, and 3b compared to AAV2.hCHM.V1 after normalizing the values to the production of endogenous GAPDH protein. See Table 9 and 10 for results.

Comparison of the expression of native CHM versus codon-optimized CHM in AAV8.V1, V2a, V3a, V2b, V3b vectors in 84-31 cells: Western blot analysis of cells transduced with AAV8.V1, AAV8.V2a, AAV8.V3a, AAV8.2b, AAV8.3b, with anti-human REP-1 antibody detected a band at ~75-80 kDa in all transduced cells (Data not shown). Anti-REP1 antibody detected negligible amount of REP-1 protein in untreated cells. Labeling of the blot with GAPDH antibody detected a band at ~39 kDa in all cell lysates, including the untreated cells. Densitometric evaluation of the blots using ImageJ software demonstrated higher expression of AAV8.hCHM.V2a; 3a; 2b; 3b compared to AAV8.V1. Values are obtained after normalizing the CHM values first, to the expression of the respective endogenous GAPDH protein and then normalized to the expression level of the average of Version 1. See Table 11 and Table 12 for results.

TABLE 9

Values of REP-1 protein in 84-31 cells after transduction with AAV2.hCHM. V1, Va, V2b, V3a or V3b for PLATE 1 (Western Blot not shown)

| CONSTRUCT | | RAW VALUE | | GAPDH NORMALIZED TO GAPDH OF V1 | REP-1 NORMALIZED TO RESPECTIVE GAPDH | REP-1 NORMALIZED TO REP-1 OF V1 (%) |
|---|---|---|---|---|---|---|
| NAME | LANE NUMBER | REP-1 | GAPDH | | | |
| AAV2.V1 | 1 | 23367.593 | 15155.602 | 1 | 23367.593 | 100 |
| AAV2.V2a | 3 | 26949.421 | 10969.581 | 0.723797115 | 37233.39103 | 159.3377248 |
| AAV2.V3a | 5 | 29867.714 | 14595.894 | 0.963069233 | 31013.0497 | 132.7182038 |
| AAV2.V2b | 7 | 32728.128 | 14133.551 | 0.932562824 | 35094.82381 | 150.1858741 |
| AAV2.V3b | 9 | 33986.543 | 13670.066 | 0.901981063 | 37679.88531 | 161.2484662 |

TABLE 10

Values of REP-1 protein in 84-31 cells after transduction with AAV2.hCHM. V1, V2a, V2b, V3a or V3b for PLATE 2 (Western blot not shown)

| CONSTRUCT | | RAW VALUE | | GAPDH NORMALIZED TO GAPDH OF V1 | REP-1 NORMALIZED TO RESPECTIVE GAPDH | REP-1 NORMALIZED TO REP-1 OF V1 (%) |
|---|---|---|---|---|---|---|
| NAME | LANE NUMBER | REP-1 | GAPDH | | | |
| AAV2.V1 | 2 | 23128.593 | 11993.823 | 1 | 23128.593 | 100 |
| AAV2.V2a | 4 | 23623.836 | 10982.798 | 0.915704526 | 25798.53582 | 111.5439051 |
| AAV2.V3a | 6 | 28832.543 | 13176.359 | 1.098595419 | 26244.91465 | 113.473892 |
| AAV2.V2b | 8 | 31349.229 | 16028.329 | 1.336381986 | 23458.28463 | 101.4254721 |
| AAV2.V3b | 10 | 33273.856 | 14760 | 1.230633469 | 27037.99047 | 116.9028763 |

TABLE 11

Values of REP-1 protein expression in 84-31 cells after transduction with AAV8 hCHM Version 1, 2a, 2b, 3a and 3b - PLATE 1 (Western blot not shown)

| CONSTRUCT NAME | LANE NUMBER | RAW VALUE REP-1 | RAW VALUE GAPDH | GAPDH NORMALIZED TO GAPDH OF V1 | REP-1 NORMALIZED TO RESPECTIVE GAPDH | REP-1 NORMALIZED TO REP-1 OF V1 (%) |
|---|---|---|---|---|---|---|
| AAV8.V1  | 11 | 3630.589  | 20309.924 | 1     | 3630.589  | 100     |
| AAV8.V2a | 13 | 7133.439  | 17051.48  | 0.839 | 8496.599  | 234.028 |
| AAV8.V3a | 15 | 5828.418  | 15801.045 | 0.777 | 7491.575  | 206.346 |
| AAV8.V2b | 17 | 11411.702 | 19249.681 | 0.947 | 12040.241 | 331.633 |
| AAV8.V3b | 19 | 17610.066 | 18727.024 | 0.922 | 19098.555 | 526.045 |

TABLE 12

Values of REP-1 protein expression in 84-31 cells after transduction with AAV8 hCHM Version 1, 2a, 2b, 3a and 3b - PLATE 2 (Western blot not shown)

| CONSTRUCT NAME | LANE NUMBER | RAW VALUE REP-1 | RAW VALUE GAPDH | GAPDH NORMALIZED TO GAPDH OF V1 | REP-1 NORMALIZED TO RESPECTIVE GAPDH | REP-1 NORMALIZED TO REP-1 OF V1 (%) |
|---|---|---|---|---|---|---|
| AAV8.V1  | 12 | 3507.468  | 19082.681 | 1           | 3507.468    | 100         |
| AAV8.V2a | 14 | 4359.296  | 13274.731 | 0.695642871 | 6266.571801 | 178.6636913 |
| AAV8.V3a | 16 | 6533.246  | 20720.246 | 1.0858142   | 6016.909708 | 171.5456765 |
| AAV8.V2b | 18 | 13962.045 | 17842.167 | 0.934992677 | 14932.7854  | 425.7425983 |
| AAV8.V3b | 20 | 16049.823 | 13836.368 | 0.725074637 | 22135.40811 | 631.0936581 |

Conclusion: Comparative expression studies demonstrated that application of AAV vectors carrying the next generation AAV.hCHM. Version 2a, 2b, 3a and 3b induced increased production of REP-1 protein compared with Version 1 (currently used in clinical trials) in both AAV2 and AAV8 serotype vectors in 84-31 cells.

Example 6: Evaluation of Lambda Stuffer's Effect on AAV Vector Production by qPCR Titer Analysis A single qPCR (quantitative polymerase chain reaction) run was performed on all 8 AAV vectors shown in Table 2, above, in order to assess the effect of lambda stuffer sequences on the amount of DNA impurities. Linearized AAV plasmid standard was used to generate the assay standard. Primer-probe sets were designed on either the CMV/CBA promoter region for quantitation of properly packaged AAV genome or the Kanamycin resistance (KanR) encoding region for reverse packaging. Standards and vector samples were run in two sets, one with the CMV/CBA primer-probe set and the other with the KanR set. Vector sample values (viral genome copy per mL) were determined from each respective standard curve. The effect of the stuffer sequence was assessed by comparing the relative amount of KanR-containing impurities in each vector lot against CMV/CBA containing sequences.

Reagents:
Transgene-Containing Viral Vector Titer:

```
Reference: CMV-CBA Promoter

Primers: CMV-F: CCC ACT TGG CAG TAC ATC AA
```

```
        -continued
CMV-R: GCC AAG TAG GAA AGT CCC ATA A

FAM-Probe: /56-FAM/CA TAA TGC C/ZEN/A GGC GGG CCA

TTT AC/3IABkFQ/
```

Impurity-Containing Viral Vector Titer
Reference: Kanamycin Resistance Gene

```
Primers: KAN-F: GAT GGT CGG AAG TGG CAT AA

KAN-R: TGC GCC AGA GTT GTT TCT

FAM-Probe: /56-FAM/CC GTC AGC C/ZEN/A GTT TAG TCT

GAC CA/3IABkFQ/
```

Dilution Reagent: Diluent Q (0.001% PF-68 in nuclease free water): Diluted 1% PF-68 solution 1000-folds with sterile water. Diluent S: Diluent Q+2 ng/μL salmon sperm DNA (Agilent technologies Cat #201190)
ABI TaqMan™ Universal Master Mix (Applied Biosystems 4304437/4326708)
Qiagen PCR Product Purification Kit (Qiagen 28104)·
  ABI QuantStudio 6 Flex System
1.2. Sample Preparation
DNase digest solution was prepared by combining the following: DNase buffer (10×) 5 μL, Nuclease-free H2O 30 μL, DNase I (Invitrogen, 18068-015) 5 μL
  Ten μL of each AAV vector sample was mixed in and incubated at ambient temperature for 10 minutes. The digest mix was inactivated by adding 50 μL of SDS/EDTA/NaCl solution (0.2% SDS/5 mM EDTA/0.2M NaCl) and incubating at 95° C. for 10 minutes. Each AAV vector sample was diluted 10-100,000 fold in Diluent S for qPCR analysis.

1.3. qPCR Standard Preparation

Reference standard DNA (linearized) was prepared by digesting plasmid p1008 (low copy transgene plasmid without stuffer) with XhoI and purifying with Qiagen PCR purification kit. Purified material was analyzed on agarose gel to confirm identity, and quantified by Nanodrop. DNA copy number was determined from the stock concentration using the following equivalence: 1 bp=1.096E−21 g. qPCR Standards were prepared according to the following table:

TABLE 13

| DNA Standard | Concentration [Copies/10 µL] | Dilution |
| --- | --- | --- |
| Standard Stock | $2 \times 10^9$ | NA |
| S1 | $1 \times 10^8$ | 10 µL Stock + 190 µL Diluent S |
| S2 | $1 \times 10^7$ | 10 µL S1 + 90 µL Diluent S |
| S3 | $1 \times 10^6$ | 10 µL S2 + 90 µL Diluent S |
| S4 | $1 \times 10^5$ | 10 µL S3 + 90 µL Diluent S |
| S5 | $1 \times 10^4$ | 10 µL S4 + 90 µL Diluent S |
| S6 | $1 \times 10^3$ | 10 µL S5 + 90 µL Diluent S |

PCR Reaction Setup

Extracted DNA samples were analyzed in triplicate (3 wells) in a single qPCR run. The run included reference DNA standards in triplicate, ranging from 103 to 108 copies per well. No-template-control (NTC) was included as negative control. Each AAV vector preparation was analyzed with both CMV/CBA and KanR primer/probe sets. Similarly, for quantitation of each set, the standards were also analyzed with both CMV/CBA and KanR primer/probe sets.

TABLE 14

PCR Reaction Setup

| Reagents | Final conc. in Reaction | Volume per 25 µL Reaction |
| --- | --- | --- |
| Universal Master Mix (2x) | 1x | 12.5 µL |
| Optimized Primer Mix (20 µM) | 0.8 µM | 1.0 µL |
| Taqman Probe (10 µM) | 0.2 µM | 0.5 µL |
| Nuclease-Free Water | NA | 1.0 µL |
| Sample/Standard | NA | 10.0 µL |

PCR reaction sequence was set up as follows: 50° C. 2 minutes 1 cycle; 95° C. 10 minutes 1 cycle; 95° C. 15 seconds 40 cycles; 60° C. 1 minutes 40 cycles Run performance. Standards were prepared and run at 103 to 108 DNA copies per well. Lower limit of the assay was set at 1000 copies since assay sensitivity was not an important factor for this experiment. A standard curve was generated for the run using the standard copy numbers and CT (threshold cycle) values of the standards. Linear regression of the standards was performed using the ABI software (data not shown). Standard curve fit had a correlation coefficient (R2 value) of 0.998 or greater indicating a reliable fit model. The slope of the standard curves was −3.5. Slope was used to calculate the efficiency of the amplification reaction, and values between −3.2 and −3.6 represented amplification efficiency between 90% and 110%. Both standard reactions were run with 92.6~93.8% efficiency. Precision of triplicate wells ranged from 2~10%, indicating good agreement among replicates. No-template-control (NTC) resulted in non-quantifiable amplification below the lower limit of the assay.

TABLE 15

Summary of standard curve fit

| Reporter | Target | Slope | Y-intercept | R | Efficiency (%) |
| --- | --- | --- | --- | --- | --- |
| FAM | CMV | −3.513 | 41.896 | 0.998 | 92.597 |
| FAM | KAN | −3.481 | 39.968 | 1.000 | 93.761 |

Results:

Sample value determination: The sample values (AAV genome and reverse-packaging copy number) were interpolated from each matching standard curve (CMV/CBA or KanR), using CT values. Interpolated DNA copy number was corrected for initial dilution and/or digest dilution. Additional correction factor of 2 was applied to account for the difference between double-stranded DNA standards and single-stranded DNA in samples.

Figure 11:
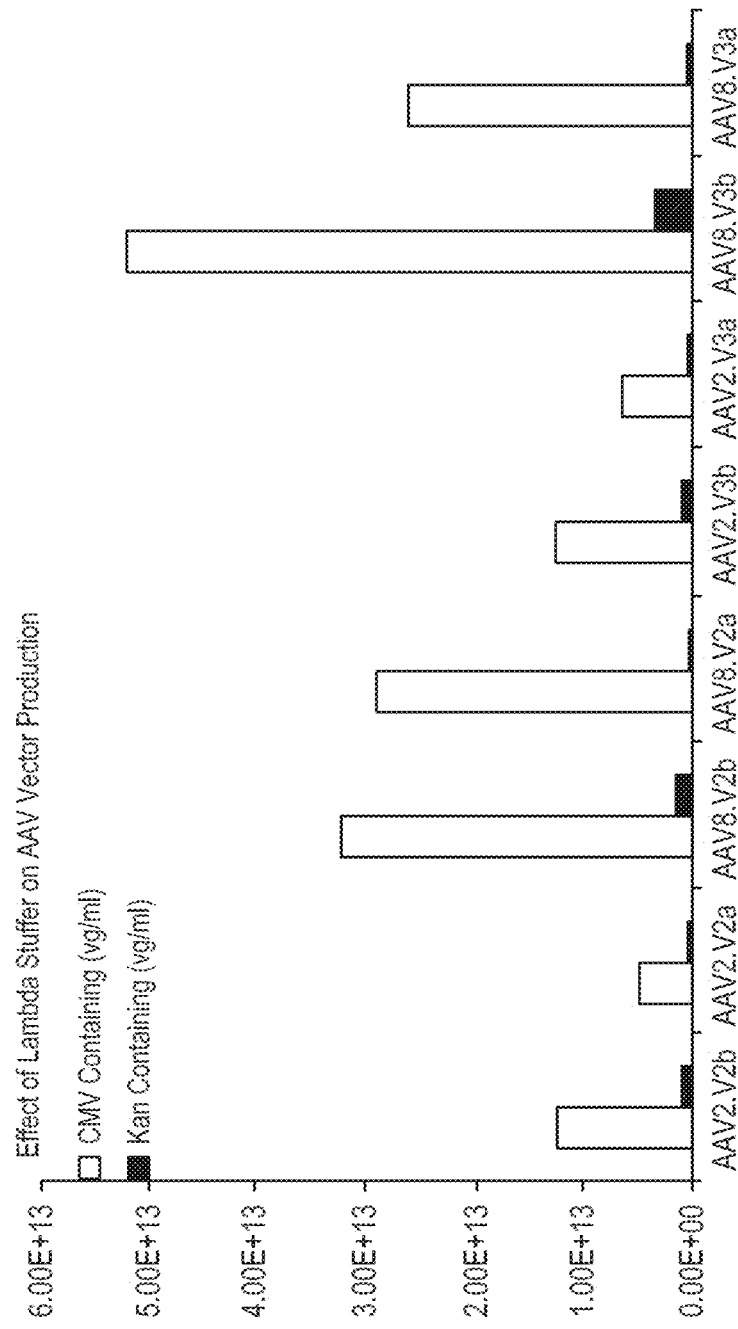
FIG. 11 is a graphic representation of the effect of lambda insert on AAV product impurity. All a-version (lambda containing) vectors have much reduced Kan+ signals from qPCR test.

Analysis results for 8 AAV vectors are summarized in the table below, with quantitative comparison between the transgene-containing AAV concentration (CMV/CBA) and the KanR-containing impurity concentration. Analysis of results demonstrate that insertion of lambda stuffer into the transgene plasmid effectively reduced the occurrence of plasmid-backbone DNA (i.e. KanR) packaging during AAV production from ~7-20 folds (FIG. 11).

TABLE 16 qPCR amplification of kanamycin versus CMV/CBA expressed as percentage

| Sample Name | Lambda Stuffer | CMV/CBA qPCR (vg/ml) | KanR qPCR (vg/ml) | Kan vs. CMV/CBA (%) |
| --- | --- | --- | --- | --- |
| AAV2.V2b | No | 1.23E+13 | 6.46E+11 | 5.25% |
| AAV2.V2a | Yes | 4.61E+12 | 3.60E+10 | 0.78% |
| AAV8.V2b | No | 3.19E+13 | 1.43E+12 | 4.48% |
| AAV8.V2a | Yes | 2.90E+13 | 1.19E+11 | 0.41% |
| AAV2.V3b | No | 1.26E+13 | 6.69E+11 | 5.31% |
| AAV2.V3a | Yes | 6.33E+12 | 4.56E+10 | 0.72% |
| AAV8.V3b | No | 5.19E+13 | 3.07E+12 | 5.92% |
| AAV8.V3a | Yes | 2.60E+13 | 8.00E+10 | 0.31% |

Example 6: In Vitro Expression of Next Generation AAV8 Vectors in iPS Cells by Western Blot The objective of this study was to evaluate the ability of AAV mediated CHM expression after gene delivery using a series of next generation AAV2 and AAV8 vectors carrying the codon optimized REP-1-encoding gene in induced pluripotent cell lines (iPSC).

Induced pluripotent stem (iPS) cell technology has been successfully utilized as a platform for testing gene therapy vectors in several proof-of-concept and gene therapy studies including ocular diseases. These patient-specific iPS cells provide a valuable in vitro model system to study disease pathogenesis and establish a model to test proof-of-concept of gene therapy where relevant animal models are unavailable. As a preliminary step to test our AAV-mediated gene augmentation therapy for Choroideremia (CHM), we have generated iPS cells from human patients harboring mutations in the causative gene, CHM, which encodes Rab Escort Protein 1 (REP-1) (See example 1) (Method is described in NCP.003). The generated iPS cells were used to evaluate the in vitro expression of our next generation AAV.codon optimized.CHM constructs.

Plasmids and vectors were as described in Example 4. Induced pluripotent stem (iPS) cells are stem cells generated in the laboratory from somatic cells, peripheral blood mononuclear cells, that were reprogrammed back to a pluripotent state. Reprogramming of blood cells enables the development of personalized in vitro cellular models for therapeutic applications. In this report, iPS cells from individuals affected by CHM were used to test the in vitro production of REP-1 protein through western blot analysis. The following table (Table 17) describes the details of iPS cells studied and their respective CHM disease-causing mutations. Table 17: An overview of the iPS cells generated from patients with CHM mutations

| Cell Line | Affected | Mutation in CHM | Method of iPSC generation |
|---|---|---|---|
| JB 588 | Affected | Arg 555 stop | Sendai virus mediated reprogramming |
| JB 527* | Affected | Exon 2-4 deletion | Sendai virus mediated reprogramming |
| JB 500* | Affected | Ex 10 c.1327_1327 del AT (Needs confirmation) | Sendai virus mediated reprogramming |

*iPS cell line qualification tests are on-going.

Study Design (e.g. Treatment Groups)

1. iPS cells plated on a 12 well cell culture plate are infected with AAV2. hCHM Version 1, Version 2a; Version 2b; Version 3a; Version 3b (AAV2.V1; V2a; V2b; V3a; V3b) at an MOI of either 1E5 or 3E5. After 24 hours of transduction, 1 ml of iPS cell culture media was added to the cells. 36-48 hours of transduction, cells were harvested, lysed and processed for SDS-PAGE followed by Western blot analysis. Production of REP-1 protein was evaluated in cells transduced with all versions of the constructs and compared with untreated controls.

2. As a pilot experiment, three different iPS cell lines plated on a 12 well cell culture plate are transduced with AAV8.hCHM Version 1 and AAV8.hCHM Version 2a (AAV8.V1; AAV8.V2a) at an MOI of 1E6. The iPS cell lines were derived from three CHM affected individuals with unrelated mutations in REP1 gene and were plated in separate plates for this purpose. After 36-48 hours, cells were harvested and lysed and subjected to Western blot analyses compared with untreated cell lysate.

Test Material Administration 3.4.1 Cell Culture

Culturing of iPS cells from CHM patient. In brief, the iPS cells were cultured on Mouse Embryonic Fibroblasts (MEFs, feeders) in iPS cell culture media at 37° C. in an environment supplied with 5% CO2 and 5% O2.

3.4.2 Preparation of Cells for Transduction

The day before seeding the cells, 12-well dishes were coated with Matrigel as described in reference NCP.003 (NCP.003: Culturing of iPS cells from CHM patient and controls). Before transduction of iPS cells with respective AAV2 or AAV8 viral vectors, the cells that are cultured on MEFs were seeded on Matrigel without MEFs (feeder free culturing). Cells were seeded at a density of 4.5+E5 to 6+E5 in 1 ml of iPS cell culture media in each well of a 12-well cell culture dish. Seeded cells were incubated at 37° C. in an environment supplied with 5% CO2, 5% O2.

3.4.3 Transduction

To infect the iPS cells with viral vectors, cells were grown to approximately 50-60% confluence. (This can take 2-4 days in feeder free conditions). Once 50-60% confluence is achieved, one well of the 12-wells is dissociated and cell counts were performed to determine the total number of cells per well. Wells of the iPS cells were then infected with AAV vectors listed below at the predetermined MOI (see Table 18 and 19). Before transduction, the old iPS cell culture media from the plates was removed and a fresh 1 ml of iPS cell culture media was added in each well. Predetermined volumes of the virus from the stock were directly added to each well. See Table 18. and Table 19. For the information on total number of cells infected, MOI and the volume of virus used for infection. Cells were then incubated at 37° C. in an environment supplied with 5% CO2, 5% O2 for 18-24 hours. After 18-24 h of transduction, cells were observed under microscope for any abnormalities or cell death. At this point, another 1 ml of fresh iPS cell culture media was added to each well containing infected and uninfected cells and were further incubated for additional 18-24 hours at 37° C. in an environment supplied with 5% CO2, 5% O2. Cells were observed under the microscope before harvesting to evaluate any cell death or abnormal appearance.

TABLE 18

Infection details and MOIs of next generation AAV2.hCHMV2a, 2B, 3a, 3b Vectors and AAV2.hCHM.V1 vectors in CHM patient-derived iPS cells.

| Vector Used | Cell Line | Cell line number | Cell density | Viral stock concentration (vg/ml) | Vector used (µL) | MOI |
|---|---|---|---|---|---|---|
| AAV2.V2a | iPSC | JB 588 | 6E5 | 2.16E+12 | 30 | 1E5 |
| | iPSC | JB 588 | 6E5 | 2.16E+12 | 90 | 3E5 |
| AAV2.V2b | iPSC | JB 588 | 6E5 | 7.4E+12 | 8.1 | 1E5 |
| | iPSC | JB 588 | 6E5 | 7.4E+12 | 24.3 | 3E5 |
| AAV2.V3a | iPSC | JB 588 | 6E5 | 4.82E+12 | 12.4 | 1E5 |
| | iPSC | JB 588 | 6E5 | 4.82E+12 | 37.3 | 3E5 |
| AAV2.V3b | iPSC | JB 588 | 6E5 | 5.91E+12 | 10.2 | 1E5 |
| | iPSC | JB 588 | 6E5 | 5.91E+12 | 30.5 | 3E5 |
| AAV2.V1 | iPSC | JB 588 | 6E5 | 4.47E+12 | 30.6 | 1E5 |
| | iPSC | JB 588 | 6E5 | 4.47E+12 | 40.9 | 3E5 |

TABLE 19

Infection dose of AAV8.V2a and AAV8.V1 vectors in three iPS cell lines derived from 3 different CHM patients.

| Vector Used | Cell Line | Cell line number | Cell density | Viral stock concentration (vg/ml) | Vector used (µL) | MOI |
|---|---|---|---|---|---|---|
| Untreated | iPSC | JB 588 | 4.5E5 | | | |
| AAV8.V2a | iPSC | JB 588 | 4.5E5 | 1.04E+13 | 43 | 1E6 |
| Untreated | iPSC | JB 500 | 4.5E5 | | | |
| AAV8.V1 | iPSC | JB 500 | 4.5E5 | 1.39E+13 | 32 | 1E6 |
| Untreated | iPSC | JB 527 | 4.5E5 | | | |
| AAV8.V1 | iPSC | JB 527 | 4.5E5 | 1.39E+13 | 32 | 1E6 |
| AAV8.V2a | iPSC | JB 527 | 4.5E5 | 1.04E+13 | 43 | 1E6 |

Outcome measurement method-Western blot analysis was performed as described herein.

Results 5.1 Expression of AAV2-hCHM V1, V2a, V2b, V3a, V3b in JB588 iPS cell line: Monoclonal human REP-1-specific antibody, detected one single ~75-80 kDa hREP-1 protein in the transduced JB 588 iPS cells (Data not shown). No band was observed in the case of the untreated control, confirming presence of the disease (data not shown). The intensity of REP-1 protein band at an MOI of 3E5 observed to be stronger in all vectors compared to an MOI of 1E5. Recombinant AAV2. hCHM viral mediated delivery of the hCHM gene, to iPS cells, resulted in a dose-dependent production of REP-1 protein. Probing of the blots with GAPDH antibody showed a band of equal density in all lysates. GAPDH detected a protein at ~39 kDa. Both REP-1 and GAPDH antibodies detected only specific bands of expected molecular weight. No nonspecific bands were observed in the blots.

Expression of AAV8-hCHM. V1, V2a in iPS cells: Monoclonal human REP-1-specific antibody, detected one single ~75-80 kDa REP-1 protein in the transduced JB527, JB500 and JB588 patient derived iPS cells (Data not shown). No protein band was observed in the case of the untreated control. (Data not shown). Probing of the blots with GAPDH antibody showed a band of equal density in all cell lysates including the cell lysates from untreated cells. Anti-GAPDH antibody detected a specific ~39 kDa protein band. Both REP-1 and GAPDH antibodies detected only specific protein bands at the expected size molecular weight. No detectable nonspecific protein bands were observed in the blot.

CONCLUSIONS

The preliminary results presented in the current report revealed the following observations: Western blot analysis confirmed presence of CHM (lack of REP-1 protein) in each one of the three patient-derived iPSCs (JB588, JB500, JB527). In vitro expression studies demonstrated that infecting iPS cells from CHM patients with AAV2.hCHM. Version 2a, 2b, 3a, 3b and AAV2.hCHM Version1 (a current clinical trial candidate) induced the production of REP-1 protein at all tested MOIs. Infecting iPS cells with AAV8.hCHM. Version 2a and AAV8.hCHMVersion1 at an MOI of 1E6 resulted in production of REP1 protein in all three CHM iPS cell lines. Level of REP1 production was higher in the iPSCs infected with AAV8.hCHM.V2a than with AAV8.hCHM.V1.

Example 7: Comparison of In Vivo Expression of AAV8.Codon Optimized.Human CHM Versus AAV.Native.Human CHM Gene therapy for a number of retinal diseases depends on efficient transduction of the appropriate target cells, which for choroideremia, are retinal pigment epithelium (RPE) cells and photoreceptor cells. This study report focuses on the comparison of in vivo expression induced by the native CHM sequence based construct, (Version 1) and four next generation transgene cassettes packaged into an AAV8 backbone in wild type mice. Here we evaluated AAV8 serotype for the purpose of improving gene transfer to photoreceptor cells.

Our experiments were designed to answer the following questions: a. How would these vectors compare for in vivo transduction of photoreceptors: In particular, how efficiently would the next generation AAV8. CHM transduce photoreceptors after subretinal injection of the respective test article compared to version.1. b. Dose response: Would the next generation AAV8. CHM and AAV8. CHM-Version1 vectors differ in dose response of gene expression.
Experimental Details:
Plasmids and vectors were as described in Example 4.
Mice (Animals): Wild type, CD1 mice were used to test the in vivo expression of CHM as assessed by production of REP-1 protein. CD1 mouse strain is an outbred Swiss mouse strain which colony we maintain in house. The details of the study are described under CAROT study protocol PCPR02.01.
3.3 Study Design (e.g. Treatment Groups)
3.3.1 Animal Husbandry: Both male and female mice (~3-4 months old) weighing ~20-30 gm were injected with the described test articles. Animals were housed in the University of Pennsylvania's John Morgan University Laboratory Animal Resources (ULAR) facility according to University of Pennsylvania's ULAR regulations. Mice were maintained on a 12-hour light/12-hour dark cycle. Food and water were provided ad libitum. All animals were identified with ear tag numbers.
3.4 Test material administration: The test article formulation provided by the CAROT Vector Core was used for dose administration. The test material was stored at −60 to −80° C. The test material was thawed on ice prior to dosing. For intra-ocular injections, the test article is diluted to the target concentration with phosphate-buffered saline as described in the formulation Table 20. A total of 60 µl of master mix was prepared.

TABLE 20

Dose Formulation table for subretinal injections of test articles.

| Identification | Lot # | Vector Conc (Vg/ml) | Volume (µl) For a total of 60 µl | Volume of PBS (µl) for a total of 60 µl | Injected Conc (vg) | Total vol. inj. (µl) |
|---|---|---|---|---|---|---|
| AAV8.V2a | CT245 | 1.04E+13 | 1.92 | 58.1 | 5E8 | 1.5 µ3 |
|  |  |  | 19.2 | 40.8 | 5E9 | 1.5 µ3 |
| AAV8.V2b | CT244 | 1.11E+13 | 1.8 | 58.2 | 5E8 | 1.5 µ3 |
|  |  |  | 18 | 42 | 5E9 | 1.5 µ3 |
| AAV8.V3a | CT259 | 8.67E+12 | 2.31 | 57.7 | 5E8 | 1.5 µ3 |
|  |  |  | 23.1 | 36.9 | 5E9 | 1.5 µ3 |
| AAV8.V3b | CT255 | 1.36E+13 | 1.47 | 58.53 | 5E8 | 1.5 µ3 |
|  |  |  | 14.7 | 45.3 | 5E9 | 1.5 µ3 |
| AAV8.V1 | KA808 | 1.39E+13 | 1.44 | 58.6 | 5E8 | 1.5 µ3 |
|  |  |  | 14.4 | 45.6 | 5E9 | 1.5 µ3 |

Preparation of Injection Log Before Subretinal Injections:
An injection log was maintained with the following information before subretinal injection of the test articles:
Cage Number/mouse number
Study Identification
Strain
Date of Birth
Date of injection
Name of investigator/injector
Eye injected into (left or right)
Injection material (vector/serotype)
Dose and Volume
Route of Administration (ROA)
Subretinal injections: Injections were performed by Subretinal Injection by the Surgeon. In brief, animals were anaesthetized before injection. Subretinal injection of the test article was performed using Hamilton 33G syringe. The details of test articles and injections are described in Table 21. From the prepared injection master mix, a volume of 1.5 µl was administered, per injection. One eye per animal was injected with 5E8 vg/eye and the contralateral eye was injected with 5E9 vg/eye.

TABLE 21

Subretinal injection scheme and injection doses

| Gr. No. | Minimum Number of Animals | ROA | Test Material Identification | Vector Dose (vg/eye) Right Eye | Vector Dose (vg/eye) Left Eye | Dose Volume (μL/eye) Right Eye | Dose Volume (μL/eye) Left Eye | Dosing Day (PD) |
|---|---|---|---|---|---|---|---|---|
| 1 | 2 | Subretinal | AAV8.V2a | 5+E8 | 5+E9 | 1.5 μl | 1.5 μl | Day 90-120 |
| 2 | 2 | Subretinal | AAV8.V2b | 5+E8 | 5+E9 | 1.5 μl | 1.5 μl | Day 90-120 |
| 3 | 2 | Subretinal | AAV8.V3a | 5+E8 | 5+E9 | 1.5 μl | 1.5 μl | Day 90-120 |
| 4 | 2 | Subretinal | AAV8.V3b | 5+E8 | 5+E9 | 1.5 μl | 1.5 μl | Day 90-120 |
| 5 | 2 | Subretinal | AAV8.V1 | 5+E8 | 5+E9 | 1.5 μl | 1.5 μl | Day 90-120 |
| 6 | 2 | Uninjected | Not Applicable (N/A) | N/A | N/A | N/A | N/A | N/A |

Outcome Measurement Methods

Animal Sacrifice: a. After injecting the animals with the test articles, all animals were observed for 48 hours for any post injection related abnormalities. b. 21-35 days of post injection, the animals were observed for ocular abnormalities using ophthalmoscopy. c. 90-12-days post injection, the animals were sacrificed and eye tissues were collected for evaluating the production of exogenous REP-1 protein by SDS-PAGE followed by western blot analysis.

Collection of Eye Tissue: Eye tissue for western blot analysis was collected after removing the lens from the eye using a sharp surgical blade. The eye (without the lens) was collected in freezer tubes that are labelled appropriately.

Western Blot Analysis

Briefly: 1. Preparation of Tissue Lysate a. Ocular tissue of animals injected with 2 different doses of next generation AAV8. CHM and AAV8.V1 along with the uninjected control animal tissues, were collected after 21-35 days of injection by sacrificing the animals. b. Tissues were then lysed on ice using RIPA buffer with protease inhibitors.

c. Tissue lysates were cleared by centrifuging at 13,000 rpm for 10 min.

2. Quantification and Preparation of Proteins a. Protein quantification of the cell lysates was carried out using ThermoFisher Micro BCA™ Protein Assay Kit following manufacturer's instructions. b. Protein concentration was determined by taking OD reading at 562 nm. c. To evaluate the in vivo expression of CHM, between 20-40 ug of measured protein was loaded on 4-12% Bis-Tris gels.

3. SDS-PAGE and Western Blot

The protein gels were transferred on to a nitrocellulose membrane, blocked in milk and incubated with the primary antibodies. Anti-human REP-1 2F1 antibody (2F1, 1:1000 dilution) and/or anti-GAPDH antibody (1:1000 dilution); were used as primary antibodies. After washing the blot, HRP conjugated anti-mouse IgG antibody and/or anti-rabbit IgG antibody at a concentration of 1:5000 were used as secondary antibodies. The blots were developed by chemiluminescence using ECL reagents according to the manufacturer's instructions.

4. Controls a) Loading controls: Anti-GAPDH antibody was used as loading controls to demonstrate equal loading of protein in each well of the gels. Anti-GAPDH antibody detects a protein of ~39 kDa. b) Positive control: AAV2. V2a transduced COS-7 cell lysates were used as positive controls. c) Negative control: Ocular tissues of uninjected animals were used as negative control.

Sample Value Determination

Quantification of Western blot analysis using Image J software. In brief, densitometric evaluations presented in this report are normalized first, to the levels of endogenous expression of GAPDH protein of the corresponding sample. Then the expression levels are normalized again, to the average REP-1 expression level of uninjected control.

The details of densitometric evaluations and fold change calculations to represent the expression of REP-1 protein are presented as Table 22 and 23.

The description in brief:

1. In table 22 and 23, Column 2 shows the raw values of REP-1 protein and column 3 shows the raw values of GAPDH protein.

2. GAPDH value of each samples was first normalized to the GAPDH values of animal-1 of AAV8.V1 and are shown in Table 22 in 4th column.

3. The values of each sample were also normalized to the GAPDH values of animal-2 of AAV8.V1 and are shown in Table 22 in 5th column.

4. The REP-1 values (Column 2) are then normalized to either to the GAPDH normalized to animal 1 (column 4) or to the GAPDH previously normalized to animal 2 (column 5). These are represented in column 6 and 7 respectively.

5. The normalized REP-1 values are then converted to fold change.

6. The respective REP-1 values are normalized to expression of REP-1 either in animal 1 or animal 2 of the AAV8.V1 injected group and are expressed as fold change (column 8 and 9)

7. Column 10 represents the average fold change in REP-1 protein expression.

Results

Comparison of the CHM expression using the native CHM AAV8.V1 versus the codon optimized CHM vectors: AAV8. V2a, V2b, V3a and V3b. Wild type CD1 mice were injected with two different doses of the each AAV8 vector: a high dose of 5E9 vg/eye and a low dose of 5E8 vg/eye. Following results describe the levels of REP1 protein after injection with high and low doses of AAV8.V1, AAV8.V2a and AAV8.V3a.

Comparison of the expression of AAV8. V1 versus AAV8. V2a and AAV8.V3a (vectors with stuffer) in animals injected with high dose (5E9 vg/eye) of viral vector. Western blot analysis with human anti REP-1 antibody detected a ~75-80 kDa hREP-1 protein band in both (low and high dose injected) ocular tissues of each animal treated with either the next generation AAV8. V2a or V3a or the original AAV8. Version1. A very faint (minimal) band is observed in the case of the uninjected control mice, both. A band of increased intensity was observed in tissues that were transduced with next generation vectors (AAV8V.2a and AAV8.V3a) compared to the tissues transduced with Version.1. Anti-GAPDH antibodies showed a ~39 kDa band of equal density in all lanes of the western blot including the uninjected controls. Pre-stained protein marker is used to compare the molecular weights of protein of interest. Densitometric evaluation (quantification of the expression level) of the blots using ImageJ software demonstrated that production of REP-1 was increased in animals injected with one of the next generation AAV8. high and low doses constructs (V2a or V3a). (See Table 22 for values.)

Comparison of the expression of AAV8.V1 versus AAV8.V2a and AAV8.V3a in animals injected with low dose (5E8 vg/eye) of viral vector Human anti REP-1 antibody, the Western blot analysis of the ocular tissues of animals injected with next generation AAV8.V2a, V3a and AAV8. Version1 at a dose of 5E8 detected a ~75-80 kDa hREP-1 protein band in tissues of injected mice. A faint (minimal) band of REP-1 was observed in ocular tissue lysates of the uninjected control mice, both. A band of increased intensity was observed in tissue lysates that are transduced with next generation vectors compared to the lysates that are transduced with Version1. Anti-GAPDH antibody detected an equal intensity protein band at ~39 kDa in all cell lysates. This data demonstrates that delivery of next generation V2a CHM through AAV8 results in robust levels of REP-1 protein in comparison with levels produced after injection of AAV8.V3a or AAV8.V1.

TABLE 22

Quantified REP-1 protein production results for treatment with high dose (5E9vg) AAV8 V1, V2a and V2b

|  | GAPDH | REP-1 | GAPDH Normalized to GAPDH of Version 1 Animal 1 | GAPDH Normalized to GAPDH of Version 2 Animal 2 | REP1 Normalized to respective GAPDH (normalized to animal 1) | REP1 Normalized to respective GAPDH (normalized to animal 2) | Fold change in REP-1 (normalized to animal 1) | Fold change in REP-1 (normalized to animal 2) | Average fold change in REP-1 expression |
|---|---|---|---|---|---|---|---|---|---|
| AAV8.V2a | 12758.589 | 10058.359 | 1.055 | 1.190 | 9533.571 | 8450.521 | 2.335 | 3.742 | 3.038 |
| AAV8.V2a | 11885.518 | 13247.510 | 0.982 | 1.108 | 13489.242 | 11956.812 | 3.303 | 5.294 | 4.299 |
| AAV8.V3a | 12139.418 | 15542.551 | 1.003 | 1.132 | 15495.152 | 13734.843 | 3.794 | 6.081 | 4.938 |
| AAV8V3a | 11113.640 | 7274.388 | 0.918 | 1.036 | 7921.575 | 7021.653 | 1.940 | 3.109 | 2.524 |
| AAV8.V1 | 12102.397 | 4083.761 | 1.000 | 1.128 | 4083.761 | 3619.830 | 1.000 |  |  |
| AAV8.V1 | 10727.518 | 2258.477 | 0.886 | 1.000 | 2547.932 | 2258.477 |  | 1.000 |  |

REP-1 expression values untreated animal was negligible see the values below:

| Name | REP-1 | GAPDH |
|---|---|---|
| Uninjected Animal-1 | 651.678 | 16633.539 |
| Animal-2 | 253.778 | 13025.397 |

TABLE 23

Quantified REP-1 protein production results for treatment with low dose (5E8 vg) AAV8 V1, V2a and V2b

|  | GAPDH | REP-1 | GAPDH Normalized to GAPDH of Version 1 Animal 1 | GAPDH Normalized to GAPDH of Version 2 Animal 2 | REP1 Normalized to respective GAPDH (normalized to animal 1) | REP1 Normalized to respective GAPDH (normalized to animal 2) | Fold change in REP-1 (normalized to animal 1) | Fold change in REP-1 (normalized to animal 2) | Average fold change in REP-1 expression |
|---|---|---|---|---|---|---|---|---|---|
| AAV8.V2a | 11815.489 | 11194.037 | 0.809 | 0.934 | 13844.203 | 11984.286 | 11.123 | 29.133 | 20.128 |
| AAV8.V2a | 12889.418 | 7162.924 | 0.882 | 1.019 | 8120.634 | 7029.658 | 6.524 | 17.089 | 11.806 |
| AAV8.V3a | 13088.418 | 1516.506 | 0.896 | 1.035 | 1693.128 | 1465.663 | 1.360 | 3.563 | 2.462 |
| AAV8V3a | 9201.075 | 593.192 | 0.630 | 0.727 | 942.084 | 815.519 | 0.757 | 1.982 | 1.370 |
| AAV8.V1 | 14612.782 | 1244.678 | 1.000 | 1.155 | 1244.678 | 1077.460 | 1.000 |  |  |
| AAV8.V1 | 12649.610 | 411.364 | 0.866 | 1.000 | 475.206 | 411.364 |  | 1.000 |  |

REP-1 expression values untreated animal was negligible see the values below:

| Name | REP-1 | GAPDH |
|---|---|---|
| Uninjected Animal-1 | 694.263 | 15930.368 |
| Animal-2 | 254.364 | 13896.246 |

Densitometric evaluation (quantification of the expression level) of the blots using ImageJ software further demonstrate an increased production of REP-1 in animals injected with next generation AAV8.CHM constructs (especially V2a) compared with Version 1. See Table 23 for values.

Expression of AAV8. V2b in CD1 Mice

This current study and the evaluation of lambda stuffer's effect on AAV vector production by qPCR titer analysis were carried out simultaneously. We performed all the animal injections for the in vivo expression study as described in the study protocol PCPR.02 and all samples were harvested. After the qPCR study on the lambda stuffer element was concluded (described above), we decided to carry out the Western blot experiments only to test the expression of AAV vectors without the stuffer such as AAV8.2b and AAV8.3b and exclude them from further analysis (such as comparison with Version 1).

Figures 12A, 12B:
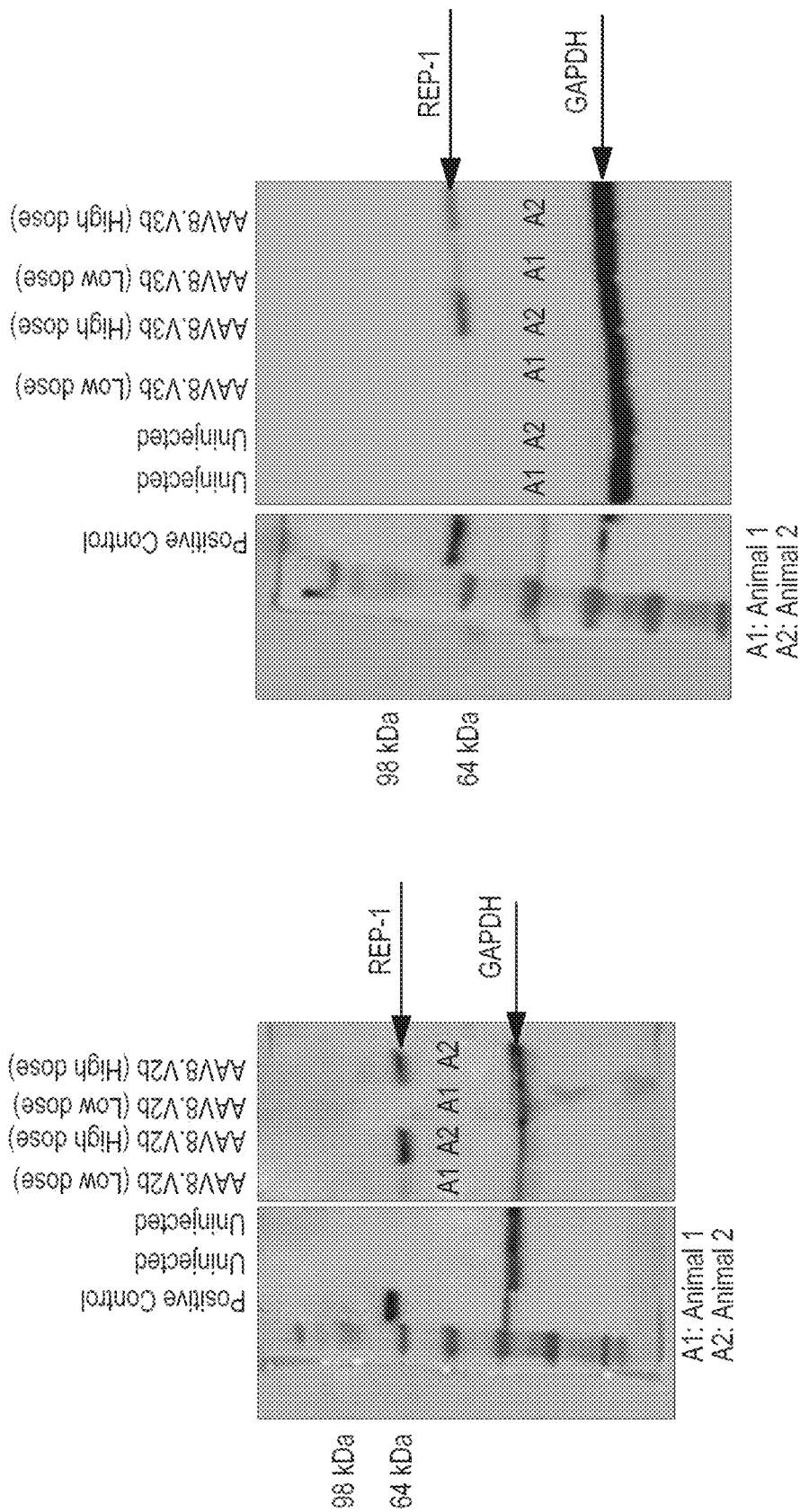
FIG. 12A is a western blot showing human anti-REP-1 antibody detection of a protein of ~75-80 kDa in ocular tissues of CD-1 mice injected with AAV8.2b at 5E9 (High dose) vector genome copies. Animals injected with AAV8.2b at 5E8 (Low dose) showed a very faint protein band at ~75-80 kDa.
FIG. 12B is a Western blot analysis of ocular tissues of AAV8.3b injected CD1 mice (2 mice/group) detected with anti-REP-1 antibody, which revealed the presence of a protein of ~75-80 kDa in one eye injected with low dose and in both eyes injected with high dose of AAV8.3b. In the ocular tissues of uninjected mice there was no REP-1 expression detected.

Human anti-REP-1 antibody detected a protein of ~75-80 kDa in ocular tissues of CD-1 mice injected with AAV8.2b at 5E9 (High dose) vector genome copies (FIG. 12A). Animals injected with AAV8.2b at 5E8 (Low dose) showed a very faint protein band at ~75-80 kDa (FIG. 12A). Lysates of ocular tissues from uninjected control animals did not show the presence of REP-1 protein. Anti-GAPDH antibody detected a protein of ~39 kDa in all ocular tissue lysates including the uninjected controls. This data may establish the minimal dose for AAV8.2b.

Expression of AAV8.V3b in CD1 Mice

We performed a Western blot analysis on ocular tissues of AAV8.3b injected CD1 mice (2 mice/group) with anti-REP-1 antibody, which revealed the presence of a protein of ~75-80 kDa in one eye injected with low dose and in both eyes injected with high dose of AAV8.3b. In the ocular tissues of uninjected mice there was no REP-1 expression detected (FIG. 12B). The level of REP-1 produced was dose dependent in animals injected with AAV8.3b. Injection with high dose of AAV8.3b (5E9 vector genomes) induced a higher amount of REP-1 compared with the low dose injected eyes (5E8 vector genomes). Anti-GAPDH antibody detected a protein of ~39 kDa in ocular tissue lysates of all injected and uninjected animals.

These results revealed the following observations:

1) The next generation vectors AAV8. Version2a, 2b, 3a and 3b are able to transduce ocular tissues efficiently. 2) Expression of the transgene (codon optimized CHM) was detectable for all of the next generation vectors. 3) Expression of transgene (codon optimized CHM) is dose dependent. 4) AAV8. Version2a and AAV8.Version.2b induced an increased production of REP-1 protein compared to AAV8. Version 1 in ocular tissues of CD-1 mice. 5) There is variation in the exact level of production of the transgenic protein between eyes injected with the same dose reflecting the variability in the surgical delivery procedure. However, differences in levels are large between the low (5E8) and high (5E9) doses. 6) AAV8.CHM.V2a and AAV8. V3a result in much higher levels of REP-1 protein production than AAV8.V1 after in vivo administration of high dose (5E9 vg) vector subretinally in mice.

All publications cited in this specification are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

| SEQ ID NO (SID) | Sequence |
|---|---|
| 1 | codon optimized REP-1 |
| 2 | AA from SID 1 |
| 3 | native REP-1 |
| 4 | AA from SID 3 |
| 5 | codon optimized REP-1 with modifications |
| 6 | AA from SID 5 |
| 7 | p584 |
| 8 | p584-REP-1 optimized |
| 9 | codon optimized CNGA3 |
| 10 | AA from SID 9 |
| 11 | codon optimized CNGA variant X1 |
| 12 | AA from SID 11 |
| 13 | native CNGA3 |
| 14 | AA from SID 13 |
| 15 | native CNGA3 variant X1 |
| 16 | codon optimized CNGA3 with modifications |
| 17 | codon optimized CNGA3 variant with modifications |
| 18 | native CNGA3 with modfications |
| 19 | native CNGB3 |
| 20 | AA from SID 19 |
| 21 | CNGB3 with modfied ORF |
| 22 | AA from SID21 |
| 23 | CNGB3 with modfied ORF with modfied ends |
| 24 | AA from SID 23 |
| 25 | Plasmid Version 2a |
| 26 | Plasmid version 2b |
| 27 | Plasmid version3a |
| 28 | Plasmid version 3b |
| 29 | Plasmid version 1 |

What is claimed is:

1. A method for treating achromatopsia in a human subject in need thereof, said method comprising administering to the human subject subretinally an AAV vector comprising an AAV capsid and a nucleic acid sequence packaged therein, wherein the nucleic acid sequence comprises i) AAV ITR sequences, ii) a nucleic acid sequence encoding human cyclic nucleotide gated channel alpha 3 (CNGA3), and iii) expression control sequences that direct expression of the CNGA3 in a host cell, wherein the nucleic acid sequence encoding the human CNGA3 sequence comprises SEQ ID NO: 9 or SEQ ID NO: 11.

2. The method of claim 1, wherein nucleic acid sequence encoding human CNGA3 sequence comprises SEQ ID NO: 9 or SEQ ID NO: 11.

3. The method of claim 1, wherein the expression control sequences comprise an ocular cell-specific promoter.

4. The method of claim 1, wherein the AAV vector is administered in combination with another therapy.

5. The method of claim 1, wherein the AAV vector is administered at a dosage of about $10^9$ to about $10^{13}$ vector genomes (VG).

6. The method of claim 1, wherein the AAV vector is administered in a volume of about 100 μL to about 500 μL.

7. The method of claim 1, wherein the AAV vector is administered more than once.

8. The method of claim 1, wherein the expression control sequences comprise a chicken β-actin (CBA) promoter with cytomegalovirus (CMV) enhancer elements.

9. The method of claim 1, wherein the expression control sequences comprise a rhodopsin kinase promoter.

10. The method of claim 1, wherein the AAV capsid is an AAV2 capsid, an AAV5 capsid, an AAV8 capsid, an AAV9 capsid, an AAV8 bp capsid, an AAV7m8 capsid, or a variant thereof.

\* \* \* \* \*

SEQUENCE LISTING

```
<160> NUMBER OF SEQ ID NOS: 24

<210> SEQ ID NO 1
<211> LENGTH: 1962
<212> TYPE: DNA
<213> ORGANISM: Artificial Sequence
<220> FEATURE:
<223> OTHER INFORMATION: codon optimized sequence
<220> FEATURE:
<221> NAME/KEY: CDS
<222> LOCATION: (1)..(1962)

<400> SEQUENCE: 1 atg gct gat acc ctg ccc tct gaa ttc gac gtg att gtg att gga acc      48
Met Ala Asp Thr Leu Pro Ser Glu Phe Asp Val Ile Val Ile Gly Thr
1               5                   10                  15
```

| | | |
|---|---|---|
| gga ctc cct gaa tcg atc atc gcc gcg gcc tgt tcc cgg tcc ggt cgg<br>Gly Leu Pro Glu Ser Ile Ile Ala Ala Ala Cys Ser Arg Ser Gly Arg<br>20            25            30 | | 96 |
| cgc gtg ctg cac gtc gat tcg aga agc tac tac gga ggg aat tgg gcc<br>Arg Val Leu His Val Asp Ser Arg Ser Tyr Tyr Gly Gly Asn Trp Ala<br>35            40            45 | | 144 |
| tca ttc tcc ttc tcc gga ctc ctc tcc tgg ctg aag gag tat cag gag<br>Ser Phe Ser Phe Ser Gly Leu Leu Ser Trp Leu Lys Glu Tyr Gln Glu<br>50            55            60 | | 192 |
| aac tcc gac att gtc tcc gac tca cct gtg tgg cag gac cag atc ctg<br>Asn Ser Asp Ile Val Ser Asp Ser Pro Val Trp Gln Asp Gln Ile Leu<br>65            70            75            80 | | 240 |
| gaa aac gag gaa gca ata gcc ctg agc cgg aag gac aag acc atc cag<br>Glu Asn Glu Glu Ala Ile Ala Leu Ser Arg Lys Asp Lys Thr Ile Gln<br>85            90            95 | | 288 |
| cac gtg gag gtg ttc tgt tat gcc tcc caa gac ctc cat gag gac gtg<br>His Val Glu Val Phe Cys Tyr Ala Ser Gln Asp Leu His Glu Asp Val<br>100           105           110 | | 336 |
| gaa gag gct gga gcg ttg cag aag aat cat gcc ctc gtg acc tcc gct<br>Glu Glu Ala Gly Ala Leu Gln Lys Asn His Ala Leu Val Thr Ser Ala<br>115           120           125 | | 384 |
| aac tcc acc gag gca gcc gac agc gcc ttc ctg ccg acc gag gat gaa<br>Asn Ser Thr Glu Ala Ala Asp Ser Ala Phe Leu Pro Thr Glu Asp Glu<br>130           135           140 | | 432 |
| tcc ctg tca act atg tcg tgc gaa atg ctg acc gaa cag act ccg agc<br>Ser Leu Ser Thr Met Ser Cys Glu Met Leu Thr Glu Gln Thr Pro Ser<br>145           150           155           160 | | 480 |
| tcc gac ccc gaa aac gcc ctg gaa gtg aac gga gcg gaa gtg acc ggc<br>Ser Asp Pro Glu Asn Ala Leu Glu Val Asn Gly Ala Glu Val Thr Gly<br>165           170           175 | | 528 |
| gaa aag gag aac cat tgc gac gac aag act tgt gtc cca tcc act tcc<br>Glu Lys Glu Asn His Cys Asp Asp Lys Thr Cys Val Pro Ser Thr Ser<br>180           185           190 | | 576 |
| gcg gag gac atg tcc gag aat gtg cct atc gcc gag gac acc acc gaa<br>Ala Glu Asp Met Ser Glu Asn Val Pro Ile Ala Glu Asp Thr Thr Glu<br>195           200           205 | | 624 |
| cag ccc aag aag aac aga atc acg tac agc cag atc atc aag gag ggg<br>Gln Pro Lys Lys Asn Arg Ile Thr Tyr Ser Gln Ile Ile Lys Glu Gly<br>210           215           220 | | 672 |
| cgg agg ttt aac atc gat ctg gtg tcg aag ctg ctg tac agc cgc ggt<br>Arg Arg Phe Asn Ile Asp Leu Val Ser Lys Leu Leu Tyr Ser Arg Gly<br>225           230           235           240 | | 720 |
| ctg ctg atc gat ctg ctc att aag tcg aac gtg tcg aga tac gcc gag<br>Leu Leu Ile Asp Leu Leu Ile Lys Ser Asn Val Ser Arg Tyr Ala Glu<br>245           250           255 | | 768 |
| ttc aag aac atc aca agg att ctc gcc ttc cgg gaa gga aga gtg gaa<br>Phe Lys Asn Ile Thr Arg Ile Leu Ala Phe Arg Glu Gly Arg Val Glu<br>260           265           270 | | 816 |
| caa gtg ccg tgc tcc cgg gcc gac gtg ttc aac tca aag caa ctt acc<br>Gln Val Pro Cys Ser Arg Ala Asp Val Phe Asn Ser Lys Gln Leu Thr<br>275           280           285 | | 864 |
| atg gtg gaa aag cgc atg ctg atg aaa ttc ctg acc ttc tgc atg gag<br>Met Val Glu Lys Arg Met Leu Met Lys Phe Leu Thr Phe Cys Met Glu<br>290           295           300 | | 912 |
| tac gaa aag tac cct gat gag tac aag ggt tac gaa gaa att act ttc<br>Tyr Glu Lys Tyr Pro Asp Glu Tyr Lys Gly Tyr Glu Glu Ile Thr Phe<br>305           310           315           320 | | 960 |
| tac gag tac ctc aag acc cag aag ctg acc ccg aat ctg cag tac att<br>Tyr Glu Tyr Leu Lys Thr Gln Lys Leu Thr Pro Asn Leu Gln Tyr Ile | | 1008 |

-continued

|  |  |  |  |  |  |  |  |  |  |  |  |  |  |  |  |
|---|---|---|---|---|---|---|---|---|---|---|---|---|---|---|---|
|  |  |  | 325 |  |  |  | 330 |  |  |  | 335 |  |  |  |  |
| gtg | atg | cac | tca | atc | gca | atg | acc | tcc | gaa | acc | gcc | tcc | tcg | acc | atc | 1056 |
| Val | Met | His | Ser | Ile | Ala | Met | Thr | Ser | Glu | Thr | Ala | Ser | Ser | Thr | Ile |  |
|  |  |  | 340 |  |  |  | 345 |  |  |  | 350 |  |  |  |  |
| gac | ggg | ctc | aag | gcc | acc | aag | aac | ttc | ctg | cac | tgt | ttg | ggg | cgc | tac | 1104 |
| Asp | Gly | Leu | Lys | Ala | Thr | Lys | Asn | Phe | Leu | His | Cys | Leu | Gly | Arg | Tyr |  |
|  |  | 355 |  |  |  |  | 360 |  |  |  |  | 365 |  |  |  |
| ggc | aac | act | ccg | ttc | ctc | ttc | ccg | ctg | tac | ggc | cag | gga | gag | ctg | cct | 1152 |
| Gly | Asn | Thr | Pro | Phe | Leu | Phe | Pro | Leu | Tyr | Gly | Gln | Gly | Glu | Leu | Pro |  |
|  | 370 |  |  |  |  | 375 |  |  |  |  | 380 |  |  |  |  |
| cag | tgt | ttc | tgc | cgg | atg | tgc | gcc | gtg | ttc | ggc | gga | atc | tac | tgt | ctc | 1200 |
| Gln | Cys | Phe | Cys | Arg | Met | Cys | Ala | Val | Phe | Gly | Gly | Ile | Tyr | Cys | Leu |  |
| 385 |  |  |  |  | 390 |  |  |  |  | 395 |  |  |  |  | 400 |
| cgc | cac | tcg | gtc | cag | tgc | ctg | gtg | gtg | gac | aag | gaa | tcc | agg | aag | tgc | 1248 |
| Arg | His | Ser | Val | Gln | Cys | Leu | Val | Val | Asp | Lys | Glu | Ser | Arg | Lys | Cys |  |
|  |  |  |  | 405 |  |  |  |  | 410 |  |  |  |  | 415 |  |
| aaa | gcc | att | att | gac | cag | ttc | gga | caa | cgg | atc | att | tcc | gag | cac | ttt | 1296 |
| Lys | Ala | Ile | Ile | Asp | Gln | Phe | Gly | Gln | Arg | Ile | Ile | Ser | Glu | His | Phe |  |
|  |  |  | 420 |  |  |  |  | 425 |  |  |  |  | 430 |  |  |
| ctt | gtg | gag | gac | tca | tac | ttc | ccg | gag | aac | atg | tgc | tct | cgg | gtc | cag | 1344 |
| Leu | Val | Glu | Asp | Ser | Tyr | Phe | Pro | Glu | Asn | Met | Cys | Ser | Arg | Val | Gln |  |
|  |  | 435 |  |  |  |  | 440 |  |  |  |  | 445 |  |  |  |
| tat | cga | cag | att | tcc | agg | gcg | gtg | ctc | att | act | gac | cgg | agc | gtc | ctc | 1392 |
| Tyr | Arg | Gln | Ile | Ser | Arg | Ala | Val | Leu | Ile | Thr | Asp | Arg | Ser | Val | Leu |  |
|  | 450 |  |  |  |  | 455 |  |  |  |  | 460 |  |  |  |  |
| aag | acc | gat | agc | gac | cag | cag | atc | tcc | atc | ctg | acc | gtg | ccg | gcg | gaa | 1440 |
| Lys | Thr | Asp | Ser | Asp | Gln | Gln | Ile | Ser | Ile | Leu | Thr | Val | Pro | Ala | Glu |  |
| 465 |  |  |  |  | 470 |  |  |  |  | 475 |  |  |  |  | 480 |
| gaa | ccc | ggc | act | ttt | gcc | gtg | cgc | gtg | atc | gag | ctt | tgc | tca | tcc | acc | 1488 |
| Glu | Pro | Gly | Thr | Phe | Ala | Val | Arg | Val | Ile | Glu | Leu | Cys | Ser | Ser | Thr |  |
|  |  |  |  | 485 |  |  |  |  | 490 |  |  |  |  | 495 |  |
| atg | act | tgc | atg | aaa | ggc | act | tac | ctg | gtg | cac | ctg | acg | tgc | acc | tca | 1536 |
| Met | Thr | Cys | Met | Lys | Gly | Thr | Tyr | Leu | Val | His | Leu | Thr | Cys | Thr | Ser |  |
|  |  |  | 500 |  |  |  |  | 505 |  |  |  |  | 510 |  |  |
| tcg | aaa | acc | gct | aga | gag | gac | ctg | gaa | tcc | gtc | gtc | caa | aag | ctg | ttc | 1584 |
| Ser | Lys | Thr | Ala | Arg | Glu | Asp | Leu | Glu | Ser | Val | Val | Gln | Lys | Leu | Phe |  |
|  |  | 515 |  |  |  |  | 520 |  |  |  |  | 525 |  |  |  |
| gtg | cct | tac | acc | gag | atg | gaa | att | gaa | aac | gaa | caa | gtg | gag | aag | ccc | 1632 |
| Val | Pro | Tyr | Thr | Glu | Met | Glu | Ile | Glu | Asn | Glu | Gln | Val | Glu | Lys | Pro |  |
|  | 530 |  |  |  |  | 535 |  |  |  |  | 540 |  |  |  |  |
| cgc | atc | ctt | tgg | gcc | ctg | tac | ttt | aac | atg | cgc | gat | tcc | tcc | gat | atc | 1680 |
| Arg | Ile | Leu | Trp | Ala | Leu | Tyr | Phe | Asn | Met | Arg | Asp | Ser | Ser | Asp | Ile |  |
| 545 |  |  |  |  | 550 |  |  |  |  | 555 |  |  |  |  | 560 |
| tcg | cgg | tcc | tgc | tat | aac | gac | ttg | cct | tcg | aac | gtc | tac | gtc | tgc | tcc | 1728 |
| Ser | Arg | Ser | Cys | Tyr | Asn | Asp | Leu | Pro | Ser | Asn | Val | Tyr | Val | Cys | Ser |  |
|  |  |  |  | 565 |  |  |  |  | 570 |  |  |  |  | 575 |  |
| ggg | cca | gac | tgc | ggt | ctt | ggc | aac | gac | aat | gcc | gtg | aag | cag | gcg | gaa | 1776 |
| Gly | Pro | Asp | Cys | Gly | Leu | Gly | Asn | Asp | Asn | Ala | Val | Lys | Gln | Ala | Glu |  |
|  |  |  | 580 |  |  |  |  | 585 |  |  |  |  | 590 |  |  |
| aca | ctg | ttc | caa | gag | atc | tgc | cct | aac | gag | gat | ttt | tgc | ccg | ccc | ccc | 1824 |
| Thr | Leu | Phe | Gln | Glu | Ile | Cys | Pro | Asn | Glu | Asp | Phe | Cys | Pro | Pro | Pro |  |
|  |  | 595 |  |  |  |  | 600 |  |  |  |  | 605 |  |  |  |
| cca | aac | ccc | gag | gat | atc | atc | ttg | gac | gga | gac | agc | ctg | cag | cca | gaa | 1872 |
| Pro | Asn | Pro | Glu | Asp | Ile | Ile | Leu | Asp | Gly | Asp | Ser | Leu | Gln | Pro | Glu |  |
|  | 610 |  |  |  |  | 615 |  |  |  |  | 620 |  |  |  |  |
| gca | tcc | gag | tcc | agc | gcc | atc | ccg | gag | gcc | aac | agc | gaa | acc | ttc | aag | 1920 |
| Ala | Ser | Glu | Ser | Ser | Ala | Ile | Pro | Glu | Ala | Asn | Ser | Glu | Thr | Phe | Lys |  |
| 625 |  |  |  |  | 630 |  |  |  |  | 635 |  |  |  |  | 640 |
| gag | agc | act | aac | ctg | ggc | aac | ctg | gaa | gag | tcc | agc | gaa | tga |  |  | 1962 |
| Glu | Ser | Thr | Asn | Leu | Gly | Asn | Leu | Glu | Glu | Ser | Ser | Glu |  |  |  |  |

-continued

Glu Ser Thr Asn Leu Gly Asn Leu Glu Glu Ser Ser Glu
            645                 650

<210> SEQ ID NO 2
<211> LENGTH: 653
<212> TYPE: PRT
<213> ORGANISM: Artificial Sequence
<220> FEATURE:
<223> OTHER INFORMATION: Synthetic Construct

<400> SEQUENCE: 2

Met Ala Asp Thr Leu Pro Ser Glu Phe Asp Val Ile Val Ile Gly Thr
1               5                   10                  15

Gly Leu Pro Glu Ser Ile Ile Ala Ala Cys Ser Arg Ser Gly Arg
            20                  25                  30

Arg Val Leu His Val Asp Ser Arg Ser Tyr Tyr Gly Gly Asn Trp Ala
            35                  40                  45

Ser Phe Ser Phe Ser Gly Leu Leu Ser Trp Leu Lys Glu Tyr Gln Glu
        50                  55                  60

Asn Ser Asp Ile Val Ser Asp Ser Pro Val Trp Gln Asp Gln Ile Leu
65                  70                  75                  80

Glu Asn Glu Glu Ala Ile Ala Leu Ser Arg Lys Asp Lys Thr Ile Gln
            85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125

Asn Ser Thr Glu Ala Ala Asp Ser Ala Phe Leu Pro Thr Glu Asp Glu
130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
            165                 170                 175

Glu Lys Glu Asn His Cys Asp Asp Lys Thr Cys Val Pro Ser Thr Ser
        180                 185                 190

Ala Glu Asp Met Ser Glu Asn Val Pro Ile Ala Glu Asp Thr Thr Glu
    195                 200                 205

Gln Pro Lys Lys Asn Arg Ile Thr Tyr Ser Gln Ile Ile Lys Glu Gly
    210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
            245                 250                 255

Phe Lys Asn Ile Thr Arg Ile Leu Ala Phe Arg Glu Gly Arg Val Glu
        260                 265                 270

Gln Val Pro Cys Ser Arg Ala Asp Val Phe Asn Ser Lys Gln Leu Thr
    275                 280                 285

Met Val Glu Lys Arg Met Leu Met Lys Phe Leu Thr Phe Cys Met Glu
    290                 295                 300

Tyr Glu Lys Tyr Pro Asp Glu Tyr Lys Gly Tyr Glu Glu Ile Thr Phe
305                 310                 315                 320

Tyr Glu Tyr Leu Lys Thr Gln Lys Leu Thr Pro Asn Leu Gln Tyr Ile
            325                 330                 335

Val Met His Ser Ile Ala Met Thr Ser Glu Thr Ala Ser Ser Thr Ile
        340                 345                 350

-continued

```
Asp Gly Leu Lys Ala Thr Lys Asn Phe Leu His Cys Leu Gly Arg Tyr
            355                 360                 365

Gly Asn Thr Pro Phe Leu Phe Pro Leu Tyr Gly Gln Gly Glu Leu Pro
        370                 375                 380

Gln Cys Phe Cys Arg Met Cys Ala Val Phe Gly Gly Ile Tyr Cys Leu
385                 390                 395                 400

Arg His Ser Val Gln Cys Leu Val Val Asp Lys Glu Ser Arg Lys Cys
                405                 410                 415

Lys Ala Ile Ile Asp Gln Phe Gly Gln Arg Ile Ile Ser Glu His Phe
            420                 425                 430

Leu Val Glu Asp Ser Tyr Phe Pro Glu Asn Met Cys Ser Arg Val Gln
        435                 440                 445

Tyr Arg Gln Ile Ser Arg Ala Val Leu Ile Thr Asp Arg Ser Val Leu
    450                 455                 460

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
                485                 490                 495

Met Thr Cys Met Lys Gly Thr Tyr Leu Val His Leu Thr Cys Thr Ser
            500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
    530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605

Pro Asn Pro Glu Asp Ile Ile Leu Asp Gly Asp Ser Leu Gln Pro Glu
    610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650
```

<210> SEQ ID NO 3
<211> LENGTH: 1962
<212> TYPE: DNA
<213> ORGANISM: Homo sapiens
<220> FEATURE:
<221> NAME/KEY: CDS
<222> LOCATION: (1)..(1962)

<400> SEQUENCE: 3

```
atg gcg gat act ctc cct tcg gag ttt gat gtg atc gta ata ggg acg    48
Met Ala Asp Thr Leu Pro Ser Glu Phe Asp Val Ile Val Ile Gly Thr
1               5                   10                  15 ggt ttg cct gaa tcc atc att gca gct gca tgt tca aga agt ggc cgg    96
Gly Leu Pro Glu Ser Ile Ile Ala Ala Ala Cys Ser Arg Ser Gly Arg
            20                  25                  30 aga gtt ctg cat gtt gat tca aga agc tac tat gga gga aac tgg gcc   144
Arg Val Leu His Val Asp Ser Arg Ser Tyr Tyr Gly Gly Asn Trp Ala
        35                  40                  45
```

```
agt ttt agc ttt tca gga cta ttg tcc tgg cta aag gaa tac cag gaa      192
Ser Phe Ser Phe Ser Gly Leu Leu Ser Trp Leu Lys Glu Tyr Gln Glu
     50              55                  60 aac agt gac att gta agt gac agt cca gtg tgg caa gac cag atc ctt      240
Asn Ser Asp Ile Val Ser Asp Ser Pro Val Trp Gln Asp Gln Ile Leu
 65              70                  75                  80 gaa aat gaa gaa gcc att gct ctt agc agg aag gac aaa act att caa      288
Glu Asn Glu Glu Ala Ile Ala Leu Ser Arg Lys Asp Lys Thr Ile Gln
                 85                  90                  95 cat gtg gaa gta ttt tgt tat gcc agt cag gat ttg cat gaa gat gtc      336
His Val Glu Val Phe Cys Tyr Ala Ser Gln Asp Leu His Glu Asp Val
             100                 105                 110 gaa gaa gct ggt gca ctg cag aaa aat cat gct ctt gtg aca tct gca      384
Glu Glu Ala Gly Ala Leu Gln Lys Asn His Ala Leu Val Thr Ser Ala
         115                 120                 125 aac tcc aca gaa gct gca gat tct gcc ttc ctg cct acg gag gat gag      432
Asn Ser Thr Glu Ala Ala Asp Ser Ala Phe Leu Pro Thr Glu Asp Glu
     130                 135                 140 tca tta agc act atg agc tgt gaa atg ctc aca gaa caa act cca agc      480
Ser Leu Ser Thr Met Ser Cys Glu Met Leu Thr Glu Gln Thr Pro Ser
145                 150                 155                 160 agc gat cca gag aat gcg cta gaa gta aat ggt gct gaa gtg aca ggg      528
Ser Asp Pro Glu Asn Ala Leu Glu Val Asn Gly Ala Glu Val Thr Gly
                 165                 170                 175 gaa aaa gaa aac cat tgt gat gat aaa act tgt gtg cca tca act tca      576
Glu Lys Glu Asn His Cys Asp Asp Lys Thr Cys Val Pro Ser Thr Ser
             180                 185                 190 gca gaa gac atg agt gaa aat gtg cct ata gca gaa gat acc aca gag      624
Ala Glu Asp Met Ser Glu Asn Val Pro Ile Ala Glu Asp Thr Thr Glu
         195                 200                 205 caa cca aag aaa aac aga att act tac tca caa att att aaa gaa ggc      672
Gln Pro Lys Lys Asn Arg Ile Thr Tyr Ser Gln Ile Ile Lys Glu Gly
     210                 215                 220 agg aga ttt aat att gat tta gta tca aag ctg ctg tat tct cga gga      720
Arg Arg Phe Asn Ile Asp Leu Val Ser Lys Leu Leu Tyr Ser Arg Gly
225                 230                 235                 240 tta cta att gat ctt cta atc aaa tct aat gtt agt cga tat gca gag      768
Leu Leu Ile Asp Leu Leu Ile Lys Ser Asn Val Ser Arg Tyr Ala Glu
                 245                 250                 255 ttt aaa aat att acc agg att ctt gca ttt cga gaa gga cga gtg gaa      816
Phe Lys Asn Ile Thr Arg Ile Leu Ala Phe Arg Glu Gly Arg Val Glu
             260                 265                 270 cag gtt ccg tgt tcc aga gca gat gtc ttt aat agc aaa caa ctt act      864
Gln Val Pro Cys Ser Arg Ala Asp Val Phe Asn Ser Lys Gln Leu Thr
         275                 280                 285 atg gta gaa aag cga atg cta atg aaa ttt ctt aca ttt tgt atg gaa      912
Met Val Glu Lys Arg Met Leu Met Lys Phe Leu Thr Phe Cys Met Glu
     290                 295                 300 tat gag aaa tat cct gat gaa tat aaa gga tat gaa gag atc aca ttt      960
Tyr Glu Lys Tyr Pro Asp Glu Tyr Lys Gly Tyr Glu Glu Ile Thr Phe
305                 310                 315                 320 tat gaa tat tta aag act caa aaa tta acc ccc aac ctc caa tat att     1008
Tyr Glu Tyr Leu Lys Thr Gln Lys Leu Thr Pro Asn Leu Gln Tyr Ile
                 325                 330                 335 gtc atg cat tca att gca atg aca tca gag aca gcc agc agc acc ata     1056
Val Met His Ser Ile Ala Met Thr Ser Glu Thr Ala Ser Ser Thr Ile
             340                 345                 350 gat ggt ctc aaa gct acc aaa aac ttt ctt cac tgt ctt ggg cgg tat     1104
Asp Gly Leu Lys Ala Thr Lys Asn Phe Leu His Cys Leu Gly Arg Tyr
```

```
                    355                 360                 365
ggc aac act cca ttt ttg ttt cct tta tat ggc caa gga gaa ctc ccc      1152
Gly Asn Thr Pro Phe Leu Phe Pro Leu Tyr Gly Gln Gly Glu Leu Pro
370                 375                 380 cag tgt ttc tgc agg atg tgt gct gtg ttt ggt gga att tat tgt ctt      1200
Gln Cys Phe Cys Arg Met Cys Ala Val Phe Gly Gly Ile Tyr Cys Leu
385                 390                 395                 400 cgc cat tca gta cag tgc ctt gta gtg gac aaa gaa tcc aga aaa tgt      1248
Arg His Ser Val Gln Cys Leu Val Val Asp Lys Glu Ser Arg Lys Cys
            405                 410                 415 aaa gca att ata gat cag ttt ggt cag aga ata atc tct gag cat ttc      1296
Lys Ala Ile Ile Asp Gln Phe Gly Gln Arg Ile Ile Ser Glu His Phe
        420                 425                 430 ctc gtg gag gac agt tac ttt cct gag aac atg tgc tca cgt gtg caa      1344
Leu Val Glu Asp Ser Tyr Phe Pro Glu Asn Met Cys Ser Arg Val Gln
    435                 440                 445 tac agg cag atc tcc agg gca gtg ctg att aca gat aga tct gtc cta      1392
Tyr Arg Gln Ile Ser Arg Ala Val Leu Ile Thr Asp Arg Ser Val Leu
450                 455                 460 aaa aca gat tca gat caa cag att tcc att ttg aca gtg cca gca gag      1440
Lys Thr Asp Ser Asp Gln Gln Ile Ser Ile Leu Thr Val Pro Ala Glu
465                 470                 475                 480 gaa cca gga act ttt gct gtt cgg gtc att gag tta tgt tct tca acg      1488
Glu Pro Gly Thr Phe Ala Val Arg Val Ile Glu Leu Cys Ser Ser Thr
            485                 490                 495 atg aca tgc atg aaa ggc acc tat ttg gtt cat ttg act tgc aca tct      1536
Met Thr Cys Met Lys Gly Thr Tyr Leu Val His Leu Thr Cys Thr Ser
        500                 505                 510 tct aaa aca gca aga gaa gat tta gaa tca gtt gtg cag aaa ttg ttt      1584
Ser Lys Thr Ala Arg Glu Asp Leu Glu Ser Val Val Gln Lys Leu Phe
    515                 520                 525 gtt cca tat act gaa atg gag ata gaa aat gaa caa gta gaa aag cca      1632
Val Pro Tyr Thr Glu Met Glu Ile Glu Asn Glu Gln Val Glu Lys Pro
530                 535                 540 aga att ctg tgg gct ctt tac ttc aat atg aga gat tcg tca gac atc      1680
Arg Ile Leu Trp Ala Leu Tyr Phe Asn Met Arg Asp Ser Ser Asp Ile
545                 550                 555                 560 agc agg agc tgt tat aat gat tta cca tcc aac gtt tat gtc tgc tct      1728
Ser Arg Ser Cys Tyr Asn Asp Leu Pro Ser Asn Val Tyr Val Cys Ser
            565                 570                 575 ggc cca gat tgt ggt tta gga aat gat aat gca gtc aaa cag gct gaa      1776
Gly Pro Asp Cys Gly Leu Gly Asn Asp Asn Ala Val Lys Gln Ala Glu
        580                 585                 590 aca ctt ttc cag gaa atc tgc ccc aat gaa gat ttc tgt ccc cct cca      1824
Thr Leu Phe Gln Glu Ile Cys Pro Asn Glu Asp Phe Cys Pro Pro Pro
    595                 600                 605 cca aat cct gaa gac att atc ctt gat gga gac agt tta cag cca gag      1872
Pro Asn Pro Glu Asp Ile Ile Leu Asp Gly Asp Ser Leu Gln Pro Glu
610                 615                 620 gct tca gaa tcc agt gcc ata cca gag gct aac tcg gag act ttc aag      1920
Ala Ser Glu Ser Ser Ala Ile Pro Glu Ala Asn Ser Glu Thr Phe Lys
625                 630                 635                 640 gaa agc aca aac ctt gga aac cta gag gag tcc tct gaa taa              1962
Glu Ser Thr Asn Leu Gly Asn Leu Glu Glu Ser Ser Glu
            645                 650

<210> SEQ ID NO 4
<211> LENGTH: 653
<212> TYPE: PRT
<213> ORGANISM: Homo sapiens
```

```
<400> SEQUENCE: 4

Met Ala Asp Thr Leu Pro Ser Glu Phe Asp Val Ile Val Ile Gly Thr
1               5                   10                  15

Gly Leu Pro Glu Ser Ile Ile Ala Ala Ala Cys Ser Arg Ser Gly Arg
            20                  25                  30

Arg Val Leu His Val Asp Ser Arg Ser Tyr Tyr Gly Gly Asn Trp Ala
        35                  40                  45

Ser Phe Ser Phe Ser Gly Leu Leu Ser Trp Leu Lys Glu Tyr Gln Glu
    50                  55                  60

Asn Ser Asp Ile Val Ser Asp Ser Pro Val Trp Gln Asp Gln Ile Leu
65                  70                  75                  80

Glu Asn Glu Glu Ala Ile Ala Leu Ser Arg Lys Asp Lys Thr Ile Gln
                85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125

Asn Ser Thr Glu Ala Ala Asp Ser Ala Phe Leu Pro Thr Glu Asp Glu
130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
                165                 170                 175

Glu Lys Glu Asn His Cys Asp Asp Lys Thr Cys Val Pro Ser Thr Ser
            180                 185                 190

Ala Glu Asp Met Ser Glu Asn Val Pro Ile Ala Glu Asp Thr Thr Glu
        195                 200                 205

Gln Pro Lys Lys Asn Arg Ile Thr Tyr Ser Gln Ile Ile Lys Glu Gly
210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
                245                 250                 255

Phe Lys Asn Ile Thr Arg Ile Leu Ala Phe Arg Glu Gly Arg Val Glu
            260                 265                 270

Gln Val Pro Cys Ser Arg Ala Asp Val Phe Asn Ser Lys Gln Leu Thr
        275                 280                 285

Met Val Glu Lys Arg Met Leu Met Lys Phe Leu Thr Phe Cys Met Glu
290                 295                 300

Tyr Glu Lys Tyr Pro Asp Glu Tyr Lys Gly Tyr Glu Glu Ile Thr Phe
305                 310                 315                 320

Tyr Glu Tyr Leu Lys Thr Gln Lys Leu Thr Pro Asn Leu Gln Tyr Ile
                325                 330                 335

Val Met His Ser Ile Ala Met Thr Ser Glu Thr Ala Ser Ser Thr Ile
            340                 345                 350

Asp Gly Leu Lys Ala Thr Lys Asn Phe Leu His Cys Leu Gly Arg Tyr
        355                 360                 365

Gly Asn Thr Pro Phe Leu Phe Pro Leu Tyr Gly Gln Gly Glu Leu Pro
        370                 375                 380

Gln Cys Phe Cys Arg Met Cys Ala Val Phe Gly Gly Ile Tyr Cys Leu
385                 390                 395                 400

Arg His Ser Val Gln Cys Leu Val Val Asp Lys Glu Ser Arg Lys Cys
```

```
                    405                 410                 415
Lys Ala Ile Ile Asp Gln Phe Gly Gln Arg Ile Ile Ser Glu His Phe
        420                 425                 430

Leu Val Glu Asp Ser Tyr Phe Pro Glu Asn Met Cys Ser Arg Val Gln
            435                 440                 445

Tyr Arg Gln Ile Ser Arg Ala Val Leu Ile Thr Asp Arg Ser Val Leu
    450                 455                 460

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
                485                 490                 495

Met Thr Cys Met Lys Gly Thr Tyr Leu Val His Leu Thr Cys Thr Ser
            500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
    530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605

Pro Asn Pro Glu Asp Ile Ile Leu Asp Gly Asp Ser Leu Gln Pro Glu
    610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650

<210> SEQ ID NO 5
<211> LENGTH: 1985
<212> TYPE: DNA
<213> ORGANISM: Artificial Sequence
<220> FEATURE:
<223> OTHER INFORMATION: constructed plasmid
<220> FEATURE:
<221> NAME/KEY: misc_feature
<222> LOCATION: (1)..(8)
<223> OTHER INFORMATION: NotI restriction site for subcloning into
      proviral plasmid
<220> FEATURE:
<221> NAME/KEY: misc_feature
<222> LOCATION: (4)..(16)
<223> OTHER INFORMATION: Kozak consensus sequence
<220> FEATURE:
<221> NAME/KEY: CDS
<222> LOCATION: (13)..(1971)
<223> OTHER INFORMATION: codon-optimized open reading frame (ORF)
<220> FEATURE:
<221> NAME/KEY: misc_feature
<222> LOCATION: (1972)..(1977)
<223> OTHER INFORMATION: BclI restriction site with embedded stop codon/
      site to add optional epitope tag
<220> FEATURE:
<221> NAME/KEY: misc_feature
<222> LOCATION: (1980)..(1985)
<223> OTHER INFORMATION: BamHI restriction site for subcloning into
      proviral plasmid

<400> SEQUENCE: 5
```

```
gcggccgcca cc atg gct gat acc ctg ccc tct gaa ttc gac gtg att gtg         51
              Met Ala Asp Thr Leu Pro Ser Glu Phe Asp Val Ile Val
               1               5                  10 att gga acc gga ctc cct gaa tcg atc atc gcc gcg gcc tgt tcc cgg           99
Ile Gly Thr Gly Leu Pro Glu Ser Ile Ile Ala Ala Ala Cys Ser Arg
 15              20              25 tcc ggt cgg cgc gtg ctg cac gtc gat tcg aga agc tac tac gga ggg          147
Ser Gly Arg Arg Val Leu His Val Asp Ser Arg Ser Tyr Tyr Gly Gly
 30              35              40              45 aat tgg gcc tca ttc tcc ttc tcc gga ctg ctc tcc tgg ctg aag gag          195
Asn Trp Ala Ser Phe Ser Phe Ser Gly Leu Leu Ser Trp Leu Lys Glu
                 50              55              60 tat cag gag aac tcc gac att gtc tcc gac tca cct gtg tgg cag gac          243
Tyr Gln Glu Asn Ser Asp Ile Val Ser Asp Ser Pro Val Trp Gln Asp
             65              70              75 cag atc ctg gaa aac gag gaa gca ata gcc ctg agc cgg aag gac aag          291
Gln Ile Leu Glu Asn Glu Glu Ala Ile Ala Leu Ser Arg Lys Asp Lys
             80              85              90 acc atc cag cac gtg gag gtg ttc tgt tat gcc tcc caa gac ctc cat          339
Thr Ile Gln His Val Glu Val Phe Cys Tyr Ala Ser Gln Asp Leu His
 95              100             105 gag gac gtg gaa gag gct gga gcg ttg cag aag aat cat gcc ctc gtg          387
Glu Asp Val Glu Glu Ala Gly Ala Leu Gln Lys Asn His Ala Leu Val
110             115             120             125 acc tcc gct aac tcc acc gag gca gcc gac agc gcc ttc ctg ccg acc          435
Thr Ser Ala Asn Ser Thr Glu Ala Ala Asp Ser Ala Phe Leu Pro Thr
                130             135             140 gag gat gaa tcc ctg tca act atg tcg tgc gaa atg ctg acc gaa cag          483
Glu Asp Glu Ser Leu Ser Thr Met Ser Cys Glu Met Leu Thr Glu Gln
                145             150             155 act ccg agc tcc gac ccc gaa aac gcc ctg gaa gtg aac gga gcg gaa          531
Thr Pro Ser Ser Asp Pro Glu Asn Ala Leu Glu Val Asn Gly Ala Glu
            160             165             170 gtg acc ggc gaa aag gag aac cat tgc gac gac aag act tgt gtc cca          579
Val Thr Gly Glu Lys Glu Asn His Cys Asp Asp Lys Thr Cys Val Pro
175             180             185 tcc act tcc gcg gag gac atg tcc gag aat gtg cct atc gcc gag gac          627
Ser Thr Ser Ala Glu Asp Met Ser Glu Asn Val Pro Ile Ala Glu Asp
190             195             200             205 acc acc gaa cag ccc aag aag aac aga atc acg tac agc cag atc atc          675
Thr Thr Glu Gln Pro Lys Lys Asn Arg Ile Thr Tyr Ser Gln Ile Ile
                210             215             220 aag gag ggg cgg agg ttt aac atc gat ctg gtg tcg aag ctg ctg tac          723
Lys Glu Gly Arg Arg Phe Asn Ile Asp Leu Val Ser Lys Leu Leu Tyr
                225             230             235 agc cgc ggt ctg ctg atc gat ctg ctc att aag tcg aac gtg tcg aga          771
Ser Arg Gly Leu Leu Ile Asp Leu Leu Ile Lys Ser Asn Val Ser Arg
            240             245             250 tac gcc gag ttc aag aac atc aca agg att ctc gcc ttc cgg gaa gga          819
Tyr Ala Glu Phe Lys Asn Ile Thr Arg Ile Leu Ala Phe Arg Glu Gly
255             260             265 aga gtg gaa caa gtg ccg tgc tcc cgg gcc gac gtg ttc aac tca aag          867
Arg Val Glu Gln Val Pro Cys Ser Arg Ala Asp Val Phe Asn Ser Lys
270             275             280             285 caa ctt acc atg gtg gaa aag cgc atg ctg atg aaa ttc ctg acc ttc          915
Gln Leu Thr Met Val Glu Lys Arg Met Leu Met Lys Phe Leu Thr Phe
                290             295             300 tgc atg gag tac gaa aag tac cct gat gag tac aag ggt tac gaa gaa          963
Cys Met Glu Tyr Glu Lys Tyr Pro Asp Glu Tyr Lys Gly Tyr Glu Glu
```

|     |     |     |     |     |     |     |     |     |     |     |     |     |     |     |     |
|---|---|---|---|---|---|---|---|---|---|---|---|---|---|---|---|
|     |     |     | 305 |     |     |     | 310 |     |     |     | 315 |     |     |     |     |
| att | act | ttc | tac | gag | tac | ctc | aag | acc | cag | aag | ctg | acc | ccg | aat | ctg | 1011 |
| Ile | Thr | Phe | Tyr | Glu | Tyr | Leu | Lys | Thr | Gln | Lys | Leu | Thr | Pro | Asn | Leu |     |
|     |     | 320 |     |     |     |     | 325 |     |     |     |     | 330 |     |     |     |     |
| cag | tac | att | gtg | atg | cac | tca | atc | gca | atg | acc | tcc | gaa | acc | gcc | tcc | 1059 |
| Gln | Tyr | Ile | Val | Met | His | Ser | Ile | Ala | Met | Thr | Ser | Glu | Thr | Ala | Ser |     |
| 335 |     |     |     |     | 340 |     |     |     |     | 345 |     |     |     |     |     |     |
| tcg | acc | atc | gac | ggg | ctc | aag | gcc | acc | aag | aac | ttc | ctg | cac | tgt | ttg | 1107 |
| Ser | Thr | Ile | Asp | Gly | Leu | Lys | Ala | Thr | Lys | Asn | Phe | Leu | His | Cys | Leu |     |
| 350 |     |     |     | 355 |     |     |     |     | 360 |     |     |     |     | 365 |     |     |
| ggg | cgc | tac | ggc | aac | act | ccg | ttc | ctc | ttc | ccg | ctg | tac | ggc | cag | gga | 1155 |
| Gly | Arg | Tyr | Gly | Asn | Thr | Pro | Phe | Leu | Phe | Pro | Leu | Tyr | Gly | Gln | Gly |     |
|     |     |     | 370 |     |     |     | 375 |     |     |     |     | 380 |     |     |     |     |
| gag | ctg | cct | cag | tgt | ttc | tgc | cgg | atg | tgc | gcc | gtg | ttc | ggc | gga | atc | 1203 |
| Glu | Leu | Pro | Gln | Cys | Phe | Cys | Arg | Met | Cys | Ala | Val | Phe | Gly | Gly | Ile |     |
|     |     | 385 |     |     |     |     | 390 |     |     |     |     | 395 |     |     |     |     |
| tac | tgt | ctc | cgc | cac | tcg | gtc | cag | tgc | ctg | gtg | gtg | gac | aag | gaa | tcc | 1251 |
| Tyr | Cys | Leu | Arg | His | Ser | Val | Gln | Cys | Leu | Val | Val | Asp | Lys | Glu | Ser |     |
| 400 |     |     |     |     | 405 |     |     |     |     | 410 |     |     |     |     |     |     |
| agg | aag | tgc | aaa | gcc | att | att | gac | cag | ttc | gga | caa | cgg | atc | att | tcc | 1299 |
| Arg | Lys | Cys | Lys | Ala | Ile | Ile | Asp | Gln | Phe | Gly | Gln | Arg | Ile | Ile | Ser |     |
| 415 |     |     |     | 420 |     |     |     |     | 425 |     |     |     |     |     |     |     |
| gag | cac | ttt | ctt | gtg | gag | gac | tca | tac | ttc | ccg | gag | aac | atg | tgc | tct | 1347 |
| Glu | His | Phe | Leu | Val | Glu | Asp | Ser | Tyr | Phe | Pro | Glu | Asn | Met | Cys | Ser |     |
| 430 |     |     |     | 435 |     |     |     |     | 440 |     |     |     |     | 445 |     |     |
| cgg | gtc | cag | tat | cga | cag | att | tcc | agg | gcg | gtg | ctc | att | act | gac | cgg | 1395 |
| Arg | Val | Gln | Tyr | Arg | Gln | Ile | Ser | Arg | Ala | Val | Leu | Ile | Thr | Asp | Arg |     |
|     |     |     | 450 |     |     |     | 455 |     |     |     |     | 460 |     |     |     |     |
| agc | gtc | ctc | aag | acc | gat | agc | gac | cag | cag | atc | tcc | atc | ctg | acc | gtg | 1443 |
| Ser | Val | Leu | Lys | Thr | Asp | Ser | Asp | Gln | Gln | Ile | Ser | Ile | Leu | Thr | Val |     |
|     |     |     | 465 |     |     |     | 470 |     |     |     | 475 |     |     |     |     |     |
| ccg | gcg | gaa | gaa | ccc | ggc | act | ttt | gcc | gtg | cgc | gtg | atc | gag | ctt | tgc | 1491 |
| Pro | Ala | Glu | Glu | Pro | Gly | Thr | Phe | Ala | Val | Arg | Val | Ile | Glu | Leu | Cys |     |
|     | 480 |     |     |     |     | 485 |     |     |     |     | 490 |     |     |     |     |     |
| tca | tcc | acc | atg | act | tgc | atg | aaa | ggc | act | tac | ctg | gtg | cac | ctg | acg | 1539 |
| Ser | Ser | Thr | Met | Thr | Cys | Met | Lys | Gly | Thr | Tyr | Leu | Val | His | Leu | Thr |     |
|     | 495 |     |     |     | 500 |     |     |     |     | 505 |     |     |     |     |     |     |
| tgc | acc | tca | tcg | aaa | acc | gct | aga | gag | gac | ctg | gaa | tcc | gtc | gtc | caa | 1587 |
| Cys | Thr | Ser | Ser | Lys | Thr | Ala | Arg | Glu | Asp | Leu | Glu | Ser | Val | Val | Gln |     |
| 510 |     |     |     |     | 515 |     |     |     |     | 520 |     |     |     |     | 525 |     |
| aag | ctg | ttc | gtg | cct | tac | acc | gag | atg | gaa | att | gaa | aac | gaa | caa | gtg | 1635 |
| Lys | Leu | Phe | Val | Pro | Tyr | Thr | Glu | Met | Glu | Ile | Glu | Asn | Glu | Gln | Val |     |
|     |     |     |     | 530 |     |     |     |     | 535 |     |     |     |     | 540 |     |     |
| gag | aag | ccc | cgc | atc | ctt | tgg | gcc | ctg | tac | ttt | aac | atg | cgc | gat | tcc | 1683 |
| Glu | Lys | Pro | Arg | Ile | Leu | Trp | Ala | Leu | Tyr | Phe | Asn | Met | Arg | Asp | Ser |     |
|     |     |     | 545 |     |     |     |     | 550 |     |     |     |     | 555 |     |     |     |
| tcc | gat | atc | tcg | cgg | tcc | tgc | tat | aac | gac | ttg | cct | tcg | aac | gtc | tac | 1731 |
| Ser | Asp | Ile | Ser | Arg | Ser | Cys | Tyr | Asn | Asp | Leu | Pro | Ser | Asn | Val | Tyr |     |
|     |     |     | 560 |     |     |     |     | 565 |     |     |     |     | 570 |     |     |     |
| gtc | tgc | tcc | ggg | cca | gac | tgc | ggt | ctt | ggc | aac | gac | aat | gcc | gtg | aag | 1779 |
| Val | Cys | Ser | Gly | Pro | Asp | Cys | Gly | Leu | Gly | Asn | Asp | Asn | Ala | Val | Lys |     |
|     | 575 |     |     |     |     | 580 |     |     |     |     | 585 |     |     |     |     |     |
| cag | gcg | gaa | aca | ctg | ttc | caa | gag | atc | tgc | cct | aac | gag | gat | ttt | tgc | 1827 |
| Gln | Ala | Glu | Thr | Leu | Phe | Gln | Glu | Ile | Cys | Pro | Asn | Glu | Asp | Phe | Cys |     |
| 590 |     |     |     |     | 595 |     |     |     |     | 600 |     |     |     |     | 605 |     |
| ccg | ccc | ccc | cca | aac | ccc | gag | gat | atc | atc | ttg | gac | gga | gac | agc | ctg | 1875 |
| Pro | Pro | Pro | Pro | Asn | Pro | Glu | Asp | Ile | Ile | Leu | Asp | Gly | Asp | Ser | Leu |     |
|     |     |     |     | 610 |     |     |     |     | 615 |     |     |     |     | 620 |     |     |
| cag | cca | gaa | gca | tcc | gag | tcc | agc | gcc | atc | ccg | gag | gcc | aac | agc | gaa | 1923 |

```
Gln Pro Glu Ala Ser Glu Ser Ser Ala Ile Pro Glu Ala Asn Ser Glu
            625                 630                 635 acc ttc aag gag agc act aac ctg ggc aac ctg gaa gag tcc agc gaa    1971
Thr Phe Lys Glu Ser Thr Asn Leu Gly Asn Leu Glu Glu Ser Ser Glu
            640                 645                 650 tgatcatagg atcc                                                     1985

<210> SEQ ID NO 6
<211> LENGTH: 653
<212> TYPE: PRT
<213> ORGANISM: Artificial Sequence
<220> FEATURE:
<223> OTHER INFORMATION: Synthetic Construct

<400> SEQUENCE: 6

Met Ala Asp Thr Leu Pro Ser Glu Phe Asp Val Ile Val Ile Gly Thr
1               5                   10                  15

Gly Leu Pro Glu Ser Ile Ile Ala Ala Cys Ser Arg Ser Gly Arg
            20                  25                  30

Arg Val Leu His Val Asp Ser Arg Ser Tyr Tyr Gly Gly Asn Trp Ala
            35                  40                  45

Ser Phe Ser Phe Ser Gly Leu Leu Ser Trp Leu Lys Glu Tyr Gln Glu
    50                  55                  60

Asn Ser Asp Ile Val Ser Asp Ser Pro Val Trp Gln Asp Gln Ile Leu
65                  70                  75                  80

Glu Asn Glu Glu Ala Ile Ala Leu Ser Arg Lys Asp Lys Thr Ile Gln
                85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125

Asn Ser Thr Glu Ala Ala Asp Ser Ala Phe Leu Pro Thr Glu Asp Glu
    130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
                165                 170                 175

Glu Lys Glu Asn His Cys Asp Asp Lys Thr Cys Val Pro Ser Thr Ser
            180                 185                 190

Ala Glu Asp Met Ser Glu Asn Val Pro Ile Ala Glu Asp Thr Thr Glu
        195                 200                 205

Gln Pro Lys Lys Asn Arg Ile Thr Tyr Ser Gln Ile Ile Lys Glu Gly
    210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
                245                 250                 255

Phe Lys Asn Ile Thr Arg Ile Leu Ala Phe Arg Glu Gly Arg Val Glu
            260                 265                 270

Gln Val Pro Cys Ser Arg Ala Asp Val Phe Asn Ser Lys Gln Leu Thr
        275                 280                 285

Met Val Glu Lys Arg Met Leu Met Lys Phe Leu Thr Phe Cys Met Glu
    290                 295                 300

Tyr Glu Lys Tyr Pro Asp Glu Tyr Lys Gly Tyr Glu Glu Ile Thr Phe
305                 310                 315                 320
```

```
Tyr Glu Tyr Leu Lys Thr Gln Lys Leu Thr Pro Asn Leu Gln Tyr Ile
            325                 330                 335

Val Met His Ser Ile Ala Met Thr Ser Glu Thr Ala Ser Ser Thr Ile
        340                 345                 350

Asp Gly Leu Lys Ala Thr Lys Asn Phe Leu His Cys Leu Gly Arg Tyr
            355                 360                 365

Gly Asn Thr Pro Phe Leu Phe Pro Leu Tyr Gly Gln Gly Glu Leu Pro
        370                 375                 380

Gln Cys Phe Cys Arg Met Cys Ala Val Phe Gly Ile Tyr Cys Leu
385                 390                 395                 400

Arg His Ser Val Gln Cys Leu Val Val Asp Lys Glu Ser Arg Lys Cys
                405                 410                 415

Lys Ala Ile Ile Asp Gln Phe Gly Gln Arg Ile Ile Ser Glu His Phe
            420                 425                 430

Leu Val Glu Asp Ser Tyr Phe Pro Glu Asn Met Cys Ser Arg Val Gln
        435                 440                 445

Tyr Arg Gln Ile Ser Arg Ala Val Leu Ile Thr Asp Arg Ser Val Leu
    450                 455                 460

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
                485                 490                 495

Met Thr Cys Met Lys Gly Thr Tyr Leu Val His Leu Thr Cys Thr Ser
            500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Glu Gln Val Glu Lys Pro
    530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605

Pro Asn Pro Glu Asp Ile Ile Leu Asp Gly Asp Ser Leu Gln Pro Glu
    610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650

<210> SEQ ID NO 7
<211> LENGTH: 9187
<212> TYPE: DNA
<213> ORGANISM: Artificial Sequence
<220> FEATURE:
<223> OTHER INFORMATION: constructed plasmid
<220> FEATURE:
<221> NAME/KEY: misc_feature
<222> LOCATION: (1)..(145)
<223> OTHER INFORMATION: 5' ITR
<220> FEATURE:
<221> NAME/KEY: promoter
<222> LOCATION: (169)..(1786)
<223> OTHER INFORMATION: CMV.CBA promoter
<220> FEATURE:
```

```
<221> NAME/KEY: misc_feature
<222> LOCATION: (1787)..(1794)
<223> OTHER INFORMATION: Not I cloning site, cuts at 1789
<220> FEATURE:
<221> NAME/KEY: misc_feature
<222> LOCATION: (1805)..(1810)
<223> OTHER INFORMATION: BamHI cloning site, cuts at 1806
<220> FEATURE:
<221> NAME/KEY: polyA_signal
<222> LOCATION: (1850)..(2052)
<223> OTHER INFORMATION: BGH PolyA
<220> FEATURE:
<221> NAME/KEY: misc_feature
<222> LOCATION: (2109)..(2252)
<223> OTHER INFORMATION: 3' ITR
<220> FEATURE:
<221> NAME/KEY: misc_feature
<222> LOCATION: (2571)..(6624)
<223> OTHER INFORMATION: lambda stuffer
<220> FEATURE:
<221> NAME/KEY: misc_feature
<222> LOCATION: (7314)..(8126)
<223> OTHER INFORMATION: Kanamycin resistance (complementary)
<220> FEATURE:
<221> NAME/KEY: misc_feature
<222> LOCATION: (8485)..(9128)
<223> OTHER INFORMATION: Origin of replication (complementary)

<400> SEQUENCE: 7
tcgctcgctc actgaggccg cccgggcaaa gcccgggcgt cgggcgacct ttggtcgccc      60
ggcctcagtg agcgagcgag cgcgcagaga gggagtggcc aactccatca ctaggggttc     120
ctgcggccta gtaggctcag aggcacacag gagtttctgc aaatctagtg caggcgttac     180
ataacttacg gtaaatggcc cgcctggctg accgcccaac gacccccgcc cattgacgtc     240
aataatgacg tatgttccca tagtaacgcc aatagggact ttccattgac gtcaatgggt     300
ggagtattta cggtaaactg cccacttggc agtacatcaa gtgtatcata tgccaagtac     360
gccccctatt gacgtcaatg acggtaaatg gcccgcctgg cattatgccc agtacatgac     420
cttatgggac tttcctactt ggcagtacat ctacgtatta gtcatcgcta ttaacatggt     480
cgaggtgagc cccacgttct gcttcactct ccccatctcc cccccctccc cacccccaat     540
tttgtattta tttattttt aattatttttg tgcagcgatg ggggcggggg ggggggggg      600 gcgcgcgcca ggcggggcgg ggcggggcga ggggcggggc gggggcgaggc ggagaggtgc     660 ggcggcagcc aatcagagcg gcgcgctccg aaagtttcct tttatggcga ggcggcggcg     720
gcggcggccc tataaaaagc gaagcgcgcg gcgggcgggg agtcgctgcg acgctgcctt     780
cgccccgtgc cccgctccgc cgccgcctcg cgccgcccgc cccggctctg actgaccgcg     840
ttactcccac aggtgagcgg gcgggacggc ccttctcctc cgggctgtaa ttagcgcttg     900
gtttaatgac ggcttgtttc ttttctgtgg ctgcgtgaaa gccttgaggg gctccgggag     960
ggccctttgt gcggggggag cggctcgggg ggtgcgtgcg tgtgtgtgtg cgtggggagc    1020
gccgcgtgcg gctccgcgct gcccggcggc tgtgagcgct gcgggcgcgg cgcggggctt    1080
tgtgcgctcc gcagtgtgcg cgaggggagc gcggccgggg gcggtgcccc gcggtgcggg    1140 ggggctgcg aggggaacaa aggctgcgtg cggggtgtgt gcgtgggggg gtgagcaggg    1200
ggtgtgggcg cgtcggtcgg gctgcaaccc cccctgcacc cccctccccg agttgctgag    1260
cacggcccgg cttcgggtgc ggggctccgt acggggcgtg gcgcggggct cgccgtgccg    1320
ggcggggggt ggcggcaggt gggggtgccg ggcggggcgg ggccgcctcg ggccggggag    1380
ggctcggggg aggggcgcgg cggccccgg agcgccggcg gctgtcgagg gcggcgagc    1440 cgcagccatt gccttttatg gtaatcgtgc gagagggcgc agggacttcc tttgtcccaa    1500
```

```
atctgtgcgg agccgaaatc tgggaggcgc cgccgcaccc cctctagcgg gcgcggggcg    1560
aagcggtgcg gcgccggcag gaaggaaatg ggcggggagg gccttcgtgc gtcgccgcgc    1620
cgccgtcccc ttctccctct ccagcctcgg ggctgtccgc ggggggacgg ctgccttcgg    1680
gggggacggg gcagggcggg gttcggcttc tggcgtgtga ccggcggctc tagacaattg    1740
tactaacctt cttctctttc ctctcctgac aggttggtgt acactagcgg ccgcatagta    1800
ctgcggatcc tgcagatctc gagccgaatt cctgcagccc gggggatcag cctcgactgt    1860
gccttctagt tgccagccat ctgttgtttg cccctccccc gtgccttcct gaccctgga    1920 aggtgccact cccactgtcc tttcctaata aaatgaggaa attgcatcgc attgtctgag    1980
taggtgtcat tctattctgg ggggtggggt ggggcaggac agcaaggggg aggattggga    2040
agacaatagc aggcatgctg gggatgcggt gggctctatg gcttctgagg cggaaagaac    2100
cagctggggc tcgagatcca ctagggccgc aggaaccccct agtgatggag ttggccactc    2160
cctctctgcg cgctcgctcg ctcactgagg ccgggcgacc aaaggtcgcc cgacgcccgg    2220
gctttgcccg gcggcctca gtgagcgagc gacctgcagg ggcagcttga aggaaatact    2280
aaggcaaagg tactgcaagt gctcgcaaca ttcgcttatg cggattattg ccgtagtgcc    2340
gcgacgccgg gggcaagatg cagagattgc catggtacag gccgtgcggt tgatattgcc    2400
aaaacagagc tgtgggggag agttgtcgag aaagagtgcg gaagatgcaa aggcgtcggc    2460
tattcaagga tgccagcaag cgcagcatat cgcgctgtga cgatgctaat cccaaacctt    2520
acccaaccca cctggtcacg cactgttaag ccgctgtatg acgctctggt ggtgcaatgc    2580
cacaaagaag agtcaatcgc agacaacatt ttgaatgcgg tcacacgtta gcagcatgat    2640
tgccacggat ggcaacatat taacggcatg atattgactt attgaataaa attgggtaaa    2700
tttgactcaa cgatgggtta attcgctcgt tgtggtagtg agatgaaaag aggcggcgct    2760
tactaccgat tccgcctagt tggtcacttc gacgtatcgt ctggaactcc aaccatcgca    2820
ggcagagagg tctgcaaaat gcaatcccga aacagttcgc aggtaatagt tagagcctgc    2880
ataacggttt cgggattttt tatatctgca caacaggtaa gagcattgag tcgataatcg    2940
tgaagagtcg gcgagcctgg ttagccagtg ctctttccgt tgtgctgaat taagcgaata    3000
ccggaagcag aaccggatca ccaaatgcgt acaggcgtca tcgccgccca gcaacagcac    3060
aacccaaact gagccgtagc cactgtctgt cctgaattca ttagtaatag ttacgctgcg    3120
gccttttaca catgaccttc gtgaaagcgg gtggcaggag gtcgcgctaa caacctcctg    3180
ccgttttgcc cgtgcatatc ggtcacgaac aaatctgatt actaaacaca gtagcctgga    3240
tttgttctat cagtaatcga ccttattcct aattaaatag agcaaatccc cttattgggg    3300
gtaagacatg aagatgccag aaaaacatga cctgttggcc gccattctcg cggcaaagga    3360
acaaggcatc ggggcaatcc ttgcgtttgc aatggcgtac cttcgcggca gatataatgg    3420
cggtgcgttt acaaaaacag taatcgacgc aacgatgtgc gccattatcg cctggttcat    3480
tcgtgacctt ctcgacttcg ccggactaag tagcaatctc gcttatataa cgagcgtgtt    3540
tatcggctac atcggtactg actcgattgg ttcgcttatc aaacgcttcg ctgctaaaaa    3600
agccggagta gaagatggta gaaatcaata atcaacgtaa ggcgttcctc gatatgctgg    3660
cgtggtcgga gggaactgat aacggacgtc agaaaaccag aaatcatggt tatgacgtca    3720
ttgtaggcgg agagctattt actgattact ccgatcaccc tcgcaaactt gtcacgctaa    3780
acccaaaact caaatcaaca ggcgccggac gctaccagct tctttcccgt tggtgggatg    3840
```

```
cctaccgcaa gcagcttggc ctgaaagact tctctccgaa aagtcaggac gctgtggcat    3900
tgcagcagat taaggagcgt ggcgctttac ctatgattga tcgtggtgat atccgtcagg    3960
caatcgaccg ttgcagcaat atctgggctt cactgccggg cgctggttat ggtcagttcg    4020
agcataaggc tgacagcctg attgcaaaat tcaaagaagc gggcggaacg gtcagagaga    4080
ttgatgtatg agcagagtca ccgcgattat ctccgctctg gttatctgca tcatcgtctg    4140
cctgtcatgg gctgttaatc attaccgtga taacgccatt acctacaaag cccagcgcga    4200
caaaaatgcc agagaactga agctggcgaa cgcggcaatt actgacatgc agatgcgtca    4260
gcgtgatgtt gctgcgctcg atgcaaaata cacgaaggag ttagctgatg ctaaagctga    4320
aaatgatgct ctgcgtgatg atgttgccgc tggtcgtcgt cggttgcaca tcaaagcagt    4380
ctgtcagtca gtgcgtgaag ccaccaccgc ctccggcgtg ataatgcag cctcccccg     4440 actggcagac accgctgaac gggattattt caccctcaga gagaggctga tcactatgca    4500
aaaacaactg gaaggaaccc agaagtatat taatgagcag tgcagataga gttgcccata    4560
tcgatgggca actcatgcaa ttattgtgag caatacacac gcgcttccag cggagtataa    4620
atgcctaaag taataaaacc gagcaatcca tttacgaatg tttgctgggt ttctgttttta   4680 acaacatttt ctgcgccgcc acaaattttg gctgcatcga cagttttctt ctgcccaatt    4740
ccagaaacga agaaatgatg ggtgatggtt cctttggtg ctactgctgc cggtttgttt     4800
tgaacagtaa acgtctgttg agcacatcct gtaataagca gggccagcgc agtagcgagt    4860 agcattttt tcatggtgtt attcccgatg cttttgaag ttcgcagaat cgtatgtgta      4920
gaaaattaaa caaaccctaa acaatgagtt gaaatttcat attgttaata tttattaatg    4980
tatgtcaggt gcgatgaatc gtcattgtat tcccggatta actatgtcca cagccctgac    5040
ggggaacttc tctgcgggag tgtccgggaa taattaaaac gatgcacaca gggtttagcg    5100
cgtacacgta ttgcattatg ccaacgcccc ggtgctgaca cggaagaaac cggacgttat    5160
gatttagcgt ggaaagattt gtgtagtgtt ctgaatgctc tcagtaaata gtaatgaatt    5220
atcaaaggta tagtaatatc ttttatgttc atggatattt gtaacccatc ggaaaactcc    5280
tgctttagca agattttccc tgtattgctg aaatgtgatt tctcttgatt tcaacctatc    5340
ataggacgtt tctataagat gcgtgtttct tgagaattta acatttacaa cctttttaag    5400 tcctttttatt aacacggtgt tatcgttttc taacacgatg tgaatattat ctgtggctag   5460
atagtaaata taatgtgaga cgttgtgacg ttttagttca gaataaaaca attcacagtc    5520
taaatctttt cgcacttgat cgaatatttc tttaaaaatg gcaacctgag ccattggtaa    5580
aaccttccat gtgatacgag ggcgcgtagt ttgcattatc gtttttatcg tttcaatctg    5640
gtctgacctc cttgtgtttt gttgatgatt tatgtcaaat attaggaatg ttttcactta    5700
atagtattgg ttgcgtaaca aagtgcggtc ctgctggcat tctggaggga aatacaaccg    5760
acagatgtat gtaaggccaa cgtgctcaaa tcttcataca gaaagatttg aagtaatatt    5820
ttaaccgcta gatgaagagc aagcgcatgg agcgacaaaa tgaataaaga acaatctgct    5880
gatgatccct ccgtggatct gattcgtgta aaaaatatgc ttaatagcac catttctatg    5940
agttaccctg atgttgtaat tgcatgtata gaacataagg tgtctctgga agcattcaga    6000
gcaattgagg cagcgttggt gaagcacgat aataatatga aggattattc cctggtggtt    6060
gactgatcac cataactgct aatcattcaa actatttagt ctgtgacaga gccaacacgc    6120
agtctgtcac tgtcaggaaa gtggtaaaac tgcaactcaa ttactgcaat gccctcgtaa    6180
ttaagtgaat ttacaatatc gtcctgttcg gagggaagaa cgcgggatgt tcattcttca    6240
```

```
tcactttaa ttgatgtata tgctctcttt tctgacgtta gtctccgacg gcaggcttca    6300
atgacccagg ctgagaaatt cccggaccct ttttgctcaa gagcgatgtt aatttgttca    6360
atcatttggt taggaaagcg gatgttgcgg gttgttgttc tgcgggttct gttcttcgtt    6420
gacatgaggt tgccccgtat tcagtgtcgc tgatttgtat tgtctgaagt tgttttacg     6480 ttaagttgat gcagatcaat taatacgata cctgcgtcat aattgattat ttgacgtggt    6540
ttgatggcct ccacgcacgt tgtgatatgt agatgataat cattatcact ttacgggtcc    6600
tttccggtga tccgacaggt tacggcctga tgcggtattt tctccttacg catctgtgcg    6660
gtatttcaca ccgcatacgt caaagcaacc atagtacgcg ccctgtagcg gcgcattaag    6720
cgcggcgggt gtggtggtta cgcgcagcgt gaccgctaca cttgccagcg ccctagcgcc    6780
cgctcctttc gctttcttcc cttcctttct cgccacgttc gccggctttc ccgtcaagc     6840 tctaaatcgg gggctccctt tagggttccg atttagtgct ttacggcacc tcgaccccaa    6900
aaaacttgat ttgggtgatg gttcacgtag tgggccatcg ccctgataga cggttttcg     6960 ccctttgacg ttggagtcca cgttctttaa tagtggactc ttgttccaaa ctggaacaac    7020
actcaaccct atctcgggct attcttttga tttagacctg caggcatgca agcttactgg    7080
ccgtcgtttt acaacgtcgt gactgggaaa accctggcgt tacccaactt aatcgccttg    7140
cagcacatcc ccctttcgcc agctggcgta atagcgaaga ggcccgcacc gatcgccctt    7200
cccaacagtt gcgcagcctg aatggcgaat gcgatttatt caacaaagcc gccgtcccgt    7260
caagtcagcg taatgctctg ccagtgttac aaccaattaa ccaattctga ttagaaaaac    7320
tcatcgagca tcaaatgaaa ctgcaattta ttcatatcag gattatcaat accatatttt    7380
tgaaaaagcc gtttctgtaa tgaaggagaa aactcaccga ggcagttcca taggatggca    7440
agatcctggt atcggtctgc gattccgact cgtccaacat caatacaacc tattaatttc    7500
ccctcgtcaa aaataaggtt atcaagtgag aaatcaccat gagtgacgac tgaatccggt    7560
gagaatggca aaagcttatg catttctttc cagacttgtt caacaggcca gccattacgc    7620
tcgtcatcaa aatcactcgc atcaaccaaa ccgttattca ttcgtgattg cgcctgagcg    7680
agacgaaata cgcgatcgct gttaaaagga caattacaaa caggaatcga atgcaaccgg    7740
cgcaggaaca ctgccagcgc atcaacaata ttttcacctg aatcaggata ttcttctaat    7800
acctggaatg ctgttttccc ggggatcgca gtggtgagta accatgcatc atcaggagta    7860
cggataaaat gcttgatggt cggaagaggc ataaattccg tcagccagtt tagtctgacc    7920
atctcatctg taacatcatt ggcaacgcta cctttgccat gtttcagaaa caactctggc    7980
gcatcgggct tcccatacaa tcgatagatt gtcgcacctg attgcccgac attatcgcga    8040
gcccatttat acccatataa atcagcatcc atgttggaat ttaatcgcgg cttcgagcaa    8100
gacgtttccc gttgaatatg gctcataaca ccccttgtat tactgtttat gtaagcagac    8160
agttttattg ttcatgatga tatttttta tcttgtgcaa tgtaacatca gagatttga     8220 gacacaacgt ggctttgttg aataaatcga acttttgctg agttgaagga tcagatcacg    8280
catcttcccg acaacgcaga ccgttccgtg gcaaagcaaa agttcaaaat caccaactgg    8340
tccacctaca caaagctct catcaaccgt ggctccctca ctttctggct ggatgatggg    8400
gcgattcagg cctggtatga gtcagcaaca ccttcttcac gaggcagacc tctcgacgga    8460
tcgttccact gagcgtcaga cccgtagaa aagatcaaag gatcttcttg agatccttt     8520 tttctgcgcg taatctgctg cttgcaaaca aaaaaaccac cgctaccagc ggtggttgt    8580
```

```
ttgccggatc aagagctacc aactcttttt ccgaaggtaa ctggcttcag cagagcgcag    8640
ataccaaata ctgtccttct agtgtagccg tagttaggcc accacttcaa gaactctgta    8700
gcaccgccta catacctcgc tctgctaatc ctgttaccag tggctgctgc cagtggcgat    8760
aagtcgtgtc ttaccgggtt ggactcaaga cgatagttac cggataaggc gcagcggtcg    8820
ggctgaacgg ggggttcgtg cacacagccc agcttggagc gaacgaccta caccgaactg    8880
agatacctac agcgtgagct atgagaaagc gccacgcttc ccgaagggag aaaggcggac    8940
aggtatccgg taagcggcag ggtcggaaca ggagagcgca cgagggagct tccaggggga    9000
aacgcctggt atctttatag tcctgtcggg tttcgccacc tctgacttga gcgtcgattt    9060
ttgtgatgct cgtcaggggg gcggagccta tggaaaaacg ccagcaacgc ggccttttta    9120
cggttcctgg ccttttgctg gccttttgct cacatgtcct gcaggcagct gcgcgccagc    9180
tgcgcgc                                                              9187

<210> SEQ ID NO 8
<211> LENGTH: 11148
<212> TYPE: DNA
<213> ORGANISM: Artificial Sequence
<220> FEATURE:
<223> OTHER INFORMATION: constructed plasmid

<400> SEQUENCE: 8
tcgctcgctc actgaggccg cccgggcaaa gcccgggcgt cgggcgacct ttggtcgccc      60
ggcctcagtg agcgagcgag cgcgcagaga gggagtggcc aactccatca ctaggggttc     120
ctgcggccta gtaggctcag aggcacacag gagtttctgc aaatctagtg caggcgttac     180
ataacttacg gtaaatggcc cgcctggctg accgcccaac gacccccgcc cattgacgtc     240
aataatgacg tatgttccca tagtaacgcc aatagggact ttccattgac gtcaatgggt     300
ggagtattta cggtaaactg cccacttggc agtacatcaa gtgtatcata tgccaagtac     360
gccccctatt gacgtcaatg acggtaaatg gcccgcctgg cattatgccc agtacatgac     420
cttatgggac tttcctactt ggcagtacat ctacgtatta gtcatcgcta ttaacatggt     480
cgaggtgagc cccacgttct gcttcactct ccccatctcc cccccctccc cacccccaat     540
tttgtattta tttatttttt aattattttg tgcagcgatg ggggcggggg gggggggggg     600
gcgcgcgcca ggcggggcgg ggcggggcga ggggcggggc gggcgaggc ggagaggtgc     660
ggcggcagcc aatcagagcg gcgcgctccg aaagtttcct tttatggcga ggcggcggcg     720
gcggcggccc tataaaaagc gaagcgcgcg gcgggcgggg agtcgctgcg acgctgcctt     780
cgccccgtgc cccgctccgc cgccgcctcg cgccgcccgc cccggctctg actgaccgcg     840
ttactcccac aggtgagcgg gcgggacggc ccttctcctc cgggctgtaa ttagcgcttg     900
gtttaatgac ggcttgtttc ttttctgtgg ctgcgtgaaa gccttgaggg gctccgggag     960
ggccctttgt gcgggggggag cggctcgggg ggtgcgtgcg tgtgtgtgtg cgtggggagc    1020
gccgcgtgcg gctccgcgct gcccggcggc tgtgagcgct gcgggcgcgg cgcggggctt    1080
tgtgcgctcc gcagtgtgcg cgaggggagc gcggccgggg gcggtgcccc gcggtgcggg    1140
gggggctgcg aggggaacaa aggctgcgtg cgggtgtgt gcgtgggggg gtgagcaggg    1200
ggtgtgggcg cgtcggtcgg gctgcaaccc cccctgcacc ccctccccg agttgctgag    1260
cacgccccgg cttcgggtgc ggggctccgt acggggcgtg gcgcggggct cgccgtgccg    1320
ggcgggggt ggcggcaggt gggggtgccg gcggggcgg ggccgcctcg ggccggggag    1380
ggctcggggg aggggcgcgg cggcccccgg agcgccggcg gctgtcgagg cgcggcgagc    1440
```

```
cgcagccatt gccttttatg gtaatcgtgc gagagggcgc agggacttcc tttgtcccaa    1500
atctgtgcgg agccgaaatc tgggaggcgc cgccgcaccc cctctagcgg gcgcggggcg    1560
aagcggtgcg gcgccggcag gaaggaaatg ggcggggagg gccttcgtgc gtcgccgcgc    1620
cgccgtcccc ttctccctct ccagcctcgg ggctgtccgc ggggggacgg ctgccttcgg    1680 ggggacggg gcagggcggg gttcggcttc tggcgtgtga ccggcggctc tagacaattg    1740
tactaacctt cttctctttc ctctcctgac aggttggtgt acactagcgg ccgccaccat    1800
ggctgatacc ctgccctctg aattcgacgt gattgtgatt ggaaccggac tccctgaatc    1860
gatcatcgcc gcggcctgtt cccggtccgg tcggcgcgtg ctgcacgtcg attcgagaag    1920
ctactacgga gggaattggg cctcattctc cttctccgga ctgctctcct ggctgaagga    1980
gtatcaggag aactccgaca ttgtctccga ctcacctgtg tggcaggacc agatcctgga    2040
aaacgaggaa gcaatagccc tgagccggaa ggacaagacc atccagcacg tggaggtgtt    2100
ctgttatgcc tcccaagacc tccatgagga cgtggaagag gctggagcgt tgcagaagaa    2160
tcatgccctc gtgacctccg ctaactccac cgaggcagcc gacagcgcct tcctgccgac    2220
cgaggatgaa tccctgtcaa ctatgtcgtg cgaaatgctg accgaacaga ctccgagctc    2280
cgaccccgaa aacgccctgg aagtgaacgg agcggaagtg accggcgaaa aggagaacca    2340
ttgcgacgac aagacttgtg tcccatccac ttccgcggag gacatgtccg agaatgtgcc    2400
tatcgccgag gacaccaccg aacagcccaa gaagaacaga atcacgtaca gccagatcat    2460
caaggagggg cggaggttta acatcgatct ggtgtcgaag ctgctgtaca gccgcggtct    2520
gctgatcgat ctgctcatta agtcgaacgt gtcgagatac gccgagttca gaacatcac    2580 aaggattctc gccttccggg aaggaagagt ggaacaagtg ccgtgctccc gggccgacgt    2640
gttcaactca aagcaactta ccatggtgga aaagcgcatg ctgatgaaat tcctgacctt    2700
ctgcatggag tacgaaaagt accctgatga gtacaagggt tacgaagaaa ttactttcta    2760
cgagtacctc aagacccaga agctgacccc gaatctgcag tacattgtga tgcactcaat    2820
cgcaatgacc tccgaaaccg cctcctcgac catcgacggg ctcaaggcca ccaagaactt    2880
cctgcactgt ttggggcgct acggcaacac tccgttcctc ttcccgctgt acggccaggg    2940
agagctgcct cagtgtttct gccggatgtg cgccgtgttc ggcggaatct actgtctccg    3000
ccactcggtc cagtgcctgg tggtggacaa ggaatccagg aagtgcaaag ccattattga    3060
ccagttcgga caacggatca tttccgagca cttttcttgtg gaggactcat acttcccgga    3120
gaacatgtgc tctcgggtcc agtatcgaca gatttccagg gcggtgctca ttactgaccg    3180
gagcgtcctc aagaccgata gcgaccagca gatctccatc ctgaccgtgc ggcggaaga    3240 acccggcact tttgccgtgc gcgtgatcga gctttgctca tccaccatga cttgcatgaa    3300
aggcacttac ctggtgcacc tgacgtgcac ctcatcgaaa accgctagag aggacctgga    3360
atccgtcgtc caaaagctgt tcgtgcctta caccagatg gaaattgaaa cgaacaagt    3420 ggagaagccc cgcatccttt gggccctgta ctttaacatg cgcgattcct ccgatatctc    3480
gcggtcctgc tataacgact tgccttcgaa cgtctacgtc tgctccgggc cagactgcgg    3540
tcttggcaac gacaatgccg tgaagcaggc ggaaacactg ttccaagaga tctgcccaa    3600 cgaggatttt tgcccgcccc ccaaaccc gaggatatc atcttggacg gagacagcct    3660
gcagccagaa gcatccgagt ccagcgccat cccggaggcc aacagcgaaa ccttcaagga    3720
gagcactaac ctgggcaacc tggaagagtc cagcgaatga tcataggatc ctgcagatct    3780
```

```
cgagccgaat tcctgcagcc cggggatca gcctcgactg tgccttctag ttgccagcca    3840
tctgttgttt gccctcccc cgtgccttcc ttgaccctgg aaggtgccac tcccactgtc    3900
ctttcctaat aaaatgagga aattgcatcg cattgtctga gtaggtgtca ttctattctg   3960
gggggtgggg tggggcagga cagcaagggg gaggattggg aagacaatag caggcatgct   4020
ggggatgcgg tgggctctat ggcttctgag gcggaaagaa ccagctgggg ctcgagatcc   4080
actagggccg caggaacccc tagtgatgga gttggccact ccctctctgc gcgctcgctc   4140
gctcactgag gccgggcgac caaaggtcgc ccgacgcccg ggctttgccc gggcggcctc   4200
agtgagcgag cgacctgcag gggcagcttg aaggaaatac taaggcaaag gtactgcaag   4260
tgctcgcaac attcgcttat gcggattatt gccgtagtgc cgcgacgccg ggggcaagat   4320
gcagagattg ccatggtaca ggccgtgcgg ttgatattgc caaaacagag ctgtggggga   4380
gagttgtcga gaaagagtgc ggaagatgca aaggcgtcgg ctattcaagg atgccagcaa   4440
gcgcagcata tcgcgctgtg acgatgctaa tcccaaacct tacccaaccc acctggtcac   4500
gcactgttaa gccgctgtat gacgctctgg tggtgcaatg ccacaaagaa gagtcaatcg   4560
cagacaacat tttgaatgcg gtcacacgtt agcagcatga ttgccacgga tggcaacata   4620
ttaacggcat gatattgact tattgaataa aattgggtaa atttgactca acgatgggtt   4680
aattcgctcg ttgtggtagt gagatgaaaa gaggcggcgc ttactaccga ttccgcctag   4740
ttggtcactt cgacgtatcg tctgaactc caaccatcgc aggcagagag gtctgcaaaa   4800
tgcaatcccg aaacagttcg caggtaatag ttagagcctg cataacggtt tcgggatttt   4860
ttatatctgc acaacaggta agagcattga gtcgataatc gtgaagagtc ggcgagcctg   4920
gttagccagt gctctttccg ttgtgctgaa ttaagcgaat accggaagca gaaccggatc   4980
accaaatgcg tacaggcgtc atcgccgccc agcaacagca caacccaaac tgagccgtag   5040
ccactgtctg tcctgaattc attagtaata gttacgctgc ggccttttac acatgacctt   5100
cgtgaaagcg ggtggcagga ggtcgcgcta acaacctcct gccgttttgc ccgtgcatat   5160
cggtcacgaa caaatctgat tactaaacac agtagcctgg atttgttcta tcagtaatcg   5220
accttattcc taattaaata gagcaaatcc cctattgggg gtaagacat gaagatgcca    5280
gaaaaacatg acctgttggc cgccattctc gcggcaaagg aacaaggcat cggggcaatc   5340
cttgcgtttg caatgcgta ccttcgcggc agatataatg gcggtgcgtt tacaaaaaca   5400
gtaatcgacg caacgatgtg cgccattatc gcctggttca ttcgtgacct tctcgacttc   5460
gccggactaa gtagcaatct cgcttatata acgagcgtgt ttatcggcta catcggtact   5520
gactcgattg gttcgcttat caaacgcttc gctgctaaaa aagccggagt agaagatggt   5580
agaaatcaat aatcaacgta aggcgttcct cgatatgctg cgtggtcgg agggaactga    5640
taacggacgt cagaaaacca gaaatcatgg ttatgacgtc attgtaggcg gagagctatt   5700
tactgattac tccgatcacc ctcgcaaact tgtcacgcta aacccaaaac tcaaatcaac   5760
aggcgccgga cgctaccagc ttcttttccg ttggtgggat gcctaccgca agcagcttgg   5820
cctgaaagac ttctctccga aaagtcagga cgctgtggca ttgcagcaga ttaaggagcg   5880
tggcgcttta cctatgattg atcgtggtga tatccgtcag gcaatcgacc gttgcagcaa   5940
tatctgggct tcactgccgg cgctggtta tggtcagttc gagcataagg ctgacagcct   6000
gattgcaaaa ttcaaagaag cgggcggaac ggtcagagag attgatgtat gagcagagtc   6060
accgcgatta tctccgctct ggttatctgc atcatcgtct gcctgtcatg ggctgttaat   6120
cattaccgtg ataacgccat tacctacaaa gcccagcgcg acaaaaatgc cagagaactg   6180
```

```
aagctggcga acgcggcaat tactgacatg cagatgcgtc agcgtgatgt tgctgcgctc    6240
gatgcaaaat acacgaagga gttagctgat gctaaagctg aaaatgatgc tctgcgtgat    6300
gatgttgccg ctggtcgtcg tcggttgcac atcaaagcag tctgtcagtc agtgcgtgaa    6360
gccaccaccg cctccggcgt ggataatgca gcctccccc gactggcaga caccgctgaa     6420
cgggattatt tcaccctcag agagaggctg atcactatgc aaaaacaact ggaaggaacc    6480
cagaagtata ttaatgagca gtgcagatag agttgcccat atcgatgggc aactcatgca    6540
attattgtga gcaatacaca cgcgcttcca gcggagtata aatgcctaaa gtaataaaac    6600
cgagcaatcc atttacgaat gtttgctggg tttctgtttt aacaacattt tctgcgccgc    6660
cacaaatttt ggctgcatcg acagttttct tctgcccaat tccagaaacg aagaaatgat    6720
gggtgatggt ttcctttggt gctactgctg ccggtttgtt ttgaacagta aacgtctgtt    6780
gagcacatcc tgtaataagc agggccagcg cagtagcgag tagcattttt ttcatggtgt    6840
tattcccgat gctttttgaa gttcgcagaa tcgtatgtgt agaaaattaa acaaaccta    6900 aacaatgagt tgaaatttca tattgttaat atttattaat gtatgtcagg tgcgatgaat    6960
cgtcattgta ttcccggatt aactatgtcc acagccctga cggggaactt ctctgcggga    7020
gtgtccggga ataattaaaa cgatgcacac agggtttagc gcgtacacgt attgcattat    7080
gccaacgccc cggtgctgac acggaagaaa ccggacgtta tgatttagcg tggaaagatt    7140
tgtgtagtgt tctgaatgct ctcagtaaat agtaatgaat tatcaaaggt atagtaatat    7200
cttttatgtt catggatatt tgtaacccat cggaaaactc ctgctttagc aagattttcc    7260
ctgtattgct gaaatgtgat ttctcttgat ttcaacctat cataggacgt ttctataaga    7320
tgcgtgtttc ttgagaattt aacatttaca accttttaa gtccttttat taacacggtg     7380
ttatcgtttt ctaacacgat gtgaatatta tctgtggcta gatagtaaat ataatgtgag    7440
acgttgtgac gttttagttc agaataaaac aattcacagt ctaaatcttt tcgcacttga    7500
tcgaatattt ctttaaaaat ggcaacctga gccattggta aaaccttcca tgtgatacga    7560
gggcgcgtag tttgcattat cgttttatc gtttcaatct ggtctgacct ccttgtgttt     7620
tgttgatgat ttatgtcaaa tattaggaat gttttcactt aatagtattg gttgcgtaac    7680
aaagtgcggt cctgctggca ttctggaggg aaatacaacc gacagatgta tgtaaggcca    7740
acgtgctcaa atcttcatac agaaagattt gaagtaatat tttaaccgct agatgaagag    7800
caagcgcatg gagcgacaaa atgaataaag aacaatctgc tgatgatccc tccgtggatc    7860
tgattcgtgt aaaaaaatatg cttaatagca ccatttctat gagttaccct gatgttgtaa    7920
ttgcatgtat agaacataag gtgtctctgg aagcattcag agcaattgag gcagcgttgg    7980
tgaagcacga taataatatg aaggattatt ccctggtggt tgactgatca ccataactgc    8040
taatcattca aactatttag tctgtgacag agccaacacg cagtctgtca ctgtcaggaa    8100
agtggtaaaa ctgcaactca attactgcaa tgccctcgta attaagtgaa tttacaatat    8160
cgtcctgttc ggagggaaga acgcgggatg ttcattcttc atcacttta attgatgtat     8220 atgctctctt ttctgacgtt agtctccgac ggcaggcttc aatgacccag gctgagaaat    8280
tcccggaccc tttttgctca agagcgatgt taatttgttc aatcatttgg ttaggaaagc    8340
ggatgttgcg ggttgttgtt ctgcgggttc tgttcttcgt tgacatgagg ttgccccgta    8400
ttcagtgtcg ctgatttgta ttgtctgaag ttgttttttac gttaagttga tgcagatcaa    8460
ttaatacgat acctgcgtca taattgatta tttgacgtgg tttgatggcc tccacgcacg    8520
```

```
ttgtgatatg tagatgataa tcattatcac tttacgggtc ctttccggtg atccgacagg    8580
ttacggcctg atgcggtatt ttctccttac gcatctgtgc ggtatttcac accgcatacg    8640
tcaaagcaac catagtacgc gccctgtagc ggcgcattaa gcgcggcggg tgtggtggtt    8700
acgcgcagcg tgaccgctac acttgccagc gccctagcgc ccgctccttt cgctttcttc    8760
ccttcctttc tcgccacgtt cgccggcttt ccccgtcaag ctctaaatcg ggggctccct    8820
ttagggttcc gatttagtgc tttacggcac ctcgacccca aaaaacttga tttgggtgat    8880
ggttcacgta gtgggccatc gccctgatag acggtttttc gccctttgac gttggagtcc    8940
acgttcttta atagtggact cttgttccaa actggaacaa cactcaaccc tatctcgggc    9000
tattcttttg atttagacct gcaggcatgc aagcttactg gccgtcgttt tacaacgtcg    9060
tgactgggaa accctggcg ttacccaact taatcgcctt gcagcacatc cccctttcgc    9120
cagctggcgt aatagcgaag aggcccgcac cgatcgccct tcccaacagt tgcgcagcct    9180
gaatggcgaa tgcgatttat tcaacaaagc cgccgtcccg tcaagtcagc gtaatgctct    9240
gccagtgtta caaccaatta accaattctg attagaaaaa ctcatcgagc atcaaatgaa    9300
actgcaattt attcatatca ggattatcaa taccatattt tgaaaaagc cgtttctgta    9360
atgaaggaga aaactcaccg aggcagttcc ataggatggc aagatcctgg tatcggtctg    9420
cgattccgac tcgtccaaca tcaatacaac ctattaattt ccctcgtca aaaataaggt     9480
tatcaagtga gaaatcacca tgagtgacga ctgaatccgg tgagaatggc aaaagcttat    9540
gcatttcttt ccagacttgt tcaacaggcc agccattacg ctcgtcatca aaatcactcg    9600
catcaaccaa accgttattc attcgtgatt gcgcctgagc gagacgaaat acgcgatcgc    9660
tgttaaaagg acaattacaa acaggaatcg aatgcaaccg gcgcaggaac actgccagcg    9720
catcaacaat atttcacct gaatcaggat attcttctaa tacctggaat gctgttttcc    9780
cggggatcgc agtggtgagt aaccatgcat catcaggagt acggataaaa tgcttgatgg    9840
tcggaagagg cataaattcc gtcagccagt ttagtctgac catctcatct gtaacatcat    9900
tggcaacgct accttgcca tgtttcagaa acaactctgg cgcatcgggc ttcccataca    9960
atcgatagat tgtcgcacct gattgcccga cattatcgcg agcccattta tacccatata   10020
aatcagcatc catgttggaa tttaatcgcg gcttcgagca agacgtttcc cgttgaatat   10080
ggctcataac acccccttgta ttactgttta tgtaagcaga cagttttatt gttcatgatg   10140
atatatttttt atcttgtgca atgtaacatc agagattttg agacacaacg tggctttgtt   10200
gaataaatcg aacttttgct gagttgaagg atcagatcac gcatcttccc gacaacgcag   10260
accgttccgt ggcaaagcaa aagttcaaaa tcaccaactg gtccacctac aacaaagctc   10320
tcatcaaccg tggctccctc actttctggc tggatgatgg ggcgattcag gcctggtatg   10380
agtcagcaac accttcttca cgaggcagac ctctcgacgg atcgttccac tgagcgtcag   10440
accccgtaga aaagatcaaa ggatcttctt gagatccttt ttttctgcgc gtaatctgct   10500
gcttgcaaac aaaaaaacca ccgctaccag cggtggtttg tttgccggat caagagctac   10560
caactctttt tccgaaggta actggcttca gcagagcgca gataccaaat actgtccttc   10620
tagtgtagcc gtagttaggc caccacttca agaactctgt agcaccgcct acatacctcg   10680
ctctgctaat cctgttacca gtggctgctg ccagtggcga taagtcgtgt cttaccgggt   10740
tggactcaag acgatagtta ccggataagg cgcagcggtc gggctgaacg gggggttcgt   10800
gcacacagcc cagcttggag cgaacgacct acaccgaact gagatacta cagcgtgagc   10860
tatgagaaag cgccacgctt cccgaaggga gaaaggcgga caggtatccg gtaagcggca   10920
```
gggtcggaac aggagagcgc acgagggagc ttccagggg aaacgcctgg tatctttata    10980
gtcctgtcgg gtttcgccac ctctgacttg agcgtcgatt tttgtgatgc tcgtcagggg    11040
ggcggagcct atggaaaaac gccagcaacg cggccttttt acggttcctg gccttttgct    11100
ggccttttgc tcacatgtcc tgcaggcagc tgcgcgccag ctgcgcgc                  11148

<210> SEQ ID NO 9
<211> LENGTH: 2085
<212> TYPE: DNA
<213> ORGANISM: Artificial Sequence
<220> FEATURE:
<223> OTHER INFORMATION: codon optimized sequence
<220> FEATURE:
<221> NAME/KEY: CDS
<222> LOCATION: (1)..(2085)
<223> OTHER INFORMATION: codon-optimized ORF

<400> SEQUENCE: 9

```
atg gct aag att aac acc cag tac tca cat cca tcc cgc act cac ctc      48
Met Ala Lys Ile Asn Thr Gln Tyr Ser His Pro Ser Arg Thr His Leu
1               5                   10                  15 aaa gtc aag acc tcc gat cgg gat ctg aac cgg gct gag aat ggg ctg      96
Lys Val Lys Thr Ser Asp Arg Asp Leu Asn Arg Ala Glu Asn Gly Leu
            20                  25                  30 tcg cgc gcc cac tcg tcg tcc gag gaa acc agc agc gtg ctc cag ccg     144
Ser Arg Ala His Ser Ser Ser Glu Glu Thr Ser Ser Val Leu Gln Pro
        35                  40                  45 ggc atc gcc atg gaa act agg ggg ctg gcg gac tcc gga cag gga tcc     192
Gly Ile Ala Met Glu Thr Arg Gly Leu Ala Asp Ser Gly Gln Gly Ser
    50                  55                  60 ttc act gga cag ggt att gcc cgg ctg agc aga ctg atc ttc ctg ctt     240
Phe Thr Gly Gln Gly Ile Ala Arg Leu Ser Arg Leu Ile Phe Leu Leu
65                  70                  75                  80 cgc cgc tgg gcg gcc aga cac gtg cac cat cag gac cag gga cct gat     288
Arg Arg Trp Ala Ala Arg His Val His His Gln Asp Gln Gly Pro Asp
                85                  90                  95 agc ttc ccc gac cgc ttt agg gga gcc gag ctg aaa gaa gtg tca agc     336
Ser Phe Pro Asp Arg Phe Arg Gly Ala Glu Leu Lys Glu Val Ser Ser
            100                 105                 110 cag gag tca aac gcg cag gcc aac gtc ggc agc caa gag cct gca gac     384
Gln Glu Ser Asn Ala Gln Ala Asn Val Gly Ser Gln Glu Pro Ala Asp
        115                 120                 125 cgg gga cgc tcg gca tgg ccg ctc gca aag tgc aac act aac act tcc     432
Arg Gly Arg Ser Ala Trp Pro Leu Ala Lys Cys Asn Thr Asn Thr Ser
    130                 135                 140 aac aac acc gaa gag gaa aag aaa acc aag aag aag gat gca att gtg     480
Asn Asn Thr Glu Glu Glu Lys Lys Thr Lys Lys Lys Asp Ala Ile Val
145                 150                 155                 160 gtg gac cct tcc tcc aac ctg tac tac cgc tgg ttg acc gcc atc gcc     528
Val Asp Pro Ser Ser Asn Leu Tyr Tyr Arg Trp Leu Thr Ala Ile Ala
                165                 170                 175 ctc ccg gtc ttt tac aat tgg tat ctc ctt atc tgc cgg gcc tgc ttc     576
Leu Pro Val Phe Tyr Asn Trp Tyr Leu Leu Ile Cys Arg Ala Cys Phe
            180                 185                 190 gac gaa ctg caa tca gag tac ctg atg ctg tgg ctg gtg ctg gac tat     624
Asp Glu Leu Gln Ser Glu Tyr Leu Met Leu Trp Leu Val Leu Asp Tyr
        195                 200                 205 agc gcc gat gtg ctc tac gtc ctg gat gtg ctc gtg cgc gcc cgg acc     672
Ser Ala Asp Val Leu Tyr Val Leu Asp Val Leu Val Arg Ala Arg Thr
    210                 215                 220
```

```
gga ttc ttg gaa caa ggc ctg atg gtg tcc gac acg aat aga ctg tgg      720
Gly Phe Leu Glu Gln Gly Leu Met Val Ser Asp Thr Asn Arg Leu Trp
225                 230                 235                 240 cag cac tat aag acc aca acc cag ttc aag ctt gac gtg ctc agc ctt      768
Gln His Tyr Lys Thr Thr Thr Gln Phe Lys Leu Asp Val Leu Ser Leu
                245                 250                 255 gtg ccg act gac ctg gcc tac ctg aaa gtc gga act aac tac ccg gaa      816
Val Pro Thr Asp Leu Ala Tyr Leu Lys Val Gly Thr Asn Tyr Pro Glu
            260                 265                 270 gtc aga ttc aac cga ctc ctg aag ttc agc agg ctg ttc gag ttc ttt      864
Val Arg Phe Asn Arg Leu Leu Lys Phe Ser Arg Leu Phe Glu Phe Phe
        275                 280                 285 gac cgc acc gag act cgg acc aac tac cct aac atg ttc cgg atc gga      912
Asp Arg Thr Glu Thr Arg Thr Asn Tyr Pro Asn Met Phe Arg Ile Gly
    290                 295                 300 aat ctg gtg ctc tac ata ctg att atc atc cat tgg aac gcc tgt atc      960
Asn Leu Val Leu Tyr Ile Leu Ile Ile Ile His Trp Asn Ala Cys Ile
305                 310                 315                 320 tat ttc gcc att tcg aag ttc atc ggt ttc gga acc gat tcc tgg gtg     1008
Tyr Phe Ala Ile Ser Lys Phe Ile Gly Phe Gly Thr Asp Ser Trp Val
                325                 330                 335 tac ccc aac atc tcg atc ccc gaa cac ggt cgc ctg tcc cgg aag tac     1056
Tyr Pro Asn Ile Ser Ile Pro Glu His Gly Arg Leu Ser Arg Lys Tyr
                340                 345                 350 atc tac tcc ctg tac tgg tcc act ctg act ctg acc acg atc ggg gaa     1104
Ile Tyr Ser Leu Tyr Trp Ser Thr Leu Thr Leu Thr Thr Ile Gly Glu
            355                 360                 365 acc cct cca ccc gtg aag gac gaa gag tac ctg ttc gtg gtg gtg gac     1152
Thr Pro Pro Pro Val Lys Asp Glu Glu Tyr Leu Phe Val Val Val Asp
        370                 375                 380 ttc ctg gtc gga gtg ttg att ttc gcc acc att gtg gga aac gtg ggc     1200
Phe Leu Val Gly Val Leu Ile Phe Ala Thr Ile Val Gly Asn Val Gly
385                 390                 395                 400 tcc atg atc tcc aac atg aac gcg tcg aga gct gag ttc caa gcc aag     1248
Ser Met Ile Ser Asn Met Asn Ala Ser Arg Ala Glu Phe Gln Ala Lys
                405                 410                 415 atc gac tcc att aag cag tac atg cag ttc aga aag gtc acc aag gac     1296
Ile Asp Ser Ile Lys Gln Tyr Met Gln Phe Arg Lys Val Thr Lys Asp
                420                 425                 430 ctg gaa acc agg gtc atc cgc tgg ttc gac tac ctg tgg gcc aac aaa     1344
Leu Glu Thr Arg Val Ile Arg Trp Phe Asp Tyr Leu Trp Ala Asn Lys
            435                 440                 445 aag act gtg gac gaa aag gaa gtg ctg aag tcg ctg ccg gat aag ctg     1392
Lys Thr Val Asp Glu Lys Glu Val Leu Lys Ser Leu Pro Asp Lys Leu
        450                 455                 460 aag gcc gaa atc gcc att aac gtg cac ctt gac acc ctg aag aaa gtc     1440
Lys Ala Glu Ile Ala Ile Asn Val His Leu Asp Thr Leu Lys Lys Val
465                 470                 475                 480 cgg atc ttc caa gac tgt gaa gcc ggc ctc ctg gtg gag ctc gtg ctc     1488
Arg Ile Phe Gln Asp Cys Glu Ala Gly Leu Leu Val Glu Leu Val Leu
                485                 490                 495 aag ctg cgg ccc acc gtg ttc agc ccg gga gat tac att tgc aag aag     1536
Lys Leu Arg Pro Thr Val Phe Ser Pro Gly Asp Tyr Ile Cys Lys Lys
                500                 505                 510 ggc gat atc ggc aaa gag atg tac atc atc aac gag gga aag ctg gcc     1584
Gly Asp Ile Gly Lys Glu Met Tyr Ile Ile Asn Glu Gly Lys Leu Ala
            515                 520                 525 gtg gtc gcg gac gac ggc gtg acc cag ttc gtg gtg ctg tcc gac gga     1632
Val Val Ala Asp Asp Gly Val Thr Gln Phe Val Val Leu Ser Asp Gly
        530                 535                 540
```

| | | |
|---|---|---|
| tcc tac ttc ggt gaa atc tca atc ctc aac atc aag ggg tcc aag tcc<br>Ser Tyr Phe Gly Glu Ile Ser Ile Leu Asn Ile Lys Gly Ser Lys Ser<br>545                        550                         555                      560 | 1680 |
| ggc aac cgg aga act gcc aac att cgc tcc atc gga tac agc gac ctg<br>Gly Asn Arg Arg Thr Ala Asn Ile Arg Ser Ile Gly Tyr Ser Asp Leu<br>                      565                        570                        575 | 1728 |
| ttt tgc ctg tcc aag gat gac ctg atg gag gct ctg act gag tac cct<br>Phe Cys Leu Ser Lys Asp Asp Leu Met Glu Ala Leu Thr Glu Tyr Pro<br>                  580                          585                        590 | 1776 |
| gaa gcg aag aag gct ttg gag gaa aag ggg cgg cag att ctg atg aag<br>Glu Ala Lys Lys Ala Leu Glu Glu Lys Gly Arg Gln Ile Leu Met Lys<br>595                        600                         605 | 1824 |
| gac aat ttg atc gac gag gag ctc gca cgg gcc ggc gcc gac ccc aag<br>Asp Asn Leu Ile Asp Glu Glu Leu Ala Arg Ala Gly Ala Asp Pro Lys<br>          610                        615                        620 | 1872 |
| gat ctc gaa gag aag gtc gaa cag ctg ggt tct tcg ctt gat acc ctg<br>Asp Leu Glu Glu Lys Val Glu Gln Leu Gly Ser Ser Leu Asp Thr Leu<br>625                        630                        635                        640 | 1920 |
| caa acc cga ttc gcg cgg ctg ctc gcc gag tac aac gcg acc cag atg<br>Gln Thr Arg Phe Ala Arg Leu Leu Ala Glu Tyr Asn Ala Thr Gln Met<br>                      645                        650                        655 | 1968 |
| aag atg aag cag aga ctg tca cag ttg gaa tcc caa gtc aag ggc gga<br>Lys Met Lys Gln Arg Leu Ser Gln Leu Glu Ser Gln Val Lys Gly Gly<br>                  660                          665                        670 | 2016 |
| ggc gac aag ccg ctg gcg gac ggg gaa gtg ccc ggg gac gcc acc aag<br>Gly Asp Lys Pro Leu Ala Asp Gly Glu Val Pro Gly Asp Ala Thr Lys<br>675                        680                         685 | 2064 |
| act gag gac aag cag cag tga<br>Thr Glu Asp Lys Gln Gln<br>    690 | 2085 |

```
<210> SEQ ID NO 10
<211> LENGTH: 694
<212> TYPE: PRT
<213> ORGANISM: Artificial Sequence
<220> FEATURE:
<223> OTHER INFORMATION: Synthetic Construct

<400> SEQUENCE: 10
```

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
                20                  25                  30

Ser Arg Ala His Ser Ser Ser Glu Glu Thr Ser Ser Val Leu Gln Pro
            35                  40                  45

Gly Ile Ala Met Glu Thr Arg Gly Leu Ala Asp Ser Gly Gln Gly Ser
        50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
    130                 135                 140

Asn Asn Thr Glu Glu Glu Lys Lys Thr Lys Lys Lys Asp Ala Ile Val

```
            145                 150                 155                 160
Val Asp Pro Ser Ser Asn Leu Tyr Tyr Arg Trp Leu Thr Ala Ile Ala
                    165                 170                 175
Leu Pro Val Phe Tyr Asn Trp Tyr Leu Leu Ile Cys Arg Ala Cys Phe
                    180                 185                 190
Asp Glu Leu Gln Ser Glu Tyr Leu Met Leu Trp Leu Val Leu Asp Tyr
                    195                 200                 205
Ser Ala Asp Val Leu Tyr Val Leu Asp Val Leu Val Arg Ala Arg Thr
                210                 215                 220
Gly Phe Leu Glu Gln Gly Leu Met Val Ser Asp Thr Asn Arg Leu Trp
225                 230                 235                 240
Gln His Tyr Lys Thr Thr Thr Gln Phe Lys Leu Asp Val Leu Ser Leu
                    245                 250                 255
Val Pro Thr Asp Leu Ala Tyr Leu Lys Val Gly Thr Asn Tyr Pro Glu
                    260                 265                 270
Val Arg Phe Asn Arg Leu Leu Lys Phe Ser Arg Leu Phe Glu Phe Phe
                    275                 280                 285
Asp Arg Thr Glu Thr Arg Thr Asn Tyr Pro Asn Met Phe Arg Ile Gly
                    290                 295                 300
Asn Leu Val Leu Tyr Ile Leu Ile Ile His Trp Asn Ala Cys Ile
305                 310                 315                 320
Tyr Phe Ala Ile Ser Lys Phe Ile Gly Phe Gly Thr Asp Ser Trp Val
                    325                 330                 335
Tyr Pro Asn Ile Ser Ile Pro Glu His Gly Arg Leu Ser Arg Lys Tyr
                    340                 345                 350
Ile Tyr Ser Leu Tyr Trp Ser Thr Leu Thr Leu Thr Thr Ile Gly Glu
                    355                 360                 365
Thr Pro Pro Pro Val Lys Asp Glu Glu Tyr Leu Phe Val Val Val Asp
                    370                 375                 380
Phe Leu Val Gly Val Leu Ile Phe Ala Thr Ile Val Gly Asn Val Gly
385                 390                 395                 400
Ser Met Ile Ser Asn Met Asn Ala Ser Arg Ala Glu Phe Gln Ala Lys
                    405                 410                 415
Ile Asp Ser Ile Lys Gln Tyr Met Gln Phe Arg Lys Val Thr Lys Asp
                    420                 425                 430
Leu Glu Thr Arg Val Ile Arg Trp Phe Asp Tyr Leu Trp Ala Asn Lys
                    435                 440                 445
Lys Thr Val Asp Glu Lys Glu Val Leu Lys Ser Leu Pro Asp Lys Leu
                    450                 455                 460
Lys Ala Glu Ile Ala Ile Asn Val His Leu Asp Thr Leu Lys Lys Val
465                 470                 475                 480
Arg Ile Phe Gln Asp Cys Glu Ala Gly Leu Leu Val Glu Leu Val Leu
                    485                 490                 495
Lys Leu Arg Pro Thr Val Phe Ser Pro Gly Asp Tyr Ile Cys Lys Lys
                    500                 505                 510
Gly Asp Ile Gly Lys Glu Met Tyr Ile Ile Asn Glu Gly Lys Leu Ala
                    515                 520                 525
Val Val Ala Asp Asp Gly Val Thr Gln Phe Val Val Leu Ser Asp Gly
                530                 535                 540
Ser Tyr Phe Gly Glu Ile Ser Ile Leu Asn Ile Lys Gly Ser Lys Ser
545                 550                 555                 560
Gly Asn Arg Arg Thr Ala Asn Ile Arg Ser Ile Gly Tyr Ser Asp Leu
                    565                 570                 575
```

```
Phe Cys Leu Ser Lys Asp Asp Leu Met Glu Ala Leu Thr Glu Tyr Pro
            580                 585                 590

Glu Ala Lys Lys Ala Leu Glu Glu Lys Gly Arg Gln Ile Leu Met Lys
        595                 600                 605

Asp Asn Leu Ile Asp Glu Glu Leu Ala Arg Ala Gly Ala Asp Pro Lys
    610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
        675                 680                 685

Thr Glu Asp Lys Gln Gln
    690

<210> SEQ ID NO 11
<211> LENGTH: 2250
<212> TYPE: DNA
<213> ORGANISM: Artificial Sequence
<220> FEATURE:
<223> OTHER INFORMATION: codon optimized sequence
<220> FEATURE:
<221> NAME/KEY: CDS
<222> LOCATION: (1)..(2250)
<223> OTHER INFORMATION: codon-optimized ORF

<400> SEQUENCE: 11 atg gct aag att aac acc cag tac tca cat cca tcc cgc act cac ctc      48
Met Ala Lys Ile Asn Thr Gln Tyr Ser His Pro Ser Arg Thr His Leu
1               5                   10                  15 aaa gtc aag acc tcc gat cgg gat ctg aac cgg gct gag aat ggg ctg      96
Lys Val Lys Thr Ser Asp Arg Asp Leu Asn Arg Ala Glu Asn Gly Leu
            20                  25                  30 tcg cgc gcc cac tcg tcg tcc gag gaa acc agc agc gtg ctc cag ccg     144
Ser Arg Ala His Ser Ser Ser Glu Glu Thr Ser Ser Val Leu Gln Pro
        35                  40                  45 ggc atc gcc atg gaa act agg ggg ctg gcg gac tcc gga cag gga tcc     192
Gly Ile Ala Met Glu Thr Arg Gly Leu Ala Asp Ser Gly Gln Gly Ser
    50                  55                  60 ttc act gga cag ggt att gcc cgg ttc ggg cgg att cag aag aag tcc     240
Phe Thr Gly Gln Gly Ile Ala Arg Phe Gly Arg Ile Gln Lys Lys Ser
65                  70                  75                  80 cag ccg gag aag gtc gtg cgg gct gcc agc agg ggc agg cca ctc att     288
Gln Pro Glu Lys Val Val Arg Ala Ala Ser Arg Gly Arg Pro Leu Ile
                85                  90                  95 ggt tgg aca cag tgg tgc gct gag gat ggt gga gat gaa tcg gaa atg     336
Gly Trp Thr Gln Trp Cys Ala Glu Asp Gly Gly Asp Glu Ser Glu Met
            100                 105                 110 gca ctg gcc ggc tct ccc gga tgc agc tcg ggc ccc caa ggg aga ctg     384
Ala Leu Ala Gly Ser Pro Gly Cys Ser Ser Gly Pro Gln Gly Arg Leu
        115                 120                 125 agc aga ctg atc ttc ctg ctt cgc cgc tgg gcg gcc aga cac gtg cac     432
Ser Arg Leu Ile Phe Leu Leu Arg Arg Trp Ala Ala Arg His Val His
    130                 135                 140 cat cag gac cag gga cct gat agc ttc ccc gac cgc ttt agg gga gcc     480
His Gln Asp Gln Gly Pro Asp Ser Phe Pro Asp Arg Phe Arg Gly Ala
145                 150                 155                 160
```

```
gag ctg aaa gaa gtg tca agc cag gag tca aac gcg cag gcc aac gtc      528
Glu Leu Lys Glu Val Ser Ser Gln Glu Ser Asn Ala Gln Ala Asn Val
                165                 170                 175 ggc agc caa gag cct gca gac cgg gga cgc tcg gca tgg ccg ctc gca      576
Gly Ser Gln Glu Pro Ala Asp Arg Gly Arg Ser Ala Trp Pro Leu Ala
            180                 185                 190 aag tgc aac act aac act tcc aac aac acc gaa gag gaa aag aaa acc      624
Lys Cys Asn Thr Asn Thr Ser Asn Asn Thr Glu Glu Glu Lys Lys Thr
        195                 200                 205 aag aag aag gat gca att gtg gtg gac cct tcc tcc aac ctg tac tac      672
Lys Lys Lys Asp Ala Ile Val Val Asp Pro Ser Ser Asn Leu Tyr Tyr
    210                 215                 220 cgc tgg ttg acc gcc atc gcc ctc ccg gtc ttt tac aat tgg tat ctc      720
Arg Trp Leu Thr Ala Ile Ala Leu Pro Val Phe Tyr Asn Trp Tyr Leu
225                 230                 235                 240 ctt atc tgc cgg gcc tgc ttc gac gaa ctg caa tca gag tac ctg atg      768
Leu Ile Cys Arg Ala Cys Phe Asp Glu Leu Gln Ser Glu Tyr Leu Met
                245                 250                 255 ctg tgg ctg gtg ctg gac tat agc gcc gat gtg ctc tac gtc ctg gat      816
Leu Trp Leu Val Leu Asp Tyr Ser Ala Asp Val Leu Tyr Val Leu Asp
            260                 265                 270 gtg ctc gtg cgc gcc cgg acc gga ttc ttg gaa caa ggc ctg atg gtg      864
Val Leu Val Arg Ala Arg Thr Gly Phe Leu Glu Gln Gly Leu Met Val
        275                 280                 285 tcc gac acg aat aga ctg tgg cag cac tat aag acc aca acc cag ttc      912
Ser Asp Thr Asn Arg Leu Trp Gln His Tyr Lys Thr Thr Thr Gln Phe
    290                 295                 300 aag ctt gac gtg ctc agc ctt gtg ccg act gac ctg gcc tac ctg aaa      960
Lys Leu Asp Val Leu Ser Leu Val Pro Thr Asp Leu Ala Tyr Leu Lys
305                 310                 315                 320 gtc gga act aac tac ccg gaa gtc aga ttc aac cga ctc ctg aag ttc     1008
Val Gly Thr Asn Tyr Pro Glu Val Arg Phe Asn Arg Leu Leu Lys Phe
                325                 330                 335 agc agg ctg ttc gag ttc ttt gac cgc acc gag act cgg acc aac tac     1056
Ser Arg Leu Phe Glu Phe Phe Asp Arg Thr Glu Thr Arg Thr Asn Tyr
            340                 345                 350 cct aac atg ttc cgg atc gga aat ctg gtg ctc tac ata ctg att atc     1104
Pro Asn Met Phe Arg Ile Gly Asn Leu Val Leu Tyr Ile Leu Ile Ile
        355                 360                 365 atc cat tgg aac gcc tgt atc tat ttc gcc att tcg aag ttc atc ggt     1152
Ile His Trp Asn Ala Cys Ile Tyr Phe Ala Ile Ser Lys Phe Ile Gly
    370                 375                 380 ttc gga acc gat tcc tgg gtg tac ccc aac atc tcg atc ccc gaa cac     1200
Phe Gly Thr Asp Ser Trp Val Tyr Pro Asn Ile Ser Ile Pro Glu His
385                 390                 395                 400 ggt cgc ctg tcc cgg aag tac atc tac tcc ctg tac tgg tcc act ctg     1248
Gly Arg Leu Ser Arg Lys Tyr Ile Tyr Ser Leu Tyr Trp Ser Thr Leu
                405                 410                 415 act ctg acc acg atc ggg gaa acc cct cca ccc gtg aag gac gaa gag     1296
Thr Leu Thr Thr Ile Gly Glu Thr Pro Pro Pro Val Lys Asp Glu Glu
            420                 425                 430 tac ctg ttc gtg gtg gtg gac ttc ctg gtc gga gtg ttg att ttc gcc     1344
Tyr Leu Phe Val Val Val Asp Phe Leu Val Gly Val Leu Ile Phe Ala
        435                 440                 445 acc att gtg gga aac gtg ggc tcc atg atc tcc aac atg aac gcg tcg     1392
Thr Ile Val Gly Asn Val Gly Ser Met Ile Ser Asn Met Asn Ala Ser
    450                 455                 460 aga gct gag ttc caa gcc aag atc gac tcc att aag cag tac atg cag     1440
Arg Ala Glu Phe Gln Ala Lys Ile Asp Ser Ile Lys Gln Tyr Met Gln
465                 470                 475                 480
```

```
ttc aga aag gtc acc aag gac ctg gaa acc agg gtc atc cgc tgg ttc      1488
Phe Arg Lys Val Thr Lys Asp Leu Glu Thr Arg Val Ile Arg Trp Phe
            485                 490                 495 gac tac ctg tgg gcc aac aaa aag act gtg gac gaa aag gaa gtg ctg      1536
Asp Tyr Leu Trp Ala Asn Lys Lys Thr Val Asp Glu Lys Glu Val Leu
        500                 505                 510 aag tcg ctg ccg gat aag ctg aag gcc gaa atc gcc att aac gtg cac      1584
Lys Ser Leu Pro Asp Lys Leu Lys Ala Glu Ile Ala Ile Asn Val His
    515                 520                 525 ctt gac acc ctg aag aaa gtc cgg atc ttc caa gac tgt gaa gcc ggc      1632
Leu Asp Thr Leu Lys Lys Val Arg Ile Phe Gln Asp Cys Glu Ala Gly
530                 535                 540 ctc ctg gtg gag ctc gtg ctc aag ctg cgg ccc acc gtg ttc agc ccg      1680
Leu Leu Val Glu Leu Val Leu Lys Leu Arg Pro Thr Val Phe Ser Pro
545                 550                 555                 560 gga gat tac att tgc aag aag ggc gat atc ggc aaa gag atg tac atc      1728
Gly Asp Tyr Ile Cys Lys Lys Gly Asp Ile Gly Lys Glu Met Tyr Ile
                565                 570                 575 atc aac gag gga aag ctg gcc gtg gtc gcg gac gac ggc gtg acc cag      1776
Ile Asn Glu Gly Lys Leu Ala Val Val Ala Asp Asp Gly Val Thr Gln
            580                 585                 590 ttc gtg gtg ctg tcc gac gga tcc tac ttc ggt gaa atc tca atc ctc      1824
Phe Val Val Leu Ser Asp Gly Ser Tyr Phe Gly Glu Ile Ser Ile Leu
        595                 600                 605 aac atc aag ggg tcc aag tcc ggc aac cgg aga act gcc aac att cgc      1872
Asn Ile Lys Gly Ser Lys Ser Gly Asn Arg Arg Thr Ala Asn Ile Arg
    610                 615                 620 tcc atc gga tac agc gac ctg ttt tgc ctg tcc aag gat gac ctg atg      1920
Ser Ile Gly Tyr Ser Asp Leu Phe Cys Leu Ser Lys Asp Asp Leu Met
625                 630                 635                 640 gag gct ctg act gag tac cct gaa gcg aag aag gct ttg gag gaa aag      1968
Glu Ala Leu Thr Glu Tyr Pro Glu Ala Lys Lys Ala Leu Glu Glu Lys
                645                 650                 655 ggg cgg cag att ctg atg aag gac aat ttg atc gac gag gag ctc gca      2016
Gly Arg Gln Ile Leu Met Lys Asp Asn Leu Ile Asp Glu Glu Leu Ala
            660                 665                 670 cgg gcc ggc gcc gac ccc aag gat ctc gaa gag aag gtc gaa cag ctg      2064
Arg Ala Gly Ala Asp Pro Lys Asp Leu Glu Glu Lys Val Glu Gln Leu
        675                 680                 685 ggt tct tcg ctt gat acc ctg caa acc cga ttc gcg cgg ctc ctc gcc      2112
Gly Ser Ser Leu Asp Thr Leu Gln Thr Arg Phe Ala Arg Leu Leu Ala
    690                 695                 700 gag tac aac gcg acc cag atg aag atg aag cag aga ctg tca cag ttg      2160
Glu Tyr Asn Ala Thr Gln Met Lys Met Lys Gln Arg Leu Ser Gln Leu
705                 710                 715                 720 gaa tcc caa gtc aag ggc gga ggc gac aag ccg ctg gcg gac ggg gaa      2208
Glu Ser Gln Val Lys Gly Gly Gly Asp Lys Pro Leu Ala Asp Gly Glu
                725                 730                 735 gtg ccc ggg gac gcc acc aag act gag gac aag cag cag tga              2250
Val Pro Gly Asp Ala Thr Lys Thr Glu Asp Lys Gln Gln
            740                 745
```

<210> SEQ ID NO 12
<211> LENGTH: 749
<212> TYPE: PRT
<213> ORGANISM: Artificial Sequence
<220> FEATURE:
<223> OTHER INFORMATION: Synthetic Construct

<400> SEQUENCE: 12

```
Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Phe Gly Arg Ile Gln Lys Lys Ser
65                  70                  75                  80

Gln Pro Glu Lys Val Val Arg Ala Ala Ser Arg Gly Arg Pro Leu Ile
                85                  90                  95

Gly Trp Thr Gln Trp Cys Ala Glu Asp Gly Asp Glu Ser Glu Met
            100                 105                 110

Ala Leu Ala Gly Ser Pro Gly Cys Ser Ser Gly Pro Gln Gly Arg Leu
            115                 120                 125

Ser Arg Leu Ile Phe Leu Leu Arg Arg Trp Ala Ala Arg His Val His
        130                 135                 140

His Gln Asp Gln Gly Pro Asp Ser Phe Pro Asp Arg Phe Arg Gly Ala
145                 150                 155                 160

Glu Leu Lys Glu Val Ser Ser Gln Glu Ser Asn Ala Gln Ala Asn Val
                165                 170                 175

Gly Ser Gln Glu Pro Ala Asp Arg Gly Arg Ser Ala Trp Pro Leu Ala
            180                 185                 190

Lys Cys Asn Thr Asn Thr Ser Asn Asn Thr Glu Glu Glu Lys Lys Thr
        195                 200                 205

Lys Lys Lys Asp Ala Ile Val Val Asp Pro Ser Ser Asn Leu Tyr Tyr
210                 215                 220

Arg Trp Leu Thr Ala Ile Ala Leu Pro Val Phe Tyr Asn Trp Tyr Leu
225                 230                 235                 240

Leu Ile Cys Arg Ala Cys Phe Asp Glu Leu Gln Ser Glu Tyr Leu Met
            245                 250                 255

Leu Trp Leu Val Leu Asp Tyr Ser Ala Asp Val Leu Tyr Val Leu Asp
            260                 265                 270

Val Leu Val Arg Ala Arg Thr Gly Phe Leu Glu Gln Gly Leu Met Val
        275                 280                 285

Ser Asp Thr Asn Arg Leu Trp Gln His Tyr Lys Thr Thr Gln Phe
            290                 295                 300

Lys Leu Asp Val Leu Ser Leu Val Pro Thr Asp Leu Ala Tyr Leu Lys
305                 310                 315                 320

Val Gly Thr Asn Tyr Pro Glu Val Arg Phe Asn Arg Leu Leu Lys Phe
            325                 330                 335

Ser Arg Leu Phe Glu Phe Phe Asp Arg Thr Glu Thr Arg Thr Asn Tyr
        340                 345                 350

Pro Asn Met Phe Arg Ile Gly Asn Leu Val Leu Tyr Ile Leu Ile Ile
            355                 360                 365

Ile His Trp Asn Ala Cys Ile Tyr Phe Ala Ile Ser Lys Phe Ile Gly
    370                 375                 380

Phe Gly Thr Asp Ser Trp Val Tyr Pro Asn Ile Ser Ile Pro Glu His
385                 390                 395                 400

Gly Arg Leu Ser Arg Lys Tyr Ile Tyr Ser Leu Tyr Trp Ser Thr Leu
            405                 410                 415

Thr Leu Thr Thr Ile Gly Glu Thr Pro Pro Pro Val Lys Asp Glu Glu
```

```
                420             425             430
Tyr Leu Phe Val Val Asp Phe Leu Val Gly Val Leu Ile Phe Ala
            435             440             445
Thr Ile Val Gly Asn Val Gly Ser Met Ile Ser Asn Met Asn Ala Ser
450             455             460
Arg Ala Glu Phe Gln Ala Lys Ile Asp Ser Ile Lys Gln Tyr Met Gln
465             470             475             480
Phe Arg Lys Val Thr Lys Asp Leu Glu Thr Arg Val Ile Arg Trp Phe
            485             490             495
Asp Tyr Leu Trp Ala Asn Lys Lys Thr Val Asp Glu Lys Glu Val Leu
        500             505             510
Lys Ser Leu Pro Asp Lys Leu Lys Ala Glu Ile Ala Ile Asn Val His
        515             520             525
Leu Asp Thr Leu Lys Lys Val Arg Ile Phe Gln Asp Cys Glu Ala Gly
    530             535             540
Leu Leu Val Glu Leu Val Leu Lys Leu Arg Pro Thr Val Phe Ser Pro
545             550             555             560
Gly Asp Tyr Ile Cys Lys Lys Gly Asp Ile Gly Lys Glu Met Tyr Ile
            565             570             575
Ile Asn Glu Gly Lys Leu Ala Val Val Ala Asp Asp Gly Val Thr Gln
            580             585             590
Phe Val Val Leu Ser Asp Gly Ser Tyr Phe Gly Glu Ile Ser Ile Leu
        595             600             605
Asn Ile Lys Gly Ser Lys Ser Gly Asn Arg Arg Thr Ala Asn Ile Arg
        610             615             620
Ser Ile Gly Tyr Ser Asp Leu Phe Cys Leu Ser Lys Asp Asp Leu Met
625             630             635             640
Glu Ala Leu Thr Glu Tyr Pro Glu Ala Lys Lys Ala Leu Glu Glu Lys
            645             650             655
Gly Arg Gln Ile Leu Met Lys Asp Asn Leu Ile Asp Glu Glu Leu Ala
            660             665             670
Arg Ala Gly Ala Asp Pro Lys Asp Leu Glu Glu Lys Val Glu Gln Leu
            675             680             685
Gly Ser Ser Leu Asp Thr Leu Gln Thr Arg Phe Ala Arg Leu Leu Ala
        690             695             700
Glu Tyr Asn Ala Thr Gln Met Lys Met Lys Gln Arg Leu Ser Gln Leu
705             710             715             720
Glu Ser Gln Val Lys Gly Gly Gly Asp Lys Pro Leu Ala Asp Gly Glu
            725             730             735
Val Pro Gly Asp Ala Thr Lys Thr Glu Asp Lys Gln Gln
            740             745

<210> SEQ ID NO 13
<211> LENGTH: 2085
<212> TYPE: DNA
<213> ORGANISM: Homo sapiens
<220> FEATURE:
<221> NAME/KEY: CDS
<222> LOCATION: (1)..(2085)
<223> OTHER INFORMATION: native open reading frame (ORF)

<400> SEQUENCE: 13 atg gcc aag atc aac acc caa tac tcc cac ccc tcc agg acc cac ctc       48
Met Ala Lys Ile Asn Thr Gln Tyr Ser His Pro Ser Arg Thr His Leu
1               5                   10                  15 aag gta aag acc tca gac cgg gat ctc aat cgc gct gaa aat ggc ctc       96
```

|   |   |   |   |   |   |   |   |   |   |   |   |   |   |   |   |
|---|---|---|---|---|---|---|---|---|---|---|---|---|---|---|---|
| Lys | Val | Lys | Thr<br>20 | Ser | Asp | Arg | Asp | Leu<br>25 | Asn | Arg | Ala | Glu | Asn<br>30 | Gly | Leu |

| | | | | | | | | | | | | | | |
|---|---|---|---|---|---|---|---|---|---|---|---|---|---|---|
| agc | aga | gcc | cac | tcg | tca | agt | gag | gag | aca | tcg | tca | gtg | ctg | cag | ccg | 144 |
| Ser | Arg | Ala<br>35 | His | Ser | Ser | Ser | Glu<br>40 | Glu | Thr | Ser | Ser<br>45 | Val | Leu | Gln | Pro |

| | | | | | | | | | | | | | | | |
|---|---|---|---|---|---|---|---|---|---|---|---|---|---|---|---|
| ggg | atc | gcc | atg | gag | acc | aga | gga | ctg | gct | gac | tcc | ggg | cag | ggc | tcc | 192 |
| Gly | Ile | Ala | Met | Glu<br>50 | Thr | Arg | Gly | Leu<br>55 | Ala | Asp | Ser | Gly<br>60 | Gln | Gly | Ser |

| | | | | | | | | | | | | | | | |
|---|---|---|---|---|---|---|---|---|---|---|---|---|---|---|---|
| ttc | acc | ggc | cag | ggg | atc | gcc | agg | ctg | tcg | cgc | ctc | atc | ttc | ttg | ctg | 240 |
| Phe<br>65 | Thr | Gly | Gln | Gly<br>70 | Ile | Ala | Arg | Leu<br>75 | Ser | Arg | Leu | Ile | Phe<br>80 | Leu | Leu |

| | | | | | | | | | | | | | | | |
|---|---|---|---|---|---|---|---|---|---|---|---|---|---|---|---|
| cgc | agg | tgg | gct | gcc | agg | cat | gtg | cac | cac | cag | gac | cag | gga | ccg | gac | 288 |
| Arg | Arg | Trp | Ala | Ala<br>85 | Arg | His | Val | His<br>90 | His | Gln | Asp | Gln<br>95 | Gly | Pro | Asp |

| | | | | | | | | | | | | | | | |
|---|---|---|---|---|---|---|---|---|---|---|---|---|---|---|---|
| tct | ttt | cct | gat | cgt | ttc | cgt | gga | gcc | gag | ctt | aag | gag | gtg | tcc | agc | 336 |
| Ser | Phe | Pro | Asp<br>100 | Arg | Phe | Arg | Gly<br>105 | Ala | Glu | Leu | Lys | Glu<br>110 | Val | Ser | Ser |

| | | | | | | | | | | | | | | | |
|---|---|---|---|---|---|---|---|---|---|---|---|---|---|---|---|
| caa | gaa | agc | aat | gcc | cag | gca | aat | gtg | ggc | agc | cag | gag | cca | gca | gac | 384 |
| Gln | Glu | Ser | Asn<br>115 | Ala | Gln | Ala | Asn | Val<br>120 | Gly | Ser | Gln | Glu<br>125 | Pro | Ala | Asp |

| | | | | | | | | | | | | | | | |
|---|---|---|---|---|---|---|---|---|---|---|---|---|---|---|---|
| aga | ggg | aga | agc | gcc | tgg | ccc | ctg | gcc | aaa | tgc | aac | act | aac | acc | agc | 432 |
| Arg | Gly | Arg | Ser<br>130 | Ala | Trp | Pro | Leu<br>135 | Ala | Lys | Cys | Asn | Thr<br>140 | Asn | Thr | Ser |

| | | | | | | | | | | | | | | | |
|---|---|---|---|---|---|---|---|---|---|---|---|---|---|---|---|
| aac | aac | acg | gag | gag | gag | aag | aag | acg | aaa | aag | aag | gat | gcg | atc | gtg | 480 |
| Asn | Asn | Thr | Glu<br>145 | Glu | Glu | Lys | Lys<br>150 | Thr | Lys | Lys | Lys | Asp<br>155 | Ala | Ile | Val<br>160 |

| | | | | | | | | | | | | | | | |
|---|---|---|---|---|---|---|---|---|---|---|---|---|---|---|---|
| gtg | gac | ccg | tcc | agc | aac | ctg | tac | tac | cgc | tgg | ctg | acc | gcc | atc | gcc | 528 |
| Val | Asp | Pro | Ser | Ser<br>165 | Asn | Leu | Tyr | Tyr<br>170 | Arg | Trp | Leu | Thr<br>175 | Ala | Ile | Ala |

| | | | | | | | | | | | | | | | |
|---|---|---|---|---|---|---|---|---|---|---|---|---|---|---|---|
| ctg | cct | gtc | ttc | tat | aac | tgg | tat | ctg | ctt | att | tgc | agg | gcc | tgt | ttc | 576 |
| Leu | Pro | Val | Phe<br>180 | Tyr | Asn | Trp | Tyr<br>185 | Leu | Leu | Ile | Cys | Arg<br>190 | Ala | Cys | Phe |

| | | | | | | | | | | | | | | | |
|---|---|---|---|---|---|---|---|---|---|---|---|---|---|---|---|
| gat | gag | ctg | cag | tcc | gag | tac | ctg | atg | ctg | tgg | ctg | gtc | ctg | gac | tac | 624 |
| Asp | Glu | Leu | Gln<br>195 | Ser | Glu | Tyr | Leu<br>200 | Met | Leu | Trp | Leu | Val<br>205 | Leu | Asp | Tyr |

| | | | | | | | | | | | | | | | |
|---|---|---|---|---|---|---|---|---|---|---|---|---|---|---|---|
| tcg | gca | gat | gtc | ctg | tat | gtc | ttg | gat | gtg | ctt | gta | cga | gct | cgg | aca | 672 |
| Ser | Ala | Asp<br>210 | Val | Leu | Tyr | Val<br>215 | Leu | Asp | Val | Leu | Val<br>220 | Arg | Ala | Arg | Thr |

| | | | | | | | | | | | | | | | |
|---|---|---|---|---|---|---|---|---|---|---|---|---|---|---|---|
| ggt | ttt | ctt | gag | caa | ggc | tta | atg | gtc | agt | gat | acc | aac | agg | ctg | tgg | 720 |
| Gly<br>225 | Phe | Leu | Glu | Gln<br>230 | Gly | Leu | Met | Val<br>235 | Ser | Asp | Thr | Asn | Arg<br>240 | Leu | Trp |

| | | | | | | | | | | | | | | | |
|---|---|---|---|---|---|---|---|---|---|---|---|---|---|---|---|
| cag | cat | tac | aag | acg | acc | acg | cag | ttc | aag | ctg | gat | gtg | ttg | tcc | ctg | 768 |
| Gln | His | Tyr | Lys | Thr<br>245 | Thr | Thr | Gln | Phe<br>250 | Lys | Leu | Asp | Val<br>255 | Leu | Ser | Leu |

| | | | | | | | | | | | | | | | |
|---|---|---|---|---|---|---|---|---|---|---|---|---|---|---|---|
| gtc | ccc | acc | gac | ctg | gct | tac | tta | aag | gtg | ggc | aca | aac | tac | cca | gaa | 816 |
| Val | Pro | Thr | Asp<br>260 | Leu | Ala | Tyr | Leu<br>265 | Lys | Val | Gly | Thr | Asn<br>270 | Tyr | Pro | Glu |

| | | | | | | | | | | | | | | | |
|---|---|---|---|---|---|---|---|---|---|---|---|---|---|---|---|
| gtg | agg | ttc | aac | cgc | cta | ctg | aag | ttt | tcc | cgg | ctc | ttt | gaa | ttc | ttt | 864 |
| Val | Arg | Phe<br>275 | Asn | Arg | Leu | Leu<br>280 | Lys | Phe | Ser | Arg | Leu<br>285 | Phe | Glu | Phe | Phe |

| | | | | | | | | | | | | | | | |
|---|---|---|---|---|---|---|---|---|---|---|---|---|---|---|---|
| gac | cgc | aca | gag | aca | agg | acc | aac | tac | ccc | aat | atg | ttc | agg | att | ggg | 912 |
| Asp | Arg | Thr | Glu<br>290 | Thr | Arg | Thr | Asn<br>295 | Tyr | Pro | Asn | Met | Phe<br>300 | Arg | Ile | Gly |

| | | | | | | | | | | | | | | | |
|---|---|---|---|---|---|---|---|---|---|---|---|---|---|---|---|
| aac | ttg | gtc | ttg | tac | att | ctc | atc | atc | atc | cac | tgg | aat | gcc | tgc | atc | 960 |
| Asn | Leu | Val | Leu | Tyr<br>305 | Ile | Leu | Ile | Ile<br>310 | Ile | His | Trp | Asn<br>315 | Ala | Cys | Ile<br>320 |

| | | | | | | | | | | | | | | | |
|---|---|---|---|---|---|---|---|---|---|---|---|---|---|---|---|
| tac | ttt | gcc | att | tcc | aag | ttc | att | ggt | ttt | ggg | aca | gac | tcc | tgg | gtc | 1008 |
| Tyr | Phe | Ala | Ile | Ser<br>325 | Lys | Phe | Ile | Gly<br>330 | Phe | Gly | Thr | Asp | Ser<br>335 | Trp | Val |

-continued

| | | |
|---|---|---|
| tac cca aac atc tca atc cca gag cat ggg cgc ctc tcc agg aag tac<br>Tyr Pro Asn Ile Ser Ile Pro Glu His Gly Arg Leu Ser Arg Lys Tyr<br>                  340                         345                        350 | 1056 | |
| att tac agt ctc tac tgg tcc acc ttg acc ctt acc acc att ggt gag<br>Ile Tyr Ser Leu Tyr Trp Ser Thr Leu Thr Leu Thr Thr Ile Gly Glu<br>                 355                          360                      365 | 1104 | |
| acc cca ccc ccc gtg aaa gat gag gag tat ctc ttt gtg gtc gta gac<br>Thr Pro Pro Pro Val Lys Asp Glu Glu Tyr Leu Phe Val Val Val Asp<br>370                           375                             380 | 1152 | |
| ttc ttg gtg ggt gtt ctg att ttt gcc acc att gtg ggc aat gtg ggc<br>Phe Leu Val Gly Val Leu Ile Phe Ala Thr Ile Val Gly Asn Val Gly<br>385                           390                                400 | 1200 | |
| tcc atg atc tcg aat atg aat gcc tca cgg gca gag ttc cag gcc aag<br>Ser Met Ile Ser Asn Met Asn Ala Ser Arg Ala Glu Phe Gln Ala Lys<br>                 405                          410                      415 | 1248 | |
| att gat tcc atc aag cag tac atg cag ttc cgc aag gtc acc aag gac<br>Ile Asp Ser Ile Lys Gln Tyr Met Gln Phe Arg Lys Val Thr Lys Asp<br>                 420                          425                      430 | 1296 | |
| ttg gag acg cgg gtt atc cgg tgg ttt gac tac ctg tgg gcc aac aag<br>Leu Glu Thr Arg Val Ile Arg Trp Phe Asp Tyr Leu Trp Ala Asn Lys<br>                   435                          440                      445 | 1344 | |
| aag acg gtg gat gag aag gag gtg ctc aag agc ctc cca gac aag ctg<br>Lys Thr Val Asp Glu Lys Glu Val Leu Lys Ser Leu Pro Asp Lys Leu<br>450                           455                             460 | 1392 | |
| aag gct gag atc gcc atc aac gtg cac ctg gac acg ctg aag aag gtt<br>Lys Ala Glu Ile Ala Ile Asn Val His Leu Asp Thr Leu Lys Lys Val<br>465                           470                            475                      480 | 1440 | |
| cgc atc ttc cag gac tgt gag gca ggc ctg ctg gtg gag ctg gtg ctg<br>Arg Ile Phe Gln Asp Cys Glu Ala Gly Leu Leu Val Glu Leu Val Leu<br>                                   485                          490                      495 | 1488 | |
| aag ctg cga ccc act gtg ttc agc cct ggg gat tat atc tgc aag aag<br>Lys Leu Arg Pro Thr Val Phe Ser Pro Gly Asp Tyr Ile Cys Lys Lys<br>                   500                          505                      510 | 1536 | |
| gga gat att ggg aag gag atg tac atc atc aac gag ggc aag ctg gcc<br>Gly Asp Ile Gly Lys Glu Met Tyr Ile Ile Asn Glu Gly Lys Leu Ala<br>                 515                          520                      525 | 1584 | |
| gtg gtg gct gat gat ggg gtc acc cag ttc gtg gtc ctc agc gat ggc<br>Val Val Ala Asp Asp Gly Val Thr Gln Phe Val Val Leu Ser Asp Gly<br>530                           535                             540 | 1632 | |
| agc tac ttc ggg gag atc agc att ctg aac atc aag ggg agc aag tcg<br>Ser Tyr Phe Gly Glu Ile Ser Ile Leu Asn Ile Lys Gly Ser Lys Ser<br>545                           550                          555                      560 | 1680 | |
| ggg aac cgc agg acg gcc aac atc cgc agc att ggc tac tca gac ctg<br>Gly Asn Arg Arg Thr Ala Asn Ile Arg Ser Ile Gly Tyr Ser Asp Leu<br>                   565                          570                      575 | 1728 | |
| ttc tgc ctc tca aag gac gat ctc atg gag gcc ctc acc gag tac ccc<br>Phe Cys Leu Ser Lys Asp Asp Leu Met Glu Ala Leu Thr Glu Tyr Pro<br>                 580                          585                      590 | 1776 | |
| gaa gcc aag aag gcc ctg gag gag aaa gga cgg cag atc ctg atg aaa<br>Glu Ala Lys Lys Ala Leu Glu Glu Lys Gly Arg Gln Ile Leu Met Lys<br>                 595                          600                      605 | 1824 | |
| gac aac ctg atc gat gag gag ctg gcc agg gcg ggc gcg gac ccc aag<br>Asp Asn Leu Ile Asp Glu Glu Leu Ala Arg Ala Gly Ala Asp Pro Lys<br>610                           615                             620 | 1872 | |
| gac ctt gag gag aaa gtg gag cag ctg ggg tcc tcc ctg gac acc ctg<br>Asp Leu Glu Glu Lys Val Glu Gln Leu Gly Ser Ser Leu Asp Thr Leu<br>625                           630                          635                      640 | 1920 | |
| cag acc agg ttt gca cgc ctc ctg gct gag tac aac gcc acc cag atg<br>Gln Thr Arg Phe Ala Arg Leu Leu Ala Glu Tyr Asn Ala Thr Gln Met<br>                 645                          650                      655 | 1968 | |

```
aag atg aag cag cgt ctc agc caa ctg gaa agc cag gtg aag ggt ggt    2016
Lys Met Lys Gln Arg Leu Ser Gln Leu Glu Ser Gln Val Lys Gly Gly
        660                 665                 670 ggg gac aag ccc ctg gct gat ggg gaa gtt ccc ggg gat gct aca aaa    2064
Gly Asp Lys Pro Leu Ala Asp Gly Glu Val Pro Gly Asp Ala Thr Lys
        675                 680                 685 aca gag gac aaa caa cag tga                                        2085
Thr Glu Asp Lys Gln Gln
        690

<210> SEQ ID NO 14
<211> LENGTH: 694
<212> TYPE: PRT
<213> ORGANISM: Homo sapiens

<400> SEQUENCE: 14

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
    130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Val Arg Ala Arg Thr
    210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
            260                 265                 270

Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
    290                 295                 300

Asn Leu Val Leu Tyr Ile Leu Ile Ile Ile His Trp Asn Ala Cys Ile
```

```
             305                 310                 315                 320
        Tyr Phe Ala Ile Ser Lys Phe Ile Gly Phe Gly Thr Asp Ser Trp Val
                        325                 330                 335

Tyr Pro Asn Ile Ser Ile Pro Glu His Gly Arg Leu Ser Arg Lys Tyr
                        340                 345                 350

Ile Tyr Ser Leu Tyr Trp Ser Thr Leu Thr Leu Thr Thr Ile Gly Glu
                        355                 360                 365

Thr Pro Pro Val Lys Asp Glu Glu Tyr Leu Phe Val Val Val Val Asp
            370                 375                 380

Phe Leu Val Gly Val Leu Ile Phe Ala Thr Ile Val Gly Asn Val Gly
        385                 390                 395                 400

Ser Met Ile Ser Asn Met Asn Ala Ser Arg Ala Glu Phe Gln Ala Lys
                        405                 410                 415

Ile Asp Ser Ile Lys Gln Tyr Met Gln Phe Arg Lys Val Thr Lys Asp
                        420                 425                 430

Leu Glu Thr Arg Val Ile Arg Trp Phe Asp Tyr Leu Trp Ala Asn Lys
                        435                 440                 445

Lys Thr Val Asp Glu Lys Glu Val Leu Lys Ser Leu Pro Asp Lys Leu
                        450                 455                 460

Lys Ala Glu Ile Ala Ile Asn Val His Leu Asp Thr Leu Lys Lys Val
        465                 470                 475                 480

Arg Ile Phe Gln Asp Cys Glu Ala Gly Leu Leu Val Glu Leu Val Leu
                        485                 490                 495

Lys Leu Arg Pro Thr Val Phe Ser Pro Gly Asp Tyr Ile Cys Lys Lys
                        500                 505                 510

Gly Asp Ile Gly Lys Glu Met Tyr Ile Ile Asn Glu Gly Lys Leu Ala
                        515                 520                 525

Val Val Ala Asp Asp Gly Val Thr Gln Phe Val Val Leu Ser Asp Gly
        530                 535                 540

Ser Tyr Phe Gly Glu Ile Ser Ile Leu Asn Ile Lys Gly Ser Lys Ser
        545                 550                 555                 560

Gly Asn Arg Arg Thr Ala Asn Ile Arg Ser Ile Gly Tyr Ser Asp Leu
                        565                 570                 575

Phe Cys Leu Ser Lys Asp Asp Leu Met Glu Ala Leu Thr Glu Tyr Pro
                        580                 585                 590

Glu Ala Lys Lys Ala Leu Glu Glu Lys Gly Arg Gln Ile Leu Met Lys
                        595                 600                 605

Asp Asn Leu Ile Asp Glu Glu Leu Ala Arg Ala Gly Ala Asp Pro Lys
                        610                 615                 620

Asp Leu Glu Glu Lys Val Glu Gln Leu Gly Ser Ser Leu Asp Thr Leu
        625                 630                 635                 640

Gln Thr Arg Phe Ala Arg Leu Leu Ala Glu Tyr Asn Ala Thr Gln Met
                        645                 650                 655

Lys Met Lys Gln Arg Leu Ser Gln Leu Glu Ser Gln Val Lys Gly Gly
                        660                 665                 670

Gly Asp Lys Pro Leu Ala Asp Gly Glu Val Pro Gly Asp Ala Thr Lys
                        675                 680                 685

Thr Glu Asp Lys Gln Gln
            690

<210> SEQ ID NO 15
<211> LENGTH: 2085
<212> TYPE: DNA
<213> ORGANISM: Homo sapiens
```

<400> SEQUENCE: 15

```
atggccaaga tcaacaccca atactcccac ccctccagga cccacctcaa ggtaaagacc        60
tcagaccgag atctcaatcg cgctgaaaat ggcctcagca gagcccactc gtcaagtgag       120
gagacatcgt cagtgctgca gccggggatc gccatgagac cagaggact ggctgactcc        180
gggcagggct ccttcaccgg ccaggggatc gccaggctgt cgcgcctcat cttcttgctg       240
cgcaggtggg ctgccaggca tgtgcaccac caggaccagg gaccggactc ttttcctgat       300
cgtttccgtg gagccgagct taaggaggtg tccagccaag aaagcaatgc ccaggcaaat       360
gtgggcagcc aggagccagc agacagaggg agaagcgcct ggcccctggc caaatgcaac       420
actaacacca gcaacaacac ggaggaggag aagaagacga aaaagaagga tgcgatcgtg       480
gtggacccgt ccagcaacct gtactaccgc tggctgaccg ccatcgccct gcctgtcttc       540
tataactggt atctgcttat ttgcagggcc tgtttcgatg agctgcagtc cgagtacctg       600
atgctgtggc tggtcctgga ctactcggca gatgtcctgt atgtcttgga tgtgcttgta       660
cgagctcgga caggttttct cgagcaaggc ttaatggtca gtgataccaa caggctgtgg       720
cagcattaca agacgaccac gcagttcaag ctggatgtgt tgtccctggt ccccaccgac       780
ctggcttact taaaggtggg cacaaactac ccagaagtga ggttcaaccg cctactgaag       840
ttttcccggc tctttgaatt cttttgaccgc acagagacaa ggaccaacta ccccaatatg       900
ttcaggattg ggaacttggt cttgtacatt ctcatcatca tccactggaa tgcctgcatc       960
tactttgcca tttccaagtt cattggtttt gggacagact cctgggtcta cccaaacatc      1020
tcaatcccag agcatgggcg cctctccagg aagtacattt acagtctcta ctggtccacc      1080
ttgacccctta ccaccattgg tgagaccccca ccccccgtga agatgaggga gtatctcttt      1140
gtggtcgtag acttcttggt gggtgttctg attttttgcca ccattgtggg caatgtgggc      1200
tccatgatct cgaatatgaa tgcctcacgg gcagagttcc aggccaagat tgattccatc      1260
aagcagtaca tgcagttccg caaggtcacc aaggacttgg agacgcgggt tatccggtgg      1320
tttgactacc tgtgggccaa caagaagacg gtggatgaga aggaggtgct caagagcctc      1380
ccagacaagc tgaaggctga gatcgccatc aacgtgcacc tggacacgct gaagaaggtt      1440
cgcatcttcc aggactgtga ggcagggctg ctggtggagc tggtgctgaa gctgcgaccc      1500
actgtgttca gccctgggga ttatatctgc aagaagggag atattgggaa ggagatgtac      1560
atcatcaacg agggcaagct ggccgtggtg gctgatgatg gggtcaccca gttcgtggtc      1620
ctcagcgatg gcagctactt cggggagatc agcattctga acatcaaggg gagcaagtcg      1680
gggaaccgca ggacggccaa catccgcagc attggctact cagacctgtt ctgcctctca      1740
aaggacgatc tcatggaggc cctcaccgag taccccgaag ccaagaaggc cctggaggag      1800
aaaggacggc agatcctgat gaaagacaac ctgatcgatg aggagctggc cagggcgggc      1860
gcggacccca aggaccttga ggagaaagtg gagcagctgg ggtcctccct ggacaccctg      1920
cagaccaggt ttgcacgcct cctggctgag tacaacgcca cccagatgaa gatgaagcag      1980
cgtctcagcc aactggaaag ccaggtgaag ggtggtgggg acaagcccct ggctgatggg      2040
gaagttcccg gggatgctac aaaaacagag gacaaacaac agtga                    2085
```

<210> SEQ ID NO 16
<211> LENGTH: 2107
<212> TYPE: DNA
<213> ORGANISM: Artificial Sequence
<220> FEATURE:

<223> OTHER INFORMATION: constructed sequence

<400> SEQUENCE: 16

```
gcggccgcca ccatggctaa gattaacacc cagtactcac atccatcccg cactcacctc    60
aaagtcaaga cctccgatcg ggatctgaac cgggctgaga atgggctgtc gcgcgcccac   120
tcgtcgtccg aggaaaccag cagcgtgctc cagccgggca tcgccatgga aactaggggg   180
ctggcggact ccggacaggg atccttcact ggacagggta ttgcccggct gagcagactg   240
atcttcctgc ttcgccgctg gcggccaga cacgtgcacc atcaggacca gggacctgat   300
agcttccccg accgctttag gggagccgag ctgaaagaag tgtcaagcca ggagtcaaac   360
gcgcaggcca acgtcggcag ccaagagcct gcagaccggg gacgctcggc atggccgctc   420
gcaaagtgca acactaacac ttccaacaac accgaagagg aaaagaaaac caagaagaag   480
gatgcaattg tggtggaccc ttcctccaac ctgtactacc gctggttgac cgccatcgcc   540
ctcccggtct tttacaattg gtatctcctt atctgccggg cctgcttcga cgaactgcaa   600
tcagagtacc tgatgctgtg gctggtgctg gactatagcg ccgatgtgct ctacgtcctg   660
gatgtgctcg tgcgcgcccg gaccggattc ttggaacaag gcctgatggt gtccgacacg   720
aatagactgt ggcagcacta taagaccaca acccagttca agcttgacgt gctcagcctt   780
gtgccgactg acctggccta cctgaaagtc ggaactaact acccggaagt cagattcaac   840
cgactcctga agttcagcag gctgttcgag ttctttgacc gcaccgagac tcggaccaac   900
taccctaaca tgttccggat cggaaatctg gtgctctaca tactgattat catccattgg   960
aacgcctgta tctatttcgc catttcgaag ttcatcggtt tcggaaccga ttcctgggtg  1020
taccccaaca tctcgatccc cgaacacggt cgcctgtccc ggaagtacat ctactccctg  1080
tactggtcca tctgactct gaccacgatc ggggaaaccc ctccacccgt gaaggacgaa  1140
gagtacctgt tcgtggtggt ggacttcctg gtcggagtgt tgattttcgc caccattgtg  1200
ggaaacgtgg gctccatgat ctccaacatg aacgcgtcga gagctgagtt ccaagccaag  1260
atcgactcca ttaagcagta catgcagttc agaaaggtca ccaaggacct ggaaaccagg  1320
gtcatccgct ggttcgacta cctgtgggcc aacaaaaaga ctgtggacga aaaggaagtg  1380
ctgaagtcgc tgccggataa gctgaaggcc gaaatcgcca ttaacgtgca ccttgacacc  1440
ctgaagaaag tccggatctt ccaagactgt gaagccggcc tcctggtgga gctcgtgctc  1500
aagctgcggc ccaccgtgtt cagcccggga gattacattt gcaagaaggg cgatatcggc  1560
aaagagatgt acatcatcaa cgagggaaag ctggccgtgg tcgcggacga cggcgtgacc  1620
cagttcgtgg tgctgtccga cggatcctac ttcggtgaaa tctcaatcct caacatcaag  1680
gggtccaagt ccggcaaccg gagaactgcc aacattcgct ccatcggata cagcgacctg  1740
ttttgcctgt ccaaggatga cctgatggag gctctgactg agtaccctga agcgaagaag  1800
gctttggagg aaaagggggcg gcagattctg atgaaggaca atttgatcga cgaggagctc  1860
gcacgggccg gcgccgaccc caaggatctc gaagagaagg tcgaacagct gggttcttcg  1920
cttgataccc tgcaaacccg attgcgcgcgg ctgctcgccg agtacaacgc gacccagatg  1980
aagatgaagc agagactgtc acagttggaa tcccaagtca agggcggagg cgacaagccg  2040
ctggcggacg gggaagtgcc cggggacgcc accaagactg aggacaagca gcagtgatca  2100
tagatct                                                             2107
```

<210> SEQ ID NO 17
<211> LENGTH: 2272

```
<212> TYPE: DNA
<213> ORGANISM: Artificial Sequence
<220> FEATURE:
<223> OTHER INFORMATION: constructed sequence

<400> SEQUENCE: 17
gcggccgcca ccatggctaa gattaacacc cagtactcac atccatcccg cactcacctc      60
aaagtcaaga cctccgatcg ggatctgaac cgggctgaga atgggctgtc gcgcgcccac     120
tcgtcgtccg aggaaaccag cagcgtgctc cagccgggca tcgccatgga aactaggggg     180
ctggcggact ccggacaggg atccttcact ggacagggta ttgcccggtt cgggcggatt     240
cagaagaagt cccagccgga gaaggtcgtg cgggctgcca gcagggcag gccactcatt      300
ggttggacac agtggtgcgc tgaggatggt ggagatgaat cggaaatggc actggccggc     360
tctcccggat gcagctcggg cccccaaggg agactgagca gactgatctt cctgcttcgc     420
cgctgggcgg ccagacacgt gcaccatcag gaccagggac ctgatagctt ccccgaccgc     480
tttaggggag ccgagctgaa agaagtgtca agccaggagt caaacgcgca ggccaacgtc     540
ggcagccaag agcctgcaga ccggggacgc tcggcatggc cgctcgcaaa gtgcaacact     600
aacacttcca acaaccga agaggaaaag aaaaccaaga agaaggatgc aattgtggtg       660
gacccttcct ccaacctgta ctaccgctgg ttgaccgcca tcgccctccc ggtcttttac     720
aattggtatc tccttatctg ccgggcctgc ttcgacgaac tgcaatcaga gtacctgatg     780
ctgtggctgg tgctggacta tagcgccgat gtgctctacg tcctggatgt gctcgtgcgc     840
gcccggaccg gattcttgga caaggcctg atggtgtccg acacgaatag actgtggcag      900
cactataaga ccacaaccca gttcaagctt gacgtgctca gccttgtgcc gactgacctg     960
gcctacctga agtcggaac taactacccg gaagtcagat tcaaccgact cctgaagttc    1020
agcaggctgt tcgagttctt tgaccgcacc gagactcgga ccaactaccc taacatgttc    1080
cggatcggaa atctggtgct ctacatactg attatcatcc attggaacgc ctgtatctat    1140
ttcgccattt cgaagttcat cggtttcgga accgattcct gggtgtaccc caacatctcg    1200
atccccgaac acgtcgcct gtcccggaag tacatctact ccctgtactg gtccactctg    1260
actctgacca cgatcgggga aaccccctcca cccgtgaagg acgaagagta cctgttcgtg    1320
gtggtggact tcctggtcgg agtgttgatt ttcgccacca ttgtgggaaa cgtgggctcc    1380
atgatctcca acatgaacgc gtcgagagct gagttccaag ccaagatcga ctccattaag    1440
cagtacatgc agttcagaaa ggtcaccaag gacctggaaa ccagggtcat ccgctggttc    1500
gactacctgt gggccaacaa aaagactgtg acgaaaagg aagtgctgaa gtcgctgccg     1560
gataagctga aggccgaaat cgccattaac gtgcaccttg acaccctgaa gaaagtccgg    1620
atcttccaag actgtgaagc cggcctcctg gtggagctcg tgctcaagct gcggccacc     1680
gtgttcagcc cggagatta catttgcaag aagggcgata tcggcaaaga gatgtacatc    1740
atcaacgagg gaaagctggc cgtggtcgcg gacgacggcg tgacccagtt cgtggtgctg    1800
tccgacggat cctacttcgg tgaaatctca atcctcaaca tcaaggggtc caagtccggc    1860
aaccggagaa ctgccaacat tcgctccatc ggatacagcg acctgttttg cctgtccaag    1920
gatgacctga tggaggctct gactgagtac cctgaagcga agaaggcttt ggaggaaaag    1980
gggcggcaga ttctgatgaa ggacaatttg atcgacgagg agctcgcacg ggccggcgcc    2040
gacccccaagg atctcgaaga gaaggtcgaa cagctgggtt cttcgcttga taccctgcaa    2100
acccgattcg cgcggctgct cgccgagtac aacgcgaccc agatgaagat gaagcagaga    2160
```

| | |
|---|---|
| ctgtcacagt tggaatccca agtcaagggc ggaggcgaca agccgctggc ggacggggaa | 2220 |
| gtgcccgggg acgccaccaa gactgaggac aagcagcagt gatcatagat ct | 2272 |

<210> SEQ ID NO 18
<211> LENGTH: 2107
<212> TYPE: DNA
<213> ORGANISM: Artificial Sequence
<220> FEATURE:
<223> OTHER INFORMATION: constructed sequence

<400> SEQUENCE: 18

| | |
|---|---|
| gcggccgcca ccatggccaa gatcaacacc caatactccc acccctccag gacccacctc | 60 |
| aaggtaaaga cctcagaccg ggatctcaat cgcgctgaaa atggcctcag cagagcccac | 120 |
| tcgtcaagtg aggagacatc gtcagtgctg cagccgggga tcgccatgga gaccagagga | 180 |
| ctggctgact ccgggcaggg ctccttcacc ggccagggga tcgccaggct gtcgcgcctc | 240 |
| atcttcttgc tgcgcaggtg ggctgccagg catgtgcacc accaggacca gggaccggac | 300 |
| tcttttcctg atcgtttccg tggagccgag cttaaggagt gtccagcca agaaagcaat | 360 |
| gcccaggcaa atgtgggcag ccaggagcca gcagacagag ggagaagcgc ctggcccctg | 420 |
| gccaaatgca acactaacac cagcaacaac acggaggagg agaagaagac gaaaaagaag | 480 |
| gatgcgatcg tggtggaccc gtccagcaac ctgtactacc gctggctgac cgccatcgcc | 540 |
| ctgcctgtct tctataactg gtatctgctt atttgcaggg cctgtttcga tgagctgcag | 600 |
| tccgagtacc tgatgctgtg gctggtcctg gactactcgg cagatgtcct gtatgtcttg | 660 |
| gatgtgcttg tacgagctcg gacaggtttt cttgagcaag gcttaatggt cagtgatacc | 720 |
| aacaggctgt ggcagcatta caagacgacc acgcagttca agctggatgt gttgtccctg | 780 |
| gtccccaccg acctggctta cttaaaggtg ggcacaaact acccagaagt gaggttcaac | 840 |
| cgcctactga agtttttccg gctctttgaa ttctttgacc gcacagagac aaggaccaac | 900 |
| taccccaata tgttcaggat tgggaacttg gtcttgtaca ttctcatcat catccactgg | 960 |
| aatgcctgca tctactttgc catttccaag ttcattggtt ttgggacaga ctcctgggtc | 1020 |
| tacccaaaca tctcaatccc agagcatggg cgcctctcca ggaagtacat ttacagtctc | 1080 |
| tactggtcca ccttgacccc taccaccatt ggtgagaccc acccccccgt gaaagatgag | 1140 |
| gagtatctct ttgtggtcgt agacttcttg gtgggtgttc tgattttttgc caccattgtg | 1200 |
| ggcaatgtgg gctccatgat ctcgaatatg aatgcctcac gggcagagtt ccaggccaag | 1260 |
| attgattcca tcaagcagta catgcagttc cgcaaggtca ccaaggactt ggagacgcgg | 1320 |
| gttatccggt ggtttgacta cctgtgggcc aacaagaaga cggtggatga aaggaggtg | 1380 |
| ctcaagagcc tcccagacaa gctgaaggct gagatcgcca tcaacgtgca cctggacacg | 1440 |
| ctgaagaagg ttcgcatctt ccaggactgt gaggcagggc tgctggtgga gctggtgctg | 1500 |
| aagctgcgac ccactgtgtt cagccctggg gattatatct gcaagaaggg agatattggg | 1560 |
| aaggagatgt acatcatcaa cgagggcaag ctggccgtgg tggctgatga tggggtcacc | 1620 |
| cagttcgtgg tcctcagcga tggcagctac ttcggggaga tcagcattct gaacatcaag | 1680 |
| gggagcaagt cggggaaccg caggacggcc aacatccgca gcattggcta ctcagacctg | 1740 |
| ttctgcctct caaaggacga tctcatggag gccctcaccg agtaccccga agccaagaag | 1800 |
| gccctggagg agaaaggacg gcagatcctg atgaaagaca acctgatcga tgaggagctg | 1860 |
| gccagggcgg gcgcggaccc caaggacctt gaggagaaag tggagcagct ggggtcctcc | 1920 |
| ctggacaccc tgcagaccag gtttgcacgc ctcctggctg agtacaacgc cacccagatg | 1980 |

```
aagatgaagc agcgtctcag ccaactggaa agccaggtga agggtggtgg ggacaagccc    2040
ctggctgatg gggaagttcc cggggatgct acaaaaacag aggacaaaca acagtgatca    2100
tagatct                                                              2107

<210> SEQ ID NO 19
<211> LENGTH: 2430
<212> TYPE: DNA
<213> ORGANISM: Homo sapiens
<220> FEATURE:
<221> NAME/KEY: CDS
<222> LOCATION: (1)..(2430)

<400> SEQUENCE: 19 atg ttt aaa tcg ctg aca aaa gtc aac aag gtg aag cct ata gga gag     48
Met Phe Lys Ser Leu Thr Lys Val Asn Lys Val Lys Pro Ile Gly Glu
1               5                   10                  15 aac aat gag aat gaa caa agt tct cgt cgg aat gaa gaa ggc tct cac     96
Asn Asn Glu Asn Glu Gln Ser Ser Arg Arg Asn Glu Glu Gly Ser His
                20                  25                  30 cca agt aat cag tct cag caa acc aca gca cag gaa gaa aac aaa ggt    144
Pro Ser Asn Gln Ser Gln Gln Thr Thr Ala Gln Glu Glu Asn Lys Gly
            35                  40                  45 gaa gag aaa tct ctc aaa acc aag tca act cca gtc acg tct gaa gag    192
Glu Glu Lys Ser Leu Lys Thr Lys Ser Thr Pro Val Thr Ser Glu Glu
50                  55                  60 cca cac acc aac ata caa gac aaa ctc tcc aag aaa aat tcc tct gga    240
Pro His Thr Asn Ile Gln Asp Lys Leu Ser Lys Lys Asn Ser Ser Gly
65                  70                  75                  80 gat ctg acc aca aac cct gac cct caa aat gca gca gaa cca act gga    288
Asp Leu Thr Thr Asn Pro Asp Pro Gln Asn Ala Ala Glu Pro Thr Gly
                85                  90                  95 aca gtg cca gag cag aag gaa atg gac ccc ggg aaa gaa ggt cca aac    336
Thr Val Pro Glu Gln Lys Glu Met Asp Pro Gly Lys Glu Gly Pro Asn
            100                 105                 110 agc cca caa aac aaa ccg cct gca gct cct gtt ata aat gag tat gcc    384
Ser Pro Gln Asn Lys Pro Pro Ala Ala Pro Val Ile Asn Glu Tyr Ala
        115                 120                 125 gat gcc cag cta cac aac ctg gtg aaa aga atg cgt caa aga aca gcc    432
Asp Ala Gln Leu His Asn Leu Val Lys Arg Met Arg Gln Arg Thr Ala
    130                 135                 140 ctc tac aag aaa aag ttg gta gag gga gat ctc tcc tca ccc gaa gcc    480
Leu Tyr Lys Lys Lys Leu Val Glu Gly Asp Leu Ser Ser Pro Glu Ala
145                 150                 155                 160 agc cca caa act gca aag ccc acg gct gta cca cca gta aaa gaa agc    528
Ser Pro Gln Thr Ala Lys Pro Thr Ala Val Pro Pro Val Lys Glu Ser
                165                 170                 175 gat gat aag cca aca gaa cat tac tac agg ctg ttg tgg ttc aaa gtc    576
Asp Asp Lys Pro Thr Glu His Tyr Tyr Arg Leu Leu Trp Phe Lys Val
            180                 185                 190 aaa aag atg cct tta aca gag tac tta aag cga att aaa ctt cca aac    624
Lys Lys Met Pro Leu Thr Glu Tyr Leu Lys Arg Ile Lys Leu Pro Asn
        195                 200                 205 agc ata gat tca tac aca gat cga ctc tat ctc ctg tgg ctc ttg ctt    672
Ser Ile Asp Ser Tyr Thr Asp Arg Leu Tyr Leu Leu Trp Leu Leu Leu
    210                 215                 220 gtc act ctt gcc tat aac tgg aac tgc tgt ttt ata cca ctg cgc ctc    720
Val Thr Leu Ala Tyr Asn Trp Asn Cys Cys Phe Ile Pro Leu Arg Leu
225                 230                 235                 240 gtc ttc cca tat caa acc gca gac aac ata cac tac tgg ctt att gcg    768
```

```
Val Phe Pro Tyr Gln Thr Ala Asp Asn Ile His Tyr Trp Leu Ile Ala
            245                 250                 255 gac atc ata tgt gat atc atc tac ctt tat gat atg cta ttt atc cag    816
Asp Ile Ile Cys Asp Ile Ile Tyr Leu Tyr Asp Met Leu Phe Ile Gln
            260                 265                 270 ccc aga ctc cag ttt gta aga gga gga gac ata ata gtg gat tca aat    864
Pro Arg Leu Gln Phe Val Arg Gly Gly Asp Ile Ile Val Asp Ser Asn
            275                 280                 285 gag cta agg aaa cac tac agg act tct aca aaa ttt cag ttg gat gtc    912
Glu Leu Arg Lys His Tyr Arg Thr Ser Thr Lys Phe Gln Leu Asp Val
            290                 295                 300 gca tca ata ata cca ttt gat att tgc tac ctc ttc ttt ggg ttt aat    960
Ala Ser Ile Ile Pro Phe Asp Ile Cys Tyr Leu Phe Phe Gly Phe Asn
305                 310                 315                 320 cca atg ttt aga gca aat agg atg tta aag tac act tca ttt ttt gaa   1008
Pro Met Phe Arg Ala Asn Arg Met Leu Lys Tyr Thr Ser Phe Phe Glu
            325                 330                 335 ttt aat cat cac cta gag tct ata atg gac aaa gca tat atc tac aga   1056
Phe Asn His His Leu Glu Ser Ile Met Asp Lys Ala Tyr Ile Tyr Arg
            340                 345                 350 gtt att cga aca act gga tac ttg ctg ttt att ctg cac att aat gcc   1104
Val Ile Arg Thr Thr Gly Tyr Leu Leu Phe Ile Leu His Ile Asn Ala
            355                 360                 365 tgt gtt tat tac tgg gct tca aac tat gaa gga att ggc act act aga   1152
Cys Val Tyr Tyr Trp Ala Ser Asn Tyr Glu Gly Ile Gly Thr Thr Arg
            370                 375                 380 tgg gtg tat gat ggg gaa gga aac gag tat ctg aga tgt tat tat tgg   1200
Trp Val Tyr Asp Gly Glu Gly Asn Glu Tyr Leu Arg Cys Tyr Tyr Trp
385                 390                 395                 400 gca gtt cga act tta att acc att ggt ggc ctt cca gaa cca caa act   1248
Ala Val Arg Thr Leu Ile Thr Ile Gly Gly Leu Pro Glu Pro Gln Thr
            405                 410                 415 tta ttt gaa att gtt ttt caa ctc ttg aat ttt ttt tct gga gtt ttt   1296
Leu Phe Glu Ile Val Phe Gln Leu Leu Asn Phe Phe Ser Gly Val Phe
            420                 425                 430 gtg ttc tcc agt tta att ggt cag atg aga gat gtg att gga gca gct   1344
Val Phe Ser Ser Leu Ile Gly Gln Met Arg Asp Val Ile Gly Ala Ala
            435                 440                 445 aca gcc aat cag aac tac ttc cgc gcc tgc atg gat gac acc att gcc   1392
Thr Ala Asn Gln Asn Tyr Phe Arg Ala Cys Met Asp Asp Thr Ile Ala
450                 455                 460 tac atg aac aat tac tcc att cct aaa ctt gtg caa aag cga gtt cgg   1440
Tyr Met Asn Asn Tyr Ser Ile Pro Lys Leu Val Gln Lys Arg Val Arg
465                 470                 475                 480 act tgg tat gaa tat aca tgg gac tct caa aga atg cta gat gag tct   1488
Thr Trp Tyr Glu Tyr Thr Trp Asp Ser Gln Arg Met Leu Asp Glu Ser
            485                 490                 495 gat ttg ctt aag acc cta cca act acg gtc cag tta gcc ctc gcc att   1536
Asp Leu Leu Lys Thr Leu Pro Thr Thr Val Gln Leu Ala Leu Ala Ile
            500                 505                 510 gat gtg aac ttc agc atc atc agc aaa gtc gac ttg ttc aag ggt tgt   1584
Asp Val Asn Phe Ser Ile Ile Ser Lys Val Asp Leu Phe Lys Gly Cys
            515                 520                 525 gat aca cag atg att tat gac atg ttg cta aga ttg aaa tcc gtt ctc   1632
Asp Thr Gln Met Ile Tyr Asp Met Leu Leu Arg Leu Lys Ser Val Leu
            530                 535                 540 tat ttg cct ggt gac ttt gtc tgc aaa aag gga gaa att ggc aag gaa   1680
Tyr Leu Pro Gly Asp Phe Val Cys Lys Lys Gly Glu Ile Gly Lys Glu
545                 550                 555                 560
```

| | | | | | | | | | | | | | | | |
|---|---|---|---|---|---|---|---|---|---|---|---|---|---|---|---|
| atg | tat | atc | atc | aag | cat | gga | gaa | gtc | caa | gtt | ctt | gga | ggc | cct | gat | 1728 |
| Met | Tyr | Ile | Ile | Lys | His | Gly | Glu | Val | Gln | Val | Leu | Gly | Gly | Pro | Asp | |
| | | | | 565 | | | | 570 | | | | | 575 | | | |
| ggt | act | aaa | gtt | ctg | gtt | act | ctg | aaa | gct | ggg | tcg | gtg | ttt | gga | gaa | 1776 |
| Gly | Thr | Lys | Val | Leu | Val | Thr | Leu | Lys | Ala | Gly | Ser | Val | Phe | Gly | Glu | |
| | | | 580 | | | | | 585 | | | | | 590 | | | |
| atc | agc | ctt | cta | gca | gca | gga | gga | gga | aac | cgt | cga | act | gcc | aat | gtg | 1824 |
| Ile | Ser | Leu | Leu | Ala | Ala | Gly | Gly | Gly | Asn | Arg | Arg | Thr | Ala | Asn | Val | |
| | | | 595 | | | | | 600 | | | | | 605 | | | |
| gtg | gcc | cac | ggg | ttt | gcc | aat | ctt | tta | act | cta | gac | aaa | aag | acc | ctc | 1872 |
| Val | Ala | His | Gly | Phe | Ala | Asn | Leu | Leu | Thr | Leu | Asp | Lys | Lys | Thr | Leu | |
| | | 610 | | | | | 615 | | | | | 620 | | | | |
| caa | gaa | att | cta | gtg | cat | tat | cca | gat | tct | gaa | agg | atc | ctc | atg | aag | 1920 |
| Gln | Glu | Ile | Leu | Val | His | Tyr | Pro | Asp | Ser | Glu | Arg | Ile | Leu | Met | Lys | |
| 625 | | | | | 630 | | | | | 635 | | | | | 640 | |
| aaa | gcc | aga | gtg | ctt | tta | aag | cag | aag | gct | aag | acc | gca | gaa | gca | acc | 1968 |
| Lys | Ala | Arg | Val | Leu | Leu | Lys | Gln | Lys | Ala | Lys | Thr | Ala | Glu | Ala | Thr | |
| | | | | 645 | | | | | 650 | | | | | 655 | | |
| cct | cca | aga | aaa | gat | ctt | gcc | ctc | ctc | ttc | cca | ccg | aaa | gaa | gag | aca | 2016 |
| Pro | Pro | Arg | Lys | Asp | Leu | Ala | Leu | Leu | Phe | Pro | Pro | Lys | Glu | Glu | Thr | |
| | | | 660 | | | | | 665 | | | | | 670 | | | |
| ccc | aaa | ctg | ttt | aaa | act | ctc | cta | gga | ggc | aca | gga | aaa | gca | agt | ctt | 2064 |
| Pro | Lys | Leu | Phe | Lys | Thr | Leu | Leu | Gly | Gly | Thr | Gly | Lys | Ala | Ser | Leu | |
| | | 675 | | | | | 680 | | | | | 685 | | | | |
| gca | aga | cta | ctc | aaa | ttg | aag | cga | gag | caa | gca | gct | cag | aag | aaa | gaa | 2112 |
| Ala | Arg | Leu | Leu | Lys | Leu | Lys | Arg | Glu | Gln | Ala | Ala | Gln | Lys | Lys | Glu | |
| | 690 | | | | | 695 | | | | | 700 | | | | | |
| aat | tct | gaa | gga | gga | gag | gaa | gaa | gga | aaa | gaa | aat | gaa | gat | aaa | caa | 2160 |
| Asn | Ser | Glu | Gly | Gly | Glu | Glu | Glu | Gly | Lys | Glu | Asn | Glu | Asp | Lys | Gln | |
| 705 | | | | | 710 | | | | | 715 | | | | | 720 | |
| aaa | gaa | aat | gaa | gat | aaa | caa | aaa | gaa | aat | gaa | gat | aaa | gga | aaa | gaa | 2208 |
| Lys | Glu | Asn | Glu | Asp | Lys | Gln | Lys | Glu | Asn | Glu | Asp | Lys | Gly | Lys | Glu | |
| | | | | 725 | | | | | 730 | | | | | 735 | | |
| aat | gaa | gat | aaa | gat | aaa | gga | aga | gag | cca | gaa | gag | aag | cca | ctg | gac | 2256 |
| Asn | Glu | Asp | Lys | Asp | Lys | Gly | Arg | Glu | Pro | Glu | Glu | Lys | Pro | Leu | Asp | |
| | | | 740 | | | | | 745 | | | | | 750 | | | |
| aga | cct | gaa | tgt | aca | gca | agt | cct | att | gca | gtg | gag | gaa | gaa | ccc | cac | 2304 |
| Arg | Pro | Glu | Cys | Thr | Ala | Ser | Pro | Ile | Ala | Val | Glu | Glu | Glu | Pro | His | |
| | | 755 | | | | | 760 | | | | | 765 | | | | |
| tca | gtt | aga | agg | aca | gtt | tta | ccc | aga | ggg | act | tct | cgt | caa | tca | ctc | 2352 |
| Ser | Val | Arg | Arg | Thr | Val | Leu | Pro | Arg | Gly | Thr | Ser | Arg | Gln | Ser | Leu | |
| | 770 | | | | | 775 | | | | | 780 | | | | | |
| att | atc | agc | atg | gct | cct | tct | gct | gag | ggc | gga | gaa | gag | gtt | ctt | act | 2400 |
| Ile | Ile | Ser | Met | Ala | Pro | Ser | Ala | Glu | Gly | Gly | Glu | Glu | Val | Leu | Thr | |
| 785 | | | | 790 | | | | | 795 | | | | | 800 | | |
| att | gaa | gtc | aaa | gaa | aag | gct | aag | caa | taa | | | | | | | 2430 |
| Ile | Glu | Val | Lys | Glu | Lys | Ala | Lys | Gln | | | | | | | | |
| | | | | 805 | | | | | | | | | | | | |

<210> SEQ ID NO 20
<211> LENGTH: 809
<212> TYPE: PRT
<213> ORGANISM: Homo sapiens

<400> SEQUENCE: 20

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly

```
                35                  40                  45
Glu Glu Lys Ser Leu Lys Thr Lys Ser Thr Pro Val Thr Ser Glu Glu
 50                  55                  60

Pro His Thr Asn Ile Gln Asp Lys Leu Ser Lys Lys Asn Ser Ser Gly
 65                  70                  75                  80

Asp Leu Thr Thr Asn Pro Asp Pro Gln Asn Ala Ala Glu Pro Thr Gly
                 85                  90                  95

Thr Val Pro Glu Gln Lys Glu Met Asp Pro Gly Lys Glu Gly Pro Asn
             100                 105                 110

Ser Pro Gln Asn Lys Pro Pro Ala Ala Pro Val Ile Asn Glu Tyr Ala
         115                 120                 125

Asp Ala Gln Leu His Asn Leu Val Lys Arg Met Arg Gln Arg Thr Ala
     130                 135                 140

Leu Tyr Lys Lys Lys Leu Val Glu Gly Asp Leu Ser Ser Pro Glu Ala
 145                 150                 155                 160

Ser Pro Gln Thr Ala Lys Pro Thr Ala Val Pro Pro Val Lys Glu Ser
                 165                 170                 175

Asp Asp Lys Pro Thr Glu His Tyr Tyr Arg Leu Leu Trp Phe Lys Val
             180                 185                 190

Lys Lys Met Pro Leu Thr Glu Tyr Leu Lys Arg Ile Lys Leu Pro Asn
         195                 200                 205

Ser Ile Asp Ser Tyr Thr Asp Arg Leu Tyr Leu Leu Trp Leu Leu Leu
     210                 215                 220

Val Thr Leu Ala Tyr Asn Trp Asn Cys Cys Phe Ile Pro Leu Arg Leu
 225                 230                 235                 240

Val Phe Pro Tyr Gln Thr Ala Asp Asn Ile His Tyr Trp Leu Ile Ala
                 245                 250                 255

Asp Ile Ile Cys Asp Ile Tyr Leu Tyr Asp Met Leu Phe Ile Gln
             260                 265                 270

Pro Arg Leu Gln Phe Val Arg Gly Gly Asp Ile Ile Val Asp Ser Asn
         275                 280                 285

Glu Leu Arg Lys His Tyr Arg Thr Ser Thr Lys Phe Gln Leu Asp Val
     290                 295                 300

Ala Ser Ile Ile Pro Phe Asp Ile Cys Tyr Leu Phe Phe Gly Phe Asn
 305                 310                 315                 320

Pro Met Phe Arg Ala Asn Arg Met Leu Lys Tyr Thr Ser Phe Phe Glu
                 325                 330                 335

Phe Asn His His Leu Glu Ser Ile Met Asp Lys Ala Tyr Ile Tyr Arg
             340                 345                 350

Val Ile Arg Thr Thr Gly Tyr Leu Leu Phe Ile Leu His Ile Asn Ala
         355                 360                 365

Cys Val Tyr Tyr Trp Ala Ser Asn Tyr Glu Gly Ile Gly Thr Thr Arg
     370                 375                 380

Trp Val Tyr Asp Gly Glu Gly Asn Glu Tyr Leu Arg Cys Tyr Tyr Trp
 385                 390                 395                 400

Ala Val Arg Thr Leu Ile Thr Ile Gly Gly Leu Pro Glu Pro Gln Thr
                 405                 410                 415

Leu Phe Glu Ile Val Phe Gln Leu Leu Asn Phe Phe Ser Gly Val Phe
             420                 425                 430

Val Phe Ser Ser Leu Ile Gly Gln Met Arg Asp Val Ile Gly Ala Ala
         435                 440                 445

Thr Ala Asn Gln Asn Tyr Phe Arg Ala Cys Met Asp Asp Thr Ile Ala
     450                 455                 460
```

```
Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
            500                 505                 510

Asp Val Asn Phe Ser Ile Ile Ser Lys Val Asp Leu Phe Lys Gly Cys
        515                 520                 525

Asp Thr Gln Met Ile Tyr Asp Met Leu Leu Arg Leu Lys Ser Val Leu
    530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Gly Asn Arg Arg Thr Ala Asn Val
        595                 600                 605

Val Ala His Gly Phe Ala Asn Leu Leu Thr Leu Asp Lys Lys Thr Leu
    610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
        675                 680                 685

Ala Arg Leu Leu Lys Leu Lys Arg Glu Gln Ala Ala Gln Lys Lys Glu
    690                 695                 700

Asn Ser Glu Gly Gly Glu Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Glu Lys Pro Leu Asp
            740                 745                 750

Arg Pro Glu Cys Thr Ala Ser Pro Ile Ala Val Glu Glu Pro His
        755                 760                 765

Ser Val Arg Arg Thr Val Leu Pro Arg Gly Thr Ser Arg Gln Ser Leu
    770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805

<210> SEQ ID NO 21
<211> LENGTH: 2430
<212> TYPE: DNA
<213> ORGANISM: Artificial Sequence
<220> FEATURE:
<223> OTHER INFORMATION: constructed sequence
<220> FEATURE:
<221> NAME/KEY: CDS
<222> LOCATION: (1)..(2430)

<400> SEQUENCE: 21
```

```
atg ttt aaa tcg ctg aca aaa gtc aac aag gtg aag cct ata gga gag    48
Met Phe Lys Ser Leu Thr Lys Val Asn Lys Val Lys Pro Ile Gly Glu
1               5                   10                  15 aac aat gag aat gaa caa agt tct cgt cgg aat gaa gaa ggc tct cac    96
Asn Asn Glu Asn Glu Gln Ser Ser Arg Arg Asn Glu Glu Gly Ser His
            20                  25                  30 cca agt aat cag tct cag caa acc aca gca cag gaa gaa aac aaa ggt   144
Pro Ser Asn Gln Ser Gln Gln Thr Thr Ala Gln Glu Glu Asn Lys Gly
        35                  40                  45 gaa gag aaa tct ctc aaa acc aag tca act cca gtc acg tct gaa gag   192
Glu Glu Lys Ser Leu Lys Thr Lys Ser Thr Pro Val Thr Ser Glu Glu
50                  55                  60 cca cac acc aac ata caa gac aaa ctc tcc aag aaa aat tcc tct gga   240
Pro His Thr Asn Ile Gln Asp Lys Leu Ser Lys Lys Asn Ser Ser Gly
65                  70                  75                  80 gat ctg acc aca aac cct gac cct caa aat gca gca gaa cca act gga   288
Asp Leu Thr Thr Asn Pro Asp Pro Gln Asn Ala Ala Glu Pro Thr Gly
                85                  90                  95 aca gtg cca gag cag aag gaa atg gac ccc ggg aaa gaa ggt cca aac   336
Thr Val Pro Glu Gln Lys Glu Met Asp Pro Gly Lys Glu Gly Pro Asn
            100                 105                 110 agc cca caa aac aaa ccg cca gca gct cct gtt ata aat gag tat gcc   384
Ser Pro Gln Asn Lys Pro Pro Ala Ala Pro Val Ile Asn Glu Tyr Ala
        115                 120                 125 gat gcc cag cta cac aac ctg gtg aaa aga atg cgt caa aga aca gcc   432
Asp Ala Gln Leu His Asn Leu Val Lys Arg Met Arg Gln Arg Thr Ala
130                 135                 140 ctc tac aag aaa aag ttg gta gag gga gat ctc tca ccc gaa gcc       480
Leu Tyr Lys Lys Lys Leu Val Glu Gly Asp Leu Ser Ser Pro Glu Ala
145                 150                 155                 160 agc cca caa act gca aag ccc acg gct gta cca cca gta aaa gaa agc   528
Ser Pro Gln Thr Ala Lys Pro Thr Ala Val Pro Pro Val Lys Glu Ser
                165                 170                 175 gat gat aag cca aca gaa cat tac tac agg ctg ttg tgg ttc aaa gtc   576
Asp Asp Lys Pro Thr Glu His Tyr Tyr Arg Leu Leu Trp Phe Lys Val
            180                 185                 190 aaa aag atg cct tta aca gag tac tta aag cga att aaa ctt cca aac   624
Lys Lys Met Pro Leu Thr Glu Tyr Leu Lys Arg Ile Lys Leu Pro Asn
        195                 200                 205 agc ata gat tca tac aca gat cga ctc tat ctc ctg tgg ctc ttg ctt   672
Ser Ile Asp Ser Tyr Thr Asp Arg Leu Tyr Leu Leu Trp Leu Leu Leu
210                 215                 220 gtc act ctt gcc tat aac tgg aac tgc tgt ttt ata cca ctg cgc ctc   720
Val Thr Leu Ala Tyr Asn Trp Asn Cys Cys Phe Ile Pro Leu Arg Leu
225                 230                 235                 240 gtc ttc cca tat caa acc gca gac aac ata cac tac tgg ctt att gcg   768
Val Phe Pro Tyr Gln Thr Ala Asp Asn Ile His Tyr Trp Leu Ile Ala
                245                 250                 255 gac atc atc tgt gat atc atc tac ctt tat gat atg cta ttt atc cag   816
Asp Ile Ile Cys Asp Ile Ile Tyr Leu Tyr Asp Met Leu Phe Ile Gln
            260                 265                 270 ccc aga ctc cag ttt gta aga gga gga gac ata ata gtg gat tca aat   864
Pro Arg Leu Gln Phe Val Arg Gly Gly Asp Ile Ile Val Asp Ser Asn
        275                 280                 285 gag cta agg aaa cac tac agg act tct aca aaa ttt cag ttg gat gtc   912
Glu Leu Arg Lys His Tyr Arg Thr Ser Thr Lys Phe Gln Leu Asp Val
290                 295                 300 gca tca ata ata cca ttt gat att tgc tac ctc ttc ttt ggg ttt aat   960
Ala Ser Ile Ile Pro Phe Asp Ile Cys Tyr Leu Phe Phe Gly Phe Asn
```

```
                                                                -continued 305                 310                 315                 320
cca atg ttt aga gca aat agg atg tta aag tac act tca ttt ttt gaa   1008
Pro Met Phe Arg Ala Asn Arg Met Leu Lys Tyr Thr Ser Phe Phe Glu
            325                 330                 335 ttt aat cat cac cta gag tct ata atg gac aaa gca tat atc tac aga   1056
Phe Asn His His Leu Glu Ser Ile Met Asp Lys Ala Tyr Ile Tyr Arg
            340                 345                 350 gtt att cga aca act gga tac ttg ctg ttt att ctg cac att aat gcc   1104
Val Ile Arg Thr Thr Gly Tyr Leu Leu Phe Ile Leu His Ile Asn Ala
            355                 360                 365 tgt gtt tat tac tgg gct tca aac tat gaa gga att ggc act act aga   1152
Cys Val Tyr Tyr Trp Ala Ser Asn Tyr Glu Gly Ile Gly Thr Thr Arg
            370                 375                 380 tgg gtg tat gat ggg gaa gga aac gag tat ctg aga tgt tat tat tgg   1200
Trp Val Tyr Asp Gly Glu Gly Asn Glu Tyr Leu Arg Cys Tyr Tyr Trp
385                 390                 395                 400 gca gtt cga act tta att acc att ggt ggc ctt cca gaa cca caa act   1248
Ala Val Arg Thr Leu Ile Thr Ile Gly Gly Leu Pro Glu Pro Gln Thr
            405                 410                 415 tta ttt gaa att gtt ttt caa ctc ttg aat ttt ttt tct gga gtt ttt   1296
Leu Phe Glu Ile Val Phe Gln Leu Leu Asn Phe Phe Ser Gly Val Phe
            420                 425                 430 gtg ttc tcc agt tta att ggt cag atg aga gat gtg att gga gca gct   1344
Val Phe Ser Ser Leu Ile Gly Gln Met Arg Asp Val Ile Gly Ala Ala
            435                 440                 445 aca gcc aat cag aac tac ttc cgc gcc tgc atg gat gac acc att gcc   1392
Thr Ala Asn Gln Asn Tyr Phe Arg Ala Cys Met Asp Asp Thr Ile Ala
            450                 455                 460 tac atg aac aat tac tcc att cct aaa ctt gtg caa aag cga gtt cgg   1440
Tyr Met Asn Asn Tyr Ser Ile Pro Lys Leu Val Gln Lys Arg Val Arg
465                 470                 475                 480 act tgg tat gaa tat aca tgg gac tct caa aga atg cta gat gag tct   1488
Thr Trp Tyr Glu Tyr Thr Trp Asp Ser Gln Arg Met Leu Asp Glu Ser
            485                 490                 495 gat ttg ctt aag acc cta cca act acg gtc cag tta gcc ctc gcc att   1536
Asp Leu Leu Lys Thr Leu Pro Thr Thr Val Gln Leu Ala Leu Ala Ile
            500                 505                 510 gat gtg aac ttc agc atc atc agc aaa gtt gac ttg ttc aag ggt tgt   1584
Asp Val Asn Phe Ser Ile Ile Ser Lys Val Asp Leu Phe Lys Gly Cys
            515                 520                 525 gat aca cag atg att tat gac atg ttg cta aga ttg aaa tcc gtt ctc   1632
Asp Thr Gln Met Ile Tyr Asp Met Leu Leu Arg Leu Lys Ser Val Leu
            530                 535                 540 tat ttg cct ggt gac ttt gtc tgc aaa aag gga gaa att ggc aag gaa   1680
Tyr Leu Pro Gly Asp Phe Val Cys Lys Lys Gly Glu Ile Gly Lys Glu
545                 550                 555                 560 atg tat atc atc aag cat gga gaa gtc caa gtt ctt gga ggc cct gat   1728
Met Tyr Ile Ile Lys His Gly Glu Val Gln Val Leu Gly Gly Pro Asp
            565                 570                 575 ggt act aaa gtt ctg gtt act ctg aaa gct ggg tcg gtg ttt gga gaa   1776
Gly Thr Lys Val Leu Val Thr Leu Lys Ala Gly Ser Val Phe Gly Glu
            580                 585                 590 atc agc ctt cta gca gca gga gga gga aac cgt cga act gcc aat gtg   1824
Ile Ser Leu Leu Ala Ala Gly Gly Gly Asn Arg Arg Thr Ala Asn Val
            595                 600                 605 gtg gcc cac ggg ttt gcc aat ctt tta act cta gac aaa aag acc ctc   1872
Val Ala His Gly Phe Ala Asn Leu Leu Thr Leu Asp Lys Lys Thr Leu
            610                 615                 620 caa gaa att cta gtg cat tat cca gat tct gaa aga atc ctc atg aag   1920
```

```
Gln Glu Ile Leu Val His Tyr Pro Asp Ser Glu Arg Ile Leu Met Lys
625                 630                 635                 640 aaa gcc aga gtg ctt tta aag cag aag gct aag acc gca gaa gca acc      1968
Lys Ala Arg Val Leu Leu Lys Gln Lys Ala Lys Thr Ala Glu Ala Thr
                    645                 650                 655 cct cca aga aaa gat ctt gcc ctc ctc ttc cca ccg aaa gaa gag aca      2016
Pro Pro Arg Lys Asp Leu Ala Leu Leu Phe Pro Pro Lys Glu Glu Thr
                660                 665                 670 ccc aaa ctg ttt aaa act ctc cta gga ggc aca gga aaa gca agt ctt      2064
Pro Lys Leu Phe Lys Thr Leu Leu Gly Gly Thr Gly Lys Ala Ser Leu
            675                 680                 685 gca aga cta ctc aaa ttg aag cga gag caa gca gct cag aag aaa gaa      2112
Ala Arg Leu Leu Lys Leu Lys Arg Glu Gln Ala Ala Gln Lys Lys Glu
        690                 695                 700 aat tct gaa gga gga gag gaa gaa gga aaa gaa aat gaa gat aaa caa      2160
Asn Ser Glu Gly Gly Glu Glu Glu Gly Lys Glu Asn Glu Asp Lys Gln
705                 710                 715                 720 aaa gaa aat gaa gat aaa caa aaa gaa aat gaa gat aaa gga aaa gaa      2208
Lys Glu Asn Glu Asp Lys Gln Lys Glu Asn Glu Asp Lys Gly Lys Glu
                725                 730                 735 aat gaa gat aaa gat aaa gga aga gag cca gaa gag aag cca ctg gac      2256
Asn Glu Asp Lys Asp Lys Gly Arg Glu Pro Glu Glu Lys Pro Leu Asp
            740                 745                 750 aga cct gaa tgt aca gca agt cct att gca gtg gag gaa gaa ccc cac      2304
Arg Pro Glu Cys Thr Ala Ser Pro Ile Ala Val Glu Glu Glu Pro His
        755                 760                 765 tca gtt aga agg aca gtt tta ccc aga ggg act tct cgt caa tca ctc      2352
Ser Val Arg Arg Thr Val Leu Pro Arg Gly Thr Ser Arg Gln Ser Leu
770                 775                 780 att atc agc atg gct cct tct gct gag ggc gga gaa gag gtt ctt act      2400
Ile Ile Ser Met Ala Pro Ser Ala Glu Gly Gly Glu Glu Val Leu Thr
785                 790                 795                 800 att gaa gtc aaa gaa aag gct aag caa tga                              2430
Ile Glu Val Lys Glu Lys Ala Lys Gln
                805

<210> SEQ ID NO 22
<211> LENGTH: 809
<212> TYPE: PRT
<213> ORGANISM: Artificial Sequence
<220> FEATURE:
<223> OTHER INFORMATION: Synthetic Construct

<400> SEQUENCE: 22

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
```

-continued

```
            115                 120                 125
Asp Ala Gln Leu His Asn Leu Val Lys Arg Met Arg Gln Arg Thr Ala
    130                 135                 140
Leu Tyr Lys Lys Lys Leu Val Glu Gly Asp Leu Ser Ser Pro Glu Ala
145                 150                 155                 160
Ser Pro Gln Thr Ala Lys Pro Thr Ala Val Pro Pro Val Lys Glu Ser
                165                 170                 175
Asp Asp Lys Pro Thr Glu His Tyr Tyr Arg Leu Leu Trp Phe Lys Val
            180                 185                 190
Lys Lys Met Pro Leu Thr Glu Tyr Leu Lys Arg Ile Lys Leu Pro Asn
            195                 200                 205
Ser Ile Asp Ser Tyr Thr Asp Arg Leu Tyr Leu Leu Trp Leu Leu Leu
    210                 215                 220
Val Thr Leu Ala Tyr Asn Trp Asn Cys Cys Phe Ile Pro Leu Arg Leu
225                 230                 235                 240
Val Phe Pro Tyr Gln Thr Ala Asp Asn Ile His Tyr Trp Leu Ile Ala
                245                 250                 255
Asp Ile Ile Cys Asp Ile Ile Tyr Leu Tyr Asp Met Leu Phe Ile Gln
            260                 265                 270
Pro Arg Leu Gln Phe Val Arg Gly Gly Asp Ile Ile Val Asp Ser Asn
        275                 280                 285
Glu Leu Arg Lys His Tyr Arg Thr Ser Thr Lys Phe Gln Leu Asp Val
    290                 295                 300
Ala Ser Ile Ile Pro Phe Asp Ile Cys Tyr Leu Phe Gly Phe Asn
305                 310                 315                 320
Pro Met Phe Arg Ala Asn Arg Met Leu Lys Tyr Thr Ser Phe Phe Glu
                325                 330                 335
Phe Asn His His Leu Glu Ser Ile Met Asp Lys Ala Tyr Ile Tyr Arg
            340                 345                 350
Val Ile Arg Thr Thr Gly Tyr Leu Leu Phe Ile Leu His Ile Asn Ala
        355                 360                 365
Cys Val Tyr Tyr Trp Ala Ser Asn Tyr Glu Gly Ile Gly Thr Thr Arg
    370                 375                 380
Trp Val Tyr Asp Gly Glu Gly Asn Glu Tyr Leu Arg Cys Tyr Tyr Trp
385                 390                 395                 400
Ala Val Arg Thr Leu Ile Thr Ile Gly Gly Leu Pro Glu Pro Gln Thr
                405                 410                 415
Leu Phe Glu Ile Val Phe Gln Leu Leu Asn Phe Phe Ser Gly Val Phe
            420                 425                 430
Val Phe Ser Ser Leu Ile Gly Gln Met Arg Asp Val Ile Gly Ala Ala
        435                 440                 445
Thr Ala Asn Gln Asn Tyr Phe Arg Ala Cys Met Asp Asp Thr Ile Ala
    450                 455                 460
Tyr Met Asn Asn Tyr Ser Ile Pro Lys Leu Val Gln Lys Arg Val Arg
465                 470                 475                 480
Thr Trp Tyr Glu Tyr Thr Trp Asp Ser Gln Arg Met Leu Asp Glu Ser
                485                 490                 495
Asp Leu Leu Lys Thr Leu Pro Thr Thr Val Gln Leu Ala Leu Ala Ile
            500                 505                 510
Asp Val Asn Phe Ser Ile Ile Ser Lys Val Asp Leu Phe Lys Gly Cys
        515                 520                 525
Asp Thr Gln Met Ile Tyr Asp Met Leu Leu Arg Leu Lys Ser Val Leu
    530                 535                 540
```

```
Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
            565                 570                 575

Gly Thr Lys Val Leu Val Thr Leu Lys Ala Gly Ser Val Phe Gly Glu
        580                 585                 590

Ile Ser Leu Leu Ala Ala Gly Gly Asn Arg Arg Thr Ala Asn Val
    595                 600                 605

Val Ala His Gly Phe Ala Asn Leu Leu Thr Leu Asp Lys Lys Thr Leu
610                 615                 620

Gln Glu Ile Leu Val His Tyr Pro Asp Ser Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
        675                 680                 685

Ala Arg Leu Leu Lys Leu Lys Arg Glu Gln Ala Ala Gln Lys Lys Glu
690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Asn Glu Asp Lys Gly Lys Glu
                725                 730                 735

Asn Glu Asp Lys Asp Lys Gly Arg Glu Pro Glu Lys Pro Leu Asp
            740                 745                 750

Arg Pro Glu Cys Thr Ala Ser Pro Ile Ala Val Glu Glu Pro His
        755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Val Leu Thr
785                 790                 795                 800

Ile Glu Val Lys Glu Lys Ala Lys Gln
                805
```

<210> SEQ ID NO 23
<211> LENGTH: 2454
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (1)..(12)
<223> OTHER INFORMATION: modified end with NotI site and Kozak
<220> FEATURE:
<221> NAME/KEY: misc_feature
<222> LOCATION: (1)..(8)
<223> OTHER INFORMATION: NotI site for subcloning
<220> FEATURE:
<221> NAME/KEY: CDS
<222> LOCATION: (13)..(2448)
<223> OTHER INFORMATION: ORF with silent mutations (stop codon and
      restriction sites BamHI, PstI, SalI, and NdeI)
<220> FEATURE:
<221> NAME/KEY: misc_feature
<222> LOCATION: (2440)..(2442)
<223> OTHER INFORMATION: modifed stop codon
<220> FEATURE:
<221> NAME/KEY: misc_feature
<222> LOCATION: (2440)..(2445)

```
<223> OTHER INFORMATION: BclI site to facilitate addition of epitope tag
<220> FEATURE:
<221> NAME/KEY: misc_feature
<222> LOCATION: (2446)..(2448)
<223> OTHER INFORMATION: additional stop codon
<220> FEATURE:
<221> NAME/KEY: misc_feature
<222> LOCATION: (2449)..(2454)
<223> OTHER INFORMATION: PstI site for subcloning

<400> SEQUENCE: 23
```

```
gcggccgcca cc atg ttt aaa tcg ctg aca aaa gtc aac aag gtg aag cct         51
              Met Phe Lys Ser Leu Thr Lys Val Asn Lys Val Lys Pro
                1               5                   10 ata gga gag aac aat gag aat gaa caa agt tct cgt cgg aat gaa gaa          99
Ile Gly Glu Asn Asn Glu Asn Glu Gln Ser Ser Arg Arg Asn Glu Glu
 15                  20                  25 ggc tct cac cca agt aat cag tct cag caa acc aca gca cag gaa gaa         147
Gly Ser His Pro Ser Asn Gln Ser Gln Gln Thr Thr Ala Gln Glu Glu
 30                  35                  40                  45 aac aaa ggt gaa gag aaa tct ctc aaa acc aag tca act cca gtc acg         195
Asn Lys Gly Glu Glu Lys Ser Leu Lys Thr Lys Ser Thr Pro Val Thr
                 50                  55                  60 tct gaa gag cca cac acc aac ata caa gac aaa ctc tcc aag aaa aat         243
Ser Glu Glu Pro His Thr Asn Ile Gln Asp Lys Leu Ser Lys Lys Asn
             65                  70                  75 tcc tct gga gat ctg acc aca aac cct gac cct caa aat gca gca gaa         291
Ser Ser Gly Asp Leu Thr Thr Asn Pro Asp Pro Gln Asn Ala Ala Glu
         80                  85                  90 cca act gga aca gtg cca gag cag aag gaa atg gac ccc ggg aaa gaa         339
Pro Thr Gly Thr Val Pro Glu Gln Lys Glu Met Asp Pro Gly Lys Glu
 95                 100                 105 ggt cca aac agc cca caa aac aaa ccg cca gca gct cct gtt ata aat         387
Gly Pro Asn Ser Pro Gln Asn Lys Pro Pro Ala Ala Pro Val Ile Asn
110                 115                 120                 125 gag tat gcc gat gcc cag cta cac aac ctg gtg aaa aga atg cgt caa         435
Glu Tyr Ala Asp Ala Gln Leu His Asn Leu Val Lys Arg Met Arg Gln
                130                 135                 140 aga aca gcc ctc tac aag aaa aag ttg gta gag gga gat ctc tcc tca         483
Arg Thr Ala Leu Tyr Lys Lys Lys Leu Val Glu Gly Asp Leu Ser Ser
            145                 150                 155 ccc gaa gcc agc cca caa act gca aag ccc acg gct gta cca cca gta         531
Pro Glu Ala Ser Pro Gln Thr Ala Lys Pro Thr Ala Val Pro Pro Val
        160                 165                 170 aaa gaa agc gat gat aag cca aca gaa cat tac tac agg ctg ttg tgg         579
Lys Glu Ser Asp Asp Lys Pro Thr Glu His Tyr Tyr Arg Leu Leu Trp
175                 180                 185 ttc aaa gtc aaa aag atg cct tta aca gag tac tta aag cga att aaa         627
Phe Lys Val Lys Lys Met Pro Leu Thr Glu Tyr Leu Lys Arg Ile Lys
190                 195                 200                 205 ctt cca aac agc ata gat tca tac aca gat cga ctc tat ctc ctg tgg         675
Leu Pro Asn Ser Ile Asp Ser Tyr Thr Asp Arg Leu Tyr Leu Leu Trp
                210                 215                 220 ctc ttg ctt gtc act ctt gcc tat aac tgg aac tgc tgt ttt ata cca         723
Leu Leu Leu Val Thr Leu Ala Tyr Asn Trp Asn Cys Cys Phe Ile Pro
            225                 230                 235 ctg cgc ctc gtc ttc cca tat caa acc gca gac aac ata cac tac tgg         771
Leu Arg Leu Val Phe Pro Tyr Gln Thr Ala Asp Asn Ile His Tyr Trp
        240                 245                 250 ctt att gcg gac atc atc tgt gat atc atc tac ctt tat gat atg cta         819
Leu Ile Ala Asp Ile Ile Cys Asp Ile Ile Tyr Leu Tyr Asp Met Leu
    255                 260                 265
```

| | |
|---|---|
| ttt atc cag ccc aga ctc cag ttt gta aga gga gga gac ata ata gtg<br>Phe Ile Gln Pro Arg Leu Gln Phe Val Arg Gly Gly Asp Ile Ile Val<br>270                        275                      280                    285 | 867 |
| gat tca aat gag cta agg aaa cac tac agg act tct aca aaa ttt cag<br>Asp Ser Asn Glu Leu Arg Lys His Tyr Arg Thr Ser Thr Lys Phe Gln<br>                     290                      295                      300 | 915 |
| ttg gat gtc gca tca ata ata cca ttt gat att tgc tac ctc ttc ttt<br>Leu Asp Val Ala Ser Ile Ile Pro Phe Asp Ile Cys Tyr Leu Phe Phe<br>               305                      310                      315 | 963 |
| ggg ttt aat cca atg ttt aga gca aat agg atg tta aag tac act tca<br>Gly Phe Asn Pro Met Phe Arg Ala Asn Arg Met Leu Lys Tyr Thr Ser<br>320                        325                      330 | 1011 |
| ttt ttt gaa ttt aat cat cac cta gag tct ata atg gac aaa gca tat<br>Phe Phe Glu Phe Asn His His Leu Glu Ser Ile Met Asp Lys Ala Tyr<br>     335                      340                      345 | 1059 |
| atc tac aga gtt att cga aca act gga tac ttg ctg ttt att ctg cac<br>Ile Tyr Arg Val Ile Arg Thr Thr Gly Tyr Leu Leu Phe Ile Leu His<br>350                        355                      360                    365 | 1107 |
| att aat gcc tgt gtt tat tac tgg gct tca aac tat gaa gga att ggc<br>Ile Asn Ala Cys Val Tyr Tyr Trp Ala Ser Asn Tyr Glu Gly Ile Gly<br>                     370                      375                      380 | 1155 |
| act act aga tgg gtg tat gat ggg gaa gga aac gag tat ctg aga tgt<br>Thr Thr Arg Trp Val Tyr Asp Gly Glu Gly Asn Glu Tyr Leu Arg Cys<br>               385                      390                      395 | 1203 |
| tat tat tgg gca gtt cga act tta att acc att ggt ggc ctt cca gaa<br>Tyr Tyr Trp Ala Val Arg Thr Leu Ile Thr Ile Gly Gly Leu Pro Glu<br>             400                      405                      410 | 1251 |
| cca caa act tta ttt gaa att gtt ttt caa ctc ttg aat ttt ttt tct<br>Pro Gln Thr Leu Phe Glu Ile Val Phe Gln Leu Leu Asn Phe Phe Ser<br>               415                      420                      425 | 1299 |
| gga gtt ttt gtg ttc tcc agt tta att ggt cag atg aga gat gtg att<br>Gly Val Phe Val Phe Ser Ser Leu Ile Gly Gln Met Arg Asp Val Ile<br>430                        435                      440                    445 | 1347 |
| gga gca gct aca gcc aat cag aac tac ttc cgc gcc tgc atg gat gac<br>Gly Ala Ala Thr Ala Asn Gln Asn Tyr Phe Arg Ala Cys Met Asp Asp<br>                     450                      455                      460 | 1395 |
| acc att gcc tac atg aac aat tac tcc att cct aaa ctt gtg caa aag<br>Thr Ile Ala Tyr Met Asn Asn Tyr Ser Ile Pro Lys Leu Val Gln Lys<br>               465                      470                      475 | 1443 |
| cga gtt cgg act tgg tat gaa tat aca tgg gac tct caa aga atg cta<br>Arg Val Arg Thr Trp Tyr Glu Tyr Thr Trp Asp Ser Gln Arg Met Leu<br>             480                      485                      490 | 1491 |
| gat gag tct gat ttg ctt aag acc cta cca act acg gtc cag tta gcc<br>Asp Glu Ser Asp Leu Leu Lys Thr Leu Pro Thr Thr Val Gln Leu Ala<br>495                        500                      505 | 1539 |
| ctc gcc att gat gtg aac ttc agc atc atc agc aaa gtt gac ttg ttc<br>Leu Ala Ile Asp Val Asn Phe Ser Ile Ile Ser Lys Val Asp Leu Phe<br>510                        515                      520                    525 | 1587 |
| aag ggt tgt gat aca cag atg att tat gac atg ttg cta aga ttg aaa<br>Lys Gly Cys Asp Thr Gln Met Ile Tyr Asp Met Leu Leu Arg Leu Lys<br>                     530                      535                      540 | 1635 |
| tcc gtt ctc tat ttg cct ggt gac ttt gtc tgc aaa aag gga gaa att<br>Ser Val Leu Tyr Leu Pro Gly Asp Phe Val Cys Lys Lys Gly Glu Ile<br>               545                      550                      555 | 1683 |
| ggc aag gaa atg tat atc atc aag cat gga gaa gtc caa gtt ctt gga<br>Gly Lys Glu Met Tyr Ile Ile Lys His Gly Glu Val Gln Val Leu Gly<br>                     560                      565                    570 | 1731 |
| ggc cct gat ggt act aaa gtt ctg gtt act ctg aaa gct ggg tcg gtg<br>Gly Pro Asp Gly Thr Lys Val Leu Val Thr Leu Lys Ala Gly Ser Val | 1779 |

```
                   575                 580                 585
ttt gga gaa atc agc ctt cta gca gca gga gga gga aac cgt cga act       1827
Phe Gly Glu Ile Ser Leu Leu Ala Ala Gly Gly Gly Asn Arg Arg Thr
590                 595                 600                 605 gcc aat gtg gtg gcc cac ggg ttt gcc aat ctt tta act cta gac aaa       1875
Ala Asn Val Val Ala His Gly Phe Ala Asn Leu Leu Thr Leu Asp Lys
                610                 615                 620 aag acc ctc caa gaa att cta gtg cat tat cca gat tct gaa aga atc       1923
Lys Thr Leu Gln Glu Ile Leu Val His Tyr Pro Asp Ser Glu Arg Ile
            625                 630                 635 ctc atg aag aaa gcc aga gtg ctt tta aag cag aag gct aag acc gca       1971
Leu Met Lys Lys Ala Arg Val Leu Leu Lys Gln Lys Ala Lys Thr Ala
        640                 645                 650 gaa gca acc cct cca aga aaa gat ctt gcc ctc ctc ttc cca ccg aaa       2019
Glu Ala Thr Pro Pro Arg Lys Asp Leu Ala Leu Leu Phe Pro Pro Lys
655                 660                 665 gaa gag aca ccc aaa ctg ttt aaa act ctc cta gga ggc aca gga aaa       2067
Glu Glu Thr Pro Lys Leu Phe Lys Thr Leu Leu Gly Gly Thr Gly Lys
670                 675                 680                 685 gca agt ctt gca aga cta ctc aaa ttg aag cga gag caa gca gct cag       2115
Ala Ser Leu Ala Arg Leu Leu Lys Leu Lys Arg Glu Gln Ala Ala Gln
                690                 695                 700 aag aaa gaa aat tct gaa gga gga gag gaa gaa gga aaa gaa aat gaa       2163
Lys Lys Glu Asn Ser Glu Gly Gly Glu Glu Gly Lys Glu Asn Glu
            705                 710                 715 gat aaa caa aaa gaa aat gaa gat aaa caa aaa gaa aat gaa gat aaa       2211
Asp Lys Gln Lys Glu Asn Glu Asp Lys Gln Lys Glu Asn Glu Asp Lys
        720                 725                 730 gga aaa gaa aat gaa gat aaa gat aaa gga aga gag cca gaa gag aag       2259
Gly Lys Glu Asn Glu Asp Lys Asp Lys Gly Arg Glu Pro Glu Glu Lys
735                 740                 745 cca ctg gac aga cct gaa tgt aca gca agt cct att gca gtg gag gaa       2307
Pro Leu Asp Arg Pro Glu Cys Thr Ala Ser Pro Ile Ala Val Glu Glu
750                 755                 760                 765 gaa ccc cac tca gtt aga agg aca gtt tta ccc aga ggg act tct cgt       2355
Glu Pro His Ser Val Arg Arg Thr Val Leu Pro Arg Gly Thr Ser Arg
                770                 775                 780 caa tca ctc att atc agc atg gct cct tct gct gag ggc gga gaa gag       2403
Gln Ser Leu Ile Ile Ser Met Ala Pro Ser Ala Glu Gly Gly Glu Glu
            785                 790                 795 gtt ctt act att gaa gtc aaa gaa aag gct aag caa tga tca taa           2448
Val Leu Thr Ile Glu Val Lys Glu Lys Ala Lys Gln     Ser
        800                 805                 810 ctgcag                                                                 2454

<210> SEQ ID NO 24
<211> LENGTH: 809
<212> TYPE: PRT
<213> ORGANISM: Artificial Sequence
<220> FEATURE:
<223> OTHER INFORMATION: Synthetic Construct

<400> SEQUENCE: 24

Met Phe Lys Ser Leu Thr Lys Val Asn Lys Val Lys Pro Ile Gly Glu
1               5                   10                  15

Asn Asn Glu Asn Glu Gln Ser Ser Arg Arg Asn Glu Glu Gly Ser His
                20                  25                  30

Pro Ser Asn Gln Ser Gln Gln Thr Thr Ala Gln Glu Glu Asn Lys Gly
            35                  40                  45
```

```
Glu Glu Lys Ser Leu Lys Thr Lys Ser Thr Pro Val Thr Ser Glu Glu
    50              55                  60
Pro His Thr Asn Ile Gln Asp Lys Leu Ser Lys Asn Ser Ser Gly
 65              70                  75                  80
Asp Leu Thr Thr Asn Pro Asp Pro Gln Asn Ala Ala Glu Pro Thr Gly
                 85                  90                  95
Thr Val Pro Glu Gln Lys Glu Met Asp Pro Gly Lys Glu Gly Pro Asn
            100             105                 110
Ser Pro Gln Asn Lys Pro Pro Ala Ala Pro Val Ile Asn Glu Tyr Ala
                115             120                 125
Asp Ala Gln Leu His Asn Leu Val Lys Arg Met Arg Gln Arg Thr Ala
        130                 135             140
Leu Tyr Lys Lys Lys Leu Val Glu Gly Asp Leu Ser Ser Pro Glu Ala
145             150                 155                 160
Ser Pro Gln Thr Ala Lys Pro Thr Ala Val Pro Pro Val Lys Glu Ser
                165             170                 175
Asp Asp Lys Pro Thr Glu His Tyr Tyr Arg Leu Leu Trp Phe Lys Val
            180             185                 190
Lys Lys Met Pro Leu Thr Glu Tyr Leu Lys Arg Ile Lys Leu Pro Asn
            195             200                 205
Ser Ile Asp Ser Tyr Thr Asp Arg Leu Tyr Leu Leu Trp Leu Leu Leu
        210             215                 220
Val Thr Leu Ala Tyr Asn Trp Asn Cys Cys Phe Ile Pro Leu Arg Leu
225             230                 235                 240
Val Phe Pro Tyr Gln Thr Ala Asp Asn Ile His Tyr Trp Leu Ile Ala
                245             250                 255
Asp Ile Ile Cys Asp Ile Ile Tyr Leu Tyr Asp Met Leu Phe Ile Gln
            260             265                 270
Pro Arg Leu Gln Phe Val Arg Gly Gly Asp Ile Ile Val Asp Ser Asn
        275             280                 285
Glu Leu Arg Lys His Tyr Arg Thr Ser Thr Lys Phe Gln Leu Asp Val
    290             295                 300
Ala Ser Ile Ile Pro Phe Asp Ile Cys Tyr Leu Phe Phe Gly Phe Asn
305             310                 315                 320
Pro Met Phe Arg Ala Asn Arg Met Leu Lys Tyr Thr Ser Phe Phe Glu
                325             330                 335
Phe Asn His His Leu Glu Ser Ile Met Asp Lys Ala Tyr Ile Tyr Arg
            340             345                 350
Val Ile Arg Thr Thr Gly Tyr Leu Leu Phe Ile Leu His Ile Asn Ala
            355             360                 365
Cys Val Tyr Tyr Trp Ala Ser Asn Tyr Glu Gly Ile Gly Thr Thr Arg
    370             375                 380
Trp Val Tyr Asp Gly Glu Gly Asn Glu Tyr Leu Arg Cys Tyr Tyr Trp
385             390                 395                 400
Ala Val Arg Thr Leu Ile Thr Ile Gly Gly Leu Pro Glu Pro Gln Thr
            405             410                 415
Leu Phe Glu Ile Val Phe Gln Leu Leu Asn Phe Phe Ser Gly Val Phe
            420             425                 430
Val Phe Ser Ser Leu Ile Gly Gln Met Arg Asp Val Ile Gly Ala Ala
            435             440                 445
Thr Ala Asn Gln Asn Tyr Phe Arg Ala Cys Met Asp Asp Thr Ile Ala
    450             455                 460
Tyr Met Asn Asn Tyr Ser Ile Pro Lys Leu Val Gln Lys Arg Val Arg
```

-continued

```
465                 470                 475                 480
Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
                500                 505                 510

Asp Val Asn Phe Ser Ile Ile Ser Lys Val Asp Leu Phe Lys Gly Cys
                515                 520                 525

Asp Thr Gln Met Ile Tyr Asp Met Leu Leu Arg Leu Lys Ser Val Leu
                530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
                580                 585                 590

Ile Ser Leu Leu Ala Ala Gly Gly Gly Asn Arg Arg Thr Ala Asn Val
                595                 600                 605

Val Ala His Gly Phe Ala Asn Leu Leu Thr Leu Asp Lys Lys Thr Leu
                610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
                660                 665                 670

Pro Lys Leu Phe Lys Thr Leu Leu Gly Gly Thr Gly Lys Ala Ser Leu
                675                 680                 685

Ala Arg Leu Leu Lys Leu Lys Arg Glu Gln Ala Ala Gln Lys Lys Glu
                690                 695                 700

Asn Ser Glu Gly Gly Glu Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Glu Lys Pro Leu Asp
                740                 745                 750

Arg Pro Glu Cys Thr Ala Ser Pro Ile Ala Val Glu Glu Glu Pro His
                755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805
```